United States Patent
Sermadiras et al.

(10) Patent No.: US 11,795,205 B2
(45) Date of Patent: Oct. 24, 2023

(54) HETERODIMERIC RELAXIN FUSIONS POLYPEPTIDES

(71) Applicant: MEDIMMUNE LIMITED, Cambridge (GB)

(72) Inventors: Isabelle Sermadiras, Cambridge (GB); Monika Anna Papworth, Cambridge (GB); Judy Christiane Paterson, Cambridge (GB); Esther Marie Martin, Cambridge (GB); Peng Ke, Cambridge (GB)

(73) Assignee: MEDIMMUNE LIMITED, Cambridge (GB)

( * ) Notice: Subject to any disclaimer, the term of this patent is extended or adjusted under 35 U.S.C. 154(b) by 121 days.

(21) Appl. No.: 17/348,825

(22) Filed: Jun. 16, 2021

(65) Prior Publication Data
US 2022/0017591 A1    Jan. 20, 2022

Related U.S. Application Data

(60) Provisional application No. 63/040,250, filed on Jun. 17, 2020.

(51) Int. Cl.
| | |
|---|---|
| *C07K 14/64* | (2006.01) |
| *A61K 38/22* | (2006.01) |
| *C07K 19/00* | (2006.01) |
| *A61P 9/04* | (2006.01) |
| *C12N 15/85* | (2006.01) |
| *A61K 47/68* | (2017.01) |

(52) U.S. Cl.
CPC .......... *C07K 14/64* (2013.01); *A61K 38/2221* (2013.01); *A61P 9/04* (2018.01); *C07K 19/00* (2013.01); *C12N 15/85* (2013.01); *A61K 47/6811* (2017.08); *C07K 2319/30* (2013.01); *C07K 2319/31* (2013.01)

(58) Field of Classification Search
CPC .... C07K 14/64; C07K 19/00; C07K 2319/30; A61K 38/2221
See application file for complete search history.

(56) References Cited

U.S. PATENT DOCUMENTS

| | | | |
|---|---|---|---|
| 2011/0130332 A1* | 6/2011 | Park | C07K 14/64 514/12.7 |
| 2013/0244938 A1 | 9/2013 | Park et al. | |

FOREIGN PATENT DOCUMENTS

| | | |
|---|---|---|
| WO | 2012/058768 A1 | 5/2012 |
| WO | 2013/004607 A1 | 1/2013 |
| WO | 2014/102179 A1 | 7/2014 |
| WO | 2015/181805 A1 | 12/2015 |
| WO | 2018/138170 A1 | 8/2018 |

OTHER PUBLICATIONS

Ha et al, 2016. Frontiers in Immunology. 7: 1-16.*
Faust, et al., "Production of a novel heterodimeric two-chain insulin-Fc fusion protein", Protein Engineering, Design and Selection, vol. 33, pp. 1-9 (2020).

* cited by examiner

*Primary Examiner* — Zachary C Howard

(57) ABSTRACT

The present invention relates to heterodimeric Relaxin fusion polypeptides, in particular to heterodimeric Relaxin 2 fusion polypeptides and uses thereof. Thus, the invention provides Relaxin fusion polypeptides, nucleic acid molecules, vectors, host cells, pharmaceutical compositions and kits comprising the same and uses of the same including methods of treatment. The polypeptides and compositions of the invention may be useful, in particular, in the treatment of cardiovascular diseases, for example for the treatment of heart failure.

5 Claims, 31 Drawing Sheets
Specification includes a Sequence Listing.

```
Relaxin A (SEQ ID NO: 80)

CAGCTCTACTCAGCGCTCGCTAATAAGTGTTGTCATGTGGGATGCACAAAGCGGTCTCTCGCCAGATTC
TGC

Relaxin B (SEQ ID NO: 81)

AGCTGGATGGAAGAAGTGATTAAACTGTGTGGCCGCGAACTGGTGCGCGCGCAGATTGCGATTTGCGGC
ATGAGCACCTGGAGC

FcH01 (SEQ ID NO: 82)

GACAAGACCCATACATGTCCTCCATGCCCGGCGCCTGAGTTCGAGGGCGGACCCTCCGTGTTCCTGTTC
CCCCCAAAGCCCAAGGACACCCTGATGATCTCCCGGACCCCCGAAGTGACCTGCGTGGTGGTGGACGTG
TCCCACGAGGACCCTGAAGTGAAGTTCAATTGGTACGTGGACGGCGTGGAAGTGCACAACGCCAAGACC
AAGCCCAGAGAGGAACAGTACAACTCCACCTACCGGGTGGTGTCCGTGCTGACCGTGCTGCACCAGGAC
TGGCTGAACGGCAAAGAGTACAAGTGCAAGGTCTCCAACAAGGCCCTGCCCGCCTCCATCGAAAAGACC
ATCTCCAAGGCCAAGGGCCAGCCCCGCGAGCCTCAGGTGTGCACACTGCCCCCAGCCGGGAAGAGATG
ACCAAGAACCAGGTGTCCCTGTCCTGTGCCGTGAAAGGCTTCTACCCCTCCGATATCGCTGTGGAATGG
GAGTCCAACGGCCAGCCCGAGAACAACTACAAGACCACCCCCCCTGTGCTGGACTCCGACGGCTCATTC
TTCCTGGTGTCCAAGCTGACCGTGGACAAGTCCCGGTGGCAGCAGGGCAACGTGTTCTCCTGCTCCGTG
ATGCACGAGGCCCTGCACAACCACTACACCCAGAAAAGCTTGTCCCTGAGCCCCGGC

FcK01 (SEQ ID NO: 83)

GACAAGACCCATACATGTCCTCCATGCCCGGCGCCTGAGTTCGAGGGCGGACCCTCCGTGTTCCTGTTC
CCCCCAAAGCCCAAGGACACCCTGATGATCTCCCGGACCCCCGAAGTGACCTGCGTGGTGGTGGACGTG
TCCCACGAGGACCCTGAAGTGAAGTTCAATTGGTACGTGGACGGCGTGGAAGTGCACAACGCCAAGACC
AAGCCCAGAGAGGAACAGTACAACTCCACCTACCGGGTGGTGTCCGTGCTGACCGTGCTGCACCAGGAC
TGGCTGAACGGCAAAGAGTACAAGTGCAAGGTCTCCAACAAGGCCCTGCCCGCCTCCATCGAAAAGACC
ATCTCCAAGGCCAAGGGCCAGCCCCGCGAGCCTCAGGTGTACACACTGCCCCCCTGCCGGGAAGAGATG
ACCAAGAACCAGGTGTCCCTGTGGTGTCTGGTGAAAGGCTTCTACCCCTCCGATATCGCTGTGGAATGG
GAGTCCAACGGCCAGCCCGAGAACAACTACAAGACCACCCCCCCTGTGCTGGACTCCGACGGCTCATTC
TTCCTGTACTCCAAGCTGACCGTGGACAAGTCCCGGTGGCAGCAGGGCAACGTGTTCTCCTGCTCCGTG
ATGCACGAGGCCCTGCACAACCACTACACCCAGAAAAGCTTGTCCCTGAGCCCCGGC

RELAX0010 (SEQ ID NO: 84)

GATAAAACCCATACCTGCCCGCCGTGCCCGGCGCCGGAACTGCTGGGCGGCCCGAGCGTGTTTCTGTTT
CCGCCGAAACCGAAAGATACCCTGATGATTAGCCGCACCCCGGAAGTGACCTGCGTGGTGGTGGATGTG
AGCCATGAAGATCCGGAAGTGAAATTTAACTGGTATGTGGATGGCGTGGAAGTGCATAACGCGAAACC
AAACCGCGCGAAGAACAGTATAACAGCACCTATCGCGTGGTGAGCGTGCTGACCGTGCTGCATCAGGAT
TGGCTGAACGGCAAAGAATATAAATGCAAAGTGAGCAACAAAGCGCTGCCGGCGCCGATTGAAAAAACC
ATTAGCAAAGCGAAAGGCCAGCCGCGCGAACCGCAGGTGTATACCCTGCCGCCGAGCCGCGATGAACTG
ACCAAAAACCAGGTGAGCCTGACCTGCCTGGTGAAAGGCTTTTATCCGAGCGATATTGCGGT
```

Figure 11 Continued

```
GGAATGGGAAAGCAACGGCCAGCCGGAAAACAACTATAAAACCACCCCGCCGGTGCTGGATAGCGATGG
CAGCTTTTTTCTGTATAGCAAACTGACCGTGGATAAAAGCCGCTGGCAGCAGGGCAACGTGTTTAGCTG
CAGCGTGATGCATGAAGCGCTGCATAACCATTATACCCAGAAAAGCCTGAGCCTGAGCCCGGGCAAAGG
CGGCGGCGGCAGCGGCGGCGGCGGCAGCGGCGGCGGCGGCAGCCAGCTGTATAGCGCGCTGGCGAACAA
ATGCTGCCATGTGGGCTGCACCAAACGCAGCCTGGCGCGCTTTTGCGGCGGCGGCGGCAGCGGCGGCGG
CGGCAGCGGCGGCGGCGGCAGCAGCTGGATGGAAGAAGTGATTAAACTGTGTGGCCGCGAACTGGTGCG
CGCGCAGATTGCGATTTGCGGCATGAGCACCTGGAGC
```

Rlx011 (SEQ ID NO: 85)

```
GGAGGAGCGGGTGGAGCTTGTCCTCCATGCCCGGCGCCTGAGTTCGAGGGCGGACCCTCCGTGTTCCTG
TTCCCCCCAAAGCCCAAGGACACCCTGATGATCTCCCGGACCCCCGAAGTGACCTGCGTGGTGGTGGAC
GTGTCCCACGAGGACCCTGAAGTGAAGTTCAATTGGTACGTGGACGGCGTGGAAGTGCACAACGCCAAG
ACCAAGCCCAGAGAGGAACAGTACAACTCCACCTACCGGGTGGTGTCCGTGCTGACCGTGCTGCACCAG
GACTGGCTGAACGGCAAAGAGTACAAGTGCAAGGTCTCCAACAAGGCCCTGCCCGCCTCCATCGAAAAG
ACCATCTCCAAGGCCAAGGGCCAGCCCCGCGAGCCTCAGGTGTACACACTGCCCCCCTGCCGGGAAGAG
ATGACCAAGAACCAGGTGTCCCTGTGGTGTCTGGTGAAAGGCTTCTACCCCTCCGATATCGCTGTGGAA
TGGGAGTCCAACGGCCAGCCCGAGAACAACTACAAGACCACCCCCCCTGTGCTGGACTCCGACGGCTCA
TTCTTCCTGTACTCCAAGCTGACCGTGGACAAGTCCCGGTGGCAGCAGGGCAACGTGTTCTCCTGCTCC
GTGATGCACGAGGCCCTGCACAACCACTACACCCAGAAGTCTCTAAGCTTGAGCCCCGGCGGAGGTGGT
GGAAGCGGAGGAGGTGGCTCTGGAGGGGGTGGAAGCGGAGGTGGAGGTGGATCCCAGCTCTACTCAGCG
CTCGCTAATAAGTGTTGTCATGTGGGATGCACAAAGCGGTCTCTCGCCAGATTCTGC
```

Rlx011b (SEQ ID NO: 86)

```
GGAGGAGCGGGTGGAGCTTGTCCTCCATGCCCGGCGCCTGAGTTCGAGGGCGGACCCTCCGTGTTCCTG
TTCCCCCCAAAGCCCAAGGACACCCTGATGATCTCCCGGACCCCCGAAGTGACCTGCGTGGTGGTGGAC
GTGTCCCACGAGGACCCTGAAGTGAAGTTCAATTGGTACGTGGACGGCGTGGAAGTGCACAACGCCAAG
ACCAAGCCCAGAGAGGAACAGTACAACTCCACCTACCGGGTGGTGTCCGTGCTGACCGTGCTGCACCAG
GACTGGCTGAACGGCAAAGAGTACAAGTGCAAGGTCTCCAACAAGGCCCTGCCCGCCTCCATCGAAAAG
ACCATCTCCAAGGCCAAGGGCCAGCCCCGCGAGCCTCAGGTGTACACACTGCCCCCCAGCCGGGAAGAG
ATGACCAAGAACCAGGTGTCCCTGTGGTGTCTGGTGAAAGGCTTCTACCCCTCCGATATCGCTGTGGAA
TGGGAGTCCAACGGCCAGCCCGAGAACAACTACAAGACCACCCCCCCTGTGCTGGACTCCGACGGCTCA
TTCTTCCTGTACTCCAAGCTGACCGTGGACAAGTCCCGGTGGCAGCAGGGCAACGTGTTCTCCTGCTCC
GTGATGCACGAGGCCCTGCACAACCACTACACCCAGAAGTCTCTAAGCTTGAGCCCCGGCGGAGGTGGT
GGAAGCGGAGGAGGTGGCTCTGGAGGGGGTGGAAGCGGAGGTGGAGGTGGATCCCAGCTCTACTCAGCG
CTCGCTAATAAGTGTTGTCATGTGGGATGCACAAAGCGGTCTCTCGCCAGATTCTGC
```

Rlx011DD (SEQ ID NO: 87)

```
GACAAGACCCACACCTGTCCTCCATGCCCGGCGCCTGAGTTCGAGGGCGGACCCTCCGTGTTCCTGTTC
CCCCCAAAGCCCAAGGACACCCTGATGATCTCCCGGACCCCCGAAGTGACCTGCGTGGTGGTGGACGTG
TCCCACGAGGACCCTGAAGTGAAGTTCAATTGGTACGTGGACGGCGTGGAAGTGCACAACGCCAAGACC
AAGCCCAGAGAGGAACAGTACAACTCCACCTACCGGGTGGTGTCCGTGCTGACCGTGCTGCACCAGGAC
TGGCTGAACGGCAAAGAGTACAAGTGCAAGGTCTCCAACAAGGCCCTGCCCGCCTCCATCGAAA
```

Figure 11 Continued

AGACCATCTCCAAGGCCAAGGGCCAGCCCCGCGAGCCTCAGGTGTACACACTGCCCCCCTGCCGGGAAG
AGATGACCAAGAACCAGGTGTCCCTGTGGTGTCTGGTGAAAGGCTTCTACCCCTCCGATATCGCTGTGG
AATGGGAGTCCAACGGCCAGCCCGAGAACAACTACAAGACCACCCCCCCTGTGCTGGACTCCGACGGCT
CATTCTTCCTGTACTCCAAGCTGACCGTGGACAAGTCCCGGTGGCAGCAGGGCAACGTGTTCTCCTGCT
CCGTGATGCACGAGGCCCTGCACAACCACTACACCCAGAAGTCTCTAAGCTTGAGCCCCGGCGGAGGTG
GTGGAAGCGGAGGAGGTGGCTCTGGAGGGGGTGGAAGCGGAGGTGGAGGTGGATCCCAGCTCTACTCAG
CGCTCGCTAATAAGTGTTGTCATGTGGGATGCACAAAGCGGTCTCTCGCCAGATTCTGC

Rlx012 (SEQ ID NO: 88)

GGAGGAGCGGGTGGAGCTTGTCCTCCATGCCCGGCGCCTGAGTTCGAGGGCGGACCCTCCGTGTTCCTG
TTCCCCCCAAAGCCCAAGGACACCCTGATGATCTCCCGGACCCCCGAAGTGACCTGCGTGGTGGTGGAC
GTGTCCCACGAGGACCCTGAAGTGAAGTTCAATTGGTACGTGGACGGCGTGGAAGTGCACAACGCCAAG
ACCAAGCCCAGAGAGGAACAGTACAACTCCACCTACCGGGTGGTGTCCGTGCTGACCGTGCTGCACCAG
GACTGGCTGAACGGCAAAGAGTACAAGTGCAAGGTCTCCAACAAGGCCCTGCCCGCCTCCATCGAAAAG
ACCATCTCCAAGGCCAAGGGCCAGCCCCGCGAGCCTCAGGTGTGCACACTGCCCCCCAGCCGGGAAGAG
ATGACCAAGAACCAGGTGTCCCTGTCCTGTGCCGTGAAAGGCTTCTACCCCTCCGATATCGCTGTGGAA
TGGGAGTCCAACGGCCAGCCCGAGAACAACTACAAGACCACCCCCCCTGTGCTGGACTCCGACGGCTCA
TTCTTCCTGGTGTCCAAGCTGACCGTGGACAAGTCCCGGTGGCAGCAGGGCAACGTGTTCTCCTGCTCC
GTGATGCACGAGGCCCTGCACAACCACTACACCCAGAAGTCTCTAAGCTTGAGCCCCGGCGGAGGTGGT
GGAAGCGGAGGAGGTGGCTCTGGAGGGGGTGGAAGCGGAGGTGGAGGTGGATCCCAGCTCTACTCAGCG
CTCGCTAATAAGTGTTGTCATGTGGGATGCACAAAGCGGTCTCTCGCCAGATTCTGC

Rlx012b (SEQ ID NO: 89)

GGAGGAGCGGGTGGAGCTTGTCCTCCATGCCCGGCGCCTGAGTTCGAGGGCGGACCCTCCGTGTTCCTG
TTCCCCCCAAAGCCCAAGGACACCCTGATGATCTCCCGGACCCCCGAAGTGACCTGCGTGGTGGTGGAC
GTGTCCCACGAGGACCCTGAAGTGAAGTTCAATTGGTACGTGGACGGCGTGGAAGTGCACAACGCCAAG
ACCAAGCCCAGAGAGGAACAGTACAACTCCACCTACCGGGTGGTGTCCGTGCTGACCGTGCTGCACCAG
GACTGGCTGAACGGCAAAGAGTACAAGTGCAAGGTCTCCAACAAGGCCCTGCCCGCCTCCATCGAAAAG
ACCATCTCCAAGGCCAAGGGCCAGCCCCGCGAGCCTCAGGTGTACACACTGCCCCCAGCCGGGAAGAG
ATGACCAAGAACCAGGTGTCCCTGTCCTGTGCCGTGAAAGGCTTCTACCCCTCCGATATCGCTGTGGAA
TGGGAGTCCAACGGCCAGCCCGAGAACAACTACAAGACCACCCCCCCTGTGCTGGACTCCGACGGCTCA
TTCTTCCTGGTGTCCAAGCTGACCGTGGACAAGTCCCGGTGGCAGCAGGGCAACGTGTTCTCCTGCTCC
GTGATGCACGAGGCCCTGCACAACCACTACACCCAGAAGTCTCTAAGCTTGAGCCCCGGCGGAGGTGGT
GGAAGCGGAGGAGGTGGCTCTGGAGGGGGTGGAAGCGGAGGTGGAGGTGGATCCCAGCTCTACTCAGCG
CTCGCTAATAAGTGTTGTCATGTGGGATGCACAAAGCGGTCTCTCGCCAGATTCTGC

Rlx012DD (SEQ ID NO: 90)

GACAAGACCCACACCTGTCCTCCATGCCCGGCGCCTGAGTTCGAGGGCGGACCCTCCGTGTTCCTGTTC
CCCCCAAAGCCCAAGGACACCCTGATGATCTCCCGGACCCCCGAAGTGACCTGCGTGGTGGTGGACGTG
TCCCACGAGGACCCTGAAGTGAAGTTCAATTGGTACGTGGACGGCGTGGAAGTGCACAACGCCAAGACC
AAGCCCAGAGAGGAACAGTACAACTCCACCTACCGGGTGGTGTCCGTGCTGACCGTGCTGCACCAGGAC
TGGCTGAACGGCAAAGAGTACAAGTGCAAGGTCTCCAACAAGGCCCTGCCCGCCTCCATCGAAA

Figure 11 Continued

```
AGACCATCTCCAAGGCCAAGGGCCAGCCCCGCGAGCCTCAGGTGTACACACTGCCCCCCTGCCGGGAAG
AGATGACCAAGAACCAGGTGTCCCTGTGGTGTCTGGTGAAAGGCTTCTACCCCTCCGATATCGCTGTGG
AATGGGAGTCCAACGGCCAGCCCGAGAACAACTACAAGACCACCCCCCCTGTGCTGGACTCCGACGGCT
CATTCTTCCTGTACTCCAAGCTGACCGTGGACAAGTCCCGGTGGCAGCAGGGCAACGTGTTCTCCTGCT
CCGTGATGCACGAGGCCCTGCACAACCACTACACCCAGAAGTCTCTAAGCTTGAGCCCCGGCGGAGGTG
GTGGAAGCGGAGGAGGTGGCTCTGGAGGGGTGGAAGCGGAGGTGGAGGTGGATCCAGCTGGATGGAAG
AAGTGATTAAACTGTGTGGCCGCGAACTGGTGCGCGCGCAGATTGCGATTTGCGGCATGAGCACCTGGA
GC
```

Rlx013 (SEQ ID NO: 91)

```
GGAGGAGCGGGTGGAGCTTGTCCTCCATGCCCGGCGCCTGAGTTCGAGGGCGGACCCTCCGTGTTCCTG
TTCCCCCCAAAGCCCAAGGACACCCTGATGATCTCCCGGACCCCCGAAGTGACCTGCGTGGTGGTGGAC
GTGTCCCACGAGGACCCTGAAGTGAAGTTCAATTGGTACGTGGACGGCGTGGAAGTGCACAACGCCAAG
ACCAAGCCCAGAGAGGAACAGTACAACTCCACCTACCGGGTGGTGTCCGTGCTGACCGTGCTGCACCAG
GACTGGCTGAACGGCAAAGAGTACAAGTGCAAGGTCTCCAACAAGGCCCTGCCCGCCTCCATCGAAAAG
ACCATCTCCAAGGCCAAGGGCCAGCCCCGCGAGCCTCAGGTGTACACACTGCCCCCCTGCCGGGAAGAG
ATGACCAAGAACCAGGTGTCCCTGTGGTGTCTGGTGAAAGGCTTCTACCCCTCCGATATCGCTGTGGAA
TGGGAGTCCAACGGCCAGCCCGAGAACAACTACAAGACCACCCCCCCTGTGCTGGACTCCGACGGCTCA
TTCTTCCTGTACTCCAAGCTGACCGTGGACAAGTCCCGGTGGCAGCAGGGCAACGTGTTCTCCTGCTCC
GTGATGCACGAGGCCCTGCACAACCACTACACCCAGAAGTCTCTAAGCTTGAGCCCCGGCGGAGGTGGT
GGAAGCGGAGGAGGTGGCTCTGGAGGGGTGGAAGCGGAGGTGGAGGTGGATCCAGCTGGATGGAAGAA
GTGATTAAACTGTGTGGCCGCGAACTGGTGCGCGCGCAGATTGCGATTTGCGGCATGAGCACCTGGAGC
```

Rlx013b (SEQ ID NO: 92)

```
GGAGGAGCGGGTGGAGCTTGTCCTCCATGCCCGGCGCCTGAGTTCGAGGGCGGACCCTCCGTGTTCCTG
TTCCCCCCAAAGCCCAAGGACACCCTGATGATCTCCCGGACCCCCGAAGTGACCTGCGTGGTGGTGGAC
GTGTCCCACGAGGACCCTGAAGTGAAGTTCAATTGGTACGTGGACGGCGTGGAAGTGCACAACGCCAAG
ACCAAGCCCAGAGAGGAACAGTACAACTCCACCTACCGGGTGGTGTCCGTGCTGACCGTGCTGCACCAG
GACTGGCTGAACGGCAAAGAGTACAAGTGCAAGGTCTCCAACAAGGCCCTGCCCGCCTCCATCGAAAAG
ACCATCTCCAAGGCCAAGGGCCAGCCCCGCGAGCCTCAGGTGTACACACTGCCCCCCAGCCGGGAAGAG
ATGACCAAGAACCAGGTGTCCCTGTGGTGTCTGGTGAAAGGCTTCTACCCCTCCGATATCGCTGTGGAA
TGGGAGTCCAACGGCCAGCCCGAGAACAACTACAAGACCACCCCCCCTGTGCTGGACTCCGACGGCTCA
TTCTTCCTGTACTCCAAGCTGACCGTGGACAAGTCCCGGTGGCAGCAGGGCAACGTGTTCTCCTGCTCC
GTGATGCACGAGGCCCTGCACAACCACTACACCCAGAAGTCTCTAAGCTTGAGCCCCGGCGGAGGTGGT
GGAAGCGGAGGAGGTGGCTCTGGAGGGGTGGAAGCGGAGGTGGAGGTGGATCCAGCTGGATGGAAGAA
GTGATTAAACTGTGTGGCCGCGAACTGGTGCGCGCGCAGATTGCGATTTGCGGCATGAGCACCTGGAGC
```

Rlx013DD (SEQ ID NO: 93)

```
GACAAGACCCAYACMTGTCCTCCATGCCCGGCGCCTGAGTTCGAGGGCGGACCCTCCGTGTTCCTGTTC
CCCCCAAAGCCCAAGGACACCCTGATGATCTCCCGGACCCCCGAAGTGACCTGCGTGGTGGTGGACG
```

Figure 11 Continued

```
TGTCCCACGAGGACCCTGAAGTGAAGTTCAATTGGTACGTGGACGGCGTGGAAGTGCACAACGCCAAGA
CCAAGCCCAGAGAGGAACAGTACAACTCCACCTACCGGGTGGTGTCCGTGCTGACCGTGCTGCACCAGG
ACTGGCTGAACGGCAAAGAGTACAAGTGCAAGGTCTCCAACAAGGCCCTGCCCGCCTCCATCGAAAAGA
CCATCTCCAAGGCCAAGGGCCAGCCCCGCGAGCCTCAGGTGTGCACACTGCCCCCCAGCCGGGAAGAGA
TGACCAAGAACCAGGTGTCCCTGTCCTGTGCCGTGAAAGGCTTCTACCCCTCCGATATCGCTGTGGAAT
GGGAGTCCAACGGCCAGCCCGAGAACAACTACAAGACCACCCCCCCTGTGCTGGACTCCGACGGCTCAT
TCTTCCTGGTGTCCAAGCTGACCGTGGACAAGTCCCGGTGGCAGCAGGGCAACGTGTTCTCCTGCTCCG
TGATGCACGAGGCCCTGCACAACCACTACACCCAGAAGTCTCTAAGCTTGAGCCCCGGCGGAGGTGGTG
GAAGCGGAGGAGGTGGCTCTGGAGGGGTGGAAGCGGAGGTGGAGGTGGATCCCAGCTCTACTCAGCGC
TCGCTAATAAGTGTTGTCATGTGGGATGCACAAAGCGGTCTCTCGCCAGATTCTGC
```

Rlx014 (SEQ ID NO: 94)

```
GGAGGAGCGGGTGGAGCTTGTCCTCCATGCCCGGCGCCTGAGTTCGAGGGCGGACCCTCCGTGTTCCTG
TTCCCCCCAAAGCCCAAGGACACCCTGATGATCTCCCGGACCCCCGAAGTGACCTGCGTGGTGGTGGAC
GTGTCCCACGAGGACCCTGAAGTGAAGTTCAATTGGTACGTGGACGGCGTGGAAGTGCACAACGCCAAG
ACCAAGCCCAGAGAGGAACAGTACAACTCCACCTACCGGGTGGTGTCCGTGCTGACCGTGCTGCACCAG
GACTGGCTGAACGGCAAAGAGTACAAGTGCAAGGTCTCCAACAAGGCCCTGCCCGCCTCCATCGAAAAG
ACCATCTCCAAGGCCAAGGGCCAGCCCCGCGAGCCTCAGGTGTGCACACTGCCCCCCAGCCGGGAAGAG
ATGACCAAGAACCAGGTGTCCCTGTCCTGTGCCGTGAAAGGCTTCTACCCCTCCGATATCGCTGTGGAA
TGGGAGTCCAACGGCCAGCCCGAGAACAACTACAAGACCACCCCCCCTGTGCTGGACTCCGACGGCTCA
TTCTTCCTGGTGTCCAAGCTGACCGTGGACAAGTCCCGGTGGCAGCAGGGCAACGTGTTCTCCTGCTCC
GTGATGCACGAGGCCCTGCACAACCACTACACCCAGAAGTCTCTAAGCTTGAGCCCCGGCGGAGGTGGT
GGAAGCGGAGGAGGTGGCTCTGGAGGGGTGGAAGCGGAGGTGGAGGTGGATCCAGCTGGATGGAAGAA
GTGATTAAACTGTGTGGCCGCGAACTGGTGCGCGCGCAGATTGCGATTTGCGGCATGAGCACCTGGAGC
```

Rlx014b (SEQ ID NO: 95)

```
GGAGGAGCGGGTGGAGCTTGTCCTCCATGCCCGGCGCCTGAGTTCGAGGGCGGACCCTCCGTGTTCCTG
TTCCCCCCAAAGCCCAAGGACACCCTGATGATCTCCCGGACCCCCGAAGTGACCTGCGTGGTGGTGGAC
GTGTCCCACGAGGACCCTGAAGTGAAGTTCAATTGGTACGTGGACGGCGTGGAAGTGCACAACGCCAAG
ACCAAGCCCAGAGAGGAACAGTACAACTCCACCTACCGGGTGGTGTCCGTGCTGACCGTGCTGCACCAG
GACTGGCTGAACGGCAAAGAGTACAAGTGCAAGGTCTCCAACAAGGCCCTGCCCGCCTCCATCGAAAAG
ACCATCTCCAAGGCCAAGGGCCAGCCCCGCGAGCCTCAGGTGTACACACTGCCCCCCAGCCGGGAAGAG
ATGACCAAGAACCAGGTGTCCCTGTCCTGTGCCGTGAAAGGCTTCTACCCCTCCGATATCGCTGTGGAA
TGGGAGTCCAACGGCCAGCCCGAGAACAACTACAAGACCACCCCCCCTGTGCTGGACTCCGACGGCTCA
TTCTTCCTGGTGTCCAAGCTGACCGTGGACAAGTCCCGGTGGCAGCAGGGCAACGTGTTCTCCTGCTCC
GTGATGCACGAGGCCCTGCACAACCACTACACCCAGAAGTCTCTAAGCTTGAGCCCCGGCGGAGGTGGT
GGAAGCGGAGGAGGTGGCTCTGGAGGGGTGGAAGCGGAGGTGGAGGTGGATCCAGCTGGATGGAAGAA
GTGATTAAACTGTGTGGCCGCGAACTGGTGCGCGCGCAGATTGCGATTTGCGGCATGAGCACCTGGAGC
```

Figure 11 Continued

Rlx014DD (SEQ ID NO: 96)

GACAAGACCCACACCTGTCCTCCATGCCCGGCGCCTGAGTTCGAGGGCGGACCCTCCGTGTTCCTGTTC
CCCCCAAAGCCCAAGGACACCCTGATGATCTCCCGGACCCCCGAAGTGACCTGCGTGGTGGTGGACGTG
TCCCACGAGGACCCTGAAGTGAAGTTCAATTGGTACGTGGACGGCGTGGAAGTGCACAACGCCAAGACC
AAGCCCAGAGAGGAACAGTACAACTCCACCTACCGGGTGGTGTCCGTGCTGACCGTGCTGCACCAGGAC
TGGCTGAACGGCAAAGAGTACAAGTGCAAGGTCTCCAACAAGGCCCTGCCCGCCTCCATCGAAAAGACC
ATCTCCAAGGCCAAGGGCCAGCCCCGCGAGCCTCAGGTGTGCACACTGCCCCCCAGCCGGGAAGAGATG
ACCAAGAACCAGGTGTCCCTGTCCTGTGCCGTGAAAGGCTTCTACCCCTCCGATATCGCTGTGGAATGG
GAGTCCAACGGCCAGCCCGAGAACAACTACAAGACCACCCCCCTGTGCTGGACTCCGACGGCTCATTC
TTCCTGGTGTCCAAGCTGACCGTGGACAAGTCCCGGTGGCAGCAGGGCAACGTGTTCTCCTGCTCCGTG
ATGCACGAGGCCCTGCACAACCACTACACCCAGAAGTCTCTAAGCTTGAGCCCCGGCGGAGGTGGTGGA
AGCGGAGGAGGTGGCTCTGGAGGGGTGGAAGCGGAGGTGGAGGTGGATCCAGCTGGATGAAGAAGTG
ATTAAACTGTGTGGCCGCGAACTGGTGCGCGCGCAGATTGCGATTTGCGGCATGAGCACCTGGAGC

Rlx020 (SEQ ID NO: 97)

GACAAGACCCACACCTGTCCTCCATGCCCGGCGCCTGAGTTCGAGGGCGGACCCTCCGTGTTCCTGTTC
CCCCCAAAGCCCAAGGACACCCTGATGATCTCCCGGACCCCCGAAGTGACCTGCGTGGTGGTGGACGTG
TCCCACGAGGACCCTGAAGTGAAGTTCAATTGGTACGTGGACGGCGTGGAAGTGCACAACGCCAAGACC
AAGCCCAGAGAGGAACAGTACAACTCCACCTACCGGGTGGTGTCCGTGCTGACCGTGCTGCACCAGGAC
TGGCTGAACGGCAAAGAGTACAAGTGCAAGGTCTCCAACAAGGCCCTGCCCGCCTCCATCGAAAAGACC
ATCTCCAAGGCCAAGGGCCAGCCCCGCGAGCCTCAGGTGTACACACTGCCCCCCTGCCGGGAAGAGATG
ACCAAGAACCAGGTGTCCCTGTGGTGTCTGGTGAAAGGCTTCTACCCCTCCGATATCGCTGTGGAATGG
GAGTCCAACGGCCAGCCCGAGAACAACTACAAGACCACCCCCCTGTGCTGGACTCCGACGGCTCATTC
TTCCTGTACTCCAAGCTGACCGTGGACAAGTCCCGGTGGCAGCAGGGCAACGTGTTCTCCTGCTCCGTG
ATGCACGAGGCCCTGCACAACCACTACACCCAGAAGTCTCTAAGCTTGAGCCCCGGCGGAGGTGGTGGA
AGCGGAGGAGGTGGCTCTGGTGGAGGGGGCGGATCCCAGCTCTACTCAGCGCTCGCTAATAAGTGTTGT
CATGTGGGATGCACAAAGCGGTCTCTCGCCAGATTCTGC

Rlx021 (SEQ ID NO: 98)

GACAAGACCCACACCTGTCCTCCATGCCCGGCGCCTGAGTTCGAGGGCGGACCCTCCGTGTTCCTGTTC
CCCCCAAAGCCCAAGGACACCCTGATGATCTCCCGGACCCCCGAAGTGACCTGCGTGGTGGTGGACGTG
TCCCACGAGGACCCTGAAGTGAAGTTCAATTGGTACGTGGACGGCGTGGAAGTGCACAACGCCAAGACC
AAGCCCAGAGAGGAACAGTACAACTCCACCTACCGGGTGGTGTCCGTGCTGACCGTGCTGCACCAGGAC
TGGCTGAACGGCAAAGAGTACAAGTGCAAGGTCTCCAACAAGGCCCTGCCCGCCTCCATCGAAAAGACC
ATCTCCAAGGCCAAGGGCCAGCCCCGCGAGCCTCAGGTGTGCACACTGCCCCCCAGCCGGGAAGAGATG
ACCAAGAACCAGGTGTCCCTGTCCTGTGCCGTGAAAGGCTTCTACCCCTCCGATATCGCTGTGGAATGG
GAGTCCAACGGCCAGCCCGAGAACAACTACAAGACCACCCCCCTGTGCTGGACTCCGACGGCTCATTC
TTCCTGGTGTCCAAGCTGACCGTGGACAAGTCCCGGTGGCAGCAGGGCAACGTGTTCTCCTGCTCCGTG
ATGCACGAGGCCCTGCACAACCACTACACCCAGAAGTCTCTAAGCTTGAGCCCCGGCGGAGGTGGTGGA
AGCGGAGGAGGTGGCTCTGGTGGAGGGGGCGGATCCAGCTGGATGAAGAAGTGATTAAACTGTGTGGC
CGCGAACTGGTGCGCGCGCAGATTGCGATTTGCGGCATGAGCACCTGGAGC

Figure 11 Continued

Rlx022 (SEQ ID NO: 99)

GACAAGACCCACACCTGTCCTCCATGCCCGGCGCCTGAGTTCGAGGGCGGACCCTCCGTGTTCCTGTTC
CCCCCAAAGCCCAAGGACACCCTGATGATCTCCCGGACCCCCGAAGTGACCTGCGTGGTGGTGGACGTG
TCCCACGAGGACCCTGAAGTGAAGTTCAATTGGTACGTGGACGGCGTGGAAGTGCACAACGCCAAGACC
AAGCCCAGAGAGGAACAGTACAACTCCACCTACCGGGTGGTGTCCGTGCTGACCGTGCTGCACCAGGAC
TGGCTGAACGGCAAAGAGTACAAGTGCAAGGTCTCCAACAAGGCCCTGCCCGCCTCCATCGAAAAGACC
ATCTCCAAGGCCAAGGGCCAGCCCCGCGAGCCTCAGGTGTACACACTGCCCCCCTGCCGGGAAGAGATG
ACCAAGAACCAGGTGTCCCTGTGGTGTCTGGTGAAAGGCTTCTACCCCTCCGATATCGCTGTGGAATGG
GAGTCCAACGGCCAGCCCGAGAACAACTACAAGACCACCCCCCTGTGCTGGACTCCGACGGCTCATTC
TTCCTGTACTCCAAGCTGACCGTGGACAAGTCCCGGTGGCAGCAGGGCAACGTGTTCTCCTGCTCCGTG
ATGCACGAGGCCCTGCACAACCACTACACCCAGAAGTCTCTAAGCTTGAGCCCCGGCGGAGGAGGTGGC
TCTGGTGGAGGGGGCGGATCCCAGCTCTACTCAGCGCTCGCTAATAAGTGTTGTCATGTGGGATGCACA
AAGCGGTCTCTCGCCAGATTCTGC

Rlx023 (SEQ ID NO: 100)

GACAAGACCCACACCTGTCCTCCATGCCCGGCGCCTGAGTTCGAGGGCGGACCCTCCGTGTTCCTGTTC
CCCCCAAAGCCCAAGGACACCCTGATGATCTCCCGGACCCCCGAAGTGACCTGCGTGGTGGTGGACGTG
TCCCACGAGGACCCTGAAGTGAAGTTCAATTGGTACGTGGACGGCGTGGAAGTGCACAACGCCAAGACC
AAGCCCAGAGAGGAACAGTACAACTCCACCTACCGGGTGGTGTCCGTGCTGACCGTGCTGCACCAGGAC
TGGCTGAACGGCAAAGAGTACAAGTGCAAGGTCTCCAACAAGGCCCTGCCCGCCTCCATCGAAAAGACC
ATCTCCAAGGCCAAGGGCCAGCCCCGCGAGCCTCAGGTGTGCACACTGCCCCCCAGCCGGGAAGAGATG
ACCAAGAACCAGGTGTCCCTGTCCTGTGCCGTGAAAGGCTTCTACCCCTCCGATATCGCTGTGGAATGG
GAGTCCAACGGCCAGCCCGAGAACAACTACAAGACCACCCCCCTGTGCTGGACTCCGACGGCTCATTC
TTCCTGGTGTCCAAGCTGACCGTGGACAAGTCCCGGTGGCAGCAGGGCAACGTGTTCTCCTGCTCCGTG
ATGCACGAGGCCCTGCACAACCACTACACCCAGAAGTCTCTAAGCTTGAGCCCCGGCGGAGGAGGTGGC
TCTGGTGGAGGGGGCGGATCCAGCTGGATGGAAGAAGTGATTAAACTGTGTGGCCGCGAACTGGTGCGC
GCGCAGATTGCGATTTGCGGCATGAGCACCTGGAGC

Rlx024 (SEQ ID NO: 101)

GACAAGACCCACACCTGTCCTCCATGCCCGGCGCCTGAGTTCGAGGGCGGACCCTCCGTGTTCCTGTTC
CCCCCAAAGCCCAAGGACACCCTGATGATCTCCCGGACCCCCGAAGTGACCTGCGTGGTGGTGGACGTG
TCCCACGAGGACCCTGAAGTGAAGTTCAATTGGTACGTGGACGGCGTGGAAGTGCACAACGCCAAGACC
AAGCCCAGAGAGGAACAGTACAACTCCACCTACCGGGTGGTGTCCGTGCTGACCGTGCTGCACCAGGAC
TGGCTGAACGGCAAAGAGTACAAGTGCAAGGTCTCCAACAAGGCCCTGCCCGCCTCCATCGAAAAGACC
ATCTCCAAGGCCAAGGGCCAGCCCCGCGAGCCTCAGGTGTACACACTGCCCCCCTGCCGGGAAGAGATG
ACCAAGAACCAGGTGTCCCTGTGGTGTCTGGTGAAAGGCTTCTACCCCTCCGATATCGCTGTGGAATGG
GAGTCCAACGGCCAGCCCGAGAACAACTACAAGACCACCCCCCTGTGCTGGACTCCGACGGCTCATTC
TTCCTGTACTCCAAGCTGACCGTGGACAAGTCCCGGTGGCAGCAGGGCAACGTGTTCTCCTGCTCCGTG
ATGCACGAGGCCCTGCACAACCACTACACCCAGAAGTCTCTAAGCTTGAGCCCCGGCGGTGGAGGGGGC
GGATCCCAGCTCTACTCAGCGCTCGCTAATAAGTGTTGTCATGTGGGATGCACAAAGCGGTCTCTCGCC
AGATTCTGC

Figure 11 Continued

Rlx025 (SEQ ID NO: 102)

GACAAGACCCACACCTGTCCTCCATGCCCGGCGCCTGAGTTCGAGGGCGGACCCTCCGTGTTCCTGTTC
CCCCCAAAGCCCAAGGACACCCTGATGATCTCCCGGACCCCCGAAGTGACCTGCGTGGTGGTGGACGTG
TCCCACGAGGACCCTGAAGTGAAGTTCAATTGGTACGTGGACGGCGTGGAAGTGCACAACGCCAAGACC
AAGCCCAGAGAGGAACAGTACAACTCCACCTACCGGGTGGTGTCCGTGCTGACCGTGCTGCACCAGGAC
TGGCTGAACGGCAAAGAGTACAAGTGCAAGGTCTCCAACAAGGCCCTGCCCGCCTCCATCGAAAAGACC
ATCTCCAAGGCCAAGGGCCAGCCCCGCGAGCCTCAGGTGTGCACACTGCCCCCCAGCCGGGAAGAGATG
ACCAAGAACCAGGTGTCCCTGTCCTGTGCCGTGAAAGGCTTCTACCCCTCCGATATCGCTGTGGAATGG
GAGTCCAACGGCCAGCCCGAGAACAACTACAAGACCACCCCCCCTGTGCTGGACTCCGACGGCTCATTC
TTCCTGGTGTCCAAGCTGACCGTGGACAAGTCCCGGTGGCAGCAGGGCAACGTGTTCTCCTGCTCCGTG
ATGCACGAGGCCCTGCACAACCACTACACCCAGAAGTCTCTAAGCTTGAGCCCCGGCGGTGGAGGGGGC
GGATCCAGCTGGATGGAAGAAGTGATTAAACTGTGTGGCCGCGAACTGGTGCGCGCGCAGATTGCGATT
TGCGGCATGAGCACCTGGAGC

Rlx026 (SEQ ID NO: 103)

GACAAGACCCACACCTGTCCTCCATGCCCGGCGCCTGAGTTCGAGGGCGGACCCTCCGTGTTCCTGTTC
CCCCCAAAGCCCAAGGACACCCTGATGATCTCCCGGACCCCCGAAGTGACCTGCGTGGTGGTGGACGTG
TCCCACGAGGACCCTGAAGTGAAGTTCAATTGGTACGTGGACGGCGTGGAAGTGCACAACGCCAAGACC
AAGCCCAGAGAGGAACAGTACAACTCCACCTACCGGGTGGTGTCCGTGCTGACCGTGCTGCACCAGGAC
TGGCTGAACGGCAAAGAGTACAAGTGCAAGGTCTCCAACAAGGCCCTGCCCGCCTCCATCGAAAAGACC
ATCTCCAAGGCCAAGGGCCAGCCCCGCGAGCCTCAGGTGTACACACTGCCCCCCTGCCGGGAAGAGATG
ACCAAGAACCAGGTGTCCCTGTGGTGTCTGGTGAAAGGCTTCTACCCCTCCGATATCGCTGTGGAATGG
GAGTCCAACGGCCAGCCCGAGAACAACTACAAGACCACCCCCCCTGTGCTGGACTCCGACGGCTCATTC
TTCCTGTACTCCAAGCTGACCGTGGACAAGTCCCGGTGGCAGCAGGGCAACGTGTTCTCCTGCTCCGTG
ATGCACGAGGCCCTGCACAACCACTACACCCAGAAGTCTCTAAGCTTGAGCCCCGGCGCACCTGCTCCC
GCACCAGCCCCTGCTCCCGCACCAGCCCCTGCTCCCGCACCAGCCGGATCCCAGCTCTACTCAGCGCTC
GCTAATAAGTGTTGTCATGTGGGATGCACAAAGCGGTCTCTCGCCAGATTCTGC

Rlx027 (SEQ ID NO: 104)

GACAAGACCCACACCTGTCCTCCATGCCCGGCGCCTGAGTTCGAGGGCGGACCCTCCGTGTTCCTGTTC
CCCCCAAAGCCCAAGGACACCCTGATGATCTCCCGGACCCCCGAAGTGACCTGCGTGGTGGTGGACGTG
TCCCACGAGGACCCTGAAGTGAAGTTCAATTGGTACGTGGACGGCGTGGAAGTGCACAACGCCAAGACC
AAGCCCAGAGAGGAACAGTACAACTCCACCTACCGGGTGGTGTCCGTGCTGACCGTGCTGCACCAGGAC
TGGCTGAACGGCAAAGAGTACAAGTGCAAGGTCTCCAACAAGGCCCTGCCCGCCTCCATCGAAAAGACC
ATCTCCAAGGCCAAGGGCCAGCCCCGCGAGCCTCAGGTGTGCACACTGCCCCCCAGCCGGGAAGAGATG
ACCAAGAACCAGGTGTCCCTGTCCTGTGCCGTGAAAGGCTTCTACCCCTCCGATATCGCTGTGGAATGG
GAGTCCAACGGCCAGCCCGAGAACAACTACAAGACCACCCCCCCTGTGCTGGACTCCGACGGCTCATTC
TTCCTGGTGTCCAAGCTGACCGTGGACAAGTCCCGGTGGCAGCAGGGCAACGTGTTCTCCTGCTCCGTG
ATGCACGAGGCCCTGCACAACCACTACACCCAGAAGTCTCTAAGCTTGAGCCCCGGCGCACCTGCTCCC
GCACCAGCCCCTGCTCCCGCACCAGCCCCTGCTCCCGCACCAGCCGGATCCAGCTGGATGGAAGAAGTG
ATTAAACTGTGTGGCCGCGAACTGGTGCGCGCGCAGATTGCGATTTGCGGCATGAGCACCTGGAGC

Figure 11 Continued

Rlx028 (SEQ ID NO: 105)

GACAAGACCCACACCTGTCCTCCATGCCCGGCGCCTGAGTTCGAGGGCGGACCCTCCGTGTTCCTGTTC
CCCCCAAAGCCCAAGGACACCCTGATGATCTCCCGGACCCCCGAAGTGACCTGCGTGGTGGTGGACGTG
TCCCACGAGGACCCTGAAGTGAAGTTCAATTGGTACGTGGACGGCGTGGAAGTGCACAACGCCAAGACC
AAGCCCAGAGAGGAACAGTACAACTCCACCTACCGGGTGGTGTCCGTGCTGACCGTGCTGCACCAGGAC
TGGCTGAACGGCAAAGAGTACAAGTGCAAGGTCTCCAACAAGGCCCTGCCCGCCTCCATCGAAAAGACC
ATCTCCAAGGCCAAGGGCCAGCCCCGCGAGCCTCAGGTGTGCACACTGCCCCCCAGCCGGGAAGAGATG
ACCAAGAACCAGGTGTCCCTGTCCTGTGCCGTGAAAGGCTTCTACCCCTCCGATATCGCTGTGGAATGG
GAGTCCAACGGCCAGCCCGAGAACAACTACAAGACCACCCCCCCTGTGCTGGACTCCGACGGCTCATTC
TTCCTGGTGTCCAAGCTGACCGTGGACAAGTCCCGGTGGCAGCAGGGCAACGTGTTCTCCTGCTCCGTG
ATGCACGAGGCCCTGCACAACCACTACACCCAGAAGTCTCTAAGCTTGAGCCCCGGCGCAGCTCCTGCT
CCCGCACCAGCCCCTGCTCCCGCACCAGCCGGATCCCAGCTCTACTCAGCGCTCGCTAATAAGTGTTGT
CATGTGGGATGCACAAAGCGGTCTCTCGCCAGATTCTGC

Rlx029 (SEQ ID NO: 106)

GACAAGACCCACACCTGTCCTCCATGCCCGGCGCCTGAGTTCGAGGGCGGACCCTCCGTGTTCCTGTTC
CCCCCAAAGCCCAAGGACACCCTGATGATCTCCCGGACCCCCGAAGTGACCTGCGTGGTGGTGGACGTG
TCCCACGAGGACCCTGAAGTGAAGTTCAATTGGTACGTGGACGGCGTGGAAGTGCACAACGCCAAGACC
AAGCCCAGAGAGGAACAGTACAACTCCACCTACCGGGTGGTGTCCGTGCTGACCGTGCTGCACCAGGAC
TGGCTGAACGGCAAAGAGTACAAGTGCAAGGTCTCCAACAAGGCCCTGCCCGCCTCCATCGAAAAGACC
ATCTCCAAGGCCAAGGGCCAGCCCCGCGAGCCTCAGGTGTACACACTGCCCCCCTGCCGGGAAGAGATG
ACCAAGAACCAGGTGTCCCTGTGGTGTCTGGTGAAAGGCTTCTACCCCTCCGATATCGCTGTGGAATGG
GAGTCCAACGGCCAGCCCGAGAACAACTACAAGACCACCCCCCCTGTGCTGGACTCCGACGGCTCATTC
TTCCTGTACTCCAAGCTGACCGTGGACAAGTCCCGGTGGCAGCAGGGCAACGTGTTCTCCTGCTCCGTG
ATGCACGAGGCCCTGCACAACCACTACACCCAGAAGTCTCTAAGCTTGAGCCCCGGCGCAGCTCCTGCT
CCCGCACCAGCCCCTGCTCCCGCACCAGCCGGATCCAGCTGGATGGAAGAAGTGATTAAACTGTGTGGC
CGCGAACTGGTGCGCGCGCAGATTGCGATTTGCGGCATGAGCACCTGGAGC

Rlx030 (SEQ ID NO: 107)

GACAAGACCCACACCTGTCCTCCATGCCCGGCGCCTGAGTTCGAGGGCGGACCCTCCGTGTTCCTGTTC
CCCCCAAAGCCCAAGGACACCCTGATGATCTCCCGGACCCCCGAAGTGACCTGCGTGGTGGTGGACGTG
TCCCACGAGGACCCTGAAGTGAAGTTCAATTGGTACGTGGACGGCGTGGAAGTGCACAACGCCAAGACC
AAGCCCAGAGAGGAACAGTACAACTCCACCTACCGGGTGGTGTCCGTGCTGACCGTGCTGCACCAGGAC
TGGCTGAACGGCAAAGAGTACAAGTGCAAGGTCTCCAACAAGGCCCTGCCCGCCTCCATCGAAAAGACC
ATCTCCAAGGCCAAGGGCCAGCCCCGCGAGCCTCAGGTGTACACACTGCCCCCCTGCCGGGAAGAGATG
ACCAAGAACCAGGTGTCCCTGTGGTGTCTGGTGAAAGGCTTCTACCCCTCCGATATCGCTGTGGAATGG
GAGTCCAACGGCCAGCCCGAGAACAACTACAAGACCACCCCCCCTGTGCTGGACTCCGACGGCTCATTC
TTCCTGTACTCCAAGCTGACCGTGGACAAGTCCCGGTGGCAGCAGGGCAACGTGTTCTCCTGCTCCGTG
ATGCACGAGGCCCTGCACAACCACTACACCCAGAAGTCTCTAAGCTTGAGCCCCGGCGCACCAGCCCCT
GCTCCCGCACCAGCCGGATCCCAGCTCTACTCAGCGCTCGCTAATAAGTGTTGTCATGTGGGATGCACA
AAGCGGTCTCTCGCCAGATTCTGC

Figure 11 Continued

Rlx031 (SEQ ID NO: 108)

GACAAGACCCACACCTGTCCTCCATGCCCGGCGCCTGAGTTCGAGGGCGGACCCTCCGTGTTCCTGTTC
CCCCAAAGCCCAAGGACACCCTGATGATCTCCCGGACCCCCGAAGTGACCTGCGTGGTGGTGGACGTG
TCCCACGAGGACCCTGAAGTGAAGTTCAATTGGTACGTGGACGGCGTGGAAGTGCACAACGCCAAGACC
AAGCCCAGAGAGGAACAGTACAACTCCACCTACCGGGTGGTGTCCGTGCTGACCGTGCTGCACCAGGAC
TGGCTGAACGGCAAAGAGTACAAGTGCAAGGTCTCCAACAAGGCCCTGCCCGCCTCCATCGAAAAGACC
ATCTCCAAGGCCAAGGGCCAGCCCCGCGAGCCTCAGGTGTGCACACTGCCCCCCAGCCGGGAAGAGATG
ACCAAGAACCAGGTGTCCCTGTCCTGTGCCGTGAAAGGCTTCTACCCCTCCGATATCGCTGTGGAATGG
GAGTCCAACGGCCAGCCCGAGAACAACTACAAGACCACCCCCCTGTGCTGGACTCCGACGGCTCATTC
TTCCTGGTGTCCAAGCTGACCGTGGACAAGTCCCGGTGGCAGCAGGGCAACGTGTTCTCCTGCTCCGTG
ATGCACGAGGCCCTGCACAACCACTACACCCAGAAGTCTCTAAGCTTGAGCCCCGGCGCACCAGCCCCT
GCTCCCGCACCAGCCGGATCCAGCTGGATGGAAGAAGTGATTAAACTGTGTGGCCGCGAACTGGTGCGC
GCGCAGATTGCGATTTGCGGCATGAGCACCTGGAGC

Rlx041E (SEQ ID NO: 109)

GACAAGACCCACACCGCTTGTCCTCCATGCCCGGCGCCTGAGTTCGAGGGCGGACCCTCCGTGTTCCTG
TTCCCCCCAAAGCCCAAGGACACCCTGATGATCTCCCGGACCCCCGAAGTGACCTGCGTGGTGGTGGAC
GTGTCCCACGAGGACCCTGAAGTGAAGTTCAATTGGTACGTGGACGGCGTGGAAGTGCACAACGCCAAG
ACCAAGCCCAGAGAGGAACAGTACAACTCCACCTACCGGGTGGTGTCCGTGCTGACCGTGCTGCACCAG
GACTGGCTGAACGGCAAAGAGTACAAGTGCAAGGTCTCCAACAAGGCCCTGCCCGCCTCCATCGAAAAG
ACCATCTCCAAGGCCAAGGGCCAGCCCCGCGAGCCTCAGGTGTACACACTGCCCCCCTGCCGGGAAGAG
ATGACCAAGAACCAGGTGTCCCTGTGGTGTCTGGTGAAAGGCTTCTACCCCTCCGATATCGCTGTGGAA
TGGGAGTCCAACGGCCAGCCCGAGAACAACTACAAGACCACCCCCCTGTGCTGGACTCCGACGGCTCA
TTCTTCCTGTACTCCAAGCTGACCGTGGACAAGTCCCGGTGGCAGCAGGGCAACGTGTTCTCCTGCTCC
GTGATGCACGAGGCCCTGCACAACCACTACACCCAGAAGTCTCTAAGCTTGAGCCCCGGCGGAGGTGGT
GGAAGCGGAGGAGGTGGCTCTGGAGGGGGTGGAAGCGGAGGTGGAGGTGGATCCCAGCTCTACTCAGCG
CTCGCTAATGAGTGTTGTCATGTGGGATGCACAAAGCGGTCTCTCGCCAGATTCTGC

Rlx041H (SEQ ID NO: 110)

GACAAGACCCACACCGCTTGTCCTCCATGCCCGGCGCCTGAGTTCGAGGGCGGACCCTCCGTGTTCCTG
TTCCCCCCAAAGCCCAAGGACACCCTGATGATCTCCCGGACCCCCGAAGTGACCTGCGTGGTGGTGGAC
GTGTCCCACGAGGACCCTGAAGTGAAGTTCAATTGGTACGTGGACGGCGTGGAAGTGCACAACGCCAAG
ACCAAGCCCAGAGAGGAACAGTACAACTCCACCTACCGGGTGGTGTCCGTGCTGACCGTGCTGCACCAG
GACTGGCTGAACGGCAAAGAGTACAAGTGCAAGGTCTCCAACAAGGCCCTGCCCGCCTCCATCGAAAAG
ACCATCTCCAAGGCCAAGGGCCAGCCCCGCGAGCCTCAGGTGTACACACTGCCCCCCTGCCGGGAAGAG
ATGACCAAGAACCAGGTGTCCCTGTGGTGTCTGGTGAAAGGCTTCTACCCCTCCGATATCGCTGTGGAA
TGGGAGTCCAACGGCCAGCCCGAGAACAACTACAAGACCACCCCCCTGTGCTGGACTCCGACGGCTCA
TTCTTCCTGTACTCCAAGCTGACCGTGGACAAGTCCCGGTGGCAGCAGGGCAACGTGTTCTCCTGCTCC
GTGATGCACGAGGCCCTGCACAACCACTACACCCAGAAGTCTCTAAGCTTGAGCCCCGGCGGAGGTGGT
GGAAGCGGAGGAGGTGGCTCTGGAGGGGGTGGAAGCGGAGGTGGAGGTGGATCCCAGCTCTACTCAGCG
CTCGCTAATCACTGTTGTCATGTGGGATGCACAAAGCGGTCTCTCGCCAGATTCTGC

Figure 11 Continued

Rlx041L (SEQ ID NO: 111)

GACAAGACCCACACCGCTTGTCCTCCATGCCCGGCGCCTGAGTTCGAGGGCGGACCCTCCGTGTTCCTG
TTCCCCCCAAAGCCCAAGGACACCCTGATGATCTCCCGGACCCCCGAAGTGACCTGCGTGGTGGTGGAC
GTGTCCCACGAGGACCCTGAAGTGAAGTTCAATTGGTACGTGGACGGCGTGGAAGTGCACAACGCCAAG
ACCAAGCCCAGAGAGGAACAGTACAACTCCACCTACCGGGTGGTGTCCGTGCTGACCGTGCTGCACCAG
GACTGGCTGAACGGCAAAGAGTACAAGTGCAAGGTCTCCAACAAGGCCCTGCCCGCCTCCATCGAAAAG
ACCATCTCCAAGGCCAAGGGCCAGCCCCGCGAGCCTCAGGTGTACACACTGCCCCCCTGCCGGGAAGAG
ATGACCAAGAACCAGGTGTCCCTGTGGTGTCTGGTGAAAGGCTTCTACCCCTCCGATATCGCTGTGGAA
TGGGAGTCCAACGGCCAGCCCGAGAACAACTACAAGACCACCCCCCTGTGCTGGACTCCGACGGCTCA
TTCTTCCTGTACTCCAAGCTGACCGTGGACAAGTCCCGGTGGCAGCAGGGCAACGTGTTCTCCTGCTCC
GTGATGCACGAGGCCCTGCACAACCACTACACCCAGAAGTCTCTAAGCTTGAGCCCCGGCGGAGGTGGT
GGAAGCGGAGGAGGTGGCTCTGGAGGGGGTGGAAGCGGAGGTGGAGGTGGATCCCAGCTCTACTCAGCG
CTCGCTAATTTGTGTTGTCATGTGGGATGCACAAAGCGGTCTCTCGCCAGATTCTGC

Rlx041M (SEQ ID NO: 112)

GACAAGACCCACACCGCTTGTCCTCCATGCCCGGCGCCTGAGTTCGAGGGCGGACCCTCCGTGTTCCTG
TTCCCCCCAAAGCCCAAGGACACCCTGATGATCTCCCGGACCCCCGAAGTGACCTGCGTGGTGGTGGAC
GTGTCCCACGAGGACCCTGAAGTGAAGTTCAATTGGTACGTGGACGGCGTGGAAGTGCACAACGCCAAG
ACCAAGCCCAGAGAGGAACAGTACAACTCCACCTACCGGGTGGTGTCCGTGCTGACCGTGCTGCACCAG
GACTGGCTGAACGGCAAAGAGTACAAGTGCAAGGTCTCCAACAAGGCCCTGCCCGCCTCCATCGAAAAG
ACCATCTCCAAGGCCAAGGGCCAGCCCCGCGAGCCTCAGGTGTACACACTGCCCCCCTGCCGGGAAGAG
ATGACCAAGAACCAGGTGTCCCTGTGGTGTCTGGTGAAAGGCTTCTACCCCTCCGATATCGCTGTGGAA
TGGGAGTCCAACGGCCAGCCCGAGAACAACTACAAGACCACCCCCCTGTGCTGGACTCCGACGGCTCA
TTCTTCCTGTACTCCAAGCTGACCGTGGACAAGTCCCGGTGGCAGCAGGGCAACGTGTTCTCCTGCTCC
GTGATGCACGAGGCCCTGCACAACCACTACACCCAGAAGTCTCTAAGCTTGAGCCCCGGCGGAGGTGGT
GGAAGCGGAGGAGGTGGCTCTGGAGGGGGTGGAAGCGGAGGTGGAGGTGGATCCCAGCTCTACTCAGCG
CTCGCTAATATGTGTTGTCATGTGGGATGCACAAAGCGGTCTCTCGCCAGATTCTGC

Rlx044E (SEQ ID NO: 113)

GACAAGACCCACACCGCTTGTCCTCCATGCCCGGCGCCTGAGTTCGAGGGCGGACCCTCCGTGTTCCTG
TTCCCCCCAAAGCCCAAGGACACCCTGATGATCTCCCGGACCCCCGAAGTGACCTGCGTGGTGGTGGAC
GTGTCCCACGAGGACCCTGAAGTGAAGTTCAATTGGTACGTGGACGGCGTGGAAGTGCACAACGCCAAG
ACCAAGCCCAGAGAGGAACAGTACAACTCCACCTACCGGGTGGTGTCCGTGCTGACCGTGCTGCACCAG
GACTGGCTGAACGGCAAAGAGTACAAGTGCAAGGTCTCCAACAAGGCCCTGCCCGCCTCCATCGAAAAG
ACCATCTCCAAGGCCAAGGGCCAGCCCCGCGAGCCTCAGGTGTACACACTGCCCCCCTGCCGGGAAGAG
ATGACCAAGAACCAGGTGTCCCTGTGGTGTCTGGTGAAAGGCTTCTACCCCTCCGATATCGCTGTGGAA
TGGGAGTCCAACGGCCAGCCCGAGAACAACTACAAGACCACCCCCCTGTGCTGGACTCCGACGGCTCA
TTCTTCCTGTACTCCAAGCTGACCGTGGACAAGTCCCGGTGGCAGCAGGGCAACGTGTTCTCCTGCTCC
GTGATGCACGAGGCCCTGCACAACCACTACACCCAGAAGTCTCTAAGCTTGAGCCCCGGCGGAGGTGGT
GGAAGCGGAGGAGGTGGCTCTGGAGGGGGTGGAAGCGGAGGTGGAGGTGGATCCCAGCTCTACTCAGCG
CTCGCTAATAAGTGTTGTCATGTGGGATGCACAAAGGAGTCTCTCGCCAGATTCTGC

Figure 11 Continued

Rlx044H (SEQ ID NO: 114)

GACAAGACCCACACCGCTTGTCCTCCATGCCCGGCGCCTGAGTTCGAGGGCGGACCCTCCGTGTTCCTG
TTCCCCCCAAAGCCCAAGGACACCCTGATGATCTCCCGGACCCCCGAAGTGACCTGCGTGGTGGTGGAC
GTGTCCCACGAGGACCCTGAAGTGAAGTTCAATTGGTACGTGGACGGCGTGGAAGTGCACAACGCCAAG
ACCAAGCCCAGAGAGGAACAGTACAACTCCACCTACCGGGTGGTGTCCGTGCTGACCGTGCTGCACCAG
GACTGGCTGAACGGCAAAGAGTACAAGTGCAAGGTCTCCAACAAGGCCCTGCCCGCCTCCATCGAAAAG
ACCATCTCCAAGGCCAAGGGCCAGCCCCGCGAGCCTCAGGTGTACACACTGCCCCCCTGCCGGGAAGAG
ATGACCAAGAACCAGGTGTCCCTGTGGTGTCTGGTGAAAGGCTTCTACCCCTCCGATATCGCTGTGGAA
TGGGAGTCCAACGGCCAGCCCGAGAACAACTACAAGACCACCCCCCTGTGCTGGACTCCGACGGCTCA
TTCTTCCTGTACTCCAAGCTGACCGTGGACAAGTCCCGGTGGCAGCAGGGCAACGTGTTCTCCTGCTCC
GTGATGCACGAGGCCCTGCACAACCACTACACCCAGAAGTCTCTAAGCTTGAGCCCCGGCGGAGGTGGT
GGAAGCGGAGGAGGTGGCTCTGGAGGGGGTGGAAGCGGAGGTGGAGGTGGATCCCAGCTCTACTCAGCG
CTCGCTAATAAGTGTTGTCATGTGGGATGCACAAAGCACTCTCTCGCCAGATTCTGC

Rlx051A (SEQ ID NO: 115)

GACAAGACCCACACCTGTCCTCCATGCCCGGCGCCTGAGTTCGAGGGCGGACCCTCCGTGTTCCTGTTC
CCCCAAAGCCCAAGGACACCCTGATGATCTCCCGGACCCCCGAAGTGACCTGCGTGGTGGTGGACGTG
TCCCACGAGGACCCTGAAGTGAAGTTCAATTGGTACGTGGACGGCGTGGAAGTGCACAACGCCAAGACC
AAGCCCAGAGAGGAACAGTACAACTCCACCTACCGGGTGGTGTCCGTGCTGACCGTGCTGCACCAGGAC
TGGCTGAACGGCAAAGAGTACAAGTGCAAGGTCTCCAACAAGGCCCTGCCCGCCTCCATCGAAAAGACC
ATCTCCAAGGCCAAGGGCCAGCCCCGCGAGCCTCAGGTGTACACACTGCCCCCCTGCCGGGAAGAGATG
ACCAAGAACCAGGTGTCCCTGTGGTGTCTGGTGAAAGGCTTCTACCCCTCCGATATCGCTGTGGAATGG
GAGTCCAACGGCCAGCCCGAGAACAACTACAAGACCACCCCCCTGTGCTGGACTCCGACGGCTCATTC
TTCCTGTACTCCAAGCTGACCGTGGACAAGTCCCGGTGGCAGCAGGGCAACGTGTTCTCCTGCTCCGTG
ATGCACGAGGCCCTGCACAACCACTACACCCAGAAGTCTCTAAGCTTGAGCCCCGGCGGAGGTGGTGGA
AGCGGAGGAGGTGGCTCTGGAGGGGGTGGAAGCGGAGGTGGAGGTGGATCCCAGCTCTACTCAGCGCTC
GCTAATAAGTGTTGTCATGTGGGATGCACAAAGCGGTCTCTCGCCGCCTTCTGC

Rlx051I (SEQ ID NO: 116)

GACAAGACCCACACCTGTCCTCCATGCCCGGCGCCTGAGTTCGAGGGCGGACCCTCCGTGTTCCTGTTC
CCCCAAAGCCCAAGGACACCCTGATGATCTCCCGGACCCCCGAAGTGACCTGCGTGGTGGTGGACGTG
TCCCACGAGGACCCTGAAGTGAAGTTCAATTGGTACGTGGACGGCGTGGAAGTGCACAACGCCAAGACC
AAGCCCAGAGAGGAACAGTACAACTCCACCTACCGGGTGGTGTCCGTGCTGACCGTGCTGCACCAGGAC
TGGCTGAACGGCAAAGAGTACAAGTGCAAGGTCTCCAACAAGGCCCTGCCCGCCTCCATCGAAAAGACC
ATCTCCAAGGCCAAGGGCCAGCCCCGCGAGCCTCAGGTGTACACACTGCCCCCCTGCCGGGAAGAGATG
ACCAAGAACCAGGTGTCCCTGTGGTGTCTGGTGAAAGGCTTCTACCCCTCCGATATCGCTGTGGAATGG
GAGTCCAACGGCCAGCCCGAGAACAACTACAAGACCACCCCCCTGTGCTGGACTCCGACGGCTCATTC
TTCCTGTACTCCAAGCTGACCGTGGACAAGTCCCGGTGGCAGCAGGGCAACGTGTTCTCCTGCTCCGTG
ATGCACGAGGCCCTGCACAACCACTACACCCAGAAGTCTCTAAGCTTGAGCCCCGGCGGAGGTGGTGGA
AGCGGAGGAGGTGGCTCTGGAGGGGGTGGAAGCGGAGGTGGAGGTGGATCCCAGCTCTACTCAGCGCTC
GCTAATAAGTGTTGTCATGTGGGATGCACAAAGCGGTCTCTCGCCATCTTCTGC

Figure 11 Continued

Rlx051M (SEQ ID NO: 117)

GACAAGACCCACACCTGTCCTCCATGCCCGGCGCCTGAGTTCGAGGGCGGACCCTCCGTGTTCCTGTTC
CCCCCAAAGCCCAAGGACACCCTGATGATCTCCCGGACCCCCGAAGTGACCTGCGTGGTGGTGGACGTG
TCCCACGAGGACCCTGAAGTGAAGTTCAATTGGTACGTGGACGGCGTGGAAGTGCACAACGCCAAGACC
AAGCCCAGAGAGGAACAGTACAACTCCACCTACCGGGTGGTGTCCGTGCTGACCGTGCTGCACCAGGAC
TGGCTGAACGGCAAAGAGTACAAGTGCAAGGTCTCCAACAAGGCCCTGCCCGCCTCCATCGAAAAGACC
ATCTCCAAGGCCAAGGGCCAGCCCCGCGAGCCTCAGGTGTACACACTGCCCCCCTGCCGGGAAGAGATG
ACCAAGAACCAGGTGTCCCTGTGGTGTCTGGTGAAAGGCTTCTACCCCTCCGATATCGCTGTGGAATGG
GAGTCCAACGGCCAGCCCGAGAACAACTACAAGACCACCCCCCTGTGCTGGACTCCGACGGCTCATTC
TTCCTGTACTCCAAGCTGACCGTGGACAAGTCCCGGTGGCAGCAGGGCAACGTGTTCTCCTGCTCCGTG
ATGCACGAGGCCCTGCACAACCACTACACCCAGAAGTCTCTAAGCTTGAGCCCCGGCGGAGGTGGTGGA
AGCGGAGGAGGTGGCTCTGGAGGGGGTGGAAGCGGAGGTGGAGGTGGATCCCAGCTCTACTCAGCGCTC
GCTAATAAGTGTTGTCATGTGGGATGCACAAAGCGGTCTCTCGCCATGTTCTGC

Rlx051Q (SEQ ID NO: 118)

GACAAGACCCACACCTGTCCTCCATGCCCGGCGCCTGAGTTCGAGGGCGGACCCTCCGTGTTCCTGTTC
CCCCCAAAGCCCAAGGACACCCTGATGATCTCCCGGACCCCCGAAGTGACCTGCGTGGTGGTGGACGTG
TCCCACGAGGACCCTGAAGTGAAGTTCAATTGGTACGTGGACGGCGTGGAAGTGCACAACGCCAAGACC
AAGCCCAGAGAGGAACAGTACAACTCCACCTACCGGGTGGTGTCCGTGCTGACCGTGCTGCACCAGGAC
TGGCTGAACGGCAAAGAGTACAAGTGCAAGGTCTCCAACAAGGCCCTGCCCGCCTCCATCGAAAAGACC
ATCTCCAAGGCCAAGGGCCAGCCCCGCGAGCCTCAGGTGTACACACTGCCCCCCTGCCGGGAAGAGATG
ACCAAGAACCAGGTGTCCCTGTGGTGTCTGGTGAAAGGCTTCTACCCCTCCGATATCGCTGTGGAATGG
GAGTCCAACGGCCAGCCCGAGAACAACTACAAGACCACCCCCCTGTGCTGGACTCCGACGGCTCATTC
TTCCTGTACTCCAAGCTGACCGTGGACAAGTCCCGGTGGCAGCAGGGCAACGTGTTCTCCTGCTCCGTG
ATGCACGAGGCCCTGCACAACCACTACACCCAGAAGTCTCTAAGCTTGAGCCCCGGCGGAGGTGGTGGA
AGCGGAGGAGGTGGCTCTGGAGGGGGTGGAAGCGGAGGTGGAGGTGGATCCCAGCTCTACTCAGCGCTC
GCTAATAAGTGTTGTCATGTGGGATGCACAAAGCGGTCTCTCGCCCAGTTCTGC

Rlx051S (SEQ ID NO: 119)

GACAAGACCCACACCTGTCCTCCATGCCCGGCGCCTGAGTTCGAGGGCGGACCCTCCGTGTTCCTGTTC
CCCCCAAAGCCCAAGGACACCCTGATGATCTCCCGGACCCCCGAAGTGACCTGCGTGGTGGTGGACGTG
TCCCACGAGGACCCTGAAGTGAAGTTCAATTGGTACGTGGACGGCGTGGAAGTGCACAACGCCAAGACC
AAGCCCAGAGAGGAACAGTACAACTCCACCTACCGGGTGGTGTCCGTGCTGACCGTGCTGCACCAGGAC
TGGCTGAACGGCAAAGAGTACAAGTGCAAGGTCTCCAACAAGGCCCTGCCCGCCTCCATCGAAAAGACC
ATCTCCAAGGCCAAGGGCCAGCCCCGCGAGCCTCAGGTGTACACACTGCCCCCCTGCCGGGAAGAGATG
ACCAAGAACCAGGTGTCCCTGTGGTGTCTGGTGAAAGGCTTCTACCCCTCCGATATCGCTGTGGAATGG
GAGTCCAACGGCCAGCCCGAGAACAACTACAAGACCACCCCCCTGTGCTGGACTCCGACGGCTCATTC
TTCCTGTACTCCAAGCTGACCGTGGACAAGTCCCGGTGGCAGCAGGGCAACGTGTTCTCCTGCTCCGTG
ATGCACGAGGCCCTGCACAACCACTACACCCAGAAGTCTCTAAGCTTGAGCCCCGGCGGAGGTGGTGGA
AGCGGAGGAGGTGGCTCTGGAGGGGGTGGAAGCGGAGGTGGAGGTGGATCCCAGCTCTACTCAGCGCTC
GCTAATAAGTGTTGTCATGTGGGATGCACAAAGCGGTCTCTCGCCTCCTTCTGC

Figure 11 Continued

Rlx051Y (SEQ ID NO: 120)

GACAAGACCCACACCTGTCCTCCATGCCCGGCGCCTGAGTTCGAGGGCGGACCCTCCGTGTTCCTGTTC
CCCCCAAAGCCCAAGGACACCCTGATGATCTCCCGGACCCCCGAAGTGACCTGCGTGGTGGTGGACGTG
TCCCACGAGGACCCTGAAGTGAAGTTCAATTGGTACGTGGACGGCGTGGAAGTGCACAACGCCAAGACC
AAGCCCAGAGAGGAACAGTACAACTCCACCTACCGGGTGGTGTCCGTGCTGACCGTGCTGCACCAGGAC
TGGCTGAACGGCAAAGAGTACAAGTGCAAGGTCTCCAACAAGGCCCTGCCCGCCTCCATCGAAAAGACC
ATCTCCAAGGCCAAGGGCCAGCCCCGCGAGCCTCAGGTGTACACACTGCCCCCCTGCCGGGAAGAGATG
ACCAAGAACCAGGTGTCCCTGTGGTGTCTGGTGAAAGGCTTCTACCCCTCCGATATCGCTGTGGAATGG
GAGTCCAACGGCCAGCCCGAGAACAACTACAAGACCACCCCCCTGTGCTGGACTCCGACGGCTCATTC
TTCCTGTACTCCAAGCTGACCGTGGACAAGTCCGGTGGCAGCAGGGCAACGTGTTCTCCTGCTCCGTG
ATGCACGAGGCCCTGCACAACCACTACACCCAGAAGTCTCTAAGCTTGAGCCCCGGCGGAGGTGGTGGA
AGCGGAGGAGGTGGCTCTGGAGGGGGTGGAAGCGGAGGTGGAGGTGGATCCCAGCTCTACTCAGCGCTC
GCTAATAAGTGTTGTCATGTGGGATGCACAAAGCGGTCTCTCGCCTACTTCTGC

Rlx052E (SEQ ID NO: 121)

GACAAGACCCACACCTGTCCTCCATGCCCGGCGCCTGAGTTCGAGGGCGGACCCTCCGTGTTCCTGTTC
CCCCCAAAGCCCAAGGACACCCTGATGATCTCCCGGACCCCCGAAGTGACCTGCGTGGTGGTGGACGTG
TCCCACGAGGACCCTGAAGTGAAGTTCAATTGGTACGTGGACGGCGTGGAAGTGCACAACGCCAAGACC
AAGCCCAGAGAGGAACAGTACAACTCCACCTACCGGGTGGTGTCCGTGCTGACCGTGCTGCACCAGGAC
TGGCTGAACGGCAAAGAGTACAAGTGCAAGGTCTCCAACAAGGCCCTGCCCGCCTCCATCGAAAAGACC
ATCTCCAAGGCCAAGGGCCAGCCCCGCGAGCCTCAGGTGTACACACTGCCCCCCTGCCGGGAAGAGATG
ACCAAGAACCAGGTGTCCCTGTGGTGTCTGGTGAAAGGCTTCTACCCCTCCGATATCGCTGTGGAATGG
GAGTCCAACGGCCAGCCCGAGAACAACTACAAGACCACCCCCCTGTGCTGGACTCCGACGGCTCATTC
TTCCTGTACTCCAAGCTGACCGTGGACAAGTCCGGTGGCAGCAGGGCAACGTGTTCTCCTGCTCCGTG
ATGCACGAGGCCCTGCACAACCACTACACCCAGAAGTCTCTAAGCTTGAGCCCCGGCGGAGGTGGTGGA
AGCGGAGGAGGTGGCTCTGGAGGGGGTGGAAGCGGAGGTGGAGGTGGATCCCAGCTCTACTCAGCGCTC
GCTAATAAGTGTTGTCATGTGGGATGCACAAAGCGGTCTCTCGCCAGAGAGTGC

Rlx052I (SEQ ID NO: 122)

GACAAGACCCACACCTGTCCTCCATGCCCGGCGCCTGAGTTCGAGGGCGGACCCTCCGTGTTCCTGTTC
CCCCCAAAGCCCAAGGACACCCTGATGATCTCCCGGACCCCCGAAGTGACCTGCGTGGTGGTGGACGTG
TCCCACGAGGACCCTGAAGTGAAGTTCAATTGGTACGTGGACGGCGTGGAAGTGCACAACGCCAAGACC
AAGCCCAGAGAGGAACAGTACAACTCCACCTACCGGGTGGTGTCCGTGCTGACCGTGCTGCACCAGGAC
TGGCTGAACGGCAAAGAGTACAAGTGCAAGGTCTCCAACAAGGCCCTGCCCGCCTCCATCGAAAAGACC
ATCTCCAAGGCCAAGGGCCAGCCCCGCGAGCCTCAGGTGTACACACTGCCCCCCTGCCGGGAAGAGATG
ACCAAGAACCAGGTGTCCCTGTGGTGTCTGGTGAAAGGCTTCTACCCCTCCGATATCGCTGTGGAATGG
GAGTCCAACGGCCAGCCCGAGAACAACTACAAGACCACCCCCCTGTGCTGGACTCCGACGGCTCATTC
TTCCTGTACTCCAAGCTGACCGTGGACAAGTCCGGTGGCAGCAGGGCAACGTGTTCTCCTGCTCCGTG
ATGCACGAGGCCCTGCACAACCACTACACCCAGAAGTCTCTAAGCTTGAGCCCCGGCGGAGGTGGTGGA
AGCGGAGGAGGTGGCTCTGGAGGGGGTGGAAGCGGAGGTGGAGGTGGATCCCAGCTCTACTCAGCGCTC
GCTAATAAGTGTTGTCATGTGGGATGCACAAAGCGGTCTCTCGCCAGAATCTGC

Figure 11 Continued

Rlx055 (SEQ ID NO: 123)

GACAAGACCCACACCTGTCCTCCATGCCCGGCGCCTGAGTTCGAGGGCGGACCCTCCGTGTTCCTGTTC
CCCCCAAAGCCCAAGGACACCCTGATGATCTCCCGGACCCCCGAAGTGACCTGCGTGGTGGTGGACGTG
TCCCACGAGGACCCTGAAGTGAAGTTCAATTGGTACGTGGACGGCGTGGAAGTGCACAACGCCAAGACC
AAGCCCAGAGAGGAACAGTACAACTCCACCTACCGGGTGGTGTCCGTGCTGACCGTGCTGCACCAGGAC
TGGCTGAACGGCAAAGAGTACAAGTGCAAGGTCTCCAACAAGGCCCTGCCCGCCTCCATCGAAAAGACC
ATCTCCAAGGCCAAGGGCCAGCCCCGCGAGCCTCAGGTGTACACACTGCCCCCCTGCCGGGAAGAGATG
ACCAAGAACCAGGTGTCCCTGTGGTGTCTGGTGAAAGGCTTCTACCCCTCCGATATCGCTGTGGAATGG
GAGTCCAACGGCCAGCCCGAGAACAACTACAAGACCACCCCCCCTGTGCTGGACTCCGACGGCTCATTC
TTCCTGTACTCCAAGCTGACCGTGGACAAGTCCCGGTGGCAGCAGGGCAACGTGTTCTCCTGCTCCGTG
ATGCACGAGGCCCTGCACAACCACTACACCCAGAAGTCTCTAAGCTTGAGCCCCGGCGGAGGTGGTGGA
AGCGGAGGAGGTGGCTCTGGAGGGGTGGAAGCGGAGGTGGAGGTGGATCCTCCTGGATGGAGGAGGTT
ATCAAGCTGTGTGGACGCGAACTGGTGCGCGCTCAGATCGCGATATGCGGGATGTCCACATGGTCAGGC
GGCGGCAGCGGCGGCGGCAGCGGCCAGCTCTACTCAGCGCTCGCTAATAAGTGTTGTCATGTGGGATGC
ACAAAGCGGTCTCTCGCCAGATTCTGC

Rlx056 (SEQ ID NO: 124)

GACAAGACCCACACCTGTCCTCCATGCCCGGCGCCTGAGTTCGAGGGCGGACCCTCCGTGTTCCTGTTC
CCCCCAAAGCCCAAGGACACCCTGATGATCTCCCGGACCCCCGAAGTGACCTGCGTGGTGGTGGACGTG
TCCCACGAGGACCCTGAAGTGAAGTTCAATTGGTACGTGGACGGCGTGGAAGTGCACAACGCCAAGACC
AAGCCCAGAGAGGAACAGTACAACTCCACCTACCGGGTGGTGTCCGTGCTGACCGTGCTGCACCAGGAC
TGGCTGAACGGCAAAGAGTACAAGTGCAAGGTCTCCAACAAGGCCCTGCCCGCCTCCATCGAAAAGACC
ATCTCCAAGGCCAAGGGCCAGCCCCGCGAGCCTCAGGTGTGCACACTGCCCCCCAGCCGGGAAGAGATG
ACCAAGAACCAGGTGTCCCTGTCCTGTGCCGTGAAAGGCTTCTACCCCTCCGATATCGCTGTGGAATGG
GAGTCCAACGGCCAGCCCGAGAACAACTACAAGACCACCCCCCCTGTGCTGGACTCCGACGGCTCATTC
TTCCTGGTGTCCAAGCTGACCGTGGACAAGTCCCGGTGGCAGCAGGGCAACGTGTTCTCCTGCTCCGTG
ATGCACGAGGCCCTGCACAACCACTACACCCAGAAGTCTCTAAGCTTGAGCCCCGGCGGAGGTGGTGGA
AGCGGAGGAGGTGGCTCTGGAGGGGTGGAAGCGGAGGTGGAGGTGGATCCTCCTGGATGGAGGAGGTT
ATCAAGCTGTGTGGACGCGAACTGGTGCGCGCTCAGATCGCGATATGCGGGATGTCCACATGGTCAGGC
GGCGGCAGCGGCGGCGGCAGCGGCCAGCTCTACTCAGCGCTCGCTAATAAGTGTTGTCATGTGGGATGC
ACAAAGCGGTCTCTCGCCAGATTCTGC

Rlx061H (SEQ ID NO: 125)

TCCTGGATGGAAGAAGTGATCAAGCTCTGCGGCAGAGAACTCGTGCGGGCCCAGATCGCTATCTGCGGC
ATGTCTACTTGGAGCGCGGCCGCGGGTGGAGGTGGATCCGGAGGAGGTGGAAGCGGAGGAGGTGGAAGC
GGAGGAGGTGGAAGCGCTTGTCCTCCATGCCCGGCGCCTGAGTTCGAGGGCGGACCCTCCGTGTTCCTG
TTCCCCCCAAAGCCCAAGGACACCCTGATGATCTCCCGGACCCCCGAAGTGACCTGCGTGGTGGTGGAC
GTGTCCCACGAGGACCCTGAAGTGAAGTTCAATTGGTACGTGGACGGCGTGGAAGTGCACAACGCCAAG
ACCAAGCCCAGAGAGGAACAGTACAACTCCACCTACCGGGTGGTGTCCGTGCTGACCGTGCTGCACCAG
GACTGGCTGAACGGCAAAGAGTACAAGTGCAAGGTCTCCAACAAGGCCCTGCCCGCCTCCATCGAAAAG
ACCATCTCCAAGGCCAAGGGCCAGCCCCGCGAGCCTCAGGTGTGCACACTGCCCCCCAGCCGGGAAGAG
ATGACCAAGAACCAGGTGTCCCTGTCCTGTGCCGTGAAAGGCTTCTACCCCTCCGATATCGCTGTGGAA
TGGGAGTCCAACGGCCAGCCCGAGAACAACTACAAGACCACCCCCCCTGTGCTGGACTC

Figure 11 Continued

CGACGGCTCATTCTTCCTGGTGTCCAAGCTGACCGTGGACAAGTCCCGGTGGCAGCAGGGCAACGTGTT
CTCCTGCTCCGTGATGCACGAGGCCCTGCACAACCACTACACCCAGAAGTCTCTGTCCCTGAGCCCCGG
C

Rlx062K (SEQ ID NO: 126)

CAGCTGTACTCTGCCCTGGCCAACAAGTGTTGCCACGTGGGCTGCACCAAGAGATCCCTGGCCAGATTC
TGTGCGGCCGCGGGTGGAGGTGGATCCGGAGGAGGTGGAAGCGGAGGAGGTGGAAGCGGAGGAGGTGGA
AGCGCTTGTCCTCCATGCCCGGCGCCTGAGTTCGAGGGCGGACCCTCCGTGTTCCTGTTCCCCCCAAAG
CCCAAGGACACCCTGATGATCTCCCGGACCCCCGAAGTGACCTGCGTGGTGGTGGACGTGTCCCACGAG
GACCCTGAAGTGAAGTTCAATTGGTACGTGGACGGCGTGGAAGTGCACAACGCCAAGACCAAGCCCAGA
GAGGAACAGTACAACTCCACCTACCGGGTGGTGTCCGTGCTGACCGTGCTGCACCAGGACTGGCTGAAC
GGCAAAGAGTACAAGTGCAAGGTCTCCAACAAGGCCCTGCCCGCCTCCATCGAAAAGACCATCTCCAAG
GCCAAGGGCCAGCCCCGCGAGCCTCAGGTGTACACACTGCCCCCCTGCCGGGAAGAGATGACCAAGAAC
CAGGTGTCCCTGTGGTGTCTGGTGAAAGGCTTCTACCCCTCCGATATCGCTGTGGAATGGGAGTCCAAC
GGCCAGCCCGAGAACAACTACAAGACCACCCCCCCTGTGCTGGACTCCGACGGCTCATTCTTCCTGTAC
TCCAAGCTGACCGTGGACAAGTCCCGGTGGCAGCAGGGCAACGTGTTCTCCTGCTCCGTGATGCACGAG
GCCCTGCACAACCACTACACCCAGAAGTCTCTGTCCCTGAGCCCCGGC

Rlx076 (SEQ ID NO: 127)

CAGCTGTACTCTGCCCTGGCCAACAAGTGTTGCCACGTGGGCTGCACCAAGAGATCCCTGGCCAGATTC
TGTGCGGCCGCGGGTGGAGGTGGATCCGGAGGAGGTGGAAGCGGAGGAGGTGGAAGCGGAGGAGGTGGA
AGCGCTTGTCCTCCATGCCCGGCGCCTGAGTTCGAGGGCGGACCCTCCGTGTTCCTGTTCCCCCCAAAG
CCCAAGGACACCCTGATGATCTCCCGGACCCCCGAAGTGACCTGCGTGGTGGTGGACGTGTCCCACGAG
GACCCTGAAGTGAAGTTCAATTGGTACGTGGACGGCGTGGAAGTGCACAACGCCAAGACCAAGCCCAGA
GAGGAACAGTACAACTCCACCTACCGGGTGGTGTCCGTGCTGACCGTGCTGCACCAGGACTGGCTGAAC
GGCAAAGAGTACAAGTGCAAGGTCTCCAACAAGGCCCTGCCCGCCTCCATCGAAAAGACCATCTCCAAG
GCCAAGGGCCAGCCCCGCGAGCCTCAGGTGTACACACTGCCCCCCTGCCGGGAAGAGATGACCAAGAAC
CAGGTGTCCCTGTGGTGTCTGGTGAAAGGCTTCTACCCCTCCGATATCGCTGTGGAATGGGAGTCCAAC
GGCCAGCCCGAGAACAACTACAAGACCACCCCCCCTGTGCTGGACTCCGACGGCTCATTCTTCCTGTAC
TCCAAGCTGACCGTGGACAAGTCCCGGTGGCAGCAGGGCAACGTGTTCTCCTGCTCCGTGATGCACGAG
GCCCTGCACAACCACTACACCCAGAAGTCTCTAAGCTTGAGCCCCGGCGGAGGTGGTGGAAGCGGAGGA
GGTGGCTCTGGAGGGGTGGAAGCGGAGGTGGAGGTGGATCCAGCTCTACTCAGCGCTCGCTAATAAG
TGTTGTCATGTGGGATGCACAAAGCGGTCTCTCGCCAGATTCTGC

Rlx077 (SEQ ID NO: 128)

TCCTGGATGGAAGAAGTGATCAAGCTCTGCGGCAGAGAACTCGTGCGGGCCCAGATCGCTATCTGCGGC
ATGTCTACTTGGAGCGCGGCCGCGGGTGGAGGTGGATCCGGAGGAGGTGGAAGCGGAGGAGGTGGAAGC
GGAGGAGGTGGAAGCGCTTGTCCTCCATGCCCGGCGCCTGAGTTCGAGGGCGGACCCTCCGTGTTCCTG
TTCCCCCCAAAGCCCAAGGACACCCTGATGATCTCCCGGACCCCCGAAGTGACCTGCGTGGTGGTGGAC
GTGTCCCACGAGGACCCTGAAGTGAAGTTCAATTGGTACGTGGACGGCGTGGAAGTGCACAACGCCAAG
ACCAAGCCCAGAGAGGAACAGTACAACTCCACCTACCGGGTGGTGTCCGTGCTGACCGTGCTGCACCAG
GACTGGCTGAACGGCAAAGAGTACAAGTGCAAGGTCTCCAACAAGGCCCTGCCCGCCTCCAT

Figure 11 Continued

CGAAAAGACCATCTCCAAGGCCAAGGGCCAGCCCCGCGAGCCTCAGGTGTGCACACTGCCCCCAGCCG
GGAAGAGATGACCAAGAACCAGGTGTCCCTGTCCTGTGCCGTGAAAGGCTTCTACCCCTCCGATATCGC
TGTGGAATGGGAGTCCAACGGCCAGCCCGAGAACAACTACAAGACCACCCCCCCTGTGCTGGACTCCGA
CGGCTCATTCTTCCTGGTGTCCAAGCTGACCGTGGACAAGTCCCGGTGGCAGCAGGGCAACGTGTTCTC
CTGCTCCGTGATGCACGAGGCCCTGCACAACCACTACACCCAGAAGTCTCTAAGCTTGAGCCCCGGCGG
AGGTGGTGGAAGCGGAGGAGGTGGCTCTGGAGGGGGTGGAAGCGGAGGTGGAGGTGGATCCAGCTGGAT
GGAAGAAGTGATTAAACTGTGTGGCCGCGAACTGGTGCGCGCGCAGATTGCGATTTGCGGCATGAGCAC
CTGGAGC

Rlx014DDdel2aa (SEQ ID NO: 129)

GACAAGACCCACACCTGTCCTCCATGCCCGGCGCCTGAGTTCGAGGGCGGACCCTCCGTGTTCCTGTTC
CCCCCAAAGCCCAAGGACACCCTGATGATCTCCCGGACCCCCGAAGTGACCTGCGTGGTGGTGGACGTG
TCCCACGAGGACCCTGAAGTGAAGTTCAATTGGTACGTGGACGGCGTGGAAGTGCACAACGCCAAGACC
AAGCCCAGAGAGGAACAGTACAACTCCACCTACCGGGTGGTGTCCGTGCTGACCGTGCTGCACCAGGAC
TGGCTGAACGGCAAAGAGTACAAGTGCAAGGTCTCCAACAAGGCCCTGCCCGCCTCCATCGAAAAGACC
ATCTCCAAGGCCAAGGGCCAGCCCCGCGAGCCTCAGGTGTGCACACTGCCCCCAGCCGGGAAGAGATG
ACCAAGAACCAGGTGTCCCTGTCCTGTGCCGTGAAAGGCTTCTACCCCTCCGATATCGCTGTGGAATGG
GAGTCCAACGGCCAGCCCGAGAACAACTACAAGACCACCCCCCCTGTGCTGGACTCCGACGGCTCATTC
TTCCTGGTGTCCAAGCTGACCGTGGACAAGTCCCGGTGGCAGCAGGGCAACGTGTTCTCCTGCTCCGTG
ATGCACGAGGCCCTGCACAACCACTACACCCAGAAGTCTCTAAGCTTGAGCCCCGGCGGAGGTGGTGGA
AGCGGAGGAGGTGGCTCTGGAGGGGGTGGAAGCGGAGGTGGAGGTGGATCCAGCTGGATGGAAGAAGTG
ATTAAACTGTGTGGCCGCGAACTGGTGCGCGCGCAGATTGCGATTTGCGGCATGAGCACC

Rlx014DDdel3aa (SEQ ID NO: 130)

GACAAGACCCACACCTGTCCTCCATGCCCGGCGCCTGAGTTCGAGGGCGGACCCTCCGTGTTCCTGTTC
CCCCCAAAGCCCAAGGACACCCTGATGATCTCCCGGACCCCCGAAGTGACCTGCGTGGTGGTGGACGTG
TCCCACGAGGACCCTGAAGTGAAGTTCAATTGGTACGTGGACGGCGTGGAAGTGCACAACGCCAAGACC
AAGCCCAGAGAGGAACAGTACAACTCCACCTACCGGGTGGTGTCCGTGCTGACCGTGCTGCACCAGGAC
TGGCTGAACGGCAAAGAGTACAAGTGCAAGGTCTCCAACAAGGCCCTGCCCGCCTCCATCGAAAAGACC
ATCTCCAAGGCCAAGGGCCAGCCCCGCGAGCCTCAGGTGTGCACACTGCCCCCAGCCGGGAAGAGATG
ACCAAGAACCAGGTGTCCCTGTCCTGTGCCGTGAAAGGCTTCTACCCCTCCGATATCGCTGTGGAATGG
GAGTCCAACGGCCAGCCCGAGAACAACTACAAGACCACCCCCCCTGTGCTGGACTCCGACGGCTCATTC
TTCCTGGTGTCCAAGCTGACCGTGGACAAGTCCCGGTGGCAGCAGGGCAACGTGTTCTCCTGCTCCGTG
ATGCACGAGGCCCTGCACAACCACTACACCCAGAAGTCTCTAAGCTTGAGCCCCGGCGGAGGTGGTGGA
AGCGGAGGAGGTGGCTCTGGAGGGGGTGGAAGCGGAGGTGGAGGTGGATCCAGCTGGATGGAAGAAGTG
ATTAAACTGTGTGGCCGCGAACTGGTGCGCGCGCAGATTGCGATTTGCGGCATGAGC

R347Rlx011DD (SEQ ID NO: 131)

GAGGTGCAGCTGCTCGAGTCAGGGGGAGGCTTGGTACAGCCGGGGGGGTCCCTGAGACTCTCCTGTACA
ACCTCTGGATTCACCTTTAACACGTATGCCATGAGTTGGGTCCGCCAGGCTCCAGGGAAGGGGCTGGAA
TGGCTCTCAGGTATTAATAACAATGGTCGGACTGCATTCTACGCAGACTCCGTGAAGGGCCGCTTC

Figure 11 Continued

```
ACCATCTCCAGAGACAACTCCAAAAACACACTTTATCTGCAAATTAATAGTCTGAGAGCGGACGACACG
GCCGTTTATTTCTGTGCGAAAGATGTCAGATTTATCGCAGTGCCTGGTGACTCCTGGGGCCAGGGAACC
CTGGTCACCGTCTCCTCAGCCTCCACCAAGGGCCCATCGGTCTTCCCCCTGGCCCCAGCAGCAAGAGC
ACCAGCGGCGGCACAGCCGCCCTGGGCTGCCTGGTGAAGGACTACTTCCCCGAGCCCGTGACCGTGTCC
TGGAACAGCGGAGCCCTGACCTCCGGCGTGCACACCTTCCCCGCCGTGCTGCAGAGCAGCGGCCTGTAC
AGCCTGAGCAGCGTGGTGACAGTGCCAAGCAGCAGCCTGGGCACCCAGACCTACATCTGCAACGTGAAC
CACAAGCCCAGCAACACCAAGGTGGACAAGAGAGTTGAGCCCAAATCTTGTGACAAGACCCACACCTGT
CCTCCATGCCCGGCGCCTGAGTTCGAGGGCGGACCCTCCGTGTTCCTGTTCCCCCCAAAGCCCAAGGAC
ACCCTGATGATCTCCCGGACCCCCGAAGTGACCTGCGTGGTGGTGGACGTGTCCCACGAGGACCCTGAA
GTGAAGTTCAATTGGTACGTGGACGGCGTGGAAGTGCACAACGCCAAGACCAAGCCCAGAGAGGAACAG
TACAACTCCACCTACCGGGTGGTGTCCGTGCTGACCGTGCTGCACCAGGACTGGCTGAACGGCAAAGAG
TACAAGTGCAAGGTCTCCAACAAGGCCCTGCCCGCCTCCATCGAAAAGACCATCTCCAAGGCCAAGGGC
CAGCCCCGCGAGCCTCAGGTGTACACACTGCCCCCTGCCGGGAAGAGATGACCAAGAACCAGGTGTCC
CTGTGGTGTCTGGTGAAAGGCTTCTACCCCTCCGATATCGCTGTGGAATGGGAGTCCAACGGCCAGCCC
GAGAACAACTACAAGACCACCCCCCCTGTGCTGGACTCCGACGGCTCATTCTTCCTGTACTCCAAGCTG
ACCGTGGACAAGTCCCGGTGGCAGCAGGGCAACGTGTTCTCCTGCTCCGTGATGCACGAGGCCCTGCAC
AACCACTACACCCAGAAGTCTCTAAGCTTGAGCCCCGGCGGAGGTGGTGGAAGCGGAGGAGGTGGCTCT
GGAGGGGGTGGAAGCGGAGGTGGAGGTGGATCCCAGCTCTACTCAGCGCTCGCTAATAAGTGTTGTCAT
GTGGGATGCACAAAGCGGTCTCTCGCCAGATTCTGC

R347R1x014DD (SEQ ID NO: 132)

GAGGTGCAGCTGCTCGAGTCAGGGGGAGGCTTGGTACAGCCGGGGGGGTCCCTGAGACTCTCCTGTACA
ACCTCTGGATTCACCTTTAACACGTATGCCATGAGTTGGGTCCGCCAGGCTCCAGGGAAGGGGCTGGAA
TGGCTCTCAGGTATTAATAACAATGGTCGGACTGCATTCTACGCAGACTCCGTGAAGGGCCGCTTCACC
ATCTCCAGAGACAACTCCAAAAACACACTTTATCTGCAAATTAATAGTCTGAGAGCGGACGACACGGCC
GTTTATTTCTGTGCGAAAGATGTCAGATTTATCGCAGTGCCTGGTGACTCCTGGGGCCAGGGAACCCTG
GTCACCGTCTCCTCAGCCTCCACCAAGGGCCCATCGGTCTTCCCCCTGGCCCCAGCAGCAAGAGCACC
AGCGGCGGCACAGCCGCCCTGGGCTGCCTGGTGAAGGACTACTTCCCCGAGCCCGTGACCGTGTCCTGG
AACAGCGGAGCCCTGACCTCCGGCGTGCACACCTTCCCCGCCGTGCTGCAGAGCAGCGGCCTGTACAGC
CTGAGCAGCGTGGTGACAGTGCCAAGCAGCAGCCTGGGCACCCAGACCTACATCTGCAACGTGAACCAC
AAGCCCAGCAACACCAAGGTGGACAAGAGAGTTGAGCCCAAATCTTGTGACAAGACCCACACCTGTCCT
CCATGCCCGGCGCCTGAGTTCGAGGGCGGACCCTCCGTGTTCCTGTTCCCCCCAAAGCCCAAGGACACC
CTGATGATCTCCCGGACCCCCGAAGTGACCTGCGTGGTGGTGGACGTGTCCCACGAGGACCCTGAAGTG
AAGTTCAATTGGTACGTGGACGGCGTGGAAGTGCACAACGCCAAGACCAAGCCCAGAGAGGAACAGTAC
AACTCCACCTACCGGGTGGTGTCCGTGCTGACCGTGCTGCACCAGGACTGGCTGAACGGCAAAGAGTAC
AAGTGCAAGGTCTCCAACAAGGCCCTGCCCGCCTCCATCGAAAAGACCATCTCCAAGGCCAAGGGCCAG
CCCCGCGAGCCTCAGGTGTGCACACTGCCCCCAGCCGGGAAGAGATGACCAAGAACCAGGTGTCCCTG
TCCTGTGCCGTGAAAGGCTTCTACCCCTCCGATATCGCTGTGGAATGGGAGTCCAACGGCCAGCCCGAG
AACAACTACAAGACCACCCCCCCTGTGCTGGACTCCGACGGCTCATTCTTCCTGGTGTCCAAGCTGACC
GTGGACAAGTCCCGGTGGCAGCAGGGCAACGTGTTCTCCTGCTCCGTGATGCACGAGGCCCTGCACAAC
CACTACACCCAGAAGTCTCTAAGCTTGAGCCCCGGCGGAGGTGGTGGAAGCGGAGGAGGTGGCTCTGGA
GGGGGTGGAAGCGGAGGTGGAGGTGGATCCAGCTGGATGGAAGAAGTGATTAAACTGTGTGGCCGCGAA
CTGGTGCGCGCGCAGATTGCGATTTGCGGCATGAGCACCTGGAGC
```

Figure 11 Continued

R347 L (SEQ ID NO: 133)

GAGCTCGTGTTGACTCAGCCTGCCTCCGTGTCTGGGTCTCCTGGACAGTCGATCACCATCTCCTGCACT
GGAACCAGCAGTGACGTTGGTGGTTATAACTATGTCTCCTGGTACCAACAGCACCCAGGCAAAGCCCCC
AAACTCATGATTTATGATGTCAGTAAGCGGCCCTCAGGGGTTTCTAATCGCTTCTCTGGCTCCAAGTCT
GGCAACACGGCCTCCCTGACCATCTCTGGGCTCCAGGCTGAGGACGAGGCTGATTATTACTGCAGCTCA
TATACAAGCAGCAGCACTTTGGTATTCGGCGGAGGGACCAAGCTGACCGTCCTAGGTCAGCCCAAGGCT
GCCCCCTCGGTCACTCTGTTCCCGCCCTCCTCTGAGGAGCTTCAAGCCAACAAGGCCACACTGGTGTGT
CTCATAAGTGACTTCTACCCGGGAGCCGTGACAGTGGCCTGGAAGGCAGATAGCAGCCCCGTCAAGGCG
GGAGTGGAGACCACCACACCCTCCAAACAAAGCAACAACAAGTACGCGGCCAGCAGCTATCTGAGCCTG
ACGCCTGAGCAGTGGAAGTCCCACAGAAGCTACAGCTGCCAGGTCACGCATGAAGGGAGCACCGTGGAG
AAGACAGTGGCCCCTACAGAATGTTCA

RELAX0126 (SEQ ID NO: 134)

GATAAAACCCATACCTGCCCGCCGTGCCCGGCGCCGGAACTGCTGGGCGGCCCGAGCGTGTTTCTGTTT
CCGCCGAAACCGAAAGATACCCTGATGATTAGCCGCACCCCGGAAGTGACCTGCGTGGTGGTGGATGTG
AGCCATGAAGATCCGGAAGTGAAATTTAACTGGTATGTGGATGGCGTGGAAGTGCATAACGCGAAAACC
AAACCGCGCGAAGAACAGTATAACAGCACCTATCGCGTGGTGAGCGTGCTGACCGTGCTGCATCAGGAT
TGGCTGAACGGCAAAGAATATAAATGCAAAGTGAGCAACAAAGCGCTGCCGGCGCCGATTGAAAAAACC
ATTAGCAAAGCGAAAGGCCAGCCGCGCGAACCGCAGGTGTATACCCTGCCGCCGAGCCGCGATGAACTG
ACCAAAAACCAGGTGAGCCTGACCTGCCTGGTGAAAGGCTTTTATCCGAGCGATATTGCGGTGGAATGG
GAAAGCAACGGCCAGCCGGAAAACAACTATAAAACCACCCCGCCGGTGCTGGATAGCGATGGCAGCTTT
TTTCTGTATAGCAAACTGACCGTGGATAAAAGCCGCTGGCAGCAGGGCAACGTGTTTAGCTGCAGCGTG
ATGCATGAAGCGCTGCATAACCATTATACCCAGAAAAGCCTGAGCCTGAGCCCGGGCAAAGGCGGCAGC
CCGCAGCTGTATAGCGCGCTGGCGAACAAATGCTGCCATGTGGGCTGCACCAAACGCAGCCTGGCGCGC
TTTTGCGGCGGCGGCAGCGGCGGCGGCAGCGGCAGCTGGATGGAAGAAGTGATTAAACTGTGTGGCCGC
GAACTGGTGCGCGCGCAGATTGCGATTTGCGGCATGAGCACCTGGAGC

RELAX0127 (SEQ ID NO: 135)

GATAAGACACACACCTGTCCTCCATGTCCTGCTCCAGAACTGCTCGGCGGACCCTCTGTGTTCCTGTTT
CCTCCAAAGCCTAAGGACACCCTGATGATCTCTCGGACCCCTGAAGTGACCTGCGTGGTGGTGGATGTG
TCTCACGAGGATCCCGAAGTGAAGTTCAATTGGTACGTGGACGGCGTGGAAGTGCACAACGCCAAGACC
AAGCCTAGAGAGGAACAGTACAACTCCACCTACAGAGTGGTGTCCGTGCTGACCGTGCTGCACCAGGAT
TGGCTGAACGGCAAAGAGTACAAGTGCAAGGTGTCCAACAAGGCCCTGCCTGCTCCTATCGAAAAGACC
ATCTCCAAGGCTAAGGGCCAGCCTCGGGAACCTCAGGTTTACACACTGCCTCCATCTCGGGACGAGCTG
ACCAAGAATCAGGTGTCCCTGACCTGCCTGGTCAAGGGCTTCTACCCTTCCGATATCGCCGTGGAATGG
GAGTCCAATGGCCAGCCTGAGAACAACTACAAGACCACACCTCCTGTGCTGGACTCCGACGGCTCATTC
TTCCTGTACTCCAAGCTGACAGTGGACAAGTCTCGGTGGCAGCAGGGCAACGTGTTCTCCTGTTCTGTG
ATGCACGAGGCCCTGCACAACCACTACACCCAGAAGTCCCTGTCTCTGTCCCTGGAAAGGCGGTTCT
GGTGGCTCTCCTCAGCTGTACTCTGCCCTGGCCAACAAGTGTTGTCACGTGGGCTGCACCAAGCGGTCC
CTGGCTAGATTTTGTGGCGGTGGAAGTGGCGGCGGATCCGGCTCTTGGATGGAAGAGGTTATCAAGCTG
TGCGGCAGAGAACTCGTGCGGGCCCAGATCGCTATCTGTGGCATGTCCACCTGGTCC

Figure 11 Continued

RELAX0128 (SEQ ID NO: 136)

GATAAGACACATACCTGTCCTCCATGTCCTGCTCCAGAGCTGCTCGGAGGCCCTTCCGTGTTTCTGTTC
CCTCCAAAGCCTAAGGACACCCTGATGATCTCTCGGACCCCTGAAGTGACCTGCGTGGTGGTGGATGTG
TCTCACGAGGATCCCGAAGTGAAGTTCAATTGGTACGTGGACGGCGTGGAAGTGCACAACGCCAAGACC
AAGCCTAGAGAGGAACAGTACAACTCCACCTACAGAGTGGTGTCCGTGCTGACCGTGCTGCACCAGGAT
TGGCTGAACGGCAAAGAGTACAAGTGCAAGGTGTCCAACAAGGCCCTGCCTGCTCCTATCGAAAGACC
ATCTCCAAGGCCAAGGGCCAGCCTAGGGAACCCCAGGTTTACACCTTGCCTCCATCTCGGGACGAGCTG
ACCAAGAACCAGGTGTCCCTGACCTGTCTGGTCAAGGGCTTCTACCCCTCCGATATCGCCGTGGAATGG
GAGTCTAATGGCCAGCCTGAGAACAACTACAAGACCACACCTCCTGTGCTGGACTCCGACGGCTCATTC
TTCCTGTACTCCAAGCTGACAGTGGACAAGTCCAGATGGCAGCAGGGCAACGTGTTCTCCTGCTCCGTG
ATGCACGAGGCCCTGCACAATCACTACACCCAGAAGTCCCTGTCTCTGTCCCTGGCAAAGGTGGCAGC
GGAGGTTCCGGAGGATCTCCTCAGCTGTACTCTGCCCTGGCCAACAAGTGTTGCCACGTGGGCTGCACC
AAGAGATCCCTGGCCAGATTTTGTGGCGGCGGATCTGGCGGAGGTTCCGGCTCTTGGATGGAAGAAGTG
ATCAAGCTCTGCGGCAGAGAACTCGTGCGGGCCCAGATCGCTATCTGCGGCATGTCTACCTGGTCC

RELAX0009 (SEQ ID NO: 137)

TTCAATTGGTACGTGGACGGCGTGGAAGTGCACAACGCCAAGACCAAGCCCAGAGAGGAACAGTACAAC
TCCACCTACCGGGTGGTGTCCGTGCTGACCGTGCTGCACCAGGACTGGCTGAACGGCAAAGAGTACAAG
TGCAAGGTCTCCAACAAGGCCCTGCCCGCCTCCATCGAAAAGACCATCTCCAAGGCCAAGGGCCAGCCC
CGCGAGCCTCAGGTGTACACACTGCCCCCAGCCGGGAAGAGATGACCAAGAACCAGGTGTCCCTGACC
TGTCTGGTGAAAGGCTTCTACCCCTCCGATATCGCTGTGGAATGGGAGTCCAACGGCCAGCCCGAGAAC
AACTACAAGACCACCCCCCTGTGCTGGACTCCGACGGCTCATTCTTCCTGTACTCCAAGCTGACCGTG
GACAAGTCCCGGTGGCAGCAGGGCAACGTGTTCTCCTGCTCCGTGATGCACGAGGCCCTGCACAACCAC
TACACCCAGAAGTCTCTGTCCCTGAGCCCCGGC

Rlx014d (SEQ ID NO: 138)

GACAAGACCCACACCGCTTGTCCTCCATGCCCGGCGCCTGAGTTCGAGGGCGGACCCTCCGTGTTCCTG
TTCCCCCCAAAGCCCAAGGACACCCTGATGATCTCCCGGACCCCCGAAGTGACCTGCGTGGTGGTGGAC
GTGTCCCACGAGGACCCTGAAGTGAAGTTCAATTGGTACGTGGACGGCGTGGAAGTGCACAACGCCAAG
ACCAAGCCCAGAGAGGAACAGTACAACTCCACCTACCGGGTGGTGTCCGTGCTGACCGTGCTGCACCAG
GACTGGCTGAACGGCAAAGAGTACAAGTGCAAGGTCTCCAACAAGGCCCTGCCCGCCTCCATCGAAAAG
ACCATCTCCAAGGCCAAGGGCCAGCCCCGCGAGCCTCAGGTGTGCACACTGCCCCCAGCCGGGAAGAG
ATGACCAAGAACCAGGTGTCCCTGTCCTGTGCCGTGAAAGGCTTCTACCCCTCCGATATCGCTGTGGAA
TGGGAGTCCAACGGCCAGCCCGAGAACAACTACAAGACCACCCCCCTGTGCTGGACTCCGACGGCTCA
TTCTTCCTGGTGTCCAAGCTGACCGTGGACAAGTCCCGGTGGCAGCAGGGCAACGTGTTCTCCTGCTCC
GTGATGCACGAGGCCCTGCACAACCACTACACCCAGAAGTCTCTAAGCTTGAGCCCCGGCGGAGGTGGT
GGAAGCGGAGGAGGTGGCTCTGGAGGGGTGGAAGCGGAGGTGGAGGTGGATCCAGCTGGATGGAAGAA
GTGATTAAACTGTGTGGCCGCGAACTGGTGCGCGCGCAGATTGCGATTTGCGGCATGAGCACCTGGAGC

Figure 11 Continued

```
Rlx042R (SEQ ID NO: 139)

GACAAGACCCACACCGCTTGTCCTCCATGCCCGGCGCCTGAGTTCGAGGGCGGACCCTCCGTGTTCCTG
TTCCCCCCAAAGCCCAAGGACACCCTGATGATCTCCCGGACCCCCGAAGTGACCTGCGTGGTGGTGGAC
GTGTCCCACGAGGACCCTGAAGTGAAGTTCAATTGGTACGTGGACGGCGTGGAAGTGCACAACGCCAAG
ACCAAGCCCAGAGAGGAACAGTACAACTCCACCTACCGGGTGGTGTCCGTGCTGACCGTGCTGCACCAG
GACTGGCTGAACGGCAAAGAGTACAAGTGCAAGGTCTCCAACAAGGCCCTGCCCGCCTCCATCGAAAAG
ACCATCTCCAAGGCCAAGGGCCAGCCCCGCGAGCCTCAGGTGTACACACTGCCCCCCTGCCGGGAAGAG
ATGACCAAGAACCAGGTGTCCCTGTGGTGTCTGGTGAAAGGCTTCTACCCCTCCGATATCGCTGTGGAA
TGGGAGTCCAACGGCCAGCCCGAGAACAACTACAAGACCACCCCCCCTGTGCTGGACTCCGACGGCTCA
TTCTTCCTGTACTCCAAGCTGACCGTGGACAAGTCCCGGTGGCAGCAGGGCAACGTGTTCTCCTGCTCC
GTGATGCACGAGGCCCTGCACAACCACTACACCCAGAAGTCTCTAAGCTTGAGCCCCGGCGGAGGTGGT
GGAAGCGGAGGAGGTGGCTCTGGAGGGGGTGGAAGCGGAGGTGGAGGTGGATCCCAGCTCTACTCAGCG
CTCGCTAATAAGTGTTGTCGAGTGGGATGCACAAAGCGGTCTCTCGCCAGATTCTGC

Rlx052A (SEQ ID NO: 140)

GACAAGACCCACACCTGTCCTCCATGCCCGGCGCCTGAGTTCGAGGGCGGACCCTCCGTGTTCCTGTTC
CCCCCAAAGCCCAAGGACACCCTGATGATCTCCCGGACCCCCGAAGTGACCTGCGTGGTGGTGGACGTG
TCCCACGAGGACCCTGAAGTGAAGTTCAATTGGTACGTGGACGGCGTGGAAGTGCACAACGCCAAGACC
AAGCCCAGAGAGGAACAGTACAACTCCACCTACCGGGTGGTGTCCGTGCTGACCGTGCTGCACCAGGAC
TGGCTGAACGGCAAAGAGTACAAGTGCAAGGTCTCCAACAAGGCCCTGCCCGCCTCCATCGAAAAGACC
ATCTCCAAGGCCAAGGGCCAGCCCCGCGAGCCTCAGGTGTACACACTGCCCCCCTGCCGGGAAGAGATG
ACCAAGAACCAGGTGTCCCTGTGGTGTCTGGTGAAAGGCTTCTACCCCTCCGATATCGCTGTGGAATGG
GAGTCCAACGGCCAGCCCGAGAACAACTACAAGACCACCCCCCCTGTGCTGGACTCCGACGGCTCATTC
TTCCTGTACTCCAAGCTGACCGTGGACAAGTCCCGGTGGCAGCAGGGCAACGTGTTCTCCTGCTCCGTG
ATGCACGAGGCCCTGCACAACCACTACACCCAGAAGTCTCTAAGCTTGAGCCCCGGCGGAGGTGGTGGA
AGCGGAGGAGGTGGCTCTGGAGGGGGTGGAAGCGGAGGTGGAGGTGGATCCCAGCTCTACTCAGCGCTC
GCTAATAAGTGTTGTCATGTGGGATGCACAAAGCGGTCTCTCGCCAGAGCGTGC
```

HETERODIMERIC RELAXIN FUSIONS POLYPEPTIDES

REFERENCE TO THE SEQUENCE LISTING

This application incorporates by reference a Sequence Listing submitted with this application as text file entitled 201011PCT_SL.txt created on Aug. 27, 2021 and having a size of 230 kilobytes.

FIELD OF THE INVENTION

The present invention relates to heterodimeric Relaxin fusions and uses thereof. In particular, the present invention relates to Relaxin-2 fusions and uses thereof.

BACKGROUND

Relaxin is a peptide hormone that belongs to the insulin superfamily. In humans, the Relaxin peptide family includes seven peptides of high structural but low sequence similarity: Relaxin 1, 2 and 3, and the insulin-like peptides INSL3, INSL4, INSL5 and INSL6. Naturally occurring Relaxins consist of A and B polypeptide chains covalently linked by two inter-chain disulphide bonds. The A chain has an additional intra-chain disulphide bond. The relaxin genes encode prohormones with structure B-C-A (B and A polypeptide chains linked by a C peptide). The prohormone undergoes endoproteolytic cleavage with PC1 and PC2 enzymes to remove the C peptide, before secretion of mature Relaxin.

Relaxin is a pleiotropic hormone known to mediate systemic haemodynamic and renal adaptive changes during pregnancy. Relaxin has also been shown to have anti-fibrotic properties and to have beneficial effects in heart failure e.g. with acute decompensated heart failure (ADHF). Heart failure is associated with significant morbidity and mortality. It is characterized by complex tissue remodeling involving increased cardiomyocyte death and interstitial fibrosis. Relaxin activates a number of signaling cascades which have been shown to be beneficial in the setting of ischemia-reperfusion and heart failure. These signaling pathways include activation of the phosphoinositide 3-kinase pathway and activation of the nitric oxide signaling pathway (Bathgate R A et al. (2013) *Physiol. Rev.* 93(1): 405-480; Mentz R J et al. (2013) *Am. Heart J.* 165(2): 193-199; Tietjens J et al. (2016) *Heart* 102: 95-99; Wilson S S et al. (2015) *Pharmacology* 35: 315-327).

Clinical trials have been conducted using unmodified recombinant human Relaxin-2, serelaxin. Continuous intravenous administration of serelaxin to hospitalized patients improved the markers of cardiac, renal and hepatic damage and congestion (Felker G M et al. (2014) *J. Am. Coll. Cardiol.* 64(15): 1591-1598; Metra M et al. (2013) *J. Am. Coll. Cardiol.* 61(2): 196-206; Teerlink J R et al. (2013) *Lancet* 381(9860): 29-39). However, due to the rapid clearance of serelaxin from the patients' circulation, the therapeutic effects were limited and the positive effects rapidly disappeared once intravenous injection stopped. Additionally, approximately one third of the patients experienced a significant blood pressure drop (>40 mm Hg) after receiving serelaxin intravenously, with the consequence that the dose had to be reduced by half or even more.

WO 2013/004607 and WO 2018/138170 describe recombinant Relaxin polypeptides in which the Relaxin A and Relaxin B are fused in a single chain with a linker peptide. WO2013/004607 describes recombinant Relaxin with a linker peptide of at least five amino acids and less than 15 amino acids. WO 2018/138170 describes recombinant Relaxin with a linker peptide of at least 15 amino acids.

Given the promising clinical studies conducted so far with unmodified recombinant Relaxin, there remains a need for further recombinant Relaxins which retain a Relaxin biological activity and provide advantages such as an extended half-life and convenient dosing.

SUMMARY OF INVENTION

The present invention relates to heterodimeric fusions having Relaxin activity.

Thus, in one aspect, the present invention provides a heterodimeric fusion comprising:
(i) a first heterodimerisation domain connected to at least one Relaxin A chain polypeptide or a variant thereof; and
(ii) a second heterodimerisation domain connected to at least one Relaxin B chain polypeptide or a variant thereof,
wherein the first heterodimerisation domain heterodimerises with the second heterodimerisation domain, and wherein the heterodimeric fusion has Relaxin activity.

In some embodiments, the Relaxin A chain and the Relaxin B chain are covalently bound by one or more (e.g. two) inter-chain bonds, preferably one or more (e.g. two) inter-chain disulphide bonds. In some embodiments, the Relaxin A chain and the Relaxin B chain are not covalently linked to each other by an amino acid linker.

In some embodiments, the Relaxin A chain is a Relaxin-2 A chain and the Relaxin B chain is a Relaxin-2 B chain.

In preferred embodiments, the first and second heterodimerisation domains are derived from an immunoglobulin Fc region, e.g. an immunoglobulin G (IgG) Fc region, ("first Fc region" and "second Fc region"). The first and second Fc regions may comprise constant domains CH2 and/or CH3. Preferably, the first and second Fc regions comprise CH2 and CH3.

In alternative embodiments, the first and second heterodimerisation domains are derived from an immunoglobulin Fab region.

In yet further alternative embodiments, the first and second heterodimerisation domains heterodimerise to form parallel coiled coils.

In some embodiments, the Relaxin A chain is connected to the first heterodimerisation domain (e.g. first Fc region) via a connector and the Relaxin B chain is connected to the second heterodimerisation domain (e.g. second Fc region) via a connector. In preferred embodiments, one or preferably both connectors are polypeptides.

In some embodiments, at least one connector is a polypeptide having a length of between 6 and 40 amino acids. Preferably, both connectors are polypeptides having a length of between 6 and 40 amino acids. In preferred embodiments, at least one connector is a polypeptide having a length of 21 amino acids. In particularly preferred embodiments, both connectors are polypeptides having a length of 21 amino acids. In certain embodiments, both connectors have the sequence GGGGSGGGGSGGGGSGGGGS [SEQ ID NO: 5].

In preferred embodiments, the C-terminus of the first heterodimerisation domain (e.g. first Fc region) is connected to the N-terminus of the Relaxin A chain and the C-terminus of the second heterodimerisation domain (e.g. second Fc region) is connected to the N-terminus of the Relaxin B chain. In alternative embodiments, the N-terminus of the first heterodimerisation domain (e.g. first Fc region) is connected to the C-terminus of the Relaxin A chain and the N-terminus of the second heterodimerisation domain (e.g. second Fc region) is connected to the C-terminus of the Relaxin B chain.

In some embodiments, the first and second heterodimerisation domains (e.g. first and second Fc regions) comprise heterodimerisation-promoting amino acid mutations and/or modifications, preferably asymmetric heterodimerisation-promoting amino acid mutations and/or modifications. In preferred embodiments, the heterodimerisation-promoting amino acid mutations are "Fc Knob" and "Fc Hole" mutations. In particularly preferred embodiments, the "Fc Knob" and "Fc Hole" mutations are present in the CH3 domains. In preferred embodiments, the first Fc region comprises "Fc Knob" mutations and the second Fc region comprises "Fc Hole" mutations. Alternatively, the first Fc region has "Fc Hole" mutations, and the second Fc region has "Fc Knob" mutations. Preferably, the heterodimerisation-promoting amino acid mutations comprise "Fc Hole" mutations Y349C, T366S, L368A and Y407V, or conservative substitutions thereof, in one CH3 domain; and "Fc Knob" mutations S354C and T366W, or conservative substitutions thereof, in the other CH3 domain, wherein the amino acid numbering is according to the EU index as in Kabat.

In embodiments of any aspect of the invention, the Relaxin-2 A chain polypeptide comprises the sequence as set forth in of SEQ ID NO: 1 or a variant thereof and the Relaxin-2 B chain polypeptide comprises the sequence as set forth in SEQ ID NO: 2 or a variant thereof. In some embodiments, the Relaxin-2 A chain polypeptide comprises the amino acid mutation K9H.

Also provided by the present invention is a heterodimeric fusion comprising:
  (i) an FcX-con-A fusion polypeptide; and
  (ii) an FcY-con-B fusion polypeptide,
  wherein:
  A is a Relaxin A chain or variant thereof, e.g. a Relaxin-2 A chain or variant thereof;
  B is a Relaxin B chain or variant thereof, e.g. a Relaxin-2 B chain or variant thereof;
  FcY is an immunoglobulin (e.g. IgG1) Fc region with "Fc Hole" amino acid mutations and/or modifications, preferably comprising a CH3 domain having the amino acid mutations Y349C:T366S:L368A:Y407V or conservative substitutions thereof;
  FcX is an immunoglobulin (e.g. IgG1) Fc region with "Fc Knob" amino acid mutations and/or modifications, preferably comprising a CH3 domain having the amino acid mutations S354C:T366W or conservative substitutions thereof; and
  con is a connector, e.g. a connector polypeptide preferably having the sequence GGGGSGGGGSGGGGSGGGGGS [SEQ ID NO: 5],
wherein the amino acid numbering is according to the EU index as in Kabat, wherein FcX heterodimerises with FcY, and wherein the heterodimeric fusion has Relaxin activity.

In particularly preferred embodiments, the heterodimeric fusion comprises a fusion polypeptide with the amino acid sequence of SEQ ID NO: 11 and a fusion polypeptide with the amino acid sequence of SEQ ID NO: 20.

In some embodiments of any aspect of the invention, the heterodimeric fusion further comprises one or more Fabs, optionally wherein the heterodimeric fusion comprises one Fab linked to the N-terminus of the first heterodimerisation domain (e.g. first Fc region) and a second Fab linked to the N-terminus of the second heterodimerisation domain (e.g. second Fc region).

In some embodiments of any aspect of the invention, the heterodimeric fusion further comprises a second Relaxin A chain polypeptide or variant thereof connected to the N-terminus of the first heterodimerisation domain (e.g. first Fc region) and a second Relaxin B chain polypeptide or variant thereof connected to the N-terminus of the second heterodimerisation domain (e.g. second Fc region), optionally wherein the second Relaxin A chain is connected to the first heterodimerisation domain (e.g. first Fc region) via a connector polypeptide and the second Relaxin B chain is connected to the second heterodimerisation domain (e.g. second Fc region) via a connector polypeptide.

In another aspect, the invention provides a heterodimeric fusion comprising
  (i) FcX-B-L-A and FcY, optionally FcY-B-L-A; or
  (ii) FcY-B-L-A and FcX, optionally FcX-B-L-A;
  wherein:
  FcY is an immunoglobulin (e.g. IgG1) Fc region with "Fc Hole" amino acid mutations and/or modifications, preferably comprising a CH3 domain having the amino acid mutations Y349C:T366S:L368A:Y407V, or conservative substitutions thereof;
  FcX is an immunoglobulin (e.g. IgG1) Fc region with "Fc Knob" amino acid mutations and/or modifications, preferably comprising a CH3 domain having the amino acid mutations S354C:T366W, or conservative substitutions thereof;
  B is a Relaxin B chain or a variant thereof, e.g. a Relaxin-2 B chain or variant thereof;
  A is a Relaxin A chain or a variant thereof, e.g. a Relaxin-2 A chain or variant thereof; and
  L is a linker polypeptide, preferably with the amino acid sequence GGGSGGGSGG [SEQ ID NO: 60],
wherein the amino acid numbering is according to the EU index as in Kabat, wherein FcX heterodimerises with FcY, and wherein the heterodimeric fusion has Relaxin activity. Alternatively, the FcX and the FcY are non-Fc heterodimerisation domains as described herein. In some embodiments, the Relaxin B chain is connected to FcX and/or FcY via a connector, optionally a connector polypeptide having a length of between 6 and 40 amino acids, e.g. a length of 21 amino acids.

In yet another aspect, the invention provides a heterodimeric fusion comprising
  (i) FcX-A-L-B and FcY, optionally FcY-A-L-B; or
  (ii) FcY-A-L-B and FcX, optionally FcX-A-L-B;
  wherein:
  FcY is an immunoglobulin (e.g. IgG1) Fc region with "Fc Hole" amino acid mutations and/or modifications, preferably comprising a CH3 domain having the amino acid mutations Y349C:T366S:L368A:Y407V, or conservative substitutions thereof;
  FcX is an immunoglobulin (e.g. IgG1) Fc region with "Fc Knob" amino acid mutations and/or modifications, preferably comprising a CH3 domain having the amino acid mutations S354C:T366W, or conservative substitutions thereof;
  A is a Relaxin A chain or a variant thereof, e.g. a Relaxin-2 A chain or variant thereof;
  B is a Relaxin B chain or a variant thereof, e.g. a Relaxin-2 B chain or variant thereof; and
  L is a linker polypeptide, preferably with the amino acid sequence GGGSGGGSGG [SEQ ID NO: 60],
wherein the amino acid numbering is according to the EU index as in Kabat, wherein FcX heterodimerises with FcY, and wherein the heterodimeric fusion has Relaxin activity. Alternatively, the FcX and the FcY are non-Fc heterodimerisation domains as described herein. In some embodiments, the Relaxin A chain is connected to FcX and/or FcY via a connector, optionally a connector polypeptide having a length of between 6 and 40 amino acids, e.g. a length of 21 amino acids.

In some embodiments of any aspect of the invention, the ratio of Relaxin activity of the heterodimeric fusion over the Relaxin activity of a reference Relaxin protein is between about 0.001 and about 10.

In related aspects, the invention provides nucleic acid molecules (e.g. DNA molecules) encoding a heterodimeric fusion of the invention, vectors comprising a nucleic acid molecule, host cells comprising a vector or nucleic acid, and methods of producing the heterodimeric fusions of the invention by culturing the host cells and collecting the fusion protein.

In another aspect, the invention provides a pharmaceutical composition comprising the heterodimeric fusion of the invention, a kit comprising the same, and uses of the heterodimeric fusion in therapy, including methods of treatment of a subject with heart failure.

Aspects and embodiments of the invention are set out in the appended claims. These and other aspects and embodiments of the invention are also described herein.

BRIEF DESCRIPTION OF FIGURES AND SEQUENCE LISTING

FIG. 1 shows exemplary formats of the heterodimeric fusions according to some embodiments of the invention. The format of each fusion polypeptide of the heterodimeric fusion is given in terms of FcX, FcY, A, B, con and L, wherein FcX ("Fc Knob") and FcY ("Fc Hole") are two Fc regions comprising heterodimerisation-promoting amino acid mutations and/or modifications; A ("Rlx A") and B ("Rlx B") are Relaxin A chain and Relaxin B chain polypeptides; "con" is a connector polypeptide; L is a linker polypeptide, HC X and HC Y—heavy chains of an antibody, LC—light chain of an antibody, hinge—the hinge region of an antibody and Fab is Fab fragment of an antibody.

FIG. 2 shows LC-MS analysis of RELAX0019 and RELAX0023 A) RELAX0019 and RELAX0023 deglycosylated and non-reduced analysis showing the mass of intact molecules B) RELAX0019 and RELAX0023 deglycosylated and reduced analysis showing masses of individual Fc-fusion chains—Knob Relaxin Chain A and Hole Relaxin Chain B.

FIG. 3 shows analysis of the C-terminal peptide of RELAX0019 and RELAX0023 by non-reduced peptide mapping using LC-MS. The amino acid sequence of the C-terminal peptide with predicted disulphide bonds represented by lines is shown in the top panel (SEQ ID NOs: 75, 76, and 77). Panels A and E—the extracted ion chromatogram of the C-terminal peptide in absence of the reducing agent (−DTT). Panels C and G—deconvoluted mass spectrum of the C-terminal peptide in absence of the reducing agent. Panels B and F—the extracted ion chromatogram in the presence of the reducing agent (+DTT) and Panels D and H—deconvoluted mass spectrum in the presence of the reducing agent.

FIG. 11 shows the nucleotide sequences encoding some of the polypeptides of the present invention (SEQ ID NOs: 80-140, respectively, in order of appearance).

TABLE 1

Figure 1:
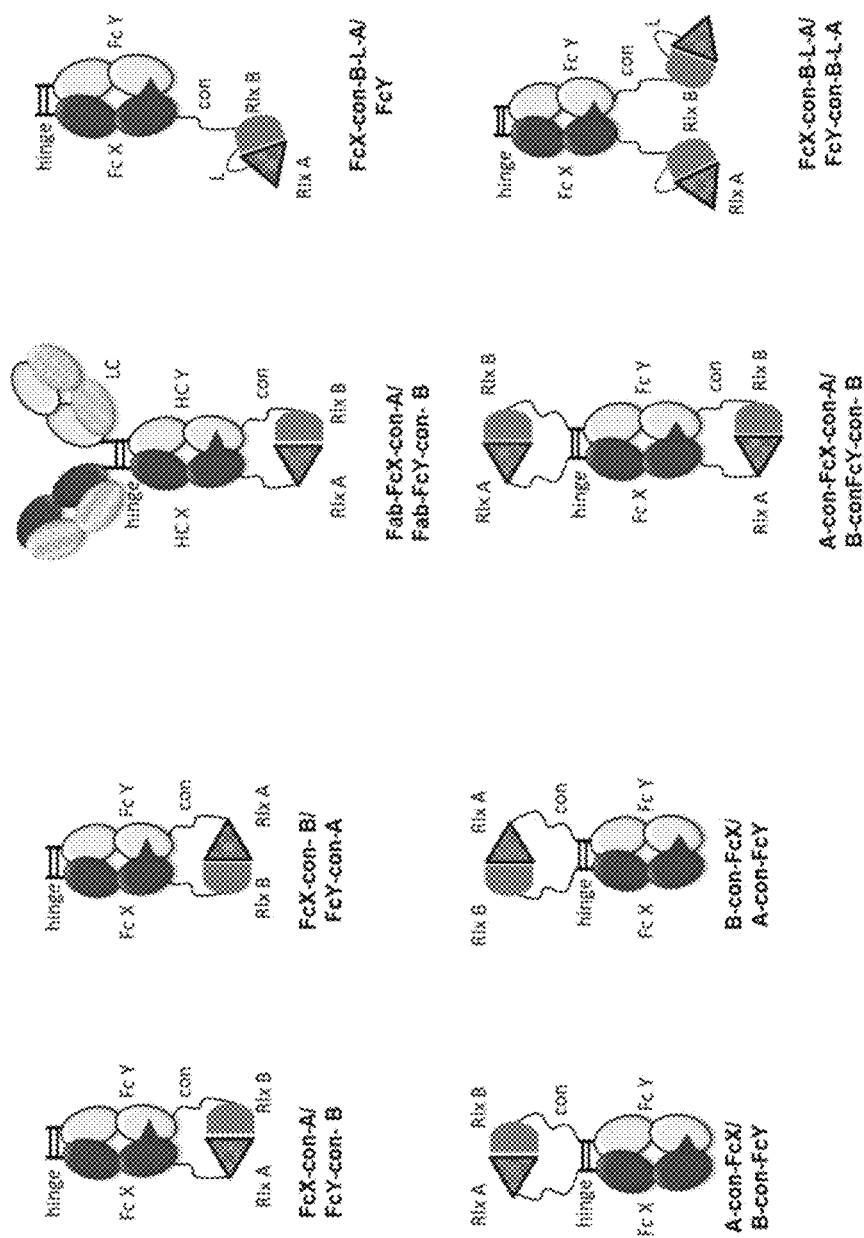

Sequence Listing.
The upper hinge region is in Italics, Relaxin A is underlined, Relaxin B is double underlined, the FC region is bold.

| SEQ ID NO: | Construct | Amino acid sequence |
|---|---|---|
| 1 | Relaxin A | QLYSALANKCCHVGCTKRSLARFC |
| 2 | Relaxin B | SWMEEVIKLCGRELVRAQIAICGMSTWS |
| 3 | FcH01 | DKTHTCPPCPAPEFEGGPSVFLFPPKPKDTLMISRTPEVT CVVVDVSHEDPEVKFNWYVDGVEVHNAKTKPREEQYNS TYRVVSVLTVLHQDWLNGKEYKCKVSNKALPASIEKTISK AKGQPREPQVCTLPPSREEMTKNQVSLSCAVKGFYPSDI AVEWESNGQPENNYKTTPPVLDSDGSFFLVSKLTVDKSR WQQGNVFSCSVMHEALHNHYTQKSLSLSPG |

TABLE 1-continued

Sequence Listing.
The upper hinge region is in Italics, Relaxin A
is underlined, Relaxin B is double underlined,
the FC region is bold.

| SEQ ID NO: | Construct | Amino acid sequence |
|---|---|---|
| 4 | FcK01 | DKTHTCPPCPAPEFEGGPSVFLFPPKPKDTLMISRTPEVT CVVVDVSHEDPEVKFNWYVDGVEVHNAKTKPREEQYNS TYRVVSVLTVLHQDWLNGKEYKCKVSNKALPASIEKTISK AKGQPREPQVYTLPPCREEMTKNQVSLWCLVKGFYPSDI AVEWESNGQPENNYKTTPPVLDSDGSFFLYSKLTVDKSR WQQGNVFSCSVMHEALHNHYTQKSLSLSPG |
| 5 | Con01 | GGGGSGGGGSGGGGSGGGGS |
| 6 | Con02 | PAPAPAPAPAPAPAPAPAG |
| 7 | RELAX0009 | SWMEEVIKLCGRELVRAQIAICGMSTWSGGGGSGGGGSG GGGSQLYSALANKCCHVGCTKRSLARFCAAAGGGGSGG GGSGGGGSGGGGSACPPCPAPEFEGGPSVFLFPPKPKD TLMISRTPEVTCVVVDVSHEDPEVKFNWYVDGVEVHNAK TKPREEQYNSTYRVVSVLTVLHQDWLNGKEYKCKVSNK ALPASIEKTISKAKGQPREPQVYTLPPSREEMTKNQVSLT CLVKGFYPSDIAVEWESNGQPENNYKTTPPVLDSDGSFF LYSKLTVDKSRWQQGNVFSCSVMHEALHNHYTQKSLSL SPG |
| 8 | RELAX0010 | DKTHTCPPCPAPELLGGPSVFLFPPKPKDTLMISRTPEVT CVVVDVSHEDPEVKFNWYVDGVEVHNAKTKPREEQYNS TYRVVSVLTVLHQDWLNGKEYKCKVSNKALPAPIEKTISK AKGQPREPQVYTLPPSRDELTKNQVSLTCLVKGFYPSDIA VEWESNGQPENNYKTTPPVLDSDGSFFLYSKLTVDKSRW QQGNVFSCSVMHEALHNHYTQKSLSLSPGKGGGGSGG GGSGGGGSQLYSALANKCCHVGCTKRSLARFCGGGGSG GGGSGGGGSSWMEEVIKLCGRELVRAQIAICGMSTWS |
| 9 | Rlx011 | GGAGGACPPCPAPEFEGGPSVFLFPPKPKDTLMISRTPE VTCVVVDVSHEDPEVKFNWYVDGVEVHNAKTKPREEQY NSTYRVVSVLTVLHQDWLNGKEYKCKVSNKALPASIEKTI SKAKGQPREPQVYTLPPCREEMTKNQVSLWCLVKGFYP SDIAVEWESNGQPENNYKTTPPVLDSDGSFFLYSKLTVD KSRWQQGNVFSCSVMHEALHNHYTQKSLSLSPGGGGG SGGGGSGGGGSGGGGSQLYSALANKCCHVGCTKRSLA RFC |
| 10 | Rlx011b | GGAGGACPPCPAPEFEGGPSVFLFPPKPKDTLMISRTPE VTCVVVDVSHEDPEVKFNWYVDGVEVHNAKTKPREEQY NSTYRVVSVLTVLHQDWLNGKEYKCKVSNKALPASIEKTI SKAKGQPREPQVYTLPPSREEMTKNQVSLWCLVKGFYP SDIAVEWESNGQPENNYKTTPPVLDSDGSFFLYSKLTVD KSRWQQGNVFSCSVMHEALHNHYTQKSLSLSPGGGGG SGGGGSGGGGSGGGGSQLYSALANKCCHVGCTKRSLA RFC |
| 11 | Rlx011DD | DKTHTCPPCPAPEFEGGPSVFLFPPKPKDTLMISRTPEVT CVVVDVSHEDPEVKFNWYVDGVEVHNAKTKPREEQYNS TYRVVSVLTVLHQDWLNGKEYKCKVSNKALPASIEKTISK AKGQPREPQVYTLPPCREEMTKNQVSLWCLVKGFYPSDI AVEWESNGQPENNYKTTPPVLDSDGSFFLYSKLTVDKSR WQQGNVFSCSVMHEALHNHYTQKSLSLSPGGGGGSGG GGSGGGGSGGGGSQLYSALANKCCHVGCTKRSLARFC |
| 12 | Rlx012 | GGAGGACPPCPAPEFEGGPSVFLFPPKPKDTLMISRTPE VTCVVVDVSHEDPEVKFNWYVDGVEVHNAKTKPREEQY NSTYRVVSVLTVLHQDWLNGKEYKCKVSNKALPASIEKTI SKAKGQPREPQVYTLPPSREEMTKNQVSLCAVKGFYP SDIAVEWESNGQPENNYKTTPPVLDSDGSFFLVSKLTVD KSRWQQGNVFSCSVMHEALHNHYTQKSLSLSPGGGGG SGGGGSGGGGSGGGGSQLYSALANKCCHVGCTKRSLA RFC |
| 13 | Rlx012b | GGAGGACPPCPAPEFEGGPSVFLFPPKPKDTLMISRTPE VTCVVVDVSHEDPEVKFNWYVDGVEVHNAKTKPREEQY NSTYRVVSVLTVLHQDWLNGKEYKCKVSNKALPASIEKTI SKAKGQPREPQVYTLPPSREEMTKNQVSLSCAVKGFYPS |

TABLE 1-continued

Sequence Listing.
The upper hinge region is in Italics, Relaxin A
is underlined, Relaxin B is double underlined,
the FC region is bold.

| SEQ ID NO: | Construct | Amino acid sequence |
|---|---|---|
| | | DIAVEWESNGQPENNYKTTPPVLDSDGSFFLVSKLTVDK SRWQQGNVFSCSVMHEALHNHYTQKSLSLSPGGGGS GGGGSGGGGSGGGGSGGGGSQLYSALANKCCHVGCTKRSLA RFC |
| 14 | Rlx012DD | *DKTHT*CPPCPAPEFEGGPSVFLFPPKPKDTLMISRTPEVT CVVVDVSHEDPEVKFNWYVDGVEVHNAKTKPREEQYNS TYRVVSVLTVLHQDWLNGKEYKCKVSNKALPASIEKTISK AKGQPREPQVYTLPPCREEMTKNQVSLWCLVKGFYPSDI AVEWESNGQPENNYKTTPPVLDSDGSFFLYSKLTVDKSR WQQGNVFSCSVMHEALHNHYTQKSLSLSPGGGGSGG GGSGGGGSGGGGS<u><u>SWMEEVIKLCGRELVRAQIAICGM STWS</u></u> |
| 15 | Rlx013 | *GGAGGA*CPPCPAPEFEGGPSVFLFPPKPKDTLMISRTPE VTCVVVDVSHEDPEVKFNVVYVDGVEVHNAKTKPREEQY NSTYRVVSVLTVLHQDWLNGKEYKCKVSNKALPASIEKTI SKAKGQPREPQVYTLPPCREEMTKNQVSLWCLVKGFYP SDIAVEWESNGQPENNYKTTPPVLDSDGSFFLYSKLTVD KSRWQQGNVFSCSVMHEALHNHYTQKSLSLSPGGGGG SGGGGSGGGGSGGGGS<u><u>SWMEEVIKLCGRELVRAQIAIC GMSTWS</u></u> |
| 16 | Rlx013b | *GGAGGA*CPPCPAPEFEGGPSVFLFPPKPKDTLMISRTPE VTCVVVDVSHEDPEVKFNWYVDGVEVHNAKTKPREEQY NSTYRVVSVLTVLHQDWLNGKEYKCKVSNKALPASIEKTI SKAKGQPREPQVYTLPPSREEMTKNQVSLWCLVKGFYP SDIAVEWESNGQPENNYKTTPPVLDSDGSFFLYSKLTVD KSRWQQGNVFSCSVMHEALHNHYTQKSLSLSPGGGGG SGGGGSGGGGSGGGGS<u><u>SWMEEVIKLCGRELVRAQIAIC GMSTWS</u></u> |
| 17 | Rlx013DD | *DKTHT*CPPCPAPEFEGGPSVFLFPPKPKDTLMISRTPEVT CVVVDVSHEDPEVKFNWYVDGVEVHNAKTKPREEQYNS TYRVVSVLTVLHQDWLNGKEYKCKVSNKALPASIEKTISK AKGQPREPQVCTLPPSREEMTKNQVSLSCAVKGFYPSDI AVEWESNGQPENNYKTTPPVLDSDGSFFLVSKLTVDKSR WQQGNVFSCSVMHEALHNHYTQKSLSLSPGGGGSGG GGSGGGGSGGGGSQLYSALANKCCHVGCTKRSLARFC |
| 18 | Rlx014 | *GGAGGA*CPPCPAPEFEGGPSVFLFPPKPKDTLMISRTPE VTCVVVDVSHEDPEVKFNWYVDGVEVHNAKTKPREEQY NSTYRVVSVLTVLHQDWLNGKEYKCKVSNKALPASIEKTI SKAKGQPREPQVCTLPPSREEMTKNQVSLSCAVKGFYP SDIAVEWESNGQPENNYKTTPPVLDSDGSFFLVSKLTVD KSRWQQGNVFSCSVMHEALHNHYTQKSLSLSPGGGGG SGGGGSGGGGSGGGGS<u><u>SWMEEVIKLCGRELVRAQIAIC GMSTWS</u></u> |
| 19 | Rlx014b | *GGAGGA*CPPCPAPEFEGGPSVFLFPPKPKDTLMISRTPE VTCVVVDVSHEDPEVKFNWYVDGVEVHNAKTKPREEQY NSTYRVVSVLTVLHQDWLNGKEYKCKVSNKALPASIEKTI SKAKGQPREPQVYTLPPSREEMTKNQVSLSCAVKGFYPS DIAVEWESNGQPENNYKTTPPVLDSDGSFFLVSKLTVDK SRWQQGNVFSCSVMHEALHNHYTQKSLSLSPGGGGS GGGGSGGGGSGGGGS<u><u>SWMEEVIKLCGRELVRAQIAIC GMSTWS</u></u> |
| 20 | Rlx014DD | *DKTHT*CPPCPAPEFEGGPSVFLFPPKPKDTLMISRTPEVT CVVVDVSHEDPEVKFNWYVDGVEVHNAKTKPREEQYNS TYRVVSVLTVLHQDWLNGKEYKCKVSNKALPASIEKTISK AKGQPREPQVCTLPPSREEMTKNQVSLSCAVKGFYPSDI AVEWESNGQPENNYKTTPPVLDSDGSFFLVSKLTVDKSR WQQGNVFSCSVMHEALHNHYTQKSLSLSPGGGGSGG GGSGGGGSGGGGS<u><u>SWMEEVIKLCGRELVRAQIAICGM STWS</u></u> |
| 21 | Rlx020 | *DKTHT*CPPCPAPEFEGGPSVFLFPPKPKDTLMISRTPEVT CVVVDVSHEDPEVKFNWYVDGVEVHNAKTKPREEQYNS TYRVVSVLTVLHQDWLNGKEYKCKVSNKALPASIEKTISK AKGQPREPQVYTLPPCREEMTKNQVSLWCLVKGFYPSDI AVEWESNGQPENNYKTTPPVLDSDGSFFLYSKLTVDKSR |

TABLE 1-continued

Sequence Listing.
The upper hinge region is in Italics, Relaxin A
is underlined, Relaxin B is double underlined,
the FC region is bold.

| SEQ ID NO: | Construct | Amino acid sequence |
|---|---|---|
|  |  | WQQGNVFSCSVMHEALHNHYTQKSLSLSPGGGGGSGG GGSGGGGSQLYSALANKCCHVGCTKRSLARFC |
| 22 | Rlx021 | DKTHTCPPCPAPEFEGGPSVFLFPPKPKDTLMISRTPEVT CVVVDVSHEDPEVKFNVVYVDGVEVHNAKTKPREEQYNS TYRVVSVLTVLHQDWLNGKEYKCKVSNKALPASIEKTISK AKGQPREPQVCTLPPSREEMTKNQVSLSCAVKGFYPSDI AVEWESNGQPENNYKTTPPVLDSDGSFFLVSKLTVDKSR WQQGNVFSCSVMHEALHNHYTQKSLSLSPGGGGGSGG GGSGGGGSSWMEEVIKLCGRELVRAQIAICGMSTWS |
| 23 | Rlx022 | DKTHTCPPCPAPEFEGGPSVFLFPPKPKDTLMISRTPEVT CVVVDVSHEDPEVKFNWYVDGVEVHNAKTKPREEQYNS TYRVVSVLTVLHQDWLNGKEYKCKVSNKALPASIEKTISK AKGQPREPQVYTLPPCREEMTKNQVSLWCLVKGFYPSDI AVEWESNGQPENNYKTTPPVLDSDGSFFLYSKLTVDKSR WQQGNVFSCSVMHEALHNHYTQKSLSLSPGGGGGSGG GGGSQLYSALANKCCHVGCTKRSLARFC |
| 24 | Rlx023 | DKTHTCPPCPAPEFEGGPSVFLFPPKPKDTLMISRTPEVT CVVVDVSHEDPEVKFNWYVDGVEVHNAKTKPREEQYNS TYRVVSVLTVLHQDWLNGKEYKCKVSNKALPASIEKTISK AKGQPREPQVCTLPPSREEMTKNQVSLSCAVKGFYPSDI AVEWESNGQPENNYKTTPPVLDSDGSFFLVSKLTVDKSR WQQGNVFSCSVMHEALHNHYTQKSLSLSPGGGGGSGG GGGSSWMEEVIKLCGRELVRAQIAICGMSTWS |
| 25 | Rlx024 | DKTHTCPPCPAPEFEGGPSVFLFPPKPKDTLMISRTPEVT CVVVDVSHEDPEVKFNWYVDGVEVHNAKTKPREEQYNS TYRVVSVLTVLHQDWLNGKEYKCKVSNKALPASIEKTISK AKGQPREPQVYTLPPCREEMTKNQVSLWCLVKGFYPSDI AVEWESNGQPENNYKTTPPVLDSDGSFFLYSKLTVDKSR WQQGNVFSCSVMHEALHNHYTQKSLSLSPGGGGGGSQ LYSALANKCCHVGCTKRSLARFC |
| 26 | Rlx025 | DKTHTCPPCPAPEFEGGPSVFLFPPKPKDTLMISRTPEVT CVVVDVSHEDPEVKFNWYVDGVEVHNAKTKPREEQYNS TYRVVSVLTVLHQDWLNGKEYKCKVSNKALPASIEKTISK AKGQPREPQVCTLPPSREEMTKNQVSLSCAVKGFYPSDI AVEWESNGQPENNYKTTPPVLDSDGSFFLVSKLTVDKSR WQQGNVFSCSVMHEALHNHYTQKSLSLSPGGGGGGSS WMEEVIKLCGRELVRAQIAICGMSTWS |
| 27 | Rlx026 | DKTHTCPPCPAPEFEGGPSVFLFPPKPKDTLMISRTPEVT CVVVDVSHEDPEVKFNWYVDGVEVHNAKTKPREEQYNS TYRVVSVLTVLHQDWLNGKEYKCKVSNKALPASIEKTISK AKGQPREPQVYTLPPCREEMTKNQVSLWCLVKGFYPSDI AVEWESNGQPENNYKTTPPVLDSDGSFFLYSKLTVDKSR WQQGNVFSCSVMHEALHNHYTQKSLSLSPGAPAPAPAP APAPAPAPAPAGSQLYSALANKCCHVGCTKRSLARFC |
| 28 | Rlx027 | DKTHTCPPCPAPEFEGGPSVFLFPPKPKDTLMISRTPEVT CVVVDVSHEDPEVKFNWYVDGVEVHNAKTKPREEQYNS TYRVVSVLTVLHQDWLNGKEYKCKVSNKALPASIEKTISK AKGQPREPQVCTLPPSREEMTKNQVSLSCAVKGFYPSDI AVEWESNGQPENNYKTTPPVLDSDGSFFLVSKLTVDKSR WQQGNVFSCSVMHEALHNHYTQKSLSLSPGAPAPAPAP APAPAPAPAPAGSSWMEEVIKLCGRELVRAQIAICGMSTW S |
| 29 | Rlx028 | DKTHTCPPCPAPEFEGGPSVFLFPPKPKDTLMISRTPEVT CVVVDVSHEDPEVKFNWYVDGVEVHNAKTKPREEQYNS TYRVVSVLTVLHQDWLNGKEYKCKVSNKALPASIEKTISK AKGQPREPQVCTLPPSREEMTKNQVSLSCAVKGFYPSDI AVEWESNGQPENNYKTTPPVLDSDGSFFLVSKLTVDKSR WQQGNVFSCSVMHEALHNHYTQKSLSLSPGAAPAPAPA PAPAPAGSQLYSALANKCCHVGCTKRSLARFC |
| 30 | Rlx029 | DKTHTCPPCPAPEFEGGPSVFLFPPKPKDTLMISRTPEVT CVVVDVSHEDPEVKFNWYVDGVEVHNAKTKPREEQYNS TYRVVSVLTVLHQDWLNGKEYKCKVSNKALPASIEKTISK AKGQPREPQVYTLPPCREEMTKNQVSLWCLVKGFYPSDI |

TABLE 1-continued

Sequence Listing.
The upper hinge region is in Italics, Relaxin A
is underlined, Relaxin B is double underlined,
the FC region is bold.

| SEQ ID NO: | Construct | Amino acid sequence |
|---|---|---|
| | | AVEWESNGQPENNYKTTPPVLDSDGSFFLYSKLTVDKSR WQQGNVFSCSVMHEALHNHYTQKSLSLSPGAAPAPAPA PAPAPAGSSWMEEVIKLCGRELVRAQIAICGMSTWS |
| 31 | Rlx030 | DKTHTCPPCPAPEFEGGPSVFLFPPKPKDTLMISRTPEVT CVVVDVSHEDPEVKFNWYVDGVEVHNAKTKPREEQYNS TYRVVSVLTVLHQDWLNGKEYKCKVSNKALPASIEKTISK AKGQPREPQVYTLPPCREEMTKNQVSLWCLVKGFYPSDI AVEWESNGQPENNYKTTPPVLDSDGSFFLYSKLTVDKSR WQQGNVFSCSVMHEALHNHYTQKSLSLSPGAPAPAPAP AGSQLYSALANKCCHVGCTKRSLARFC |
| 32 | Rlx031 | DKTHTCPPCPAPEFEGGPSVFLFPPKPKDTLMISRTPEVT CVVVDVSHEDPEVKFNWYVDGVEVHNAKTKPREEQYNS TYRVVSVLTVLHQDWLNGKEYKCKVSNKALPASIEKTISK AKGQPREPQVCTLPPSREEMTKNQVSLSCAVKGFYPSDI AVEWESNGQPENNYKTTPPVLDSDGSFFLVSKLTVDKSR WQQGNVFSCSVMHEALHNHYTQKSLSLSPGAPAPAPAP AGSSWMEEVIKLCGRELVRAQIAICGMSTWS |
| 33 | Rlx041E | DKTHTACPPCPAPEFEGGPSVFLFPPKPKDTLMISRTPEV TCVVVDVSHEDPEVKFNWYVDGVEVHNAKTKPREEQYN STYRVVSVLTVLHQDWLNGKEYKCKVSNKALPASIEKTIS KAKGQPREPQVYTLPPCREEMTKNQVSLWCLVKGFYPS DIAVEWESNGQPENNYKTTPPVLDSDGSFFLYSKLTVDK SRWQQGNVFSCSVMHEALHNHYTQKSLSLSPGGGGGS GGGGSGGGGSGGGGSQLYSALANECCHVGCTKRSLA RFC |
| 34 | Rlx041H | DKTHTACPPCPAPEFEGGPSVFLFPPKPKDTLMISRTPEV TCVVVDVSHEDPEVKFNWYVDGVEVHNAKTKPREEQYN STYRVVSVLTVLHQDWLNGKEYKCKVSNKALPASIEKTIS KAKGQPREPQVYTLPPCREEMTKNQVSLWCLVKGFYPS DIAVEWESNGQPENNYKTTPPVLDSDGSFFLYSKLTVDK SRWQQGNVFSCSVMHEALHNHYTQKSLSLSPGGGGGS GGGGSGGGGSGGGGSQLYSALANHCCHVGCTKRSLA RFC |
| 35 | Rlx041L | DKTHTACPPCPAPEFEGGPSVFLFPPKPKDTLMISRTPEV TCVVVDVSHEDPEVKFNWYVDGVEVHNAKTKPREEQYN STYRVVSVLTVLHQDWLNGKEYKCKVSNKALPASIEKTIS KAKGQPREPQVYTLPPCREEMTKNQVSLWCLVKGFYPS DIAVEWESNGQPENNYKTTPPVLDSDGSFFLYSKLTVDK SRWQQGNVFSCSVMHEALHNHYTQKSLSLSPGGGGGS GGGGSGGGGSGGGGSQLYSALANLCCHVGCTKRSLAR FC |
| 36 | Rlx041M | DKTHTACPPCPAPEFEGGPSVFLFPPKPKDTLMISRTPEV TCVVVDVSHEDPEVKFNWYVDGVEVHNAKTKPREEQYN STYRVVSVLTVLHQDWLNGKEYKCKVSNKALPASIEKTIS KAKGQPREPQVYTLPPCREEMTKNQVSLWCLVKGFYPS DIAVEWESNGQPENNYKTTPPVLDSDGSFFLYSKLTVDK SRWQQGNVFSCSVMHEALHNHYTQKSLSLSPGGGGGS GGGGSGGGGSGGGGSQLYSALANMCCHVGCTKRSLA RFC |
| 37 | Rlx044E | DKTHTACPPCPAPEFEGGPSVFLFPPKPKDTLMISRTPEV TCVVVDVSHEDPEVKFNWYVDGVEVHNAKTKPREEQYN STYRVVSVLTVLHQDWLNGKEYKCKVSNKALPASIEKTIS KAKGQPREPQVYTLPPCREEMTKNQVSLWCLVKGFYPS DIAVEWESNGQPENNYKTTPPVLDSDGSFFLYSKLTVDK SRWQQGNVFSCSVMHEALHNHYTQKSLSLSPGGGGGS GGGGSGGGGSGGGGSQLYSALANKCCHVGCTKESLAR FC |
| 38 | Rlx044H | DKTHTACPPCPAPEFEGGPSVFLFPPKPKDTLMISRTPEV TCVVVDVSHEDPEVKFNWYVDGVEVHNAKTKPREEQYN STYRVVSVLTVLHQDWLNGKEYKCKVSNKALPASIEKTIS KAKGQPREPQVYTLPPCREEMTKNQVSLWCLVKGFYPS |

TABLE 1-continued

Sequence Listing.
The upper hinge region is in Italics, Relaxin A
is underlined, Relaxin B is double underlined,
the FC region is bold.

| SEQ ID NO: | Construct | Amino acid sequence |
|---|---|---|
|  |  | DIAVEWESNGQPENNYKTTPPVLDSDGSFFLYSKLTVDK SRWQQGNVFSCSVMHEALHNHYTQKSLSLSPGGGGS GGGGSGGGGSGGGGS<u>QLYSALANKCCHVGCTKHSLA RFC</u> |
| 39 | Rlx051A | *DKTHT*CPPCPAPEFEGGPSVFLFPPKPKDTLMISRTPEVT CVVVDVSHEDPEVKFNWYVDGVEVHNAKTKPREEQYNS TYRVVSVLTVLHQDWLNGKEYKCKVSNKALPASIEKTISK AKGQPREPQVYTLPPCREEMTKNQVSLWCLVKGFYPSDI AVEWESNGQPENNYKTTPPVLDSDGSFFLYSKLTVDKSR WQQGNVFSCSVMHEALHNHYTQKSLSLSPGGGGGSGG GGSGGGGSGGGGS<u>QLYSALANKCCHVGCTKRSLAAFC</u> |
| 40 | Rlx051I | *DKTHT*CPPCPAPEFEGGPSVFLFPPKPKDTLMISRTPEVT CVVVDVSHEDPEVKFNWYVDGVEVHNAKTKPREEQYNS TYRVVSVLTVLHQDWLNGKEYKCKVSNKALPASIEKTISK AKGQPREPQVYTLPPCREEMTKNQVSLWCLVKGFYPSDI AVEWESNGQPENNYKTTPPVLDSDGSFFLYSKLTVDKSR WQQGNVFSCSVMHEALHNHYTQKSLSLSPGGGGGSGG GGSGGGGSGGGGS<u>QLYSALANKCCHVGCTKRSLAIFC</u> |
| 41 | Rlx051M | *DKTHT*CPPCPAPEFEGGPSVFLFPPKPKDTLMISRTPEVT CVVVDVSHEDPEVKFNWYVDGVEVHNAKTKPREEQYNS TYRVVSVLTVLHQDWLNGKEYKCKVSNKALPASIEKTISK AKGQPREPQVYTLPPCREEMTKNQVSLWCLVKGFYPSDI AVEWESNGQPENNYKTTPPVLDSDGSFFLYSKLTVDKSR WQQGNVFSCSVMHEALHNHYTQKSLSLSPGGGGGSGG GGSGGGGSGGGGS<u>QLYSALANKCCHVGCTKRSLAMFC</u> |
| 42 | Rlx051Q | *DKTHT*CPPCPAPEFEGGPSVFLFPPKPKDTLMISRTPEVT CVVVDVSHEDPEVKFNWYVDGVEVHNAKTKPREEQYNS TYRVVSVLTVLHQDWLNGKEYKCKVSNKALPASIEKTISK AKGQPREPQVYTLPPCREEMTKNQVSLWCLVKGFYPSDI AVEWESNGQPENNYKTTPPVLDSDGSFFLYSKLTVDKSR WQQGNVFSCSVMHEALHNHYTQKSLSLSPGGGGGSGG GGSGGGGSGGGGS<u>QLYSALANKCCHVGCTKRSLAQFC</u> |
| 43 | Rlx051S | *DKTHT*CPPCPAPEFEGGPSVFLFPPKPKDTLMISRTPEVT CVVVDVSHEDPEVKFNWYVDGVEVHNAKTKPREEQYNS TYRVVSVLTVLHQDWLNGKEYKCKVSNKALPASIEKTISK AKGQPREPQVYTLPPCREEMTKNQVSLWCLVKGFYPSDI AVEWESNGQPENNYKTTPPVLDSDGSFFLYSKLTVDKSR WQQGNVFSCSVMHEALHNHYTQKSLSLSPGGGGGSGG GGSGGGGSGGGGS<u>QLYSALANKCCHVGCTKRSLASFC</u> |
| 44 | Rlx052E | *DKTHT*CPPCPAPEFEGGPSVFLFPPKPKDTLMISRTPEVT CVVVDVSHEDPEVKFNWYVDGVEVHNAKTKPREEQYNS TYRVVSVLTVLHQDWLNGKEYKCKVSNKALPASIEKTISK AKGQPREPQVYTLPPCREEMTKNQVSLWCLVKGFYPSDI AVEWESNGQPENNYKTTPPVLDSDGSFFLYSKLTVDKSR WQQGNVFSCSVMHEALHNHYTQKSLSLSPGGGGGSGG GGSGGGGSGGGGS<u>QLYSALANKCCHVGCTKRSLAREC</u> |
| 45 | Rlx052I | *DKTHT*CPPCPAPEFEGGPSVFLFPPKPKDTLMISRTPEVT CVVVDVSHEDPEVKFNWYVDGVEVHNAKTKPREEQYNS TYRVVSVLTVLHQDWLNGKEYKCKVSNKALPASIEKTISK AKGQPREPQVYTLPPCREEMTKNQVSLWCLVKGFYPSDI AVEWESNGQPENNYKTTPPVLDSDGSFFLYSKLTVDKSR WQQGNVFSCSVMHEALHNHYTQKSLSLSPGGGGGSGG GGSGGGGSGGGGS<u>QLYSALANKCCHVGCTKRSLARIC</u> |
| 46 | Rlx055 | *DKTHT*CPPCPAPEFEGGPSVFLFPPKPKDTLMISRTPEVT CVVVDVSHEDPEVKFNWYVDGVEVHNAKTKPREEQYNS TYRVVSVLTVLHQDWLNGKEYKCKVSNKALPASIEKTISK AKGQPREPQVYTLPPCREEMTKNQVSLWCLVKGFYPSDI AVEWESNGQPENNYKTTPPVLDSDGSFFLYSKLTVDKSR WQQGNVFSCSVMHEALHNHYTQKSLSLSPGGGGGSGG GGSGGGGSGGGGS<u><u>SWMEEVIKLCGRELVRAQIAICGM STWS</u></u>GGGSGGGGSG<u>QLYSALANKCCHVGCTKRSLARFC</u> |
| 47 | Rlx056 | *DKTHT*CPPCPAPEFEGGPSVFLFPPKPKDTLMISRTPEVT CVVVDVSHEDPEVKFNWYVDGVEVHNAKTKPREEQYNS |

TABLE 1-continued

Sequence Listing.
The upper hinge region is in Italics, Relaxin A
is underlined, Relaxin B is double underlined,
the FC region is bold.

| SEQ ID NO: | Construct | Amino acid sequence |
|---|---|---|
| | | TYRVVSVLTVLHQDWLNGKEYKCKVSNKALPASIEKTISK AKGQPREPQVCTLPPSREEMTKNQVSLSCAVKGFYPSDI AVEWESNGQPENNYKTTPPVLDSDGSFFLVSKLTVDKSR WQQGNVFSCSVMHEALHNHYTQKSLSLSPGGGGSGG GGSGGGGSGGGGSSWMEEVIKLCGRELVRAQIAICGM STWSGGGSGGGSGQLYSALANKCCHVGCTKRSLARFC |
| 48 | Rlx061H | SWMEEVIKLCGRELVRAQIAICGMSTWSAAAGGGGSGGG GSGGGGSGGGGSACPPCPAPEFEGGPSVFLFPPKPKDT LMISRTPEVTCVVVDVSHEDPEVKFNWYVDGVEVHNAKT KPREEQYNSTYRVVSVLTVLHQDWLNGKEYKCKVSNKA LPASIEKTISKAKGQPREPQVCTLPPSREEMTKNQVSLSC AVKGFYPSDIAVEWESNGQPENNYKTTPPVLDSDGSFFL VSKLTVDKSRWQQGNVFSCSVMHEALHNHYTQKSLSLS PG |
| 49 | Rlx062K | QLYSALANKCCHVGCTKRSLARFCAAAGGGGSGGGGSG GGGSGGGGSACPPCPAPEFEGGPSVFLFPPKPKDTLMIS RTPEVTCVVVDVSHEDPEVKFNWYVDGVEVHNAKTKPRE EQYNSTYRVVSVLTVLHQDWLNGKEYKCKVSNKALPASI EKTISKAKGQPREPQVYTLPPCREEMTKNQVSLWCLVKG FYPSDIAVEWESNGQPENNYKTTPPVLDSDGSFFLYSKLT VDKSRWQQGNVFSCSVMHEALHNHYTQKSLSLSPG |
| 50 | Rlx076 | QLYSALANKCCHVGCTKRSLARFCAAAGGGGSGGGGSG GGGSGGGGSACPPCPAPEFEGGPSVFLFPPKPKDTLMIS RTPEVTCVVVDVSHEDPEVKFNWYVDGVEVHNAKTKPRE EQYNSTYRVVSVLTVLHQDWLNGKEYKCKVSNKALPASI EKTISKAKGQPREPQVYTLPPCREEMTKNQVSLWCLVKG FYPSDIAVEWESNGQPENNYKTTPPVLDSDGSFFLYSKLT VDKSRWQQGNVFSCSVMHEALHNHYTQKSLSLSPGGGG GSGGGGSGGGGSGGGGSQLYSALANKCCHVGCTKRS LARFC |
| 51 | Rlx077 | SWMEEVIKLCGRELVRAQIAICGMSTWSAAAGGGGSGGG GSGGGGSGGGGSACPPCPAPEFEGGPSVFLFPPKPKDT LMISRTPEVTCVVVDVSHEDPEVKFNWYVDGVEVHNAKT KPREEQYNSTYRVVSVLTVLHQDWLNGKEYKCKVSNKA LPASIEKTISKAKGQPREPQVCTLPPSREEMTKNQVSLSC AVKGFYPSDIAVEWESNGQPENNYKTTPPVLDSDGSFFL VSKLTVDKSRWQQGNVFSCSVMHEALHNHYTQKSLSLS PGGGGSGGGGSGGGGSGGGGSSWMEEVIKLCGREL VRAQIAICGMSTWS |
| 52 | Rlx014DDdel2 aa | DKTHTCPPCPAPEFEGGPSVFLFPPKPKDTLMISRTPEVT CVVVDVSHEDPEVKFNWYVDGVEVHNAKTKPREEQYNS TYRVVSVLTVLHQDWLNGKEYKCKVSNKALPASIEKTISK AKGQPREPQVCTLPPSREEMTKNQVSLSCAVKGFYPSDI AVEWESNGQPENNYKTTPPVLDSDGSFFLVSKLTVDKSR WQQGNVFSCSVMHEALHNHYTQKSLSLSPGGGGSGG GGSGGGGSGGGGSSWMEEVIKLCGRELVRAQIAICGM ST |
| 53 | Rlx014DDdel3 aa | DKTHTCPPCPAPEFEGGPSVFLFPPKPKDTLMISRTPEVT CVVVDVSHEDPEVKFNWYVDGVEVHNAKTKPREEQYNS TYRVVSVLTVLHQDWLNGKEYKCKVSNKALPASIEKTISK AKGQPREPQVCTLPPSREEMTKNQVSLSCAVKGFYPSDI AVEWESNGQPENNYKTTPPVLDSDGSFFLVSKLTVDKSR WQQGNVFSCSVMHEALHNHYTQKSLSLSPGGGGSGG GGSGGGGSGGGGSSWMEEVIKLCGRELVRAQIAICGM S |
| 54 | R347 L | ELVLTQPASVSGSPGQSITISCTGTSSDVGGYNYVSWYQQ HPGKAPKLMIYDVSKRPSGVSNRFSGSKSGNTASLTISGQ AEDEADYYCSSYTSSSTLVFGGGTKLTVLGQPKAAPSVTL FPPSSEELQANKATLVCLISDFYPGAVTVAWKADSSPVAG VETTTPSKQSNNKYAASSYLSLTPEQWKSHRSYSCQTHE GSTVEKTVAPTECS |
| 55 | R347Rlx011DD | EVQLLESGGGLVQPGGSLRLSCTTSGFTFNTYAMSVVVRQ APGKGLEWLSGINNNGRTAFYADSVKGRFTISRDNSKNTL YLQINSLRADDTAVYFCAKDVRFIAVPGDSWGQGTLVTVS |

TABLE 1-continued

Sequence Listing.
The upper hinge region is in Italics, Relaxin A
is underlined, Relaxin B is double underlined,
the FC region is bold.

| SEQ ID NO: | Construct | Amino acid sequence |
|---|---|---|
|  |  | SASTKGPSVFPLAPSSKSTSGGTAALGCLVKDYFPEPVTV<br>SWNSGALTSGVHTFPAVLQSSGLYSLSSVVTVPSSSLGTQ<br>TYICNVNHKPSNTKVDKRVEPKS*CDKTHT*CPPCPAPEFEG<br>GPSVFLFPPKPKDTLMISRTPEVTCVVVDVSHEDPEVKFN<br>WYVDGVEVHNAKTKPREEQYNSTYRVVSVLTVLHQDWL<br>NGKEYKCKVSNKALPASIEKTISKAKGQPREPQVYTLPPC<br>REEMTKNQVSLWCLVKGFYPSDIAVEWESNGQPENNYK<br>TTPPVLDSDGSFFLYSKLTVDKSRWQQGNVFSCSVMHEA<br>LHNHYTQKSLSLSPGGGGGSGGGGSGGGGSGGGGSQ<br>LYSALANKCCHVGCTKRSLARFC |
| 56 | R347Rlx014DD | *EVQLLESGGGLVQPGGSLRLSCTTSGFTFNTYAMSWVRQ<br>APGKGLEWLSGINNNGRTAFYADSVKGRFTISRDNSKNTL<br>YLQINSLRADDTAVYFCAKDVRFIAVPGDSWGQGTLVTVS<br>SASTKGPSVFPLAPSSKSTSGGTAALGCLVKDYFPEPVTV<br>SWNSGALTSGVHTFPAVLQSSGLYSLSSVVTVPSSSLGTQ<br>TYICNVNHKPSNTKVDKRVEPKS*CDKTHT*CPPCPAPEFEG<br>GPSVFLFPPKPKDTLMISRTPEVTCVVVDVSHEDPEVKFN<br>WYVDGVEVHNAKTKPREEQYNSTYRVVSVLTVLHQDWL<br>NGKEYKCKVSNKALPASIEKTISKAKGQPREPQVCTLPPS<br>REEMTKNQVSLSCAVKGFYPSDIAVEWESNGQPENNYKT<br>TPPVLDSDGSFFLVSKLTVDKSRWQQGNVFSCSVMHEAL<br>HNHYTQKSLSLSPGGGGGSGGGGSGGGGSGGGGSS<br>WMEEVIKLCGRELVRAQIAICGMSTWS |
| 57 | RELAX0126 | *DKTHT*CPPCPAPELLGGPSVFLFPPKPKDTLMISRTPEVT<br>CVVVDVSHEDPEVKFNWYVDGVEVHNAKTKPREEQYNS<br>TYRVVSVLTVLHQDWLNGKEYKCKVSNKALPAPIEKTISK<br>AKGQPREPQVYTLPPSRDELTKNQVSLTCLVKGFYPSDIA<br>VEWESNGQPENNYKTTPPVLDSDGSFFLYSKLTVDKSRW<br>QQGNVFSCSVMHEALHNHYTQKSLSLSPGKGGSPQLYS<br>ALANKCCHVGCTKRSLARFCGGGSGGGSGSWMEEVIKL<br>CGRELVRAQIAICGMSTWS |
| 58 | RELAX0127 | *DKTHT*CPPCPAPELLGGPSVFLFPPKPKDTLMISRTPEVT<br>CVVVDVSHEDPEVKFNWYVDGVEVHNAKTKPREEQYNS<br>TYRVVSVLTVLHQDWLNGKEYKCKVSNKALPAPIEKTISK<br>AKGQPREPQVYTLPPSRDELTKNQVSLTCLVKGFYPSDIA<br>VEWESNGQPENNYKTTPPVLDSDGSFFLYSKLTVDKSRW<br>QQGNVFSCSVMHEALHNHYTQKSLSLSPGKGGSGGSPQ<br>LYSALANKCCHVGCTKRSLARFCGGGSGGGSGSWMEEVI<br>KLCGRELVRAQIAICGMSTWS |
| 59 | RELAX0128 | *DKTHT*CPPCPAPELLGGPSVFLFPPKPKDTLMISRTPEVT<br>CVVVDVSHEDPEVKFNWYVDGVEVHNAKTKPREEQYNS<br>TYRVVSVLTVLHQDWLNGKEYKCKVSNKALPAPIEKTISK<br>AKGQPREPQVYTLPPSRDELTKNQVSLTCLVKGFYPSDIA<br>VEWESNGQPENNYKTTPPVLDSDGSFFLYSKLTVDKSRW<br>QQGNVFSCSVMHEALHNHYTQKSLSLSPGKGGSGGSGG<br>SPQLYSALANKCCHVGCTKRSLARFCGGGSGGGSGSWM<br>EEVIKLCGRELVRAQIAICGMSTWS |
| 60 | Linker 01 | GGGSGGGSGG |
| 61 | Rlx052A | *DKTHT*CPPCPAPEFEGGPSVFLFPPKPKDTLMISRTPEVT<br>CVVVDVSHEDPEVKFNWYVDGVEVHNAKTKPREEQYNS<br>TYRVVSVLTVLHQDWLNGKEYKCKVSNKALPASIEKTISK<br>AKGQPREPQVYTLPPCREEMTKNQVSLWCLVKGFYPSDI<br>AVEWESNGQPENNYKTTPPVLDSDGSFFLYSKLTVDKSR<br>WQQGNVFSCSVMHEALHNHYTQKSLSLSPGGGGGSGG<br>GGSGGGGSGGGGSQLYSALANKCCHVGCTKRSLARAC |
| 62 | RELAX0013 B chain | DSWMEEVIKLCGRELVRAQIAICGMSTWS |
| 63 | RELAX0013 A chain | QLYSALANKCCHVGCTKRSLARFC |
| 64 | RELAX0014 B chain | MRVSEEWMDGFIRMCGREYARELIKICGASVGR |

TABLE 1-continued

Sequence Listing.
The upper hinge region is in Italics, Relaxin A
is underlined, Relaxin B is double underlined,
the FC region is bold.

| SEQ ID NO: | Construct | Amino acid sequence |
|---|---|---|
| 65 | RELAX0014 A chain | ESGGLMSQQCCHVGCSRRSIAKLYC |
| 66 | Rlx042R | *DKTHT*ACPPCPAPEFEGGPSVFLFPPKPKDTLMISRTPEV TCVVVDVSHEDPEVKFNWYVDGVEVHNAKTKPREEQYN STYRVVSVLTVLHQDWLNGKEYKCKVSNKALPASIEKTIS KAKGQPREPQVYTLPPCREEMTKNQVSLWCLVKGFYPS DIAVEWESNGQPENNYKTTPPVLDSDGSFFLYSKLTVDK SRWQQGNVFSCSVMHEALHNHYTQKSLSLSPGGGGGS GGGGSGGGGSGGGGSQLYSALANKCCRVGCTKRSLA RFC |
| 67 | Rlx014d | *DKTHT*ACPPCPAPEFEGGPSVFLFPPKPKDTLMISRTPEV TCVVVDVSHEDPEVKFNWYVDGVEVHNAKTKPREEQYN STYRVVSVLTVLHQDWLNGKEYKCKVSNKALPASIEKTIS KAKGQPREPQVCTLPPSREEMTKNQVSLSCAVKGFYPS DIAVEWESNGQPENNYKTTPPVLDSDGSFFLVSKLTVDK SRWQQGNVFSCSVMHEALHNHYTQKSLSLSPGGGGGS GGGGSGGGGSGGGGSSWMEEVIKLCGRELVRAQIAIC GMSTWS |
| 68 | Rlx051Y | *DKTHT*CPPCPAPEFEGGPSVFLFPPKPKDTLMISRTPEVT CVVVDVSHEDPEVKFNWYVDGVEVHNAKTKPREEQYNS TYRVVSVLTVLHQDWLNGKEYKCKVSNKALPASIEKTISK AKGQPREPQVYTLPPCREEMTKNQVSLWCLVKGFYPSDI AVEWESNGQPENNYKTTPPVLDSDGSFFLYSKLTVDKSR WQQGNVFSCSVMHEALHNHYTQKSLSLSPGGGGSGG GGSGGGGSGGGGSQLYSALANKCCHVGCTKRSLAYFC |

DETAILED DESCRIPTION

Relaxin

The present invention is based, at least in part, on the finding that heterodimeric fusions described herein may exhibit Relaxin activity when the Relaxin A chain and the Relaxin B chain are not covalently linked to each other through an amino acid linker. This is surprising based on the disclosures of WO 2013/004607 and WO 2018/138170, which describe recombinant Relaxin in which the Relaxin A and Relaxin B are fused in a single chain. The present inventors have further found that heterodimerisation of the heterodimerisation domains induces correct folding and heterodimerisation of the Relaxin A and Relaxin B chains (see Example 2). In addition, unlike wild-type Relaxin proteins, the fusion polypeptides of the invention do not require endoproteolytic processing for biological activity.

As used herein, the term "heterodimeric fusion" refers to a heterodimer of fusion polypeptides, wherein one fusion polypeptide comprises a first heterodimerisation domain connected to a first subunit of a heterodimeric protein (e.g. Relaxin A chain), and the other fusion polypeptide comprises a second heterodimerisation domain connected to a second subunit of a heterodimeric protein (e.g. Relaxin B chain).

The heterodimeric fusions of the present invention may comprise Relaxin A and B chain polypeptides from the group of Relaxins selected from Relaxin-1, Relaxin-2 and Relaxin-3. In preferred embodiments, the Relaxin A chain polypeptide of the invention is a Relaxin-2 A chain polypeptide or a variant thereof; and the Relaxin B chain polypeptide of the invention a Relaxin-2 B chain polypeptide or a variant thereof. In particular embodiments, the Relaxin A chain polypeptide comprises a human Relaxin-2 A chain polypeptide or a variant thereof and a human Relaxin-2 B chain polypeptide or a variant thereof.

The terms "chain", "polypeptide" and "peptide" may be used interchangeably herein to refer to a chain of two or more amino acids linked through peptide bonds.

In some embodiments, the Relaxin-2 A chain polypeptide has the sequence as set forth in SEQ ID NO: 1 or a variant thereof and the Relaxin-2 B chain polypeptide has the sequence as set forth in SEQ ID NO: 2 or a variant thereof. Variants may comprise one or more amino acid substitutions, deletions and/or insertions. In some embodiments, the Relaxin-2 A chain polypeptide comprises one or more amino acid mutations selected from K9E, K9H, K9L, K9M, R18E, R18H, R22A, R22I, R22M, R22Q, R22S, R22Y, F23E, F23A and F23I. In a preferred embodiment Relaxin-2 A chain comprises the amino acid mutation K9H.

Relaxin A and B chain variants are known in the art. In addition, guidance on the design of Relaxin A and B chain variants is available to the skilled person. For example, it will be understood that variants may retain those amino acids that are required for Relaxin function. For example, Relaxin-2 B chain variants may comprise the conserved motif Arg-X-X-X-Arg-X-X-Ile (Claasz A A et al. (2002) *Eur. J. Biochem.* 269(24): 6287-6293) or Arg-X-X-X-Arg-X-X-Val (Bathgate R A et al. (2013) *Physiol Rev.* 93(1): 405-480). Variants may comprise one or more amino acid substitutions and/or insertions. For example, Relaxin-2 B chain variants may have one or more additional amino acids for example K30 and R31 and N-terminal V-2, A-1 and M-1 compared to SEQ ID NO: 62. Alternatively or in addition, variants may comprise one or more amino acid derivatives. For example, the first amino acid of Relaxin-2 B chain variants may be pyroglutamate.

In preferred embodiments, the Relaxin A chain and the Relaxin B chain are covalently bound by two inter-chain disulphide bonds (see Example 2).

The Relaxin family of peptides mediate their biological effects, at least in part, through the activation of G protein-coupled receptors (GPCRs), and the subsequent stimulation or inhibition of the cAMP signaling pathway by the Gs or Gi protein subunit, respectively. Relaxin-2 is known to activate the GPCR RXFP1 (also known as LGR7) and, to a lesser degree, the GPCR RXFP2 (also known as LGR8), thus stimulating the Gs-cAMP-dependent signaling pathway, leading to an increase in the second messenger molecule cAMP.

As used herein, the term "Relaxin activity" refers to the ability of a Relaxin molecule to bind to a Relaxin receptor, and/or activate said Relaxin receptor and/or initiate a signaling cascade inside the cell. In embodiments in which the Relaxin activity is Relaxin-2 activity, Relaxin activity may refer to the ability to bind and/or activate the receptor RXFP1 and/or RXFP2. The term "Relaxin activity" may be used interchangeably with "biological activity".

Relaxin activity may be determined by measuring binding of a Relaxin molecule to a Relaxin receptor, and/or by measuring downstream events from binding to a Relaxin receptor.

Relaxin activity may be determined in vitro and/or in vivo. In some embodiments, Relaxin activity is determined in vitro.

Relaxin activity may be determined by measuring the amount and/or presence of a molecule downstream from Relaxin activation of a receptor. For example, Relaxin activity may be determined by measuring cAMP production following Relaxin activation of a receptor. Methods for the detection of Relaxin-induced cAMP generation are known in the art. Such methods include cAMP ELISA, HTRF cAMP assays and the HitHunter® cAMP assay. In some embodiments, Relaxin activity is determined by measuring Relaxin-induced cAMP production by HTRF cAMP assay, e.g. as performed in Example 3. Relaxin activity may also be determined by measuring nitric oxide (NO) production following Relaxin activation of a receptor. Relaxin activity may also be determined by measuring the activation of a molecule downstream from Relaxin activation of a receptor. For example, Relaxin activity may be determined by measuring activation of p42/44 MAPK.

Alternatively or in addition, Relaxin activity may be determined by measuring the activation of a known Relaxin target gene. For example, Relaxin activity may be determined by measuring the activation of the transcription of the known Relaxin target gene, VEGF, in THP-1 cells. Methods to determine activation of transcription of a gene are known in the art and include quantitative PCR analysis of the mRNA. The relative expression of VEGF mRNA can be measured by quantitative real-time PCR induction of VEGF transcripts following incubation of THP-1 cells with Relaxin as described in Xiao et al. (2013) *Nat Commun.* 4: 1953.

Alternatively or in addition, Relaxin activity may be determined by measuring one or more downstream effects of Relaxin. For example, reduction of cardiac hypertrophy can be measured by echocardiography, left ventricular weight relative to body weight and/or tibia length according to standard methods. In another example, Relaxin activity may be determined by measuring fibrosis reduction by Masson's Trichrome stain. In another example, Relaxin activity may be determined by measuring modulation of connective tissue metabolism, such as the inhibition of profibrotic factors (such as TGF-beta), inhibition of fibroblast proliferation and differentiation, and/or activation of MMP-mediated extracellular matrix degradation (Bathgate R A et al. (2013) *Physiol Rev.* 93(1): 405-480).

In some embodiments, Relaxin activity is determined by measuring reversal of isoproterenol-induced cardiac hypertrophy (measured as heart weight relative to tibial length) and fibrosis (measured as collagen content relative to heart weight), e.g. as performed in Example 7.

The activity of the heterodimeric fusions of the invention may be determined in relation to a reference Relaxin protein. In some embodiments, the reference Relaxin protein is a recombinant protein. In preferred embodiments, the reference Relaxin protein is a Relaxin protein having the Relaxin A chain and Relaxin B chain array of a mature Relaxin protein. Recombinant Relaxins having the Relaxin A chain and Relaxin B chain array of a mature Relaxin protein are commercially available. For example, recombinant human Relaxin-2, murine Relaxin-1 and INSL3 are available from R&D systems (catalogue numbers 6586-RN, 6637-RN and 4544-NS, respectively).

In some embodiments, the reference Relaxin protein has the same Relaxin A and B chains as the heterodimeric fusion of the invention or differs from the Relaxin A and B chains of the heterodimeric fusion of the invention by up to 10 amino acids, for example 1 or 2 amino acids. In some embodiments, the first amino acid of the B chain of the reference Relaxin-2 is D and this amino acid is deleted in the Relaxin B chain of the heterodimeric fusion of the invention.

The reference Relaxin protein may be selected from:
(i) recombinant human Relaxin-2 (referred to herein as RELAX0013); and
(ii) recombinant murine Relaxin-1 (referred to herein as RELAX0014); and
(iii) recombinant Fc-fused Relaxin-2 in which the Relaxin A and Relaxin B are fused in a single chain, and wherein Fc is a half-life extending Fc region (referred to herein as RELAX0010 and described in WO2018/138170); and
(iv) recombinant Fc-fused Relaxin-2 in which the Relaxin A and Relaxin B are fused in a single chain, and wherein Fc is a half-life extending Fc region (referred to herein as RELAX0009 and described in WO2018/138170); and
(v) recombinant Fc-fused Relaxin-2 in which the Relaxin A and Relaxin B are fused in a single chain (referred to herein as RELAX0126 and described in WO 2013/004607); and
(vi) recombinant Fc-fused Relaxin-2 in which the Relaxin A and Relaxin B are fused in a single chain (referred to herein as RELAX0127 and described in WO 2013/004607); and
(vii) recombinant Fc-fused Relaxin in which the Relaxin A and Relaxin B are fused in a single chain (referred to herein as RELAX0128 and described in WO 2013/004607).

In particularly preferred embodiments, the reference Relaxin protein is a Relaxin-2 protein having the Relaxin-2 chain A and Relaxin-2 B chain array of a mature Relaxin-2 protein as disclosed under UniProtKB/Swiss-Prot Accession Number P04090.1.

The heterodimeric fusions of the invention may be considered to have Relaxin activity if they show at least a proportion of the activity of a reference Relaxin protein. For example, a fusion polypeptide may be considered to have Relaxin activity if it has at least about half of the activity of a reference Relaxin protein. A heterodimeric fusion of the invention may be considered to have Relaxin activity if the ratio of the activity of said fusion polypeptide over the activity of a reference Relaxin protein is between about $10^{-5}$ and about 1, between about $10^{-4}$ and about 1, between about $10^{-3}$ and about 1, between about $10^{-2}$ and about 1, between about 1/50 and about 1, between about 1/20 and about 1, between about 1/15 and about 1, between about 1/10 and about 1, between about 1/5 and about 1, or between about 1/2 and about 1. Alternatively, a heterodimeric fusion of the invention may be considered to have Relaxin activity if the ratio of the activity of said fusion polypeptide over the activity of a reference Relaxin protein is between about 1 and about $10^5$, between about 1 and about $10^4$, between about 1 and about $10^3$, between about 1 about 100, between about 1 and about 50, between about 1 and about 20, between about 1 and about 15, between about 1 and about 10, between about 1 and about 5, or between about 1 and about 2.

In some embodiments, the Relaxin activity of the heterodimeric fusion over the Relaxin activity of a reference Relaxin protein is between about 0.001 and about 10.

Relaxin activity may be determined as an EC50 value. As used herein the term "EC50" (half maximal effective concentration) refers to the effective concentration of a therapeutic compound which induces a response halfway between the baseline and maximum after a specified exposure time.

Heterodimerisation Domains

The heterodimeric fusions of the invention comprise a first heterodimerisation domain and a second heterodimerisation domain. In preferred embodiments, the first and second heterodimerisation domains are derived from an immunoglobulin Fc region.

The term "Fc region" defines the C-terminal region of an immunoglobulin heavy chain, which may be generated by papain digestion of an intact antibody. The Fc region of an immunoglobulin generally comprises two constant domains, a CH2 domain and a CH3 domain, and optionally comprises a CH4 domain.

The first and second Fc regions may comprise the immunoglobulin domains CH2 and/or CH3. In preferred embodiments, the first and second Fc regions comprise the immunoglobulin domains CH2 and CH3.

The Fc region may be derived from an immunoglobulin (e.g. IgG) from any species, preferably human (e.g. human IgG). In embodiments in which the Fc region is derived from IgG, the Fc region may be derived from an IgG of any subclass (e.g. IgG1, IgG2, IgG3, IgG4), preferably IgG1. Preferably, the first and second Fc regions are derived from a human IgG1 immunoglobulin. In other embodiments, the first and second Fc regions are derived from a human IgG4 immunoglobulin.

In preferred embodiments, the first and second Fc regions comprise heterodimerisation-promoting amino acid mutations and/or modifications. Such modifications may include the introduction of asymmetric complementary modifications into each of the first and second Fc regions, such that both chains are compatible with each other and thus able to form a heterodimer, but each chain is not able to dimerize with itself. Such modifications may encompass insertions, deletions, conservative and non-conservative substitutions and rearrangements. Incorporating such modifications provides a method for increasing the yield of heterodimers produced by recombinant cell culture over other unwanted end-products such as homodimers.

The first and second Fc regions may comprise any heterodimerisation-promoting amino acid mutations and/or modifications known in the art. A combination of modifications may be used to maximise the efficiency of assembly while minimising the impact on antibody stability.

In the "knob in hole" method, heterodimerisation may be promoted by the introduction of steric hindrance between contacting residues. A "protrusion' is generated by replacing one or more small amino acid side chains from the interface of one Fc region ("Fc Knob") with larger side chains (e.g. tyrosine or tryptophan). Compensatory "cavities" of identical or similar size to the large side chain(s) are created on the interface of the other Fc region ("Fc Hole") by replacing amino acid having large side chains with amino acids having smaller ones (e.g. alanine or valine). "Knob-in-holes" modifications are described in detail e.g. Ridgway J B et al. (1996) *Protein Eng.* 9(7) 617-621; Merchant A M et al. (1998) *Nat. Biotechnol.* 16(7): 677-681.

Other modifications which may be used to generate heterodimers include but are not limited to those which create favourable electrostatic interactions between the two Fc regions. For example, one or more positively charged amino acids may be introduced into one Fc region, and one or more negatively charged amino acids may be introduced into a corresponding position in the other Fc region. Alternatively or in addition, the Fc regions may be modified to include mutations that introduce cysteine residues capable of forming a disulphide bond. Alternatively or in addition, the Fc regions may comprise one or more modification(s) to the hydrophilic and hydrophobic residues at the interface between chains, in order make heterodimer formation more entropically and enthalpically favourable than homodimer formation.

Thus, in some embodiments, the heterodimerisation-promoting amino acid mutations and/or modifications create steric hindrance between contacting residues (e.g. by "knob-in-hole"), create favourable electrostatic interactions between the two Fc regions, introduce cysteine residues capable of forming a disulphide bond and/or modify the hydrophilic and hydrophobic residues at the interface between the two Fc regions.

In preferred embodiments, the heterodimerisation-promoting amino acid mutations are "Fc Knob" and "Fc Hole" mutations. In preferred embodiments, the "Fc Knob" and "Fc Hole" mutations are present in the CH3 domains.

In some embodiments, the first and second Fc regions are derived from a human IgG1 immunoglobulin and comprise "Fc X" and "Fc Y" with mutations in the CH3 domains, wherein the "Fc X" and "Fc Y" mutations are selected from the combinations set forth in Table 2 (or conservative substitutions thereof).

TABLE 2

"FcX" and "Fc Y" mutations

| Combination No. | Fc X mutation(s)* | Fc Y mutation(s)* |
|---|---|---|
| 1 | D399C | K392C |
| 2 | D399S | K392S |
| 3 | Y349C | S354C |
| 4 | Y349C | E356C |
| 5 | Y349C | E357C |
| 6 | L351C | S354C |
| 7 | T394C | V397C |
| 8 | T366W | T366S: L368A: Y407V |
| 9 | T366W: D399C | T366S: L368A: K392C: Y407V |
| 10 | T366W: K392C | T366S: 0099C: L368A: Y407V |
| 11 | S354C: T366W | Y349C: T366S: L368A: Y407V |

TABLE 2-continued

"FcX" and "Fc Y" mutations

| Combination No. | Fc X mutation(s)* | Fc Y mutation(s)* |
|---|---|---|
| 12 | Y349C: T366W | S354C: T366S: L368A: Y407V |
| 13 | E356C: T366W | Y349C: T366S: L368A: Y407V |
| 14 | Y349C: T366W | E356C: T366S: L368A: Y41J7V |
| 15 | E357C: T366W | Y349C: T366S: L368A: Y407V |
| 16 | Y349C: T366W | E357C: T366S: L368A: Y407V |
| 17 | S364H/F405A | Y349T/T394F |
| 18 | T350V/L351Y/F405A/Y407V | T350V/T366L/K392L/T394W |
| 19 | K360D/D399M/Y407A | E345R/Q347R/T366V/K409V |
| 20 | K409D/K392D | D399K/E356K |
| 21 | K360E/K409W | Q347R/D399V/F405T |
| 22 | K360E/K409W/Y349C | Q347R/D399V/F405T/S354C |
| 23 | K370E/K409W | E357N/D399V/F405T |
| 24 | T366Y | Y407T |

*wherein the amino acid numbering is according to the EU index as in Kabat.

In preferred embodiments the "Fc Y" is the "Fc Hole" with mutations Y349C, T366S, L368A and Y407V, or conservative substitutions thereof, and the "Fc X" is the "Fc Knob" with mutations S354C and T366W, or conservative substitutions thereof, wherein the amino acid numbering is according to the EU index as in Kabat.

The term "EU index as in Kabat" refers to the numbering system of the human IgG1 EU antibody described in Kabat E A et al. (1991) Sequences of Proteins of Immunological Interest, 5th ed. Public Health Service. National Institutes of Health. Bethesda, Md. All amino acid positions referenced in the present application refer to EU index positions.

In some embodiments, the first Fc region has "Fc Hole" mutations, and the second Fc region has "Fc Knob" mutations. In alternative and preferred embodiments, the first Fc region has "Fc Knob" mutations, and the second Fc region has "Fc Hole" mutations.

It will be understood that the Fc regions may further comprise other amino acid modifications relative to a wild-type Fc region. The Fc region may be modified to e.g. increase the affinity of the IgG molecule for the FcRn. WO 02/060919 discloses modified immunoglobulins comprising an Fc region having one or more amino acid modifications and is incorporated herein in its entirety by reference. Methods of making Fc regions with one or more amino acid modifications are known in the art.

In some embodiments, the first and/or second Fc region may comprise one or more amino acid modifications to reduce or abolish the effector function of the Fc region. In some embodiments, the amino acid modifications reduce or circumvent cytotoxicity, for example antibody-dependent cell-mediated cytotoxicity (ADCC) and complement-dependent cytotoxicity (CDC).

In some embodiments, the first and/or second Fc region may comprise one or more amino acid modifications to increase the half-life of the heterodimeric fusion.

In some embodiments, the first and/or second Fc region comprises at least one of the following combinations of amino acid mutations:

(i) M252Y, S254T and T256E, or conservative substitutions thereof;
(ii) L234F, L235Q and K322Q, or conservative substitutions thereof;
(iii) L234F, L235E and P331S, or conservative substitutions thereof;
(iv) M252Y, S254T, T256E, L234F, L235Q and K322Q, or conservative substitutions thereof; or
(v) M252Y, S254T, T256E, L234F, L235E and P331S, or conservative substitutions thereof, wherein the amino acid numbering is according to the EU index as in Kabat.

In some embodiments, the first and/or second Fc region may comprise the amino acid mutations L234F, L235E and P331S, or conservative substitutions thereof, wherein the amino acid numbering is according to the EU index as in Kabat.

In some embodiments, the Fc region comprising "Fc Hole" mutations has the sequence set forth in SEQ ID NO: 3 or variants thereof, and the Fc region comprising "Fc Knob" mutations has the sequence set forth in SEQ ID NO:4 or variants thereof.

In some embodiments, the Fc regions comprise a SEQ ID NO: 3 variant having the amino acid mutation Y349C reverted to Y349 and a SEQ ID NO: 4 variant having the amino acid mutation S354C reverted to S354, such that the Fc regions are unable to form a stabilising disulphide bond.

In some embodiments, the Fc regions comprise a SEQ ID NO: 3 variant and/or SEQ ID NO: 4 variant, wherein the first five residues DKTHTCPPC (SEQ ID NO: 69) are modified. In some embodiments, this region is replaced with the sequence DKTHTACPPC SEQ ID NO: 70). In alternative embodiments, this region is replaced with the sequence GGAGGACPPC (SEQ ID NO: 71). In alternative embodiments, this region is replaced with the sequence ACPPC (SEQ ID NO: 72).

In alternative embodiments, the first and second heterodimerisation domains are derived from an immunoglobulin Fab region. In some embodiments, the heterodimerisation domains comprise CH1 and CL regions. It has been found that Fab regions comprising L and Fd chains mediate efficient heterodimerisation (Schoonjans R et al. (2000) J. Immunol. 165 (12): 7050-7057). Thus, in alternative embodiments, the heterodimerisation domains comprise L and Fd chains. In some embodiments, the L and Fd chains heterodimerise to form a disulphide-bridge stabilised heterodimer.

In yet further alternative embodiments, the first and second heterodimerisation domains heterodimerise to form parallel coiled coils. Heterodimeric coiled coils are described e.g. in Aronsson et al. (2015) Sci. Rep. 5: 14063. In some embodiments, the heterodimerisation domains comprise amino acid mutations and/or modifications to prevent formation of undesired folded assemblies and/or to promote formation of parallel coiled coils.

The first and second heterodimerisation domains (e.g. first and second Fc regions) may form a half-life extending moiety. Thus, in some embodiments the heterodimeric fusions of the invention have an extended half-life compared to a reference Relaxin.

As used herein, the term "half-life" is used to refer to the time taken for the concentration of fusion protein in plasma to decline to 50% of its original level. The "half-life" of a protein in plasma may depend on different factors such as the size of the protein, its stability, its clearance rate, turnover rate, in vivo proteolytic degradation, the rate of absorption by the body or specific tissues, etc. Methods to determine the half-life of proteins are known in the art and are described in the Examples below.

The inventors have shown that heterodimeric fusions of the invention having first and second heterodimerisation domains derived from an immunoglobulin Fc have a half-life of at least 5 hours in mouse models (see Example 6). In comparison, the half-life of human Relaxin-2 following IV administration is about 0.09+/−0.04 hours, i.e. 5.4+/−2.4 minutes in humans (Chen S A et al. (1993) *Pharm. Res.* 10(6): 834-838).

It will be recognised that an extended half-life is advantageous, as it permits the therapeutic proteins to be administered according to a safe and convenient dosing schedule, e.g. lower doses that can be administered less frequently. Moreover, the achievement of lower doses may provide further advantages such as the provision of an improved safety profile and/or the activation of multiple mechanisms of action in vivo.

Connectors

One or both of the Relaxin A and B chains may be connected to their respective heterodimerisation domains by a connector polypeptide. In some embodiments, the Relaxin A chain is connected to the first heterodimerisation domain (e.g. first Fc region) via a connector polypeptide, and the Relaxin B chain is connected to the second heterodimerisation domain (e.g. second Fc region) via a connector polypeptide.

The connector polypeptide may be any suitable length, for example between about 6 and 40 amino acids in length, preferably between about 6 and 21 amino acids in length. In some embodiments, the connector polypeptide is at least 6 amino acid residues in length, preferably at least 11 amino acids in length, preferably at least 16 amino acids in length. In some embodiments, the connector polypeptide is less than 40 amino acids in length. Connector polypeptides of different or the same lengths can be used for each arm of the heterodimeric fusions of the invention. In some embodiments, at least one connector polypeptide has a length of 21 amino acids. In preferred embodiments, both connector polypeptides have a length of 21 amino acids. The connector polypeptides can have any amino acid sequence. Connector polypeptides of different or the same amino acid compositions can be used for each arm of the heterodimeric fusions of the invention.

In some embodiments, one or preferably both connector polypeptides comprise proline and alanine repeats (PA)x (SEQ ID NO: 73), preferably wherein x is of between 3 and 15, preferably wherein the connector polypeptide has a length greater than 16 amino acids, preferably wherein the connector polypeptide is composed of the 21 amino acid sequence PAPAPAPAPAPAPAPAPAPAG (SEQ ID NO: 6).

In some embodiments, one or preferably both connector polypeptides comprise glycine and serine repeats such as those described in Chen X et al. (2013) *Adv. Drug. Deliv. Rev.* 65(10): 1357-1369. In some embodiments, one or both connector polypeptides comprise the motif (GGGGS)n (SEQ ID NO: 74), wherein n may be between 1 and 8, for instance wherein n is 4. In some embodiments, one or more connector polypeptide is composed of the 21 amino acid sequence GGGGSGGGGSGGGGSGGGGGS (SEQ ID NO: 5). In certain embodiments, both connector polypeptides are composed of the 21 amino acid sequence GGGGSGGGGSGGGGSGGGGGS (SEQ ID NO: 5).

In some embodiments, one connector polypeptide comprises proline and alanine repeats as described herein, and the other connector polypeptide comprises glycine and serine repeats as described herein.

Alternatively, one or both of the Relaxin A and B chains may be connected to their respective heterodimerisation domains by a synthetic connector polypeptide, such as a polyethylene glycol (PEG) polymer chain. Thus, the Relaxin A chain may be connected to the first heterodimerisation domain (e.g. first Fc region) via a synthetic connector, such as a polyethylene glycol (PEG) polymer chain, and the Relaxin B chain may be connected to the second heterodimerisation domain (e.g. second Fc region) via a synthetic connector, such as a polyethylene glycol (PEG) polymer chain, wherein the synthetic connector may be covalently or non-covalently attached to the heterodimerisation domain (e.g. Fc region). PEGylation, that is the process of attaching PEG polymer chains to a molecule, can be carried out according to methods known in the art.

Stability

The present inventors have shown that heterodimeric fusions of the invention have unexpected superior physical and chemical stability. Thus, in some embodiments the heterodimeric fusions of the invention have superior physical and/or chemical stability compared to a reference Relaxin protein.

Physical stability of Relaxin may be determined by measuring purity and aggregation, for example by HP-SEC as in Example 9. Chemical stability of Relaxin may be determined by measuring fragmentation and modification of the molecule, for example by LC-MS as in Example 9.

Surprisingly, the present inventors have shown that heterodimeric fusions of the invention have superior physical and chemical stability compared to recombinant Fc-fused Relaxin in which the Relaxin A and Relaxin B are fused in a single chain (as opposed to Relaxin A and B in separate fusion polypeptides). WO 2013/004607 describes recombinant single chain Relaxin fusion polypeptides fused to an immunoglobulin Fc region, for example the fusion polypeptides referred to herein as RELAX0127 and RELAX0128. Thus, in some embodiments, the heterodimeric fusions of the invention have superior physical and/or chemical stability compared to RELAX0127 and RELAX0128.

The heterodimeric fusion may comprise a half-life extending moiety in addition to the first and second heterodimerisation domains. In some embodiments, the half-life extending moiety is a proteinaceous half-life extending moiety. The proteinaceous half-life extending moiety may be selected from the group consisting of an Fc region of an immunoglobulin, albumin-binding domain and serum albumin. In further embodiments, the half-life extending moiety is a chemical entity that is not a protein or peptide, such as a polyethylene glycol (PEG) polymer chain.

The half-life extending moiety may be attached at the N-terminus or the C-terminus of the first or second heterodimerisation domain. In some embodiments, the half-life extending moiety is attached at the N-terminus of the first or second heterodimerisation domain. In other embodiments, the half-life extending moiety is attached at the C-terminus of the first or second heterodimerisation domain. Methods for attaching the half-life extending moiety to the heterodimeric fusion are known in the art. For example, the half-life extending moiety may be attached by chemical conjugation or recombinant technology. The half-life extending moiety may be attached to the heterodimeric fusion directly or through a connector (e.g. connector polypeptide). The use of a connector polypeptide may be particularly appropriate when the fusion polypeptide comprises a proteinaceous half-life extending moiety such as an Fc region.

Exemplary Embodiments

The heterodimeric fusions of the invention may have a variety of formats and/or sequences.

The term "fusion polypeptide of the invention" and "fusion polypeptides of the invention" may be used to refer to the first heterodimerisation domain fused to a Relaxin A chain, and/or the second heterodimerisation domain fused to a Relaxin B chain. The fusion polypeptides of the invention may be recombinant fusion polypeptides, i.e. which have been created by recombinant DNA technology.

In preferred embodiments, the C-terminus of the first heterodimerisation domain (e.g. first Fc region) is connected to the N-terminus of the Relaxin A chain and the C-terminus of the second heterodimerisation domain (e.g. second Fc region) is connected to the N-terminus of the Relaxin B chain. In some embodiments, the Relaxin A chain polypeptide and/or the Relaxin B chain polypeptide have a free C-terminus.

In alternative embodiments, the N-terminus of the first heterodimerisation domain (e.g. first Fc region) is connected to the C-terminus of the Relaxin A chain and the N-terminus of the second heterodimerisation domain (e.g. second Fc region) is connected to the C-terminus of the Relaxin B chain. In some embodiments, the Relaxin A chain polypeptide and/or the Relaxin B chain polypeptide have a free N-terminus.

The heterodimeric fusion of the invention may further comprise one or more Fabs. In some embodiments, the heterodimeric fusion comprises one Fab linked to the N-terminus of the first heterodimerisation domain (e.g. first Fc region) and a second Fab linked to the N-terminus of the second heterodimerisation domain (e.g. second Fc region).

The heterodimeric fusion of the invention may further comprise a second Relaxin A chain polypeptide or variant thereof and a second Relaxin B chain polypeptide or variant thereof. In some embodiments, the second Relaxin A chain polypeptide or variant thereof is connected to the N-terminus of the first heterodimerisation domain (e.g. first Fc region) and the second Relaxin B chain polypeptide or variant thereof is connected to the N-terminus of the second heterodimerisation domain (e.g. second Fc region), optionally wherein the second Relaxin A chain is connected to the first heterodimerisation domain (e.g. first Fc region) via a connector (e.g. connector polypeptide) and the second Relaxin B chain is connected to the second heterodimerisation domain (e.g. second Fc region) via a connector (e.g. connector polypeptide).

Thus, in some embodiments, the format of the heterodimeric fusion is selected from:
(i) FcX-con-A/FcY-con-B (e.g. see FIG. 1);
(ii) FcX-con-B/FcY-con-A (e.g. see FIG. 1);
(iii) A-con-FcX/B-con-FcY (e.g. see FIG. 1);
(iv) B-con-FcX/A-con-FcY (e.g. see FIG. 1);
(v) Fab-FcX-con-A/Fab-FcY-con-B (e.g. see FIG. 1);
(vi) Fab-FcX-con-B/Fab-FcY-con-A;
(vii) A-con-FcX-con-A/B-con-FcY-con-B (e.g. see FIG. 1);
(ix) B-con-FcX-con-B/A-con-FcY-con-A;
(ix) FcX-con-B-L-A, and FcY, optionally FcY-con-B-L-A (e.g. see FIG. 1);
(x) FcY-con-B-L-A, and FcX, optionally FcX-con-B-L-A;
(xi) FcX-con-A-L-B, and FcY, optionally FcY-con-A-L-B; and
(xii) FcY-con-A-L-B, and FcX, optionally FcX-con-A-L-B, wherein:
FcY is an immunoglobulin Fc region with "Fc Hole" amino acid mutations and/or modifications, preferably comprising a CH3 domain having the amino acid mutations Y349C:T366S:L368A:Y407V, or conservative substitutions thereof;
FcX is an Fc region with "Fc Knob" amino acid mutations and/or modifications, preferably comprising a CH3 domain having the amino acid mutations S3540:T366W, or conservative substitutions thereof;
"con" is a connector polypeptide;
B is a Relaxin B chain or a variant thereof;
A is a Relaxin A chain or a variant thereof; and
L is a linker polypeptide, preferably with the amino acid sequence GGGSGGGSGG (SEQ ID NO: 60).

In another aspect, the invention provides a heterodimeric fusion comprising
(i) X-B-L-A and Y, optionally Y-B-L-A; or
(ii) Y-B-L-A and X, optionally X-B-L-A,
wherein:
X and Y are heterodimerisation domains as described herein;
B is a Relaxin B chain or a variant thereof, e.g. a Relaxin-2 B chain or variant thereof;
A is a Relaxin A chain or a variant thereof, e.g. a Relaxin-2 A chain or variant thereof; and
L is a linker polypeptide, preferably with the amino acid sequence GGGSGGGSGG (SEQ ID NO: 60),
wherein X heterodimerises with Y, and wherein the heterodimeric fusion has Relaxin activity.

In yet another aspect, the invention provides a heterodimeric fusion comprising
(i) X-A-L-B and Y, optionally Y-A-L-B or
(ii) Y-A-L-B and X, optionally X-A-L-B,
wherein:
X and Y are heterodimerisation domains as described herein;
A is a Relaxin A chain or a variant thereof, e.g. a Relaxin-2 A chain or variant thereof;
B is a Relaxin B chain or a variant thereof, e.g. a Relaxin-2 B chain or variant thereof; and
L is a linker polypeptide, preferably with the amino acid sequence GGGSGGGSGG (SEQ ID NO: 60),
wherein X heterodimerises with Y, and wherein the heterodimeric fusion has Relaxin activity.

In particularly preferred embodiments, the heterodimeric fusion comprises the fusion polypeptides RIx011DD as set forth in SEQ ID NO: 11 and RIx014DD as set forth in SEQ ID NO: 20. In alternative preferred embodiments, the heterodimeric fusion comprises the fusion polypeptides RIx013DD as set forth in SEQ ID NO: 17 and RIx012DD as set forth in SEQ ID NO: 14.

In an aspect of the invention, there is provided heterodimeric fusions comprising a fusion polypeptide combination selected from the FcX and FcY combinations set forth in Table 3.

TABLE 3

Fusion polypeptide combinations in heterodimeric fusions of the invention

| Heterodimeric Fusion | FcX (knob) fusion polypeptide* | FcY (hole) fusion polypeptide* |
| --- | --- | --- |
| RELAX0019 | RIx011 | RIx014 |
| RELAX0020 | RIx013 | RIx012 |
| RELAX0021 | RIx011b | RIx014b |

TABLE 3-continued

Fusion polypeptide combinations in heterodimeric fusions of the invention

| Heterodimeric Fusion | FcX (knob) fusion polypeptide* | FcY (hole) fusion polypeptide* |
|---|---|---|
| RELAX0022 | Rlx12b | Rlx13b |
| RELAX0023 | Rlx011DD | Rlx014DD |
| RELAX0024 | Rlx013DD | Rlx012DD |
| RELAX0034 | Rlx041H | Rlx014d |
| RELAX0039 | Rlx041M | Rlx014DD |
| RELAX0040 | Rlx041L | Rlx014DD |
| RELAX0041 | Rlx041H | Rlx014DD |
| RELAX0043 | Rlx041E | Rlx014DD |
| RELAX0046 | Rlx042R | Rlx014DD |
| RELAX0052 | Rlx044E | Rlx014DD |
| RELAX0053 | Rlx044H | Rlx014DD |
| RELAX0054 | Rlx028 | Rlx029 |
| RELAX0055 | Rlx030 | Rlx031 |
| RELAX0056 | Rlx026 | Rlx027 |
| RELAX0063 | Rlx052A | Rlx014DD |
| RELAX0069 | Rlx051M | Rlx014DD |
| RELAX0070 | Rlx051I | Rlx014DD |
| RELAX0071 | Rlx051Q | Rlx014DD |
| RELAX0072 | Rlx051A | Rlx014DD |
| RELAX0073 | Rlx051Y | Rlx014DD |
| RELAX0074 | Rlx051S | Rlx014DD |
| RELAX0075 | Rlx052I | Rlx014DD |
| RELAX0076 | Rlx052E | Rlx014DD |
| RELAX0081 | Rlx020 | Rlx021 |
| RELAX0082 | Rlx022 | Rlx023 |
| RELAX0083 | Rlx024 | Rlx025 |
| RELAX0084 | Rlx026 | Rlx014DD |
| RELAX0085 | Rlx011DD | Rlx027 |
| RELAX0086 | Rlx020 | Rlx014DD |
| RELAX0087 | Rlx011DD | Rlx021 |
| RELAX0088 | Rlx055 | FcH01 |
| RELAX0091 | Rlx062K | Rlx061H |
| RELAX0105 | Rlx020 | Rlx027 |
| RELAX0106 | Rlx022 | Rlx027 |
| RELAX0107 | Rlx024 | Rlx027 |
| RELAX0109 | Rlx020 | Rlx029 |
| RELAX0110 | Rlx022 | Rlx029 |
| RELAX0111 | Rlx024 | Rlx029 |
| RELAX0117 | Rlx076 | Rlx077 |
| RELAX0122 | Rlx055 | Rlx056 |
| RELAX0123 | Rlx011DD | Rlx014DDdel2aa |
| RELAX0124 | Rlx011DD | Rlx014DDdel3aa |
| RELAX0130** | R347Rlx011DD | R347Rlx014DD |

*The sequences of the fusion polypeptides listed are set forth in Table 1.
**In this particular embodiment the heterodimeric fusion is an IgG and comprises an additional polypeptide corresponding to the Light Chain set forth in SEQ ID NO: 54

In an aspect, there is provided a heterodimeric fusion comprising the fusion polypeptides set forth in SEQ ID NO: 11 and SEQ ID NO: 20.

In an alternative aspect, there is provided a heterodimeric fusion comprising the fusion polypeptides set forth in SEQ ID NO: 17 and SEQ ID NO: 14.

The fusion polypeptides of the invention may be produced by any method known in the art. In some embodiments, the fusion polypeptides of the invention are produced by recombinant expression of a nucleic acid molecule encoding a fusion polypeptide in a host cell.

Methods that are known to those skilled in the art can be used to construct expression vectors containing the nucleic acid molecules of the invention. Suitable vectors include, for example, plasmids, phagemids, phages or viral vectors.

Vectors containing the nucleic acid molecules of the invention may be transferred to a host cell by conventional techniques. Suitable host cells are known in the art. In some embodiments, the host cells are mammalian cells such as HEK293 cells or CHO cells.

The transfected cells may be cultured by conventional techniques to produce the fusion polypeptides of the invention.

Once a fusion polypeptide of the invention has been produced, for example by recombinant expression, it may be purified by any method known in the art. Exemplary protein purification techniques include chromatography (e.g. ion exchange, affinity and/or sizing column chromatography), centrifugation and differential solubility. The present invention provides isolated fusion polypeptides that have been separated from the cell culture, optionally by at least one purification step.

Therapeutic Methods

The fusion polypeptides of the invention may be provided in a pharmaceutical composition.

The pharmaceutical compositions of the invention may comprise one or more excipient(s). Pharmaceutically acceptable excipients are known in the art, see for instance Remington's Pharmaceutical Sciences (by Joseph P. Remington, 18th ed., Mack Publishing Co., Easton, Pa.), which is incorporated herein in its entirety.

The present invention encompasses therapies which involve administering the fusion polypeptides of the invention to an animal, in particular a mammal, for instance a human, for preventing, treating, or ameliorating symptoms associated with a disease, disorder, or infection.

Accordingly, the fusion polypeptides or a pharmaceutical composition of the invention may be used in therapy, for example for treating a disease or disorder. Also provided is a method of treating a disease or disorder comprising administering to a subject or patient in need thereof a therapeutically effective amount of the fusion polypeptides of the invention. The use or method may comprise administering a therapeutically effective schedule that has less frequent doses of the fusion polypeptides of the invention than the therapeutically effective dosing schedule of a wild-type Relaxin molecule.

It will be understood that the fusion polypeptides of the invention may be used in the treatment of cardiovascular diseases, for example for the treatment of heart failure.

As used herein, the term "heart failure" includes acute heart failure, chronic heart failure (CHF) and acute decompensated heart failure (ADHF). The term "heart failure" may also include more specific diagnoses such as heart failure with preserved ejection fraction (HFpEF), heart failure with mid-range ejection fraction or heart failure with reduced ejection fraction (HFrEF).

The fusion polypeptides of the invention may also be used in the treatment of kidney disease, lung disease and fibrotic disorders, for example fibrotic disorders of the kidney, heart, lung and liver, and in wound healing (Sherwood O D (2004) *Endocrine Reviews* 25(2): 205-234). The fusion polypeptides of the invention may also be used in the reversal of insulin resistance in diabetic patients (Bonner J S et al. (2013) *Diabetes* 62(9):3251-3260). The fusion polypeptides of the invention may also be used in various forms of pulmonary hypertension. The fusion polypeptides of the invention may also be used in disorders that are a result of or a cause of arterial stiffness, reduced arterial elasticity, reduced arterial compliance and distensibility including hypertension, kidney disease, peripheral arterial disease, carotid and cerebrovascular disease (i.e. stroke and dementia), diabetes, microvascular disease resulting in end organ damage, coronary artery disease, and heart failure.

The fusion polypeptides and/or pharmaceutical compositions of the invention are suitable for parenteral administration to a subject or patient. In some embodiments the subject or patient is a mammal, in particular a human.

Wild-type human Relaxin-2 has a half-life of minutes in vivo. As a consequence, it has to be administered by continuous intravenous infusion in hospitalized patients and presents severe side effects including blood pressure drop. In contrast, it will be understood that embodiments of the fusion polypeptides and/or pharmaceutical compositions of the invention may be administered by injection, such as by intravenous, subcutaneous or intramuscular injection, to a subject or patient. In some embodiments, the fusion polypeptides and/or pharmaceutical compositions are administered by subcutaneous injection. Administration by injection, such as by subcutaneous injection, offers the advantage of better comfort for the subject or patient and the opportunity to administer to a subject or patient outside of a hospital setting. In some embodiments the fusion polypeptide or pharmaceutical composition is administered by self-administration.

In some embodiments, the fusion polypeptides of the invention have an increased half-life compared to wild-type Relaxin, which permits lower overall exposure based on molar concentration. For example, the fusion polypeptides of the invention may be administered less frequently than wild-type Relaxin, thus providing a more convenient dosing schedule.

The present invention provides a kit comprising the pharmaceutical compositions of the invention. The kit may comprise a package containing the pharmaceutical compositions of the invention and instructions. In some embodiments, the pharmaceutical compositions of the invention are formulated in single dose vials or a container closure system (e.g. pre-filled syringe). Optionally associated with such container(s) can be a notice in the form prescribed by a governmental agency regulating the manufacture, use or sale of pharmaceuticals or biological products, which notice reflects approval by the agency of manufacture, use or sale for human administration.

As used herein, the articles "a" and "an" may refer to one or to more than one (e.g. to at least one) of the grammatical object of the article.

"About" may generally mean an acceptable degree of error for the quantity measured given the nature or precision of the measurements. Exemplary degrees of error are within percent (%), typically, within 10%, and more typically, within 5% of a given value or range of values.

Embodiments described herein as "comprising" one or more features may also be considered as disclosure of the corresponding embodiments "consisting of" such features.

The term "pharmaceutically acceptable" as used herein means approved by a regulatory agency of the Federal or a state government, or listed in the U.S. Pharmacopeia, European Pharmacopeia or other generally recognized pharmacopeia for use in animals, and more particularly in humans.

Concentrations, amounts, volumes, percentages and other numerical values may be presented herein in a range format. It is also to be understood that such range format is used merely for convenience and brevity and should be interpreted flexibly to include not only the numerical values explicitly recited as the limits of the range but also to include all the individual numerical values or sub-ranges encompassed within that range as if each numerical value and sub-range is explicitly recited.

The above embodiments are to be understood as illustrative examples. Further embodiments are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

In the context of the present disclosure other examples and variations of the fusion polypeptides and methods described herein will be apparent to a person of skill in the art.

Other examples and variations are within the scope of the disclosure, as set out in the appended claims. All documents cited herein are each entirely incorporated by reference herein, including all data, tables, figures, and text presented in the cited documents.

EXAMPLES

Example 1: Generation of Recombinant Heterodimeric Fc Relaxin-2 Fusion Proteins

The Fc Relaxin-2 fusion proteins described herewith have been designed using the heterodimerisation properties of the knob-in-hole Fc domains (Fc Knob and Fc Hole) to induce correct folding and heterodimerisation of chains A and B of Relaxin-2.

More precisely, Relaxin-2 chains A and B have been genetically fused to two complementary Fcs (at the N- and/or C-terminus of the Fc) via connectors, as illustrated in FIG. 1. CHO cells were then co-transfected with two expression vectors comprising each of the single Fc-Relaxin chains (A and/or B). The two complementary Fc moieties assemble within the CHO cells and, thus, facilitate the assembly and correct folding of Relaxin-2. As demonstrated in the following Example 2, disulphide bonds are then formed between complementary Fc chains and between the chain A and the chain B, recreating the natural Relaxin-2 structure.

The heterodimeric Fc Relaxin-2 fusion proteins were secreted in the supernatant, then purified using an automated system by affinity chromatography, wherein the Fc region of the protein binds to the column matrix.

Example 2: LC-MS Analysis of Fc Relaxin-2 Knob-in-Hole Heterodimers

LC-MS analysis was performed on both non-reduced and reduced deglycosylated Fc-Relaxin-2 heterodimers. For deglycosylation, samples were diluted to 1 mg/ml and buffered at pH 7.80 using 10 mM Tris-Cl. PNGase F (Roche) was added to the sample at a concentration of 1 unit of enzyme per 50 μg of Fc-Relaxin-2 and incubated overnight at 37° C. For non-reduced analysis, the sample was diluted to 0.05 mg/ml in water and 20 μL loaded into an LC-MS-certified total recovery vial with a pre-slit cap (Waters part number: 186005663CV). For reduced analysis, 10 mM TCEP was added and the sample incubated at 37° C. for a further 30 minutes prior to analysis.

Experiments were performed using an ACQUITY I-Class UPLC coupled to a Xevo G2-XS Q-TOF instrument (Waters, Milford, Mass.), both operated using UNIFI Scientific Information System. For the LC system, Solvent A was water with 0.1% formic acid and solvent B was acetonitrile with 0.1% formic acid (both UPLC-MS grade, BioSolve). The UV detector was set to measure at wavelengths of 220 nm and 280 nm and the vials placed in a sample chamber maintaining a temperature of 4° C. A volume of 1 μL was injected onto a reverse phase ACQUITY UPLC Protein BEH C4 Column, 300A-pore column (Waters part number: 186004495) and proteins were eluted using an increasing gradient of solvent B from 5% to 75% over 6 minutes.

The mass spectrometer was calibrated from 500-5000 m/z by infusing 2 µg/µL sodium iodide in 50% 2-propanol and the lockspray was 200 pg/µL Leucine Enkephalin. The instrument was operated in positive ionisation mode and sensitivity analyser mode with the following key settings: capillary voltage=3.0 V; sample cone voltage=40 V; source temperature=120° C.; desolvation temperature=450° C.; cone gas flow=120 L/h; desolvation gas flow=1000 L/h; mass range=500-5000 m/z, scan time=1.0 sec.

Data were processed in UNIFI software. The spectra were combined from the retention time in the chromatogram where the protein of interest eluted. The raw data was background subtracted and deconvoluted using MaxEnt1 algorithm for large molecules. The experimental data was compared to the mass of theoretical sequences which took into consideration disulphide bonds for non-reduced analysis and free cysteines for reduced analysis. Deamidation of asparagine (+1 Da) was also considered following PNGaseF deglycosylation.

Figure 2:
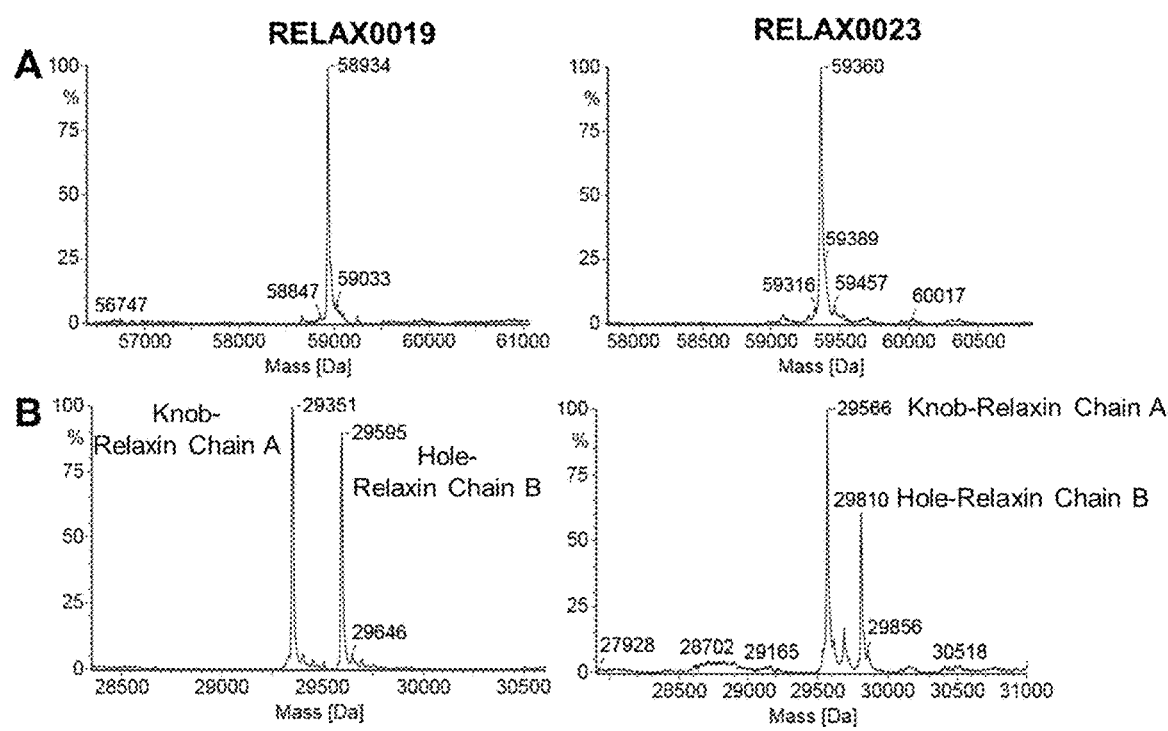

LC-MS analysis confirmed disulphide bonds are formed between complementary Fc chains and between the chain A and the chain B, recreating the natural Relaxin-2 structure. FIG. 2A shows, as an example, LC-MS data for RELAX0019 and RELAX0023. Non-reduced analysis confirmed the formation of the heterodimers with expected masses of 58932 Da and 59361Da respectively for RELAX0019 and RELAX0023: no homodimers were detected. Reduced analysis (FIG. 2B) confirmed the sequence identity of both chains and showed they had no modifications.

Non-Reduced Peptide Mapping to Identify Disulphide Bonds

Heterodimeric Fc-Relaxin (50 µg) was placed into a clean sample tube and diluted in 17 µL of 100 mM sodium phosphate pH 7.0. Alkylation of free cysteines was achieved by addition of 0.5 µL of 5 mg/ml iodoacetamide followed by incubation at room temperature for 20 minutes. Following the alkylation, a further 2.5 µL of 100 mM sodium phosphate buffer pH 7.0 was added amd 2.5 µL of sodium chloride. The protein was denatured by addition of 40 µL 8.0 M Guanidine HCl and incubated at 37° C. for 30 minutes. Dilution was achieved by addition of 125 µL of 100 mM sodium phosphate buffer pH 7.0 followed by addition of 0.5 µL of 40 mM EDTA. Endoproteinase Lys-C (Wako Chemicals) was reconstituted in water at a concentration of 1 mg/ml and 5 µL added to Fc-Relaxin-2. Digestion was carried out at 37° C. for 2 hours after which time an additional 5 µL of Lys-C was added and the incubation continued for a further 2 hours. For peptide analysis, 42.5 µL of sample was transferred to a UPLC vial and 2.5 µL of water added. For reduction of disulphide bonds, 2.5 µL of 500 mM DTT was added to another 42.5 µL aliquot of sample and left at room temperature for 15 minutes before LC-MS analysis.

Analysis of the peptides was performed using an ACQUITY I-Class UPLC coupled to a Xevo G2-XS Q-TOF instrument (Waters, Milford, Mass.), both operated using UNIFI Scientific Information System. For the LC system, Solvent A was water with 0.1% formic acid and solvent B was acetonitrile with 0.1% formic acid (both UPLC-MS grade, BioSolve). The UV detector was set to measure at a wavelength of 214 nm and the vials placed in a sample chamber maintaining a temperature of 4° C. A volume of 10 µl was injected onto a reverse phase ACQUITY BEH C18 300 Å-pore column (Waters part number: 186003687) and proteins were eluted using an increasing gradient of solvent B from 5% to 37% B over 73.5 minutes and then increased to 60% B over a further 2.5 minutes. After 77.5 minutes the column was held at 95% B for 5 minutes.

The mass spectrometer was calibrated from 100-2600 m/z by infusing 2 µg/µL sodium iodide in 50% 2-propanol and the lockspray was 200 pg/µL Leucine Enkephalin. The instrument was operated in positive ionisation mode and sensitivity analyser mode with the following key settings: capillary voltage=3.0 V; sample cone voltage=25 V; source temperature=100° C.; desolvation temperature=250° C.; cone gas flow=0 L/h; desolvation gas flow=500 L/h; mass range=100-2600 m/z, scan time=0.5 sec.

Data were processed in UNIFI software by importing the sequence with expected disulphide bonds and performing a search for matching Lys-C generated peptides. The chromatograms obtained in the absence and presence of reducing agent were overlaid to verify that the disulphide-bonded peptides identified were no longer observed once reduced.

Figure 3:
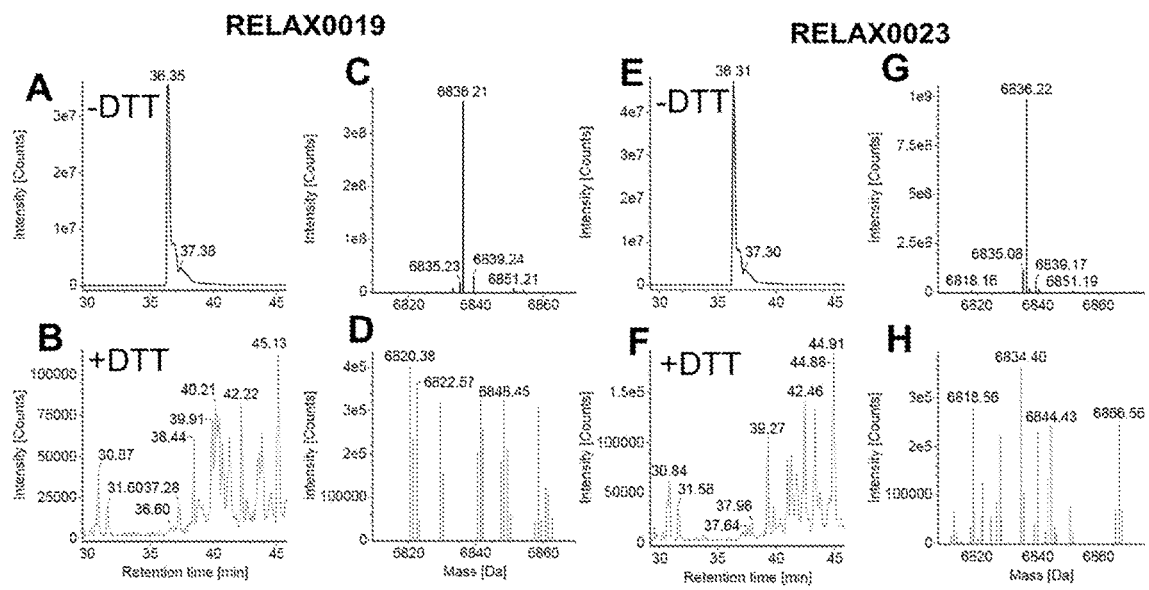

A peptide matching the expected mass for the disulphide-bonded Relaxin-2 peptide incorporating both chains A and B was identified as depicted on the top of FIG. 3 (SLSL-SPGGGGGSGGGGSGGGGSGGGGGSQLYSALANKC-CHVGCTK (SEQ ID NO: 75)=LCGRELVRAQIA-ICGMSTWS (SEQ ID NO: 76)=RSLARFC (SEQ ID NO: 77). expected mass including 3 disulphide bonds 6836.23 Da). FIG. 3 (A-D) shows the identification of this peptide for RELAX0019 and confirmation that the peptide was no longer observed when reducing agent was added: panels A and B show extracted ion chromatograms in the absence and presence of DTT and panels C and D show the corresponding mass spectrum of the peptide. FIG. 3 (E-H) shows the identification of the same peptide for RELAX0023 and confirmation that the peptide was no longer observed when reducing agent was added: panels E and F show extracted ion chromatograms in the absence and presence of DTT and panels G and H show the corresponding mass spectra of the peptide. These data confirm that Relaxin chains A and B are interacting through disulphide bonds within the heterodimers RELAX0019 and RELAX0023.

Example 3: In Vitro Activity of Fc-Relaxin-2 Fusion Proteins (Cell Based cAMP Activity Assay)

The Relaxin-2 fusion polypeptides produced as described above were tested for biological activity, e.g. stimulation of one or more cellular receptor responses, by the following methods.

Stable cell lines expressing human or mouse receptors generated in CHO cells were purchased from DiscoverX.
cAMP Hunter™ CHO-K1 RXFP1 Gs, cell line (DiscoverX catalogue number 95-0127C2)
cAMP Hunter™ CHO-K1 RXFP2 Gs cell line (DiscoverX catalogue number 95-0140C2)
cAMP Hunter™ CHO-K1 mRXFP1 Gs cell line (DiscoverX catalogue number 95-0180C2)

Activation of these receptors results in downstream production of cAMP second messenger that can be measured in a functional activity assay.

Routine cAMP assays were performed using bovine serum albumin (BSA)-based assay buffer: Hanks Balanced Salt Solution (Sigma #H8264) supplemented with 0.1% BSA (Sigma #A9418) and 0.5 mM IBMX (Sigma #17018), adjusted to pH 7.4 with 1 M NaOH.

A frozen cryo-vial of cells expressing the receptor of interest was thawed rapidly in a water-bath, transferred to pre-warmed cell media and spun at 240×g for 5 minutes. Cells were re-suspended in cell media at an optimized concentration (e.g. hRXFP1 at $3.33 \times 10^4$ cells/mL), and 30 µL cell suspension was added to Poly-D-Lysine-coated 384-well plates (Greiner #781946) and allowed to adhere overnight. The next day the media was flicked out of the plates and replaced with 5 uL assay buffer. Eleven-point serial dilutions of test recombinant peptide or Fc fusion samples were added to the cells using a non-contact liquid dispenser (ECHO™, Labcyte). All sample dilutions were made in duplicate. An additional 5 µL assay buffer was added to each well and the plates incubated at room temperature for 30 minutes.

cAMP levels were measured using a commercially available cAMP dynamic $G_s$ HTRF kit (Cisbio, Cat #62AM4PEJ), following the two-step protocol as per manufacturer's recommendations. In brief, anti-cAMP cryptate (donor fluorophore) and cAMP-d2 (acceptor fluorophore) were made up separately by diluting each 1/20 in conjugate & lysis buffer provided in the kit. 5 µL anti-cAMP cryptate was added to all wells of the assay plate, and 5 µL cAMP-d2 added to all wells except non-specific binding (NSB) wells, to which conjugate and lysis buffer was added. Plates were incubated at room temperature for one hour and then read on an Envision (Perkin Elmer) using excitation wavelength of 320 nm and emission wavelengths of 620 nm & 665 nm. Data was transformed to % Delta F as described in manufacturer's guidelines and then transformed to percent activation of maximal native agonist response and analysed by 4-parameter logistic fit to determine EC50 values. The results are compared to corresponding results for recombinant hRelaxin-2 (R&D Systems Cat #6586 RN) in the case of hRXFP1 cells, mRelaxin-1 (R&D Systems Cat #6637 RN) in mRXFP1 cells and INSL3 (R&D Systems Cat #4544 NS) in hRXFP2 cells.

Data analysis was performed using statistical analysis software (GraphPad Prism, V6).

Figure 4:
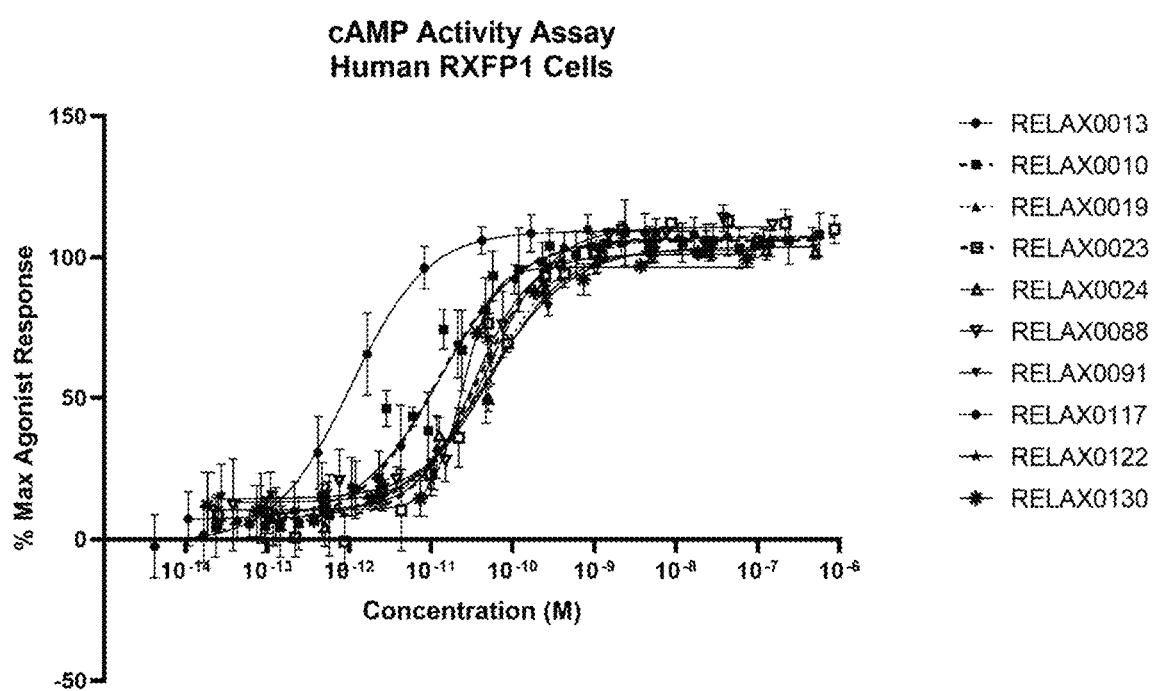
FIG. 4 shows the in vitro biological activity of some heterodimeric fusions of the invention measured by cAMP induction in cells expressing recombinant human RXFP1.

The biological activity of the tested constructs is provided in Table 4 and in FIG. 4. The average EC50 measurements for both the recombinant human Relaxin-2 and fusion polypeptides from several assays has been summarized in Table 4.

RELAX0013, RELAX0014 and RELAX0010 are proteins of reference, where RELAX0013 is the recombinant human Relaxin-2, RELAX0014 is the recombinant murine Relaxin-1 and RELAX0010 is a single chain fusion protein comprising chain A, linker of 15 amino acids, chain B, connector of 15 amino acids, and Fc, comprising the amino acid sequence of SEQ ID NO. 8, described in WO2018/138170.

TABLE 4

Biological activity of heterodimeric Fc Relaxin fusion polypeptides (n: number of repeats).

| Name | n | EC50 hRXFP1 (M) | EC50 mRXFP1 (M) | EC50 hRXFP2 (M) |
|---|---|---|---|---|
| RELAX0013 | 23 | 1.15E−12 | 7.54E−13 | 1.75E−09 |
| RELAX0014 | 23 | 4.47E−12 | 2.37E−12 | 1.78E−12 |
| RELAX0010 | 10 | 8.3E−12 | 7.64E−12 | 2.88E−07 |
| RELAX0019 | 8 | 3.57E−11 | 9.10E−12 | 3.42E−08 |
| RELAX0020 | 4 | 4.41E−11 | 2.79E−11 | 3.54E−08 |
| RELAX0023 | 11 | 3.77E−11 | 3.27E−11 | 3.24E−08 |
| RELAX0024 | 2 | 4.60E−11 | 1.56E−11 | 4.26E−08 |
| RELAX0021 | 4 | 8.27E−11 | 4.14E−11 | Not tested |
| RELAX0022 | 2 | 4.74E−11 | 3.28E−11 | Not tested |
| RELAX0091 | 2 | 5.88E−11 | 2.88E−11 | >1.09E−7 |
| RELAX0117 | 6 | 1.06E−11 | 1.74E−11 | 1.61E−08 |

From the results presented in Table 4, it can be concluded that the heterodimeric Fc Relaxin fusion proteins tested were less potent than the single chain fusion RELAX0010 or the recombinant human Relaxin-2 peptide, but they still retained high levels of biological activity (ranging from ~10 pM to ~80 pM in the human RXFP1 cell line).

These results show that the Relaxin A and B chains can be fused to either/both termini (connector can be attached to either N or C terminus of the Relaxin chain) and either chain of the heterodimeric Fc (X or Y) and retain biological activity. The format of the heterodimeric Fc Relaxin fusion proteins described herewith thus constitutes a robust format for generating a long half-life active Relaxin.

The presence of the disulphide bond to stabilise the heterodimeric Fc did not affect potency of the fusion protein (compare RELAX0023 versus RELAX0021, and RELAX0024 versus RELAX0022).

The two upper hinge regions used (GGAGGA (SEQ ID NO: 78) and native DKTHT (SEQ ID NO: 79)) did not affect potency (compare RELAX0023 versus RELAX0019, and RELAX0024 versus RELAX0020). The exact amino acid sequence of the upper hinge is not critical for the activity of the fusion protein.

Example 4: The Effect of the Connector Composition and Length in the Heterodimeric Relaxin-2 Fc Fusion Proteins The connectors can be composed of glycine and serine residues (GS) or can be composed of proline and alanine repeats (PA). The connectors used herewith had lengths between 6 and 21 residues. An example of a long GS connector is: GGGGSGGGGSGGGGSGGGGGS (SEQ ID NO: 5) (21 amino acids). An example of a long PA connector is: PAPAPAPAPAPAPAPAPAPAG (SEQ ID NO: 6) (21 amino acids).

Connectors of different lengths and compositions can be placed on each Fc-chain of the heterodimeric Relaxin-2 Fc fusion polypeptides.

Examples of heterodimeric Relaxin-2 Fc fusion proteins with a variety of connectors are shown in Table 5. This table also indicates information regarding developability/manufacturability (expression yield and percentage of monomeric/non-aggregated Relaxin-2 Fc fusion proteins after protein A capture from cell culture supernatant), and biological activity.

TABLE 5

Effect of connectors on biological activity and developability properties of heterodimeric Fc Relaxin-2 fusion proteins during small scale expression.

| Name | Expression yield (mg/l) | % monomers | n | EC50 hRXFP1 (M) | EC50 mRXFP1 (M) | EC50 hRXFP2 (M) |
|---|---|---|---|---|---|---|
| RELAX0013 | | | 23 | 1.15E−12 | 7.54E−13 | 1.75E−09 |
| RELAX0014 | | | 23 | 4.47E−12 | 2.37E−12 | 1.78E−12 |
| RELAX0010 | No data | No data | 10 | 8.3E−12 | 7.64E−12 | 2.88E−07 |
| RELAX0019 | 147 | 78 | 25 | 5.81E−11 | 2.24E−11 | 4.40E−08 |
| RELAX0023 | No data | No data | 15 | 3.32E−11 | 1.36E−11 | 4.20E−08 |
| RELAX0081 | 164 | 82 | 3 | 4.51E−11 | 4.73E−11 | 4.92E−08 |
| RELAX0082 | 226 | 83 | 3 | 5.68E−11 | 4.90E−11 | 3.81E−08 |
| RELAX0083 | 83 | 94 | 6 | 2.81E−11 | 1.34E−11 | 2.42E−08 |
| RELAX0056 | 466 | 75 | 4 | 3.87E−11 | 3.27E−11 | 6.48E−08 |
| RELAX0054 | 6 | 89 | 2 | 2.89E−11 | 1.59E−11 | 1.53E−08 |
| RELAX0055 | 9 | 92 | 2 | 1.88E−11 | 1.51E−11 | 3.39E−08 |
| RELAX0084 | 91 | 93 | 2 | 5.34E−11 | 3.48E−11 | 1.20E−08 |
| RELAX0085 | 261 | 81 | 2 | 6.37E−11 | 3.09E−11 | 4.67E−08 |
| RELAX0086 | 150 | 92 | 2 | 4.49E−11 | 2.68E−11 | 4.88E−08 |
| RELAX0087 | 179 | 82 | 2 | 4.89E−11 | 3.48E−11 | 3.63E−08 |
| RELAX0105 | 231 | 76 | 2 | 7.12E−11 | 1.49E−11 | 3.33E−08 |
| RELAX0106 | 269 | 76 | 2 | 6.96E−11 | 1.98E−11 | 4.94E−08 |
| RELAX0107 | 301 | 77 | 2 | 8.09E−11 | 3.87E−11 | 1.22E−07 |
| RELAX0109 | 60 | 33 | 3 | 1.72E−09 | 8.22E−10 | |
| RELAX0110 | 61 | 34 | 3 | 1.88E−09 | 1.11E−09 | >6.07E−8 |
| RELAX0111 | 60 | 36 | 3 | 1.93E−09 | 1.24E−09 | >6.06E−8 |

The length and composition of the connectors does have an impact on the developability aspect of the molecules. As shown in Table 5, heterodimeric Relaxin-2 Fc fusion polypeptides with PA connectors of less than or equal to 16 amino acids did not express well. In contrast, a 21-residue long PA connector increased the expression yield significantly. Expression yields of constructs with GS connectors are more consistent.

Heterodimeric Relaxin-2 Fc fusion proteins with short and asymmetric (different) connectors retained potency. Reduction in biological activity was only observed in fusion proteins with low monomeric content (RELAX0109, RELAX0110 and RELAX0111).

Example 5: Point Mutations in the Relaxin-2 Sequence

Relaxin single point mutation analogues were made as heterodimeric Fc Relaxin-2 fusion proteins. Table 6 shows examples of such molecules which retained potency and favourable developability properties.

The native residues targeted are positively charged and could be liable to proteolysis but are not involved in the binding of Relaxin to its receptor.

For instance, R22X analogues heterodimeric Fc Relaxin-2 fusion proteins seem to consistently have improved developability/manufacturability properties.

TABLE 6

Examples of Relaxin-2 analogues which retain potency and favourable developability properties during small scale expression.

| Name | Expression yield (mg/l) | % Monomers | n | EC50 hRXFP1 (M) | EC50 mRXFP1 (M) | EC50 hRXFP2 (M) |
|---|---|---|---|---|---|---|
| RELAX0013 | | | 23 | 1.15E−12 | 7.54E−13 | 1.75E−09 |
| RELAX0014 | | | 23 | 4.47E−12 | 2.37E−12 | 1.78E−12 |
| RELAX0019 | 147 | 78 | 25 | 5.81E−11 | 2.24E−11 | 4.40E−08 |
| RELAX0039 | 188.0 | 87 | 2 | 6.54E−11 | 4.25E−11 | 1.08E−07 |
| RELAX0040 | 128.8 | 88 | 2 | 5.92E−11 | 2.92E−11 | >1.27E−7 |
| RELAX0041 | 162.5 | 82 | 2 | 6.22E−11 | 3.17E−11 | 1.18E−07 |
| RELAX0043 | 160.2 | 79 | 2 | 7.98E−11 | 5.58E−11 | >1.58E−7 |
| RELAX0052 | 162.4 | 81 | 4 | 9.67E−11 | 5.69E−11 | 1.05E−07 |
| RELAX0053 | 181.0 | 80 | 2 | 7.15E−11 | 4.36E−11 | >1.79E−7 |
| RELAX0063 | 157.2 | 84 | 2 | 1.96E−10 | 4.46E−11 | >1.38E−7 |
| RELAX0069 | 163.0 | 86 | 3 | 5.76E−11 | 3.69E−11 | >1.62E−7 |
| RELAX0070 | 145.5 | 91 | 3 | 6.67E−11 | 5.02E−11 | 1.07E−07 |
| RELAX0071 | 174.7 | 85 | 3 | 6.87E−11 | 3.93E−11 | 1.15E−07 |
| RELAX0072 | 232.3 | 78 | 2 | 8.53E−11 | 4.03E−11 | >2.3E−7 |
| RELAX0073 | 174.7 | 87 | 3 | 5.70E−11 | 4.15E−11 | 8.63E−08 |
| RELAX0074 | 170.0 | 88 | 2 | 5.45E−11 | 4.53E−11 | 9.21E−08 |
| RELAX0075 | 144.4 | 79 | 3 | 9.47E−11 | 6.14E−11 | >1.43E−7 |

The results presented in Table 6 demonstrate that some variability in the amino acid sequence of the Relaxin-2 chain A is tolerated without the loss of potency while retaining favourable developability properties.

Example 6: PK Profile of Fc-Relaxin-2 Fusion Proteins

The pharmacokinetic (PK) profiles of Relaxin-2 fusion polypeptides were determined using a Relaxin ELISA assay and/or cAMP assay. Relaxin-2 fusion polypeptides were administered to 6-10-week-old male C57BL/6J (Jax) mice (Jackson Laboratories) by either the subcutaneous (SC) and/or intravenous (IV) route at 6 mg/kg. For the IV route of administration, serum samples were collected at 5 minutes, 30 minutes and 60 minutes followed by either 3 hours and/or 6 hours and/or 8 hours and 24 hours followed by a series of minimum 1-day intervals to a maximum of 21 days post drug administration. A similar schedule was followed for the SC route of administration with less frequent collections within the first 8 hours; for example, collecting the first sample at 30 minutes then at 3 hours, 8 hours, 24 hours, 30 hours and 48 hours, followed by a series of minimum 1-day intervals to a maximum of 21 days. Samples were collected by cardiac puncture into a serum tube and were kept at room temperature for 15 to 30 minutes then centrifuged for 10 minutes at 10000 rpm within 30 minutes of collection. Aliquoted samples were stored at <−80° C. and later tested by ELISA or cAMP activity assay.

For the majority of molecules, the PK samples were tested in an ELISA using an anti-hRelaxin-2 capture (pre-coated Human Relaxin-2 Quantikine ELISA Kit, R&D Systems Cat #DRL200) and anti-human Fc detection antibody (AU003 labelled with HRP), with the exception of RELAX0010 (described in WO2018/138170) which was tested in an ELISA using anti-human Fc capture and anti-hRelaxin-2 detection (using the polyclonal HRP-labelled antibody from the Human Relaxin-2 ELISA kit, R&D Systems Cat #DRL200). In both assays, plates coated with the capture antibody were blocked with 100 µL RD1-19 assay diluent for one hour at room temperature. 50 µL of standard or sample was added to each well and incubated for two hours at room temperature. Samples were aspirated and wells washed three times with assay wash buffer. 50 µL of HRP-labelled detection antibody was added per well, diluted either 1:1000 in PBS/1% BSA in the case of anti-human Fc-specific detection or used undiluted in the case of anti-hRelaxin-2 detection. Following 1 hour incubation at room temperature and three washes, 50 µL per well TMB (SureBlue Reserve KPL 53-00-03) was added and once the colour change had occurred the reaction was stopped by adding 50 µL per well TMB stop solution (KPL 50-85-06).

Biological Activity of PK Samples in Cell-Based cAMP Activity Assay.

Serum samples collected from animals as outlined above were tested for biological activity in order to measure functional Relaxin-2 to assess integrity of Fc-Relaxin-2 fusion polypeptides. A stable cell line expressing human RXFP1 receptor generated in CHO cells was purchased from DiscoverX. Activation of this receptor results in downstream production of cAMP second messenger that can be measured in a functional activity assay.

cAMP assays were performed using bovine serum albumin (BSA)-based assay buffer: Hanks Balanced Salt Solution (Sigma #H8264) supplemented with 0.1% BSA (Sigma #A9418) and 0.5 mM IBMX (Sigma #17018), adjusted to pH 7.4 with 1 M NaOH.

Dosing solutions of the Relaxin-2 fusion polypeptides or recombinant Relaxin-2 peptide (R&D Systems Cat #6586-RN) were diluted in assay buffer and a non-contact liquid dispenser (ECHO, Labcyte) used to create 11-point standard curves in four matrix concentrations. The matrix used was blank serum from mock-dosed animals and was added manually to wells at twice the required concentration to allow for the addition of cells. Test samples were transferred from serum tubes to a 384-well source plate which was used by a non-contact liquid dispenser (ECHO, Labcyte) to set up four dilutions in assay buffer. All sample dilutions were made in duplicate.

A frozen cryo-vial of cells expressing hRXFP1 was thawed rapidly in a water-bath, transferred to pre-warmed cell media and spun at 240×g for 5 minutes. Cells were re-suspended in 8 mL cell culture medium, seeded in a T75 flask containing 10 mL culture medium and allowed to attach overnight. The following day the cells were detached using accutase and spun at 240×g for 5 minutes. The resulting cell pellet was resuspended at an optimized concentration, and 2.5 µL cell suspension was added to each well of the assay plates using a Combi-drop dispenser.

cAMP levels were measured using a commercially available cAMP dynamic 2 HTRF kit (Cisbio, Cat #62AM4PEJ), following the two-step protocol as per manufacturer's recommendations. In brief, anti-cAMP cryptate (donor fluorophore) and cAMP-d2 (acceptor fluorophore) were made up separately by diluting each ½₀ in conjugate & lysis buffer provided in the kit. 2.5 µL anti-cAMP cryptate was added to all wells of the assay plate, and 2.5 µL cAMP-d2 added to all wells except non-specific binding (NSB) wells, to which conjugate and lysis buffer was added. Plates were incubated at room temperature for one hour and then read on an Envision (Perkin Elmer) using excitation wavelength of 320 nm and emission wavelengths of 620 nm & 665 nm. Data was transformed to % Delta F as described in manufacturer's guidelines and sample values calculated from the linear part of the standard curves.

Results and Conclusion

Figure 5:
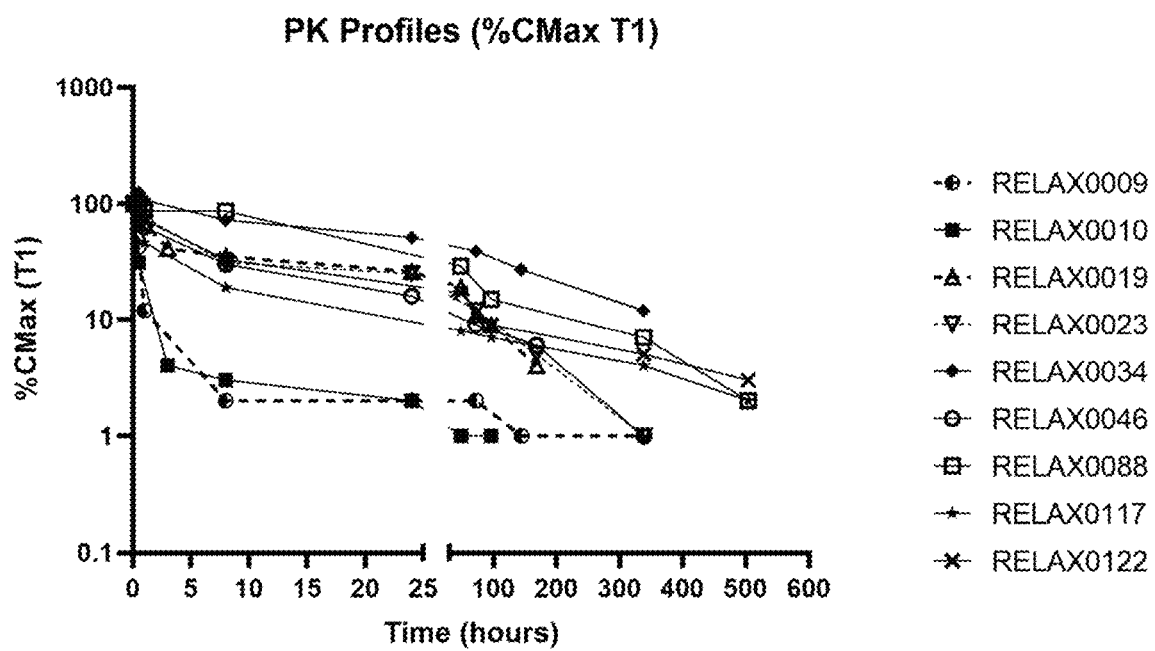
FIG. 5 shows in vivo pharmacokinetic (PK) profiles from a series of ELISA experiments where heterodimeric fusions of the invention were administered to mice intravenously. Data is normalised as a % cMax at the 5 min time point (T1).

FIG. 5 shows a summary of data from a series of in vivo PK experiments where Fc-Relaxin-2 polypeptides were administered to mice IV. Data is normalised for 5 minute time point.

The half-life of human Relaxin-2 following IV administration is about 0.09+/−0.04 hours, i.e. 5.4+/−2.4 minutes in humans (Chen et al. 1993). Recombinant Relaxin Fc fusion polypeptides are all showing half-life improvements compared to native Relaxin-2. The Fc-Relaxin polypeptides where Relaxin A-chain and B-chain are connected to different heterodimeric Fc-chains (exemplified by RELAX0019, RELAX0023, RELAX0034, RELAX0046 and RELAX0117) have improved PK properties compared to those Fc-Relaxin polypeptides in which the Relaxin chains are connected with a linker (exemplified by RELAX0010 and RELAX0009). However, the presence of the connecting linker between Relaxin chain A and chain B by itself is not directly linked to quick in vivo elimination of Fc-Relaxin polypeptides since linker-containing molecules RELAX0088 and RELAX0122 both show good in vivo stability.

Unexpectedly in this study, the heterodimeric Fc-Relaxin fusion polypeptides (RELAX0019, RELAX0023, RELAX0034, RELAX0046, RELAX0117, RELAX0088 and RELAX0122) all have significantly improved pharmacokinetic properties compared to the Fc-Relaxin fusion polypeptides RELAX0010 and RELAX0009.

Example 7: Reversal of Established Hypertrophy and Fibrosis by RELAX0019 and RELAX0023

Figure 6:
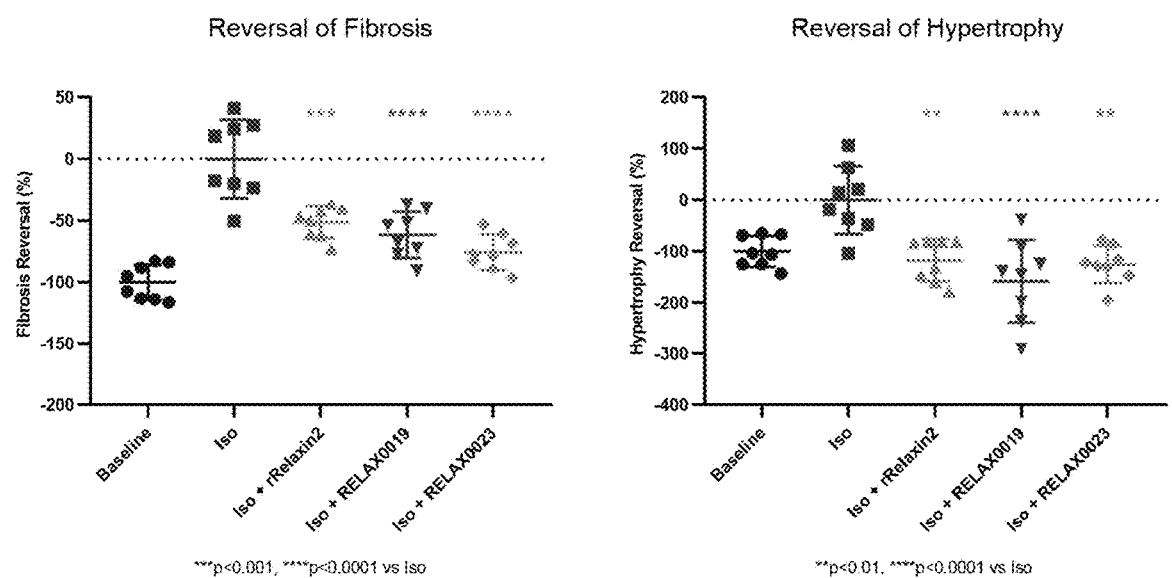
FIG. 6 shows reversal of isoproterenol-induced cardiac fibrosis and hypertrophy in mice treated with RELAX0019 and RELAX0023. Levels of fibrosis and hypertrophy for (1) vehicle (baseline), (2) isoproterenol, (3) isoproterenol+Relaxin-2, (4) isoproterenol+RELAX0019, and (5) isoproterenol+RELAX0023 are shown.

Isoproterenol was infused via minipump (15 mg/kg/day) into C57B6 mice for 10 days to induce cardiac hypertrophy and fibrosis. Mice infused with vehicle for the same duration were used as baseline controls. After 10 days, the minipumps were removed and mice were either given a new minipump containing rRelaxin-2 (500 ug/kg/day) or received the first of two, once-weekly (QW), subcutaneous injections of RELAX0019 (20 mg/kg) or RELAX0023 (20 mg/kg). After the 14-day treatment period, mice were sacrificed, and their hearts were collected for analysis of hypertrophy and fibrosis. Hearts from baseline control mice were collected after removal of the vehicle minipump. Hypertrophy was determined as a measure of heart weight relative to tibial length and fibrosis was established by quantitation of collagen content relative to heart weight. Infusion of isoproterenol significantly induced both hypertrophy and fibrosis in this model. QW dosing of RELAX0019 and RELAX0023 returned the isoproterenol-induced hypertrophy to baseline levels, as did constant infusion of rRelaxin-2. All Relaxin treatments also reduced cardiac fibrosis by more than 50%. N=8 for each group. $p<0.01, *p<0.001, ****p<0.0001$ Recombinant Relaxin Fc fusion proteins RELAX0019 and RELAX0023 were able to reverse hypertrophy and fibrosis in a similar manner to native hRelaxin-2 (FIG. 6)

Example 8: Assessing Non-Specific Binding of Fc-Relaxin-2 Proteins Using Baculovirus ELISA RELAX proteins were expressed in CHO cells and purified as described above. A Baculovirus ELISA developed for assessing non-specific binding of monoclonal antibodies (Ref: Hotzel et al 2012 mAbs 4:6, 753-760) was adapted to determine a non-specific binding of Fc-Relaxin polypeptides with the modification whereby instead of calculating a 'BV score' (Baculovirus plate absorbance/blank plate absorbance) a non-specific binding was calculated separately for Baculovirus plate and blank plate as signal over background (where background is a value obtained in absence of Fc-Relaxin polypeptide). This measure was introduced to reflect increased, when compared to monoclonal antibodies, non-specific binding of some Fc-peptides to both coated and un-coated (blank) plates. Preparations of each protein were made at either 100 nM or 10 nM in PBS (Gibco 14190-086)+0.5% BSA (Sigma A9576) and used in duplicates in the ELISA assay on 96-well Nunc Maxisorp F plates coated overnight at 4° C. with 50 µL/well of either 1% Baculovirus extract in 50 mM sodium carbonate (BV plate) or with 50 mM sodium carbonate (blank plate). Following a wash with PBS, plates were blocked with 300 µL/well of PBS+0.5% BSA for 1 hour at room temperature and washed three times with PBS. 50 µL/well of either PBS+0.5% BSA (background) or RELAX proteins dilutions were added and incubated for 1 h at room temperature. Following three washes in PBS a detection antibody (anti-human Fc-specific-HRP Sigma A0170) diluted 1:5000 in PBS+0.5% BSA was added at 50 µL/well. Samples were incubated for 1 hour at room temperature and plates were washed three times in PBS. The HRP substrate—TMB (SureBlue Reserve KPL 53-00-03) was then added at 50 µL/well and following the colour change, the reaction was stopped by adding 50 µL/well of 0.5M sulphuric acid. Absorbance was measured at 450 nm and for each sample non-specific binding was determined. Non-specific binding (fold binding over background) was defined as a ratio of non-specific binding in the presence of Fc Relaxin-2 proteins and absence of Fc Relaxin-2 proteins (background). Data for Fc-Relaxin-2 proteins tested at 2 different concentrations of either 100 nM or 10 nM are shown in Table 7.

TABLE 7

Binding of Fc-Relaxin fusion proteins in the Baculovirus ELISA at 100 nM and 10 nM (-001, 002, 003 refer to different batches of the same protein)

| Fusion name | non-specific binding BV plate (signal/background) at 100 nM | non-specific binding BLANK plate (signal/background)) at 100 nM | non-specific binding BV plate (signal/background)) at 10 nM | non-specific binding BLANK plate (signal/background)) at 10 nM |
| --- | --- | --- | --- | --- |
| RELAX0019-001 | 2.0 | 1.8 | 1.0 | 1.2 |
| RELAX0019-002 | 1.5 | 1.9 | 1.1 | 1.1 |
| RELAX0020 | 2.2 | 2.5 | 1.1 | 1.3 |
| RELAX0021 | 2.7 | 5.3 | 1.0 | 2.0 |
| RELAX0022 | 4.9 | 8.2 | 1.3 | 2.9 |
| RELAX0023-001 | 1.7 | 1.8 | 1.0 | 1.0 |
| RELAX0023-002 | 2.4 | 3.7 | 1.1 | 0.8 |
| RELAX0024 | 1.8 | 5.3 | 0.9 | 1.5 |
| RELAX0039 | 6.3 | 3.2 | 1.7 | 1.8 |
| RELAX0040 | 7.5 | 3.0 | 2.6 | 2.1 |
| RELAX0041 | 7.0 | 4.4 | 1.9 | 2.0 |
| RELAX0043 | 3.7 | 1.6 | 1.3 | 1.3 |
| RELAX0052 | 2.9 | 1.1 | 1.5 | 1.3 |
| RELAX0053 | 5.5 | 3.8 | 1.7 | 2.2 |
| RELAX0054 | 3.2 | 4.1 | 1.5 | 1.8 |
| RELAX0055 | 1.4 | 4.6 | 0.7 | 1.7 |
| RELAX0056 | 5.4 | 9.1 | 1.3 | 1.2 |
| RELAX0069 | 1.7 | 1.8 | 1.1 | 6.5 |
| RELAX0070 | 2.7 | 3.2 | 0.9 | 1.3 |
| RELAX0071 | 1.3 | 1.7 | 0.8 | 0.9 |
| RELAX0072 | 1.4 | 2.4 | 0.7 | 1.3 |
| RELAX0073 | 1.7 | 1.6 | 0.7 | 1.1 |
| RELAX0074 | 1.4 | 1.8 | 0.9 | 1.5 |
| RELAX0075 | 4.7 | 7.9 | 3.3 | 4.8 |
| RELAX0076 | 3.3 | 5.0 | 1.5 | 3.6 |
| RELAX0081 | 3.2 | 4.9 | 0.8 | 1.5 |
| RELAX0082 | 3.4 | 6.1 | 1.0 | 2.9 |
| RELAX0083 | 2.9 | 5.7 | 2.6 | 1.5 |
| RELAX0084 | 3.2 | 7.8 | 1.2 | 1.7 |
| RELAX0085 | 5.4 | 12.3 | 1.4 | 2.2 |
| RELAX0086 | 3.1 | 7.2 | 1.3 | 1.6 |
| RELAX0087 | 4.1 | 17.3 | 1.4 | 2.7 |
| RELAX0088-001 | 3.5 | 5.6 | 1.4 | 1.4 |
| RELAX0088-002 | 1.9 | 2.2 | 1.1 | 0.8 |
| RELAX0091 | 5.6 | 39.3 | 1.6 | 6.8 |
| RELAX0105 | 12.9 | 8.3 | 2.4 | 1.1 |
| RELAX0106 | 14.6 | 8.3 | 2.4 | 1.0 |
| RELAX0107 | 11.6 | 7.0 | 1.8 | 0.9 |
| RELAX0109 | 27.1 | 19.7 | 5.8 | 2.5 |
| RELAX0110 | 26.8 | 23.9 | 8.3 | 2.6 |
| RELAX0111 | 29.0 | 24.3 | 7.0 | 2.9 |
| RELAX0117 | 18.5 | 47.4 | 3.0 | 8.2 |
| RELAX0122 | 2.2 | 2.4 | 1.1 | 0.7 |
| RELAX0123 | 2.5 | 4.8 | 1.1 | 0.9 |
| RELAX0124-001 | 1.8 | 1.7 | 1.1 | 0.7 |
| RELAX0124-002 | 6.4 | 4.6 | 1.5 | 0.9 |
| RELAX0126-001 | 20.0 | 41.5 | 10.2 | 16.9 |
| RELAX0126-002 | 21.3 | 40.4 | 10.9 | 14.3 |
| RELAX0127 | 23.5 | 42.8 | 13.3 | 19.8 |
| RELAX0128 | 23.5 | 42.4 | 13.2 | 19.2 |
| RELAX0130 | 2.2 | 6.1 | 1.1 | 1.6 |
| RELAX0010-001 | 6.3 | 13.7 | 1.5 | 5.0 |
| RELAX0010-002 | 6.0 | 13.2 | 1.8 | 4.2 |

TABLE 7-continued

Binding of Fc-Relaxin fusion proteins in the Baculovirus
ELISA at 100 nM and 10 nM (-001, 002, 003 refer
to different batches of the same protein)

| Fusion name | non-specific binding BV plate (signal/background) at 100 nM | non-specific binding BLANK plate (signal/background)) at 100 nM | non-specific binding BV plate (signal/background)) at 10 nM | non-specific binding BLANK plate (signal/background)) at 10 nM |
|---|---|---|---|---|
| RELAX0010-003 | 2.4 | 21.0 | 0.8 | 7.7 |
| RELAX0009 | 17.8 | 22.2 | 4.8 | 21.5 |

Figure 7:
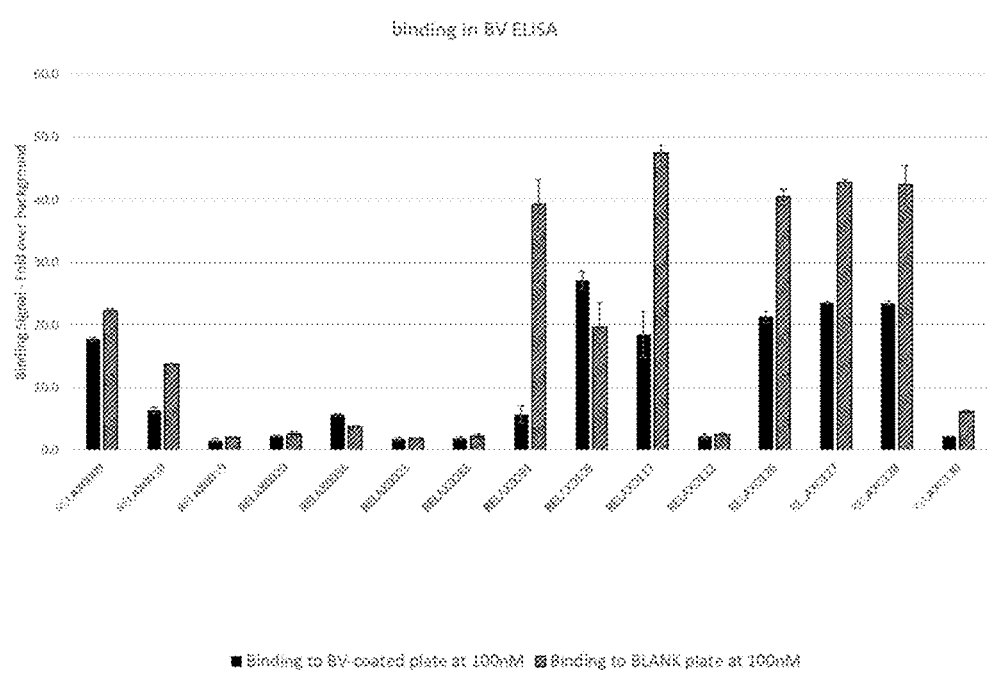
FIG. 7 shows the in vitro non-specific binding of heterodimeric fusions of the invention in Baculovirus (BV) ELISA assay.

As shown in Table 7 and FIG. 7, heterodimeric Relaxin-2 Fc fusion polypeptides exhibit lower non-specific binding when Relaxin chains are attached to the C-terminus using GS connectors. Some asymmetric and PA connectors, certain point mutations and positioning Relaxin chains at the N-termini, particularly in the context of a bivalent molecule (RELAX0117), increase non-specific binding to both blank and BV-coated plates. Some Fc-Relaxin proteins with particularly high non-specific binding exhibit greater non-specific binding to blank plates than to BV-coated plates at both high (100 nM) and low (10 nM) concentrations. Although the control molecules—the linker-containing bivalent RELAX0009, RELAX0010, RELAX0126, RELAX0127 and RELAX0128 all demonstrate high non-specific binding, neither the presence of the linker between chains A and B of Relaxin nor the bi-valency per se, drive high non-specific binding as can be demonstrated by low non-specific binding of RELAX0122.

Example 9: Stability in Solution

Figure 8:
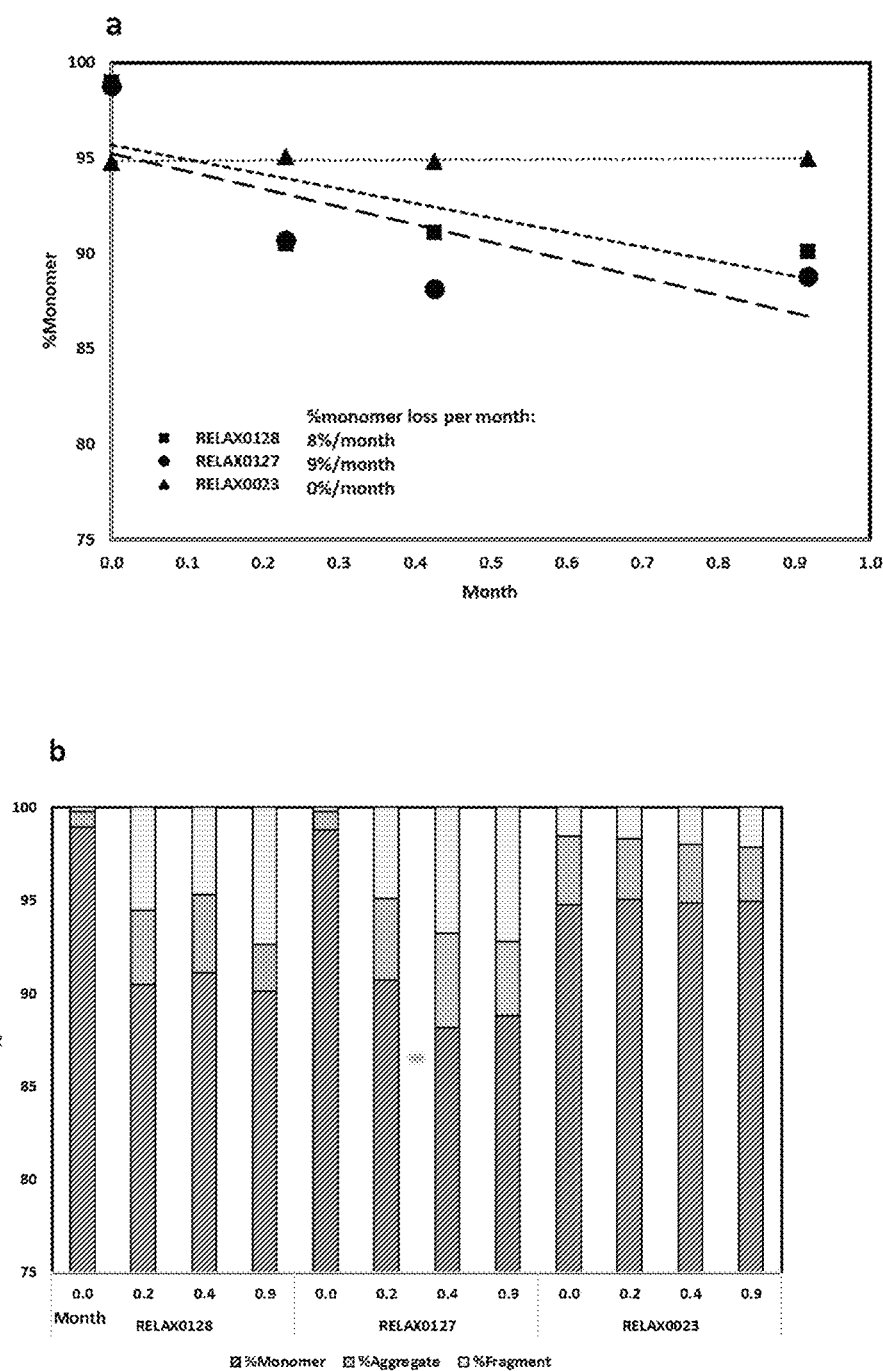
FIG. 8 shows the percentage of purity loss, aggregation and fragmentation of RELAX0023, RELAX0127 and RELAX0128 in solution upon storage.

Stability of RELAX0023 was assessed using High Performance Size Exclusion Chromatography (HP-SEC) and liquid chromatography-mass spectrometry (LC-MS) and compared to RELAX0127 and RELAX0128. HP-SEC with detection by absorbance at 280 nm can be used to measure purity, aggregation and fragmentation. The molecules were buffer exchanged into an optimised formulation composition and then concentrated up to 10 mg/mL. All samples were placed at a stressed temperature condition (40° C.) for up to 4 weeks. At the time points of 1, 2 and 4 weeks, the samples were collected and injected onto a size exclusion column and were eluted with an aqueous mobile phase isocratically at a fixed flow rate. Larger molecules are excluded from the pores of the size exclusion column to a greater extent than smaller molecules, and therefore elute earlier. Peaks eluting earlier than the monomer peak are recorded as aggregates. Peaks eluting after the monomer peak (excluding the buffer-related peak) are recorded as fragments. Results are reported as percent purity; percent aggregate; and percent fragment and shown in FIG. 8. RELAX0023 is the most stable molecule with a %purity loss rate of only 0.1% per month compared to 7.7% and 9.3% respectively for RELAX0128 and RELAX0127. Both RELAX0127 and RELAX0128 showed signs of aggregation, however the aggregate level for RELAX0023 did not increase, indicating a better physical solution stability. Fragmentation appeared to be the main factor for the purity loss with RELAX0127 having a 6.6% fragmentation per month and 6.8% for RELAX0128. RELAX0023 only has a fragmentation rate of 0.7% per month. At the meantime, after 4 weeks of storage at 40° C., the total peak area of RELAX0128 dropped from 22403 to 18216 (a decrease of 19%), and RELAX0127 dropped from 22225 to 18823 (a decrease of 15%). This significant loss in total peak area, together with a high fragmentation rate, indicated a potential high chemical degradation with these two molecules. It should be pointed out that, this loss in total areas had a strong impact to the chromatogram profiles of these two molecules. This explains why, despite an obvious increase in the aggregate peak areas after storage, RELAX0128 and RELAX0127 showed a lower percent aggregate at 4 weeks compared to previous timepoints. In contrast, the total peak area of RELAX0023 only dropped by 0.03%, from 21828 to 21761, indicating a better stability profile compared to RELAX0128 and RELAX0127.

Figure 9:
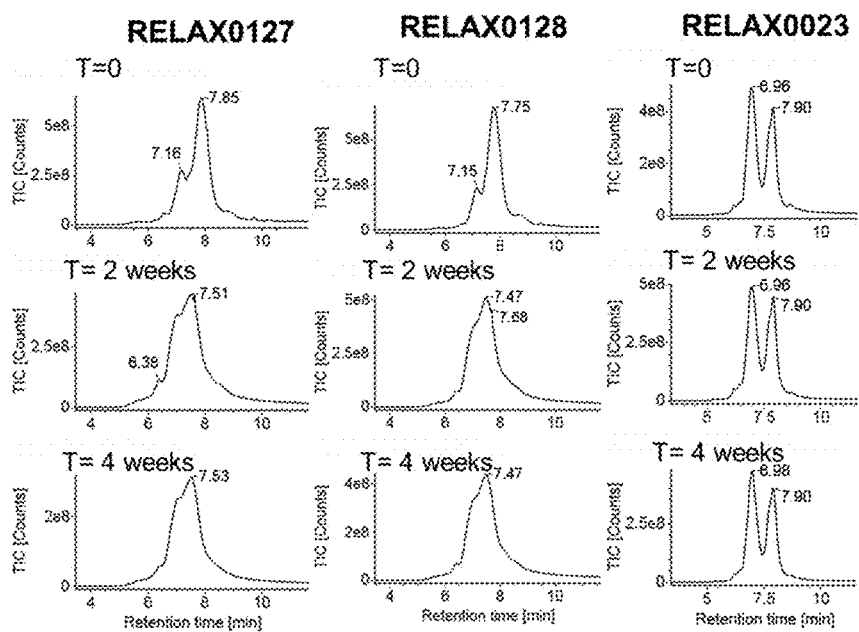
FIG. 9 shows the stability of RELAX0023, RELAX0127 and RELAX0128 in solution over time assessed by reduced LC-MS analysis. A) Total ion chromatograms B) Mass spectra of reduced molecules
Figure 9:
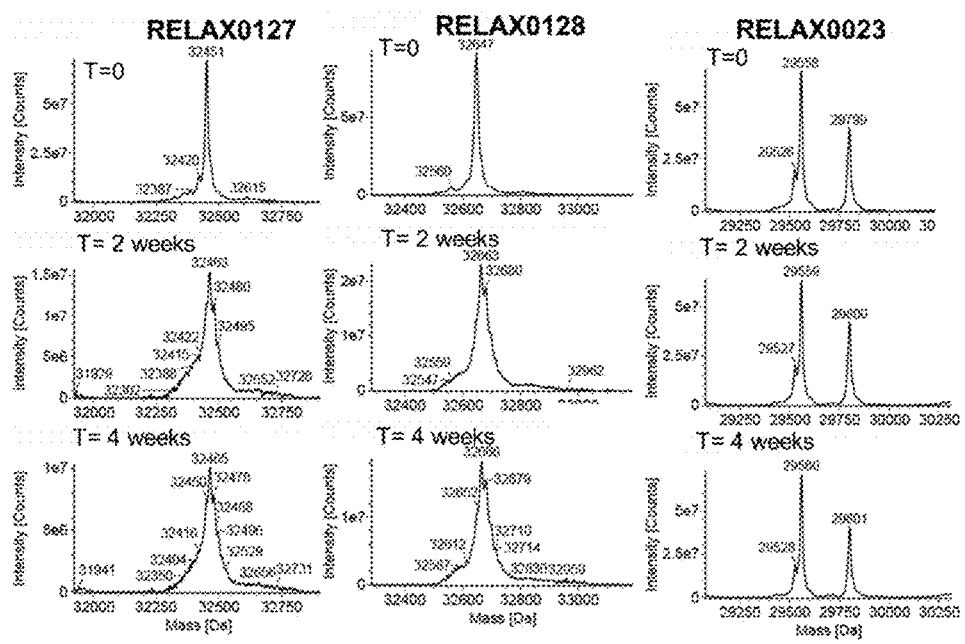

The fragmentation of the molecules was further verified by LC-MS using reduced mass analysis which showed that the fragment peaks of RELAX0127 and RELAX0128 increased in intensity after storage at 40° C. (FIG. 9A). In contrast, the fragment peak for RELAX0023 remained unchanged after stress. The mass spectra under reducing conditions also showed modification of RELAX0127 and RELAX0128 over time which is evidenced by a shift of the peak to a larger mass and a broadening of the peak indicating greater heterogeneity (FIG. 9B). In contrast, the intact mass spectra of RELAX0023 remained unchanged indicating no modification occurred. This study indicates that RELAX0023 has superior physical and chemical stability compared to RELAX0127 and RELAX0128.

Example 10: PK Profile of RELAX0023 in Cynomolgus Monkeys

The pharmacokinetic (PK) profile of RELAX0023 in cynomolgus monkeys was determined using a sandwich ELISA-based immunoassay. RELAX0023 was administered to a total of 12 female cynomolgus monkeys that were randomly assigned to 4 groups of 3 animals per group. Animals in Groups 1, 2, and 3 were administered 0.1, 1, and 10 mg/kg of RELAX0023 SC, respectively. Animals in Group 4 were given 10 mg/kg IV bolus of RELAX0023. Serum samples were collected 0.25 hour, 1 hour, 2 hours, 4 hours, 8 hours, 24 hours, 48 hours, 96 hours, 7 days, 14 days and 21 days post drug administration.

Assay plates were coated with goat anti-human IgG antibody and were incubated with cynomolgus monkey sera from group 1-4 animals. RELAX0023 bound to the plates was detected by an anti-relaxin antibody conjugated with HRP. Cynomolgus serum was diluted 1:10 prior to addition to plates. The lower limit of quantitation is 0.010 µg/mL and upper limit of quantitation is 0.300 µg/mL in 100% serum.

Results and Conclusion

Figure 10:
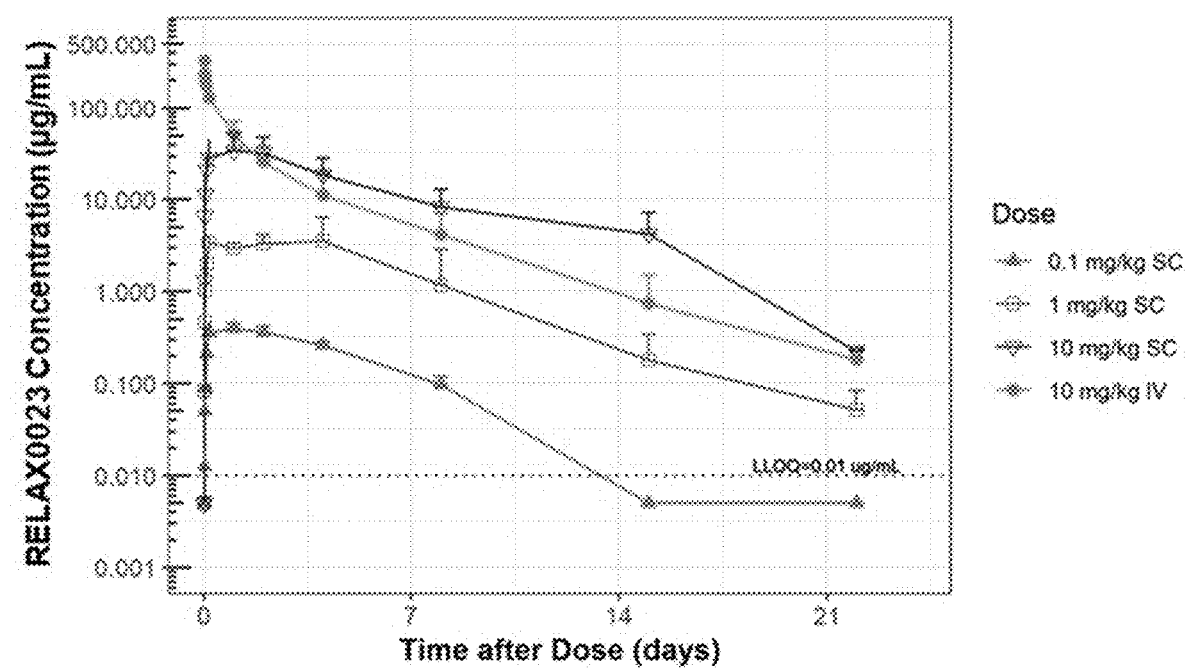
FIG. 10 shows the PK profile of RELAX0023 in cynomolgus monkeys following intravenous and subcutaneous injections.

FIG. 10 shows the mean serum concentration-time profiles of RELAX0023 in cynomolgus monkeys following a single dose. Following a single dose administered SC, RELAX0023 exhibited linear PK in a dose range of 0.01 to 10 mg/kg. A dose-proportional increase in $C_{max}$ was observed. Mean $C_{max}$ values were 0.400, 4.69, 34.8 µg/mL for 0.1, 1, and 10 mg/kg SC dose groups, respectively. A dose-proportional increase in $AUC_{0\text{-}last}$ values were also observed from 0.1 mg/kg to 10 mg/kg SC group. Mean $AUC_{0\text{-}last}$ values were 2.01, 25.5, 193 µg·day/mL for 0.1, 1, and 10 mg/kg SC dose groups, respectively. Overall, RELAX0023 PK is linear in the range of 0.1 mg/kg to 10 mg/kg with the mean CL/F of 51.0 mL/day/kg and mean $t_{1/2}$ of 3.07 days. SC bioavailability of RELAX0023 was estimated as 88.2%.

The invention claimed is:

1. A heterodimeric fusion comprising:
   (i) a polypeptide according to SEQ ID NO: 11; and
   (ii) a polypeptide according to SEQ ID NO: 20,
   wherein SEQ ID NO: 11 comprises a first heterodimerisation domain connected to a Relaxin A chain polypeptide;
   wherein SEQ ID NO: 20 comprises a second heterodimerisation domain connected to a Relaxin B chain polypeptide;
   wherein the first heterodimerisation domain heterodimerises with the second heterodimerisation domain, and wherein the heterodimeric fusion has Relaxin activity.

2. The heterodimeric fusion according to claim 1, wherein the Relaxin A chain polypeptide and the Relaxin B chain polypeptide are covalently bound by at least one inter-chain disulphide bond.

3. The heterodimeric fusion according to claim 1, wherein the Relaxin A chain polypeptide and the Relaxin B chain polypeptide are not covalently linked to each other by an amino acid linker.

4. A pharmaceutical composition comprising the heterodimeric fusion of claim 1 and a pharmaceutically acceptable excipient.

5. A kit comprising the pharmaceutical composition of claim 4.

* * * * *

SEQUENCE LISTING

<160> NUMBER OF SEQ ID NOS: 140

<210> SEQ ID NO 1
<211> LENGTH: 24
<212> TYPE: PRT
<213> ORGANISM: Unknown
<220> FEATURE:
<221> NAME/KEY: source
<223> OTHER INFORMATION: /note="Description of Unknown: Relaxin A Sequence"

<400> SEQUENCE: 1

Gln Leu Tyr Ser Ala Leu Ala Asn Lys Cys Cys His Val Gly Cys Thr
1               5                   10                  15

Lys Arg Ser Leu Ala Arg Phe Cys
            20

<210> SEQ ID NO 2
<211> LENGTH: 28
<212> TYPE: PRT
<213> ORGANISM: Unknown
<220> FEATURE:
<221> NAME/KEY: source
<223> OTHER INFORMATION: /note="Description of Unknown: Relaxin B Sequence"

<400> SEQUENCE: 2

Ser Trp Met Glu Glu Val Ile Lys Leu Cys Gly Arg Glu Leu Val Arg
1               5                   10                  15

Ala Gln Ile Ala Ile Cys Gly Met Ser Thr Trp Ser
            20                  25

<210> SEQ ID NO 3
<211> LENGTH: 226
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 3

Asp Lys Thr His Thr Cys Pro Pro Cys Pro Ala Pro Glu Phe Glu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

```
Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225
```

<210> SEQ ID NO 4
<211> LENGTH: 226
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

```
Asp Lys Thr His Thr Cys Pro Pro Cys Pro Ala Pro Glu Phe Glu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Glu Glu Met Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225
```

<210> SEQ ID NO 5
<211> LENGTH: 21
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 5

Gly Gly Gly Gly Ser Gly Gly Gly Gly Ser Gly Gly Gly Gly Ser Gly
1               5                   10                  15

Gly Gly Gly Gly Ser
            20

<210> SEQ ID NO 6
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Pro Ala Pro Ala Pro Ala Pro Ala Pro Ala Pro Ala Pro Ala Pro Ala
1               5                   10                  15

Pro Ala Pro Ala Gly
            20

<210> SEQ ID NO 7
<211> LENGTH: 312
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Ser Trp Met Glu Glu Val Ile Lys Leu Cys Gly Arg Glu Leu Val Arg
1               5                   10                  15

Ala Gln Ile Ala Ile Cys Gly Met Ser Thr Trp Ser Gly Gly Gly Gly
            20                  25                  30

Ser Gly Gly Gly Gly Ser Gly Gly Gly Ser Gln Leu Tyr Ser Ala
        35                  40                  45

Leu Ala Asn Lys Cys Cys His Val Gly Cys Thr Lys Arg Ser Leu Ala
    50                  55                  60

Arg Phe Cys Ala Ala Ala Gly Gly Gly Gly Ser Gly Gly Gly Gly Ser
65                  70                  75                  80

Gly Gly Gly Gly Ser Gly Gly Gly Ser Ala Cys Pro Pro Cys Pro
                85                  90                  95

Ala Pro Glu Phe Glu Gly Gly Pro Ser Val Phe Leu Phe Pro Pro Lys
            100                 105                 110

Pro Lys Asp Thr Leu Met Ile Ser Arg Thr Pro Glu Val Thr Cys Val
        115                 120                 125

Val Val Asp Val Ser His Glu Asp Pro Glu Val Lys Phe Asn Trp Tyr
130                 135                 140

Val Asp Gly Val Glu Val His Asn Ala Lys Thr Lys Pro Arg Glu Glu
145                 150                 155                 160

Gln Tyr Asn Ser Thr Tyr Arg Val Val Ser Val Leu Thr Val Leu His
            165                 170                 175

Gln Asp Trp Leu Asn Gly Lys Glu Tyr Lys Cys Lys Val Ser Asn Lys
        180                 185                 190

Ala Leu Pro Ala Ser Ile Glu Lys Thr Ile Ser Lys Ala Lys Gly Gln
```

```
                    195                 200                 205

Pro Arg Glu Pro Gln Val Tyr Thr Leu Pro Pro Ser Arg Glu Glu Met
210                 215                 220

Thr Lys Asn Gln Val Ser Leu Thr Cys Leu Val Lys Gly Phe Tyr Pro
225                 230                 235                 240

Ser Asp Ile Ala Val Glu Trp Glu Ser Asn Gly Gln Pro Glu Asn Asn
                245                 250                 255

Tyr Lys Thr Thr Pro Pro Val Leu Asp Ser Asp Gly Ser Phe Phe Leu
            260                 265                 270

Tyr Ser Lys Leu Thr Val Asp Lys Ser Arg Trp Gln Gln Gly Asn Val
        275                 280                 285

Phe Ser Cys Ser Val Met His Glu Ala Leu His Asn His Tyr Thr Gln
    290                 295                 300

Lys Ser Leu Ser Leu Ser Pro Gly
305                 310

<210> SEQ ID NO 8
<211> LENGTH: 309
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Ser Gly Gly Gly Gly Ser Gly Gly Gly
225                 230                 235                 240
```

```
Gly Ser Gln Leu Tyr Ser Ala Leu Ala Asn Lys Cys Cys His Val Gly
                245                 250                 255

Cys Thr Lys Arg Ser Leu Ala Arg Phe Cys Gly Gly Gly Ser Gly
            260                 265                 270

Gly Gly Gly Ser Gly Gly Gly Ser Ser Trp Met Glu Glu Val Ile
        275                 280                 285

Lys Leu Cys Gly Arg Glu Leu Val Arg Ala Gln Ile Ala Ile Cys Gly
290                 295                 300

Met Ser Thr Trp Ser
305
```

<210> SEQ ID NO 9
<211> LENGTH: 272
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 9

```
Gly Gly Ala Gly Ala Cys Pro Pro Cys Pro Ala Pro Glu Phe Glu
1               5                   10                  15

Gly Gly Pro Ser Val Phe Leu Phe Pro Pro Lys Pro Lys Asp Thr Leu
                20                  25                  30

Met Ile Ser Arg Thr Pro Glu Val Thr Cys Val Val Val Asp Val Ser
            35                  40                  45

His Glu Asp Pro Glu Val Lys Phe Asn Trp Tyr Val Asp Gly Val Glu
50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Ser
            100                 105                 110

Ile Glu Lys Thr Ile Ser Lys Ala Lys Gly Gln Pro Arg Glu Pro Gln
        115                 120                 125

Val Tyr Thr Leu Pro Pro Cys Arg Glu Glu Met Thr Lys Asn Gln Val
130                 135                 140

Ser Leu Trp Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
210                 215                 220

Ser Pro Gly Gly Gly Gly Ser Gly Gly Gly Ser Gly Gly Gly
225                 230                 235                 240

Gly Ser Gly Gly Gly Gly Ser Gln Leu Tyr Ser Ala Leu Ala Asn
                245                 250                 255

Lys Cys Cys His Val Gly Cys Thr Lys Arg Ser Leu Ala Arg Phe Cys
            260                 265                 270
```

<210> SEQ ID NO 10
<211> LENGTH: 272
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Gly Gly Ala Gly Gly Ala Cys Pro Pro Cys Pro Ala Pro Glu Phe Glu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Ser
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Trp Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Gly Gly Gly Ser Gly Gly Gly Ser Gly Gly Gly
225                 230                 235                 240

Gly Ser Gly Gly Gly Gly Ser Gln Leu Tyr Ser Ala Leu Ala Asn
                245                 250                 255

Lys Cys Cys His Val Gly Cys Thr Lys Arg Ser Leu Ala Arg Phe Cys
            260                 265                 270

<210> SEQ ID NO 11
<211> LENGTH: 271
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Asp Lys Thr His Thr Cys Pro Pro Cys Pro Ala Pro Glu Phe Glu Gly
1               5                   10                  15

Gly Pro Ser Val Phe Leu Phe Pro Pro Lys Pro Lys Asp Thr Leu Met

-continued

```
                20                  25                  30
Ile Ser Arg Thr Pro Glu Val Thr Cys Val Val Val Asp Val Ser His
         35                  40                  45
Glu Asp Pro Glu Val Lys Phe Asn Trp Tyr Val Asp Gly Val Glu Val
 50                  55                  60
His Asn Ala Lys Thr Lys Pro Arg Glu Glu Gln Tyr Asn Ser Thr Tyr
 65                  70                  75                  80
Arg Val Val Ser Val Leu Thr Val Leu His Gln Asp Trp Leu Asn Gly
                 85                  90                  95
Lys Glu Tyr Lys Cys Lys Val Ser Asn Lys Ala Leu Pro Ala Ser Ile
            100                 105                 110
Glu Lys Thr Ile Ser Lys Ala Lys Gly Gln Pro Arg Glu Pro Gln Val
        115                 120                 125
Tyr Thr Leu Pro Pro Cys Arg Glu Glu Met Thr Lys Asn Gln Val Ser
    130                 135                 140
Leu Trp Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
Pro Gly Gly Gly Gly Ser Gly Gly Gly Gly Ser Gly Gly Gly Gly
225                 230                 235                 240
Ser Gly Gly Gly Gly Ser Gln Leu Tyr Ser Ala Leu Ala Asn Lys
                245                 250                 255
Cys Cys His Val Gly Cys Thr Lys Arg Ser Leu Ala Arg Phe Cys
            260                 265                 270
```

<210> SEQ ID NO 12
<211> LENGTH: 272
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 12

```
Gly Gly Ala Gly Gly Ala Cys Pro Pro Cys Pro Ala Pro Glu Phe Glu
 1               5                  10                  15
Gly Gly Pro Ser Val Phe Leu Phe Pro Pro Lys Pro Lys Asp Thr Leu
                20                  25                  30
Met Ile Ser Arg Thr Pro Glu Val Thr Cys Val Val Val Asp Val Ser
            35                  40                  45
His Glu Asp Pro Glu Val Lys Phe Asn Trp Tyr Val Asp Gly Val Glu
         50                  55                  60
Val His Asn Ala Lys Thr Lys Pro Arg Glu Glu Gln Tyr Asn Ser Thr
 65                  70                  75                  80
Tyr Arg Val Val Ser Val Leu Thr Val Leu His Gln Asp Trp Leu Asn
                 85                  90                  95
Gly Lys Glu Tyr Lys Cys Lys Val Ser Asn Lys Ala Leu Pro Ala Ser
            100                 105                 110
```

Ile Glu Lys Thr Ile Ser Lys Ala Lys Gly Gln Pro Arg Glu Pro Gln
            115                 120                 125

Val Cys Thr Leu Pro Pro Ser Arg Glu Glu Met Thr Lys Asn Gln Val
        130                 135                 140

Ser Leu Ser Cys Ala Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                    165                 170                 175

Pro Val Leu Asp Ser Asp Gly Ser Phe Phe Leu Val Ser Lys Leu Thr
                180                 185                 190

Val Asp Lys Ser Arg Trp Gln Gln Gly Asn Val Phe Ser Cys Ser Val
            195                 200                 205

Met His Glu Ala Leu His Asn His Tyr Thr Gln Lys Ser Leu Ser Leu
        210                 215                 220

Ser Pro Gly Gly Gly Gly Ser Gly Gly Gly Ser Gly Gly Gly
225                 230                 235                 240

Gly Ser Gly Gly Gly Gly Ser Gln Leu Tyr Ser Ala Leu Ala Asn
                    245                 250                 255

Lys Cys Cys His Val Gly Cys Thr Lys Arg Ser Leu Ala Arg Phe Cys
                260                 265                 270

<210> SEQ ID NO 13
<211> LENGTH: 272
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 13

Gly Gly Ala Gly Gly Ala Cys Pro Pro Cys Pro Ala Pro Glu Phe Glu
1               5                   10                  15

Gly Gly Pro Ser Val Phe Leu Phe Pro Pro Lys Pro Lys Asp Thr Leu
                20                  25                  30

Met Ile Ser Arg Thr Pro Glu Val Thr Cys Val Val Val Asp Val Ser
            35                  40                  45

His Glu Asp Pro Glu Val Lys Phe Asn Trp Tyr Val Asp Gly Val Glu
        50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                    85                  90                  95

Gly Lys Glu Tyr Lys Cys Lys Val Ser Asn Lys Ala Leu Pro Ala Ser
                100                 105                 110

Ile Glu Lys Thr Ile Ser Lys Ala Lys Gly Gln Pro Arg Glu Pro Gln
            115                 120                 125

Val Tyr Thr Leu Pro Pro Ser Arg Glu Glu Met Thr Lys Asn Gln Val
        130                 135                 140

Ser Leu Ser Cys Ala Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                    165                 170                 175

Pro Val Leu Asp Ser Asp Gly Ser Phe Phe Leu Val Ser Lys Leu Thr
                180                 185                 190

```
Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Gly Gly Gly Ser Gly Gly Gly Ser Gly Gly Gly
225                 230                 235                 240

Gly Ser Gly Gly Gly Gly Ser Gln Leu Tyr Ser Ala Leu Ala Asn
                245                 250                 255

Lys Cys Cys His Val Gly Cys Thr Lys Arg Ser Leu Ala Arg Phe Cys
            260                 265                 270

<210> SEQ ID NO 14
<211> LENGTH: 275
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Asp Lys Thr His Thr Cys Pro Pro Cys Pro Ala Pro Glu Phe Glu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Glu Glu Met Thr Lys Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Ser Gly Gly Gly Gly Ser Gly Gly Gly Gly
225                 230                 235                 240

Ser Gly Gly Gly Gly Ser Ser Trp Met Glu Glu Val Ile Lys Leu
                245                 250                 255

Cys Gly Arg Glu Leu Val Arg Ala Gln Ile Ala Ile Cys Gly Met Ser
            260                 265                 270

Thr Trp Ser
```

```
<210> SEQ ID NO 15
<211> LENGTH: 276
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Gly Gly Ala Gly Gly Ala Cys Pro Pro Cys Pro Ala Pro Glu Phe Glu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Ser
            100                 105                 110

Ile Glu Lys Thr Ile Ser Lys Ala Lys Gly Gln Pro Arg Glu Pro Gln
        115                 120                 125

Val Tyr Thr Leu Pro Pro Cys Arg Glu Glu Met Thr Lys Asn Gln Val
    130                 135                 140

Ser Leu Trp Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Gly Gly Gly Ser Gly Gly Gly Ser Gly Gly Gly Gly Gly
225                 230                 235                 240

Gly Ser Gly Gly Gly Gly Ser Ser Trp Met Glu Glu Val Ile Lys
                245                 250                 255

Leu Cys Gly Arg Glu Leu Val Arg Ala Gln Ile Ala Ile Cys Gly Met
            260                 265                 270

Ser Thr Trp Ser
        275

<210> SEQ ID NO 16
<211> LENGTH: 276
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16
```

-continued

```
Gly Gly Ala Gly Gly Ala Cys Pro Pro Cys Pro Ala Pro Glu Phe Glu
1               5                   10                  15

Gly Gly Pro Ser Val Phe Leu Phe Pro Pro Lys Pro Lys Asp Thr Leu
                20                  25                  30

Met Ile Ser Arg Thr Pro Glu Val Thr Cys Val Val Val Asp Val Ser
            35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Ser
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Trp Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Gly Gly Gly Ser Gly Gly Gly Ser Gly Gly Gly
225                 230                 235                 240

Gly Ser Gly Gly Gly Gly Ser Ser Trp Met Glu Val Ile Lys
                245                 250                 255

Leu Cys Gly Arg Glu Leu Val Arg Ala Gln Ile Ala Ile Cys Gly Met
            260                 265                 270

Ser Thr Trp Ser
        275
```

<210> SEQ ID NO 17
<211> LENGTH: 271
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 17

```
Asp Lys Thr His Thr Cys Pro Pro Cys Pro Ala Pro Glu Phe Glu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60
```

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Ser Gly Gly Gly Ser Gly Gly Gly Gly
225                 230                 235                 240

Ser Gly Gly Gly Gly Ser Gln Leu Tyr Ser Ala Leu Ala Asn Lys
                245                 250                 255

Cys Cys His Val Gly Cys Thr Lys Arg Ser Leu Ala Arg Phe Cys
    260                 265                 270

<210> SEQ ID NO 18
<211> LENGTH: 276
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Gly Gly Ala Gly Gly Ala Cys Pro Pro Cys Pro Ala Pro Glu Phe Glu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Ser
            100                 105                 110

Ile Glu Lys Thr Ile Ser Lys Ala Lys Gly Gln Pro Arg Glu Pro Gln
        115                 120                 125

Val Cys Thr Leu Pro Pro Ser Arg Glu Glu Met Thr Lys Asn Gln Val
    130                 135                 140

Ser Leu Ser Cys Ala Val Lys Gly Phe Tyr Pro Ser Asp Ile Ala Val

```
                145                 150                 155                 160
Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Val Ser Lys Leu Thr
            180                 185                 190

Val Asp Lys Ser Arg Trp Gln Gln Gly Asn Val Phe Ser Cys Ser Val
            195                 200                 205

Met His Glu Ala Leu His Asn His Tyr Thr Gln Lys Ser Leu Ser Leu
    210                 215                 220

Ser Pro Gly Gly Gly Gly Ser Gly Gly Gly Ser Gly Gly Gly
225                 230                 235                 240

Gly Ser Gly Gly Gly Gly Ser Ser Trp Met Glu Glu Val Ile Lys
                245                 250                 255

Leu Cys Gly Arg Glu Leu Val Arg Ala Gln Ile Ala Ile Cys Gly Met
            260                 265                 270

Ser Thr Trp Ser
        275

<210> SEQ ID NO 19
<211> LENGTH: 276
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Gly Gly Ala Gly Gly Ala Cys Pro Pro Cys Pro Ala Pro Glu Phe Glu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Ser
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Ser Cys Ala Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Val Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220
```

```
Ser Pro Gly Gly Gly Gly Ser Gly Gly Gly Ser Gly Gly
225                 230                 235                 240

Gly Ser Gly Gly Gly Gly Ser Ser Trp Met Glu Glu Val Ile Lys
            245                 250                 255

Leu Cys Gly Arg Glu Leu Val Arg Ala Gln Ile Ala Ile Cys Gly Met
            260                 265                 270

Ser Thr Trp Ser
            275
```

<210> SEQ ID NO 20
<211> LENGTH: 275
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 20

```
Asp Lys Thr His Thr Cys Pro Pro Cys Pro Ala Pro Glu Phe Glu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
            85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
            115                 120                 125

Cys Thr Leu Pro Pro Ser Arg Glu Glu Met Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
            165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
210                 215                 220

Pro Gly Gly Gly Gly Ser Gly Gly Gly Ser Gly Gly Gly
225                 230                 235                 240

Ser Gly Gly Gly Gly Ser Ser Trp Met Glu Glu Val Ile Lys Leu
            245                 250                 255

Cys Gly Arg Glu Leu Val Arg Ala Gln Ile Ala Ile Cys Gly Met Ser
            260                 265                 270

Thr Trp Ser
        275
```

<210> SEQ ID NO 21
<211> LENGTH: 266
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 21

```
Asp Lys Thr His Thr Cys Pro Pro Cys Pro Ala Pro Glu Phe Glu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Glu Glu Met Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Ser Gly Gly Gly Gly Ser Gly Gly Gly Gly Gly
225                 230                 235                 240

Gly Ser Gln Leu Tyr Ser Ala Leu Ala Asn Lys Cys Cys His Val Gly
                245                 250                 255

Cys Thr Lys Arg Ser Leu Ala Arg Phe Cys
            260                 265
```

<210> SEQ ID NO 22
<211> LENGTH: 270
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 22

```
Asp Lys Thr His Thr Cys Pro Pro Cys Pro Ala Pro Glu Phe Glu Gly
1               5                   10                  15

Gly Pro Ser Val Phe Leu Phe Pro Pro Lys Pro Lys Asp Thr Leu Met
```

```
            20                  25                  30

Ile Ser Arg Thr Pro Glu Val Thr Cys Val Val Asp Val Ser His
        35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Glu Glu Met Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Gly Gly Gly Ser Gly Gly Gly Ser Gly Gly Gly Gly
225                 230                 235                 240

Gly Ser Ser Trp Met Glu Glu Val Ile Lys Leu Cys Gly Arg Glu Leu
                245                 250                 255

Val Arg Ala Gln Ile Ala Ile Cys Gly Met Ser Thr Trp Ser
            260                 265                 270

<210> SEQ ID NO 23
<211> LENGTH: 261
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Asp Lys Thr His Thr Cys Pro Pro Cys Pro Ala Pro Glu Phe Glu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Asp Val Ser His
        35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Ser Ile
            100                 105                 110
```

```
Glu Lys Thr Ile Ser Lys Ala Lys Gly Gln Pro Arg Glu Pro Gln Val
            115                 120                 125

Tyr Thr Leu Pro Pro Cys Arg Glu Glu Met Thr Lys Asn Gln Val Ser
        130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
        210                 215                 220

Pro Gly Gly Gly Gly Ser Gly Gly Gly Gly Ser Gln Leu Tyr
225                 230                 235                 240

Ser Ala Leu Ala Asn Lys Cys Cys His Val Gly Cys Thr Lys Arg Ser
                245                 250                 255

Leu Ala Arg Phe Cys
            260

<210> SEQ ID NO 24
<211> LENGTH: 265
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 24

Asp Lys Thr His Thr Cys Pro Pro Cys Pro Ala Pro Glu Phe Glu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190
```

-continued

```
Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
        210                 215                 220

Pro Gly Gly Gly Gly Ser Gly Gly Gly Gly Ser Ser Trp Met
225                 230                 235                 240

Glu Glu Val Ile Lys Leu Cys Gly Arg Glu Leu Val Arg Ala Gln Ile
                245                 250                 255

Ala Ile Cys Gly Met Ser Thr Trp Ser
            260                 265

<210> SEQ ID NO 25
<211> LENGTH: 256
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Asp Lys Thr His Thr Cys Pro Pro Cys Pro Ala Pro Glu Phe Glu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Glu Glu Met Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Gly Ser Gln Leu Tyr Ser Ala Leu Ala Asn
225                 230                 235                 240

Lys Cys Cys His Val Gly Cys Thr Lys Arg Ser Leu Ala Arg Phe Cys
                245                 250                 255

<210> SEQ ID NO 26
<211> LENGTH: 260
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Asp Lys Thr His Thr Cys Pro Pro Cys Pro Ala Pro Glu Phe Glu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Glu Glu Met Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Gly Ser Ser Trp Met Glu Glu Val Ile Lys
225                 230                 235                 240

Leu Cys Gly Arg Glu Leu Val Arg Ala Gln Ile Ala Ile Cys Gly Met
                245                 250                 255

Ser Thr Trp Ser
            260

<210> SEQ ID NO 27
<211> LENGTH: 271
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Asp Lys Thr His Thr Cys Pro Pro Cys Pro Ala Pro Glu Phe Glu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45
```

Glu Asp Pro Glu Val Lys Phe Asn Trp Tyr Val Asp Gly Val Glu Val
              50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                     85                  90                  95

Lys Glu Tyr Lys Cys Lys Val Ser Asn Lys Ala Leu Pro Ala Ser Ile
                100                 105                 110

Glu Lys Thr Ile Ser Lys Ala Lys Gly Gln Pro Arg Glu Pro Gln Val
            115                 120                 125

Tyr Thr Leu Pro Pro Cys Arg Glu Glu Met Thr Lys Asn Gln Val Ser
        130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
        210                 215                 220

Pro Gly Ala Pro Ala Pro Ala Pro Ala Pro Ala Pro Ala Pro Ala Pro
225                 230                 235                 240

Ala Pro Ala Pro Ala Gly Ser Gln Leu Tyr Ser Ala Leu Ala Asn Lys
                245                 250                 255

Cys Cys His Val Gly Cys Thr Lys Arg Ser Leu Ala Arg Phe Cys
            260                 265                 270

<210> SEQ ID NO 28
<211> LENGTH: 275
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Asp Lys Thr His Thr Cys Pro Pro Cys Pro Ala Pro Glu Phe Glu Gly
 1               5                  10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                     85                  90                  95

Lys Glu Tyr Lys Cys Lys Val Ser Asn Lys Ala Leu Pro Ala Ser Ile
                100                 105                 110

Glu Lys Thr Ile Ser Lys Ala Lys Gly Gln Pro Arg Glu Pro Gln Val
            115                 120                 125

```
Cys Thr Leu Pro Pro Ser Arg Glu Glu Met Thr Lys Asn Gln Val Ser
            130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Ala Pro Ala Pro Ala Pro Ala Pro Ala Pro Ala Pro Ala Pro
225                 230                 235                 240

Ala Pro Ala Pro Ala Gly Ser Ser Trp Met Glu Val Ile Lys Leu
                245                 250                 255

Cys Gly Arg Glu Leu Val Arg Ala Gln Ile Ala Ile Cys Gly Met Ser
            260                 265                 270

Thr Trp Ser
        275

<210> SEQ ID NO 29
<211> LENGTH: 266
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Asp Lys Thr His Thr Cys Pro Pro Cys Pro Ala Pro Glu Phe Glu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
```

```
            195                 200                 205
His Glu Ala Leu His Asn His Tyr Thr Gln Lys Ser Leu Ser Leu Ser
    210                 215                 220

Pro Gly Ala Ala Pro Ala Pro Ala Pro Ala Pro Ala Pro Ala Pro Ala
225                 230                 235                 240

Gly Ser Gln Leu Tyr Ser Ala Leu Ala Asn Lys Cys Cys His Val Gly
                245                 250                 255

Cys Thr Lys Arg Ser Leu Ala Arg Phe Cys
                260                 265

<210> SEQ ID NO 30
<211> LENGTH: 270
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Asp Lys Thr His Thr Cys Pro Pro Cys Pro Ala Pro Glu Phe Glu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Glu Glu Met Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Ala Ala Pro Ala Pro Ala Pro Ala Pro Ala Pro Ala Pro Ala
225                 230                 235                 240

Gly Ser Ser Trp Met Glu Glu Val Ile Lys Leu Cys Gly Arg Glu Leu
                245                 250                 255

Val Arg Ala Gln Ile Ala Ile Cys Gly Met Ser Thr Trp Ser
            260                 265                 270

<210> SEQ ID NO 31
```

<211> LENGTH: 261
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 31

```
Asp Lys Thr His Thr Cys Pro Pro Cys Pro Ala Pro Glu Phe Glu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Glu Glu Met Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Ala Pro Ala Pro Ala Pro Ala Gly Ser Gln Leu Tyr
225                 230                 235                 240

Ser Ala Leu Ala Asn Lys Cys Cys His Val Gly Cys Thr Lys Arg Ser
                245                 250                 255

Leu Ala Arg Phe Cys
            260
```

<210> SEQ ID NO 32
<211> LENGTH: 265
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 32

```
Asp Lys Thr His Thr Cys Pro Pro Cys Pro Ala Pro Glu Phe Glu Gly
1               5                   10                  15

Gly Pro Ser Val Phe Leu Phe Pro Pro Lys Pro Lys Asp Thr Leu Met
            20                  25                  30
```

```
Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
            115                 120                 125

Cys Thr Leu Pro Pro Ser Arg Glu Glu Met Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Ala Pro Ala Pro Ala Pro Ala Gly Ser Ser Trp Met
225                 230                 235                 240

Glu Glu Val Ile Lys Leu Cys Gly Arg Glu Leu Val Arg Ala Gln Ile
                245                 250                 255

Ala Ile Cys Gly Met Ser Thr Trp Ser
            260                 265

<210> SEQ ID NO 33
<211> LENGTH: 272
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Asp Lys Thr His Thr Ala Cys Pro Pro Cys Pro Ala Pro Glu Phe Glu
 1               5                  10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
 65                  70                  75                  80

Tyr Arg Val Val Ser Val Leu Thr Val Leu His Gln Asp Trp Leu Asn
                 85                  90                  95

Gly Lys Glu Tyr Lys Cys Lys Val Ser Asn Lys Ala Leu Pro Ala Ser
            100                 105                 110

Ile Glu Lys Thr Ile Ser Lys Ala Lys Gly Gln Pro Arg Glu Pro Gln
```

```
                115                 120                 125
Val Tyr Thr Leu Pro Pro Cys Arg Glu Glu Met Thr Lys Asn Gln Val
        130                 135                 140

Ser Leu Trp Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
        180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
        210                 215                 220

Ser Pro Gly Gly Gly Gly Ser Gly Gly Gly Ser Gly Gly Gly Gly Gly
225                 230                 235                 240

Gly Ser Gly Gly Gly Gly Ser Gln Leu Tyr Ser Ala Leu Ala Asn
                245                 250                 255

Glu Cys Cys His Val Gly Cys Thr Lys Arg Ser Leu Ala Arg Phe Cys
                260                 265                 270

<210> SEQ ID NO 34
<211> LENGTH: 272
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Asp Lys Thr His Thr Ala Cys Pro Pro Cys Pro Ala Pro Glu Phe Glu
1               5                   10                  15

Gly Gly Pro Ser Val Phe Leu Phe Pro Pro Lys Pro Lys Asp Thr Leu
                20                  25                  30

Met Ile Ser Arg Thr Pro Glu Val Thr Cys Val Val Val Asp Val Ser
            35                  40                  45

His Glu Asp Pro Glu Val Lys Phe Asn Trp Tyr Val Asp Gly Val Glu
        50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Ser
            100                 105                 110

Ile Glu Lys Thr Ile Ser Lys Ala Lys Gly Gln Pro Arg Glu Pro Gln
        115                 120                 125

Val Tyr Thr Leu Pro Pro Cys Arg Glu Glu Met Thr Lys Asn Gln Val
        130                 135                 140

Ser Leu Trp Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
        180                 185                 190

Val Asp Lys Ser Arg Trp Gln Gln Gly Asn Val Phe Ser Cys Ser Val
        195                 200                 205
```

```
Met His Glu Ala Leu His Asn His Tyr Thr Gln Lys Ser Leu Ser Leu
    210                 215                 220

Ser Pro Gly Gly Gly Gly Ser Gly Gly Gly Ser Gly Gly Gly
225                 230                 235                 240

Gly Ser Gly Gly Gly Gly Ser Gln Leu Tyr Ser Ala Leu Ala Asn
            245                 250                 255

His Cys Cys His Val Gly Cys Thr Lys Arg Ser Leu Ala Arg Phe Cys
            260                 265                 270

<210> SEQ ID NO 35
<211> LENGTH: 272
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Asp Lys Thr His Thr Ala Cys Pro Pro Cys Pro Ala Pro Glu Phe Glu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Ser
            100                 105                 110

Ile Glu Lys Thr Ile Ser Lys Ala Lys Gly Gln Pro Arg Glu Pro Gln
        115                 120                 125

Val Tyr Thr Leu Pro Pro Cys Arg Glu Glu Met Thr Lys Asn Gln Val
    130                 135                 140

Ser Leu Trp Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Gly Gly Gly Ser Gly Gly Gly Ser Gly Gly Gly
225                 230                 235                 240

Gly Ser Gly Gly Gly Gly Ser Gln Leu Tyr Ser Ala Leu Ala Asn
            245                 250                 255

Leu Cys Cys His Val Gly Cys Thr Lys Arg Ser Leu Ala Arg Phe Cys
            260                 265                 270

<210> SEQ ID NO 36
<211> LENGTH: 272
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Asp Lys Thr His Thr Ala Cys Pro Pro Cys Pro Ala Pro Glu Phe Glu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Ser
            100                 105                 110

Ile Glu Lys Thr Ile Ser Lys Ala Lys Gly Gln Pro Arg Glu Pro Gln
        115                 120                 125

Val Tyr Thr Leu Pro Pro Cys Arg Glu Glu Met Thr Lys Asn Gln Val
    130                 135                 140

Ser Leu Trp Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Gly Gly Gly Ser Gly Gly Gly Ser Gly Gly Gly
225                 230                 235                 240

Gly Ser Gly Gly Gly Gly Ser Gln Leu Tyr Ser Ala Leu Ala Asn
            245                 250                 255

Met Cys Cys His Val Gly Cys Thr Lys Arg Ser Leu Ala Arg Phe Cys
    260                 265                 270

<210> SEQ ID NO 37
<211> LENGTH: 272
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Asp Lys Thr His Thr Ala Cys Pro Pro Cys Pro Ala Pro Glu Phe Glu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
```

```
              35                  40                  45
His Glu Asp Pro Glu Val Lys Phe Asn Trp Tyr Val Asp Gly Val Glu
     50                  55                  60

Val His Asn Ala Lys Thr Lys Pro Arg Glu Glu Gln Tyr Asn Ser Thr
 65                  70                  75                  80

Tyr Arg Val Val Ser Val Leu Thr Val Leu His Gln Asp Trp Leu Asn
                 85                  90                  95

Gly Lys Glu Tyr Lys Cys Lys Val Ser Asn Lys Ala Leu Pro Ala Ser
                100                 105                 110

Ile Glu Lys Thr Ile Ser Lys Ala Lys Gly Gln Pro Arg Glu Pro Gln
            115                 120                 125

Val Tyr Thr Leu Pro Pro Cys Arg Glu Glu Met Thr Lys Asn Gln Val
        130                 135                 140

Ser Leu Trp Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
                180                 185                 190

Val Asp Lys Ser Arg Trp Gln Gln Gly Asn Val Phe Ser Cys Ser Val
            195                 200                 205

Met His Glu Ala Leu His Asn His Tyr Thr Gln Lys Ser Leu Ser Leu
        210                 215                 220

Ser Pro Gly Gly Gly Gly Ser Gly Gly Gly Ser Gly Gly Gly
225                 230                 235                 240

Gly Ser Gly Gly Gly Gly Ser Gln Leu Tyr Ser Ala Leu Ala Asn
                245                 250                 255

Lys Cys Cys His Val Gly Cys Thr Lys Glu Ser Leu Ala Arg Phe Cys
                260                 265                 270

<210> SEQ ID NO 38
<211> LENGTH: 272
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Asp Lys Thr His Thr Ala Cys Pro Pro Cys Pro Ala Pro Glu Phe Glu
1                5                  10                  15

Gly Gly Pro Ser Val Phe Leu Phe Pro Pro Lys Pro Lys Asp Thr Leu
                20                  25                  30

Met Ile Ser Arg Thr Pro Glu Val Thr Cys Val Val Val Asp Val Ser
            35                  40                  45

His Glu Asp Pro Glu Val Lys Phe Asn Trp Tyr Val Asp Gly Val Glu
     50                  55                  60

Val His Asn Ala Lys Thr Lys Pro Arg Glu Glu Gln Tyr Asn Ser Thr
 65                  70                  75                  80

Tyr Arg Val Val Ser Val Leu Thr Val Leu His Gln Asp Trp Leu Asn
                 85                  90                  95

Gly Lys Glu Tyr Lys Cys Lys Val Ser Asn Lys Ala Leu Pro Ala Ser
                100                 105                 110

Ile Glu Lys Thr Ile Ser Lys Ala Lys Gly Gln Pro Arg Glu Pro Gln
            115                 120                 125
```

```
Val Tyr Thr Leu Pro Pro Cys Arg Glu Glu Met Thr Lys Asn Gln Val
    130                 135                 140

Ser Leu Trp Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
                180                 185                 190

Val Asp Lys Ser Arg Trp Gln Gln Gly Asn Val Phe Ser Cys Ser Val
            195                 200                 205

Met His Glu Ala Leu His Asn His Tyr Thr Gln Lys Ser Leu Ser Leu
            210                 215                 220

Ser Pro Gly Gly Gly Gly Ser Gly Gly Gly Ser Gly Gly Gly
225                 230                 235                 240

Gly Ser Gly Gly Gly Gly Ser Gln Leu Tyr Ser Ala Leu Ala Asn
                245                 250                 255

Lys Cys Cys His Val Gly Cys Thr Lys His Ser Leu Ala Arg Phe Cys
                260                 265                 270
```

<210> SEQ ID NO 39
<211> LENGTH: 271
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 39

```
Asp Lys Thr His Thr Cys Pro Pro Cys Pro Ala Pro Glu Phe Glu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Ser Ile
                100                 105                 110

Glu Lys Thr Ile Ser Lys Ala Lys Gly Gln Pro Arg Glu Pro Gln Val
            115                 120                 125

Tyr Thr Leu Pro Pro Cys Arg Glu Glu Met Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205
```

```
His Glu Ala Leu His Asn His Tyr Thr Gln Lys Ser Leu Ser Leu Ser
    210                 215                 220

Pro Gly Gly Gly Gly Ser Gly Gly Gly Ser Gly Gly Gly Gly
225                 230                 235                 240

Ser Gly Gly Gly Gly Ser Gln Leu Tyr Ser Ala Leu Ala Asn Lys
                245                 250                 255

Cys Cys His Val Gly Cys Thr Lys Arg Ser Leu Ala Ala Phe Cys
                260                 265                 270

<210> SEQ ID NO 40
<211> LENGTH: 271
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Asp Lys Thr His Thr Cys Pro Pro Cys Pro Ala Pro Glu Phe Glu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Glu Glu Met Thr Lys Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Ser Gly Gly Gly Ser Gly Gly Gly Gly
225                 230                 235                 240

Ser Gly Gly Gly Gly Ser Gln Leu Tyr Ser Ala Leu Ala Asn Lys
                245                 250                 255

Cys Cys His Val Gly Cys Thr Lys Arg Ser Leu Ala Ile Phe Cys
                260                 265                 270

<210> SEQ ID NO 41
<211> LENGTH: 271
<212> TYPE: PRT
```

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 41

Asp Lys Thr His Thr Cys Pro Pro Cys Pro Ala Pro Glu Phe Glu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Glu Glu Met Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Ser Gly Gly Gly Ser Gly Gly Gly Gly
225                 230                 235                 240

Ser Gly Gly Gly Gly Ser Gln Leu Tyr Ser Ala Leu Ala Asn Lys
            245                 250                 255

Cys Cys His Val Gly Cys Thr Lys Arg Ser Leu Ala Met Phe Cys
        260                 265                 270

<210> SEQ ID NO 42
<211> LENGTH: 271
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 42

Asp Lys Thr His Thr Cys Pro Pro Cys Pro Ala Pro Glu Phe Glu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Glu Glu Met Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Ser Gly Gly Gly Ser Gly Gly Gly Gly
225                 230                 235                 240

Ser Gly Gly Gly Gly Ser Gln Leu Tyr Ser Ala Leu Ala Asn Lys
                245                 250                 255

Cys Cys His Val Gly Cys Thr Lys Arg Ser Leu Ala Gln Phe Cys
            260                 265                 270

<210> SEQ ID NO 43
<211> LENGTH: 271
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Asp Lys Thr His Thr Cys Pro Pro Cys Pro Ala Pro Glu Phe Glu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Glu Glu Met Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
210                 215                 220

Pro Gly Gly Gly Gly Ser Gly Gly Gly Ser Gly Gly Gly Gly
225                 230                 235                 240

Ser Gly Gly Gly Gly Ser Gln Leu Tyr Ser Ala Leu Ala Asn Lys
                245                 250                 255

Cys Cys His Val Gly Cys Thr Lys Arg Ser Leu Ala Ser Phe Cys
            260                 265                 270

<210> SEQ ID NO 44
<211> LENGTH: 271
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Asp Lys Thr His Thr Cys Pro Pro Cys Pro Ala Pro Glu Phe Glu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Glu Glu Met Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser

```
                210                 215                 220
Pro Gly Gly Gly Gly Ser Gly Gly Gly Ser Gly Gly Gly
225                 230                 235                 240

Ser Gly Gly Gly Gly Ser Gln Leu Tyr Ser Ala Leu Ala Asn Lys
                245                 250                 255

Cys Cys His Val Gly Cys Thr Lys Arg Ser Leu Ala Arg Glu Cys
                260                 265                 270

<210> SEQ ID NO 45
<211> LENGTH: 271
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Asp Lys Thr His Thr Cys Pro Pro Cys Pro Ala Pro Glu Phe Glu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Glu Glu Met Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Ser Gly Gly Gly Ser Gly Gly Gly Gly
225                 230                 235                 240

Ser Gly Gly Gly Gly Ser Gln Leu Tyr Ser Ala Leu Ala Asn Lys
                245                 250                 255

Cys Cys His Val Gly Cys Thr Lys Arg Ser Leu Ala Arg Ile Cys
                260                 265                 270

<210> SEQ ID NO 46
<211> LENGTH: 308
<212> TYPE: PRT
<213> ORGANISM: Artificial Sequence
```

<220> FEATURE:
<221> NAME/KEY: source
<223> OTHER INFORMATION: /note="Description of Artificial Sequence: Synthetic polypeptide"

<400> SEQUENCE: 46

```
Asp Lys Thr His Thr Cys Pro Pro Cys Pro Ala Pro Glu Phe Glu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
            85                  90                  95

Lys Glu Tyr Lys Cys Lys Val Ser Asn Lys Ala Leu Pro Ala Ser Ile
        100                 105                 110

Glu Lys Thr Ile Ser Lys Ala Lys Gly Gln Pro Arg Glu Pro Gln Val
    115                 120                 125

Tyr Thr Leu Pro Pro Cys Arg Glu Glu Met Thr Lys Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
            165                 170                 175

Val Leu Asp Ser Asp Gly Ser Phe Phe Leu Tyr Ser Lys Leu Thr Val
        180                 185                 190

Asp Lys Ser Arg Trp Gln Gln Gly Asn Val Phe Ser Cys Ser Val Met
    195                 200                 205

His Glu Ala Leu His Asn His Tyr Thr Gln Lys Ser Leu Ser Leu Ser
210                 215                 220

Pro Gly Gly Gly Gly Ser Gly Gly Gly Ser Gly Gly Gly Gly
225                 230                 235                 240

Ser Gly Gly Gly Gly Ser Ser Trp Met Glu Glu Val Ile Lys Leu
            245                 250                 255

Cys Gly Arg Glu Leu Val Arg Ala Gln Ile Ala Ile Cys Gly Met Ser
        260                 265                 270

Thr Trp Ser Gly Gly Ser Gly Gly Ser Gly Gln Leu Tyr Ser
    275                 280                 285

Ala Leu Ala Asn Lys Cys Cys His Val Gly Cys Thr Lys Arg Ser Leu
290                 295                 300

Ala Arg Phe Cys
305
```

<210> SEQ ID NO 47
<211> LENGTH: 308
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 47

```
Asp Lys Thr His Thr Cys Pro Pro Cys Pro Ala Pro Glu Phe Glu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Ser Gly Gly Gly Gly Ser Gly Gly Gly Gly
225                 230                 235                 240

Ser Gly Gly Gly Gly Ser Ser Trp Met Glu Glu Val Ile Lys Leu
                245                 250                 255

Cys Gly Arg Glu Leu Val Arg Ala Gln Ile Ala Ile Cys Gly Met Ser
            260                 265                 270

Thr Trp Ser Gly Gly Ser Gly Gly Ser Gly Gln Leu Tyr Ser
        275                 280                 285

Ala Leu Ala Asn Lys Cys Cys His Val Gly Cys Thr Lys Arg Ser Leu
    290                 295                 300

Ala Arg Phe Cys
305
```

<210> SEQ ID NO 48
<211> LENGTH: 273
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 48

```
Ser Trp Met Glu Glu Val Ile Lys Leu Cys Gly Arg Glu Leu Val Arg
1               5                   10                  15

Ala Gln Ile Ala Ile Cys Gly Met Ser Thr Trp Ser Ala Ala Ala Gly
            20                  25                  30

Gly Gly Gly Ser Gly Gly Gly Gly Ser Gly Gly Gly Gly Ser Gly Gly
```

-continued

```
                35                  40                  45
Gly Gly Ser Ala Cys Pro Pro Cys Pro Ala Pro Glu Phe Glu Gly Gly
 50                  55                  60

Pro Ser Val Phe Leu Phe Pro Pro Lys Pro Lys Asp Thr Leu Met Ile
 65                  70                  75                  80

Ser Arg Thr Pro Glu Val Thr Cys Val Val Val Asp Val Ser His Glu
                 85                  90                  95

Asp Pro Glu Val Lys Phe Asn Trp Tyr Val Asp Gly Val Glu Val His
                100                 105                 110

Asn Ala Lys Thr Lys Pro Arg Glu Glu Gln Tyr Asn Ser Thr Tyr Arg
            115                 120                 125

Val Val Ser Val Leu Thr Val Leu His Gln Asp Trp Leu Asn Gly Lys
        130                 135                 140

Glu Tyr Lys Cys Lys Val Ser Asn Lys Ala Leu Pro Ala Ser Ile Glu
145                 150                 155                 160

Lys Thr Ile Ser Lys Ala Lys Gly Gln Pro Arg Glu Pro Gln Val Cys
                165                 170                 175

Thr Leu Pro Pro Ser Arg Glu Glu Met Thr Lys Asn Gln Val Ser Leu
            180                 185                 190

Ser Cys Ala Val Lys Gly Phe Tyr Pro Ser Asp Ile Ala Val Glu Trp
        195                 200                 205

Glu Ser Asn Gly Gln Pro Glu Asn Asn Tyr Lys Thr Thr Pro Pro Val
    210                 215                 220

Leu Asp Ser Asp Gly Ser Phe Phe Leu Val Ser Lys Leu Thr Val Asp
225                 230                 235                 240

Lys Ser Arg Trp Gln Gln Gly Asn Val Phe Ser Cys Ser Val Met His
                245                 250                 255

Glu Ala Leu His Asn His Tyr Thr Gln Lys Ser Leu Ser Leu Ser Pro
            260                 265                 270

Gly

<210> SEQ ID NO 49
<211> LENGTH: 269
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Gln Leu Tyr Ser Ala Leu Ala Asn Lys Cys Cys His Val Gly Cys Thr
 1               5                  10                  15

Lys Arg Ser Leu Ala Arg Phe Cys Ala Ala Ala Gly Gly Gly Gly Ser
                20                  25                  30

Gly Gly Gly Gly Ser Gly Gly Gly Ser Gly Gly Gly Ser Ala
            35                  40                  45

Cys Pro Pro Cys Pro Ala Pro Glu Phe Glu Gly Gly Pro Ser Val Phe
 50                  55                  60

Leu Phe Pro Pro Lys Pro Lys Asp Thr Leu Met Ile Ser Arg Thr Pro
 65                  70                  75                  80

Glu Val Thr Cys Val Val Val Asp Val Ser His Glu Asp Pro Glu Val
                 85                  90                  95

Lys Phe Asn Trp Tyr Val Asp Gly Val Glu Val His Asn Ala Lys Thr
                100                 105                 110
```

```
Lys Pro Arg Glu Glu Gln Tyr Asn Ser Thr Tyr Arg Val Val Ser Val
            115                 120                 125

Leu Thr Val Leu His Gln Asp Trp Leu Asn Gly Lys Glu Tyr Lys Cys
130                 135                 140

Lys Val Ser Asn Lys Ala Leu Pro Ala Ser Ile Glu Lys Thr Ile Ser
145                 150                 155                 160

Lys Ala Lys Gly Gln Pro Arg Glu Pro Gln Val Tyr Thr Leu Pro Pro
                165                 170                 175

Cys Arg Glu Glu Met Thr Lys Asn Gln Val Ser Leu Trp Cys Leu Val
            180                 185                 190

Lys Gly Phe Tyr Pro Ser Asp Ile Ala Val Glu Trp Glu Ser Asn Gly
            195                 200                 205

Gln Pro Glu Asn Asn Tyr Lys Thr Thr Pro Pro Val Leu Asp Ser Asp
            210                 215                 220

Gly Ser Phe Phe Leu Tyr Ser Lys Leu Thr Val Asp Lys Ser Arg Trp
225                 230                 235                 240

Gln Gln Gly Asn Val Phe Ser Cys Ser Val Met His Glu Ala Leu His
                245                 250                 255

Asn His Tyr Thr Gln Lys Ser Leu Ser Leu Ser Pro Gly
            260                 265

<210> SEQ ID NO 50
<211> LENGTH: 314
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Gln Leu Tyr Ser Ala Leu Ala Asn Lys Cys Cys His Val Gly Cys Thr
1               5                   10                  15

Lys Arg Ser Leu Ala Arg Phe Cys Ala Ala Gly Gly Gly Gly Gly Ser
            20                  25                  30

Gly Gly Gly Gly Ser Gly Gly Gly Gly Ser Gly Gly Gly Gly Ser Ala
            35                  40                  45

Cys Pro Pro Cys Pro Ala Pro Glu Phe Glu Gly Gly Pro Ser Val Phe
50                  55                  60

Leu Phe Pro Pro Lys Pro Lys Asp Thr Leu Met Ile Ser Arg Thr Pro
65                  70                  75                  80

Glu Val Thr Cys Val Val Val Asp Val Ser His Glu Asp Pro Glu Val
            85                  90                  95

Lys Phe Asn Trp Tyr Val Asp Gly Val Glu Val His Asn Ala Lys Thr
            100                 105                 110

Lys Pro Arg Glu Glu Gln Tyr Asn Ser Thr Tyr Arg Val Val Ser Val
            115                 120                 125

Leu Thr Val Leu His Gln Asp Trp Leu Asn Gly Lys Glu Tyr Lys Cys
130                 135                 140

Lys Val Ser Asn Lys Ala Leu Pro Ala Ser Ile Glu Lys Thr Ile Ser
145                 150                 155                 160

Lys Ala Lys Gly Gln Pro Arg Glu Pro Gln Val Tyr Thr Leu Pro Pro
                165                 170                 175

Cys Arg Glu Glu Met Thr Lys Asn Gln Val Ser Leu Trp Cys Leu Val
            180                 185                 190

Lys Gly Phe Tyr Pro Ser Asp Ile Ala Val Glu Trp Glu Ser Asn Gly
```

```
            195                 200                 205
Gln Pro Glu Asn Asn Tyr Lys Thr Thr Pro Val Leu Asp Ser Asp
    210                 215                 220

Gly Ser Phe Phe Leu Tyr Ser Lys Leu Thr Val Asp Lys Ser Arg Trp
225                 230                 235                 240

Gln Gln Gly Asn Val Phe Ser Cys Ser Val Met His Glu Ala Leu His
                245                 250                 255

Asn His Tyr Thr Gln Lys Ser Leu Ser Leu Ser Pro Gly Gly Gly Gly
                260                 265                 270

Gly Ser Gly Gly Gly Ser Gly Gly Gly Ser Gly Gly Gly Gly
                275                 280                 285

Gly Ser Gln Leu Tyr Ser Ala Leu Ala Asn Lys Cys Cys His Val Gly
    290                 295                 300

Cys Thr Lys Arg Ser Leu Ala Arg Phe Cys
305                 310

<210> SEQ ID NO 51
<211> LENGTH: 322
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Ser Trp Met Glu Glu Val Ile Lys Leu Cys Gly Arg Glu Leu Val Arg
1               5                   10                  15

Ala Gln Ile Ala Ile Cys Gly Met Ser Thr Trp Ser Ala Ala Ala Gly
                20                  25                  30

Gly Gly Gly Ser Gly Gly Gly Gly Ser Gly Gly Gly Ser Gly Gly
                35                  40                  45

Gly Gly Ser Ala Cys Pro Pro Cys Pro Ala Pro Glu Phe Glu Gly Gly
            50                  55                  60

Pro Ser Val Phe Leu Phe Pro Pro Lys Pro Lys Asp Thr Leu Met Ile
65                  70                  75                  80

Ser Arg Thr Pro Glu Val Thr Cys Val Val Val Asp Val Ser His Glu
                85                  90                  95

Asp Pro Glu Val Lys Phe Asn Trp Tyr Val Asp Gly Val Glu Val His
                100                 105                 110

Asn Ala Lys Thr Lys Pro Arg Glu Glu Gln Tyr Asn Ser Thr Tyr Arg
            115                 120                 125

Val Val Ser Val Leu Thr Val Leu His Gln Asp Trp Leu Asn Gly Lys
130                 135                 140

Glu Tyr Lys Cys Lys Val Ser Asn Lys Ala Leu Pro Ala Ser Ile Glu
145                 150                 155                 160

Lys Thr Ile Ser Lys Ala Lys Gly Gln Pro Arg Glu Pro Gln Val Cys
                165                 170                 175

Thr Leu Pro Pro Ser Arg Glu Glu Met Thr Lys Asn Gln Val Ser Leu
            180                 185                 190

Ser Cys Ala Val Lys Gly Phe Tyr Pro Ser Asp Ile Ala Val Glu Trp
        195                 200                 205

Glu Ser Asn Gly Gln Pro Glu Asn Asn Tyr Lys Thr Thr Pro Pro Val
    210                 215                 220

Leu Asp Ser Asp Gly Ser Phe Phe Leu Val Ser Lys Leu Thr Val Asp
225                 230                 235                 240
```

```
Lys Ser Arg Trp Gln Gln Gly Asn Val Phe Ser Cys Ser Val Met His
                245                 250                 255

Glu Ala Leu His Asn His Tyr Thr Gln Lys Ser Leu Ser Leu Ser Pro
            260                 265                 270

Gly Gly Gly Gly Gly Ser Gly Gly Gly Ser Gly Gly Gly Gly Ser
        275                 280                 285

Gly Gly Gly Gly Ser Ser Trp Met Glu Glu Val Ile Lys Leu Cys
        290                 295                 300

Gly Arg Glu Leu Val Arg Ala Gln Ile Ala Ile Cys Gly Met Ser Thr
305                 310                 315                 320

Trp Ser

<210> SEQ ID NO 52
<211> LENGTH: 273
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

Asp Lys Thr His Thr Cys Pro Pro Cys Pro Ala Pro Glu Phe Glu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Ser Gly Gly Gly Ser Gly Gly Gly Gly
225                 230                 235                 240

Ser Gly Gly Gly Gly Ser Ser Trp Met Glu Glu Val Ile Lys Leu
                245                 250                 255

Cys Gly Arg Glu Leu Val Arg Ala Gln Ile Ala Ile Cys Gly Met Ser
```

Thr

<210> SEQ ID NO 53
<211> LENGTH: 272
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 53

Asp Lys Thr His Thr Cys Pro Pro Cys Pro Ala Pro Glu Phe Glu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Ser Gly Gly Gly Ser Gly Gly Gly Gly
225                 230                 235                 240

Ser Gly Gly Gly Gly Ser Ser Trp Met Glu Glu Val Ile Lys Leu
                245                 250                 255

Cys Gly Arg Glu Leu Val Arg Ala Gln Ile Ala Ile Cys Gly Met Ser
            260                 265                 270

<210> SEQ ID NO 54
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 54

Glu Leu Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Gln
65                  70                  75                  80

Ala Glu Asp Glu Ala Asp Tyr Tyr Cys Ser Ser Tyr Thr Ser Ser Ser
                85                  90                  95

Thr Leu Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Thr His Glu Gly Ser Thr Val Glu Lys Thr Val Ala
        195                 200                 205

Pro Thr Glu Cys Ser
    210

<210> SEQ ID NO 55
<211> LENGTH: 494
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

Glu Val Gln Leu Leu Glu Ser Gly Gly Gly Leu Val Gln Pro Gly Gly
1               5                   10                  15

Ser Leu Arg Leu Ser Cys Thr Thr Ser Gly Phe Thr Phe Asn Thr Tyr
            20                  25                  30

Ala Met Ser Trp Val Arg Gln Ala Pro Gly Lys Gly Leu Glu Trp Leu
        35                  40                  45

Ser Gly Ile Asn Asn Asn Gly Arg Thr Ala Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Ile Asn Ser Leu Arg Ala Asp Asp Thr Ala Val Tyr Phe Cys
                85                  90                  95

Ala Lys Asp Val Arg Phe Ile Ala Val Pro Gly Asp Ser Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala

```
                130                 135                 140
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
        210                 215                 220

Lys Thr His Thr Cys Pro Pro Cys Pro Ala Pro Glu Phe Glu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Ser Ile Glu
                325                 330                 335

Lys Thr Ile Ser Lys Ala Lys Gly Gln Pro Arg Glu Pro Gln Val Tyr
                340                 345                 350

Thr Leu Pro Pro Cys Arg Glu Glu Met Thr Lys Asn Gln Val Ser Leu
            355                 360                 365

Trp Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Gly Gly Gly Gly Ser Gly Gly Gly Ser Gly Gly Gly Gly Ser
        450                 455                 460

Gly Gly Gly Gly Ser Gln Leu Tyr Ser Ala Leu Ala Asn Lys Cys
465                 470                 475                 480

Cys His Val Gly Cys Thr Lys Arg Ser Leu Ala Arg Phe Cys
                485                 490

<210> SEQ ID NO 56
<211> LENGTH: 498
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56
```

-continued

```
Glu Val Gln Leu Leu Glu Ser Gly Gly Gly Leu Val Gln Pro Gly Gly
1               5                   10                  15

Ser Leu Arg Leu Ser Cys Thr Thr Ser Gly Phe Thr Phe Asn Thr Tyr
            20                  25                  30

Ala Met Ser Trp Val Arg Gln Ala Pro Gly Lys Gly Leu Glu Trp Leu
        35                  40                  45

Ser Gly Ile Asn Asn Asn Gly Arg Thr Ala Phe Tyr Ala Asp Ser Val
    50                  55                  60

Lys Gly Arg Phe Thr Ile Ser Arg Asp Asn Ser Lys Asn Thr Leu Tyr
65              70                  75                  80

Leu Gln Ile Asn Ser Leu Arg Ala Asp Asp Thr Ala Val Tyr Phe Cys
                85                  90                  95

Ala Lys Asp Val Arg Phe Ile Ala Val Pro Gly Asp Ser Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Phe Glu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Ser Ile Glu
                325                 330                 335

Lys Thr Ile Ser Lys Ala Lys Gly Gln Pro Arg Glu Pro Gln Val Cys
            340                 345                 350

Thr Leu Pro Pro Ser Arg Glu Glu Met Thr Lys Asn Gln Val Ser Leu
        355                 360                 365

Ser Cys Ala Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415
```

```
Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Gly Gly Gly Gly Ser Gly Gly Gly Ser Gly Gly Gly Gly Ser
    450                 455                 460

Gly Gly Gly Gly Ser Ser Trp Met Glu Glu Val Ile Lys Leu Cys
465                 470                 475                 480

Gly Arg Glu Leu Val Arg Ala Gln Ile Ala Ile Cys Gly Met Ser Thr
                485                 490                 495

Trp Ser

<210> SEQ ID NO 57
<211> LENGTH: 292
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 57

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Ser Pro Gln Leu Tyr Ser Ala Leu Ala Asn Lys
225                 230                 235                 240

Cys Cys His Val Gly Cys Thr Lys Arg Ser Leu Ala Arg Phe Cys Gly
                245                 250                 255

Gly Gly Ser Gly Gly Gly Ser Gly Ser Trp Met Glu Glu Val Ile Lys
            260                 265                 270
```

```
Leu Cys Gly Arg Glu Leu Val Arg Ala Gln Ile Ala Ile Cys Gly Met
        275                 280                 285

Ser Thr Trp Ser
    290

<210> SEQ ID NO 58
<211> LENGTH: 295
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Ser Gly Gly Ser Pro Gln Leu Tyr Ser Ala Leu
225                 230                 235                 240

Ala Asn Lys Cys Cys His Val Gly Cys Thr Lys Arg Ser Leu Ala Arg
                245                 250                 255

Phe Cys Gly Gly Gly Ser Gly Gly Ser Gly Ser Trp Met Glu Glu
            260                 265                 270

Val Ile Lys Leu Cys Gly Arg Glu Leu Val Arg Ala Gln Ile Ala Ile
        275                 280                 285

Cys Gly Met Ser Thr Trp Ser
    290                 295

<210> SEQ ID NO 59
<211> LENGTH: 298
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 59

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Ser Gly Gly Ser Gly Gly Ser Pro Gln Leu Tyr
225                 230                 235                 240

Ser Ala Leu Ala Asn Lys Cys Cys His Val Gly Cys Thr Lys Arg Ser
                245                 250                 255

Leu Ala Arg Phe Cys Gly Gly Ser Gly Gly Gly Ser Gly Gly Ser Trp
            260                 265                 270

Met Glu Glu Val Ile Lys Leu Cys Gly Arg Glu Leu Val Arg Ala Gln
        275                 280                 285

Ile Ala Ile Cys Gly Met Ser Thr Trp Ser
    290                 295

<210> SEQ ID NO 60
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Gly Gly Gly Ser Gly Gly Gly Ser Gly Gly
```

<210> SEQ ID NO 61
<211> LENGTH: 271
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 61

Asp Lys Thr His Thr Cys Pro Pro Cys Pro Ala Pro Glu Phe Glu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Glu Glu Met Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Ser Gly Gly Gly Gly Ser Gly Gly Gly Gly
225                 230                 235                 240

Ser Gly Gly Gly Gly Ser Gln Leu Tyr Ser Ala Leu Ala Asn Lys
                245                 250                 255

Cys Cys His Val Gly Cys Thr Lys Arg Ser Leu Ala Arg Ala Cys
            260                 265                 270

<210> SEQ ID NO 62
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 62

Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser
            20                  25

<210> SEQ ID NO 63
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Gln Leu Tyr Ser Ala Leu Ala Asn Lys Cys Cys His Val Gly Cys Thr
1               5                   10                  15

Lys Arg Ser Leu Ala Arg Phe Cys
            20

<210> SEQ ID NO 64
<211> LENGTH: 33
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 64

Met Arg Val Ser Glu Glu Trp Met Asp Gly Phe Ile Arg Met Cys Gly
1               5                   10                  15

Arg Glu Tyr Ala Arg Glu Leu Ile Lys Ile Cys Gly Ala Ser Val Gly
            20                  25                  30

Arg

<210> SEQ ID NO 65
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Glu Ser Gly Gly Leu Met Ser Gln Gln Cys Cys His Val Gly Cys Ser
1               5                   10                  15

Arg Arg Ser Ile Ala Lys Leu Tyr Cys
            20                  25

<210> SEQ ID NO 66
<211> LENGTH: 272
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66

Asp Lys Thr His Thr Ala Cys Pro Pro Cys Pro Ala Pro Glu Phe Glu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser

```
                35                  40                  45
His Glu Asp Pro Glu Val Lys Phe Asn Trp Tyr Val Asp Gly Val Glu
            50                  55                  60
Val His Asn Ala Lys Thr Lys Pro Arg Glu Glu Gln Tyr Asn Ser Thr
65                  70                  75                  80
Tyr Arg Val Val Ser Val Leu Thr Val Leu His Gln Asp Trp Leu Asn
                85                  90                  95
Gly Lys Glu Tyr Lys Cys Lys Val Ser Asn Lys Ala Leu Pro Ala Ser
            100                 105                 110
Ile Glu Lys Thr Ile Ser Lys Ala Lys Gly Gln Pro Arg Glu Pro Gln
        115                 120                 125
Val Tyr Thr Leu Pro Pro Cys Arg Glu Glu Met Thr Lys Asn Gln Val
130                 135                 140
Ser Leu Trp Cys Leu Val Lys Gly Phe Tyr Pro Ser Asp Ile Ala Val
145                 150                 155                 160
Glu Trp Glu Ser Asn Gly Gln Pro Glu Asn Asn Tyr Lys Thr Thr Pro
                165                 170                 175
Pro Val Leu Asp Ser Asp Gly Ser Phe Phe Leu Tyr Ser Lys Leu Thr
            180                 185                 190
Val Asp Lys Ser Arg Trp Gln Gln Gly Asn Val Phe Ser Cys Ser Val
        195                 200                 205
Met His Glu Ala Leu His Asn His Tyr Thr Gln Lys Ser Leu Ser Leu
210                 215                 220
Ser Pro Gly Gly Gly Gly Ser Gly Gly Gly Ser Gly Gly Gly Gly
225                 230                 235                 240
Gly Ser Gly Gly Gly Gly Ser Gln Leu Tyr Ser Ala Leu Ala Asn
                245                 250                 255
Lys Cys Cys Arg Val Gly Cys Thr Lys Arg Ser Leu Ala Arg Phe Cys
            260                 265                 270

<210> SEQ ID NO 67
<211> LENGTH: 276
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67

Asp Lys Thr His Thr Ala Cys Pro Pro Cys Pro Ala Pro Glu Phe Glu
1               5                   10                  15
Gly Gly Pro Ser Val Phe Leu Phe Pro Pro Lys Pro Lys Asp Thr Leu
            20                  25                  30
Met Ile Ser Arg Thr Pro Glu Val Thr Cys Val Val Val Asp Val Ser
        35                  40                  45
His Glu Asp Pro Glu Val Lys Phe Asn Trp Tyr Val Asp Gly Val Glu
    50                  55                  60
Val His Asn Ala Lys Thr Lys Pro Arg Glu Glu Gln Tyr Asn Ser Thr
65                  70                  75                  80
Tyr Arg Val Val Ser Val Leu Thr Val Leu His Gln Asp Trp Leu Asn
                85                  90                  95
Gly Lys Glu Tyr Lys Cys Lys Val Ser Asn Lys Ala Leu Pro Ala Ser
            100                 105                 110
Ile Glu Lys Thr Ile Ser Lys Ala Lys Gly Gln Pro Arg Glu Pro Gln
        115                 120                 125
```

```
Val Cys Thr Leu Pro Pro Ser Arg Glu Glu Met Thr Lys Asn Gln Val
    130                 135                 140

Ser Leu Ser Cys Ala Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Val Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Gly Gly Gly Ser Gly Gly Gly Ser Gly Gly Gly
225                 230                 235                 240

Gly Ser Gly Gly Gly Gly Ser Ser Trp Met Glu Glu Val Ile Lys
                245                 250                 255

Leu Cys Gly Arg Glu Leu Val Arg Ala Gln Ile Ala Ile Cys Gly Met
            260                 265                 270

Ser Thr Trp Ser
        275
```

<210> SEQ ID NO 68
<211> LENGTH: 271
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 68

```
Asp Lys Thr His Thr Cys Pro Pro Cys Pro Ala Pro Glu Phe Glu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Glu Glu Met Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190
```

-continued

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Gly Gly Gly Ser Gly Gly Gly Ser Gly Gly Gly Gly
225                 230                 235                 240

Ser Gly Gly Gly Gly Ser Gln Leu Tyr Ser Ala Leu Ala Asn Lys
                245                 250                 255

Cys Cys His Val Gly Cys Thr Lys Arg Ser Leu Ala Tyr Phe Cys
            260                 265                 270

<210> SEQ ID NO 69
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

Asp Lys Thr His Thr Cys Pro Pro Cys
1               5

<210> SEQ ID NO 70
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

Asp Lys Thr His Thr Ala Cys Pro Pro Cys
1               5                   10

<210> SEQ ID NO 71
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Gly Gly Ala Gly Gly Ala Cys Pro Pro Cys
1               5                   10

<210> SEQ ID NO 72
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 72

Ala Cys Pro Pro Cys
1               5

<210> SEQ ID NO 73
<211> LENGTH: 30
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (1)..(30)
<223> OTHER INFORMATION: /note="This sequence may encompass 3-15 'Pro
      Ala' repeating units"

<400> SEQUENCE: 73

Pro Ala Pro Ala Pro Ala Pro Ala Pro Ala Pro Ala Pro Ala Pro Ala
1               5                   10                  15

Pro Ala Pro Ala Pro Ala Pro Ala Pro Ala Pro Ala Pro Ala
            20                  25                  30

<210> SEQ ID NO 74
<211> LENGTH: 40
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (1)..(30)
<223> OTHER INFORMATION: /note="This sequence may encompass 1-8 'Gly
      Gly Gly Gly Ser' repeating units"

<400> SEQUENCE: 74

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser
        35                  40

<210> SEQ ID NO 75
<211> LENGTH: 45
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 75

Ser Leu Ser Leu Ser Pro Gly Gly Gly Gly Ser Gly Gly Gly Gly
1               5                   10                  15

Ser Gly Gly Gly Gly Ser Gly Gly Gly Gly Ser Gln Leu Tyr Ser
            20                  25                  30

Ala Leu Ala Asn Lys Cys Cys His Val Gly Cys Thr Lys
        35                  40                  45

<210> SEQ ID NO 76
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Leu Cys Gly Arg Glu Leu Val Arg Ala Gln Ile Ala Ile Cys Gly Met
```

-continued

```
1               5                   10                  15
Ser Thr Trp Ser
            20
```

<210> SEQ ID NO 77
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 77

```
Arg Ser Leu Ala Arg Phe Cys
1               5
```

<210> SEQ ID NO 78
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 78

```
Gly Gly Ala Gly Gly Ala
1               5
```

<210> SEQ ID NO 79
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 79

```
Asp Lys Thr His Thr
1               5
```

<210> SEQ ID NO 80
<211> LENGTH: 72
<212> TYPE: DNA
<213> ORGANISM: Unknown
<220> FEATURE:
<221> NAME/KEY: source
<223> OTHER INFORMATION: /note="Description of Unknown: Relaxin A Sequence"

<400> SEQUENCE: 80

```
cagctctact cagcgctcgc taataagtgt tgtcatgtgg gatgcacaaa gcggtctctc    60
gccagattct gc                                                       72
```

<210> SEQ ID NO 81
<211> LENGTH: 84
<212> TYPE: DNA
<213> ORGANISM: Unknown
<220> FEATURE:
<221> NAME/KEY: source
<223> OTHER INFORMATION: /note="Description of Unknown: Relaxin B Sequence"

<400> SEQUENCE: 81

```
agctggatgg aagaagtgat taaactgtgt ggccgcgaac tggtgcgcgc gcagattgcg    60
```

<210> SEQ ID NO 82
<211> LENGTH: 678
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 82

```
gacaagaccc atacatgtcc tccatgcccg gcgcctgagt tcgagggcgg accctccgtg      60
ttcctgttcc ccccaaagcc caaggacacc ctgatgatct cccggacccc cgaagtgacc     120
tgcgtggtgg tggacgtgtc ccacgaggac cctgaagtga agttcaattg gtacgtggac     180
ggcgtggaag tgcacaacgc caagaccaag cccagagagg aacagtacaa ctccacctac     240
cgggtggtgt ccgtgctgac cgtgctgcac caggactggc tgaacggcaa agagtacaag     300
tgcaaggtct ccaacaaggc cctgcccgcc tccatcgaaa agaccatctc caaggccaag     360
ggccagcccc gcgagcctca ggtgtgcaca ctgccccca gcgggaaga gatgaccaag      420
aaccaggtgt ccctgtcctg tgccgtgaaa ggcttctacc cctccgatat cgctgtggaa     480
tgggagtcca acggccagcc cgagaacaac tacaagacca cccccctgt gctggactcc      540
gacggctcat tcttcctggt gtccaagctg accgtggaca agtcccggtg gcagcagggc     600
aacgtgttct cctgctccgt gatgcacgag gccctgcaca accactacac ccagaaaagc     660
ttgtccctga gccccggc                                                   678
```

<210> SEQ ID NO 83
<211> LENGTH: 678
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 83

```
gacaagaccc atacatgtcc tccatgcccg gcgcctgagt tcgagggcgg accctccgtg      60
ttcctgttcc ccccaaagcc caaggacacc ctgatgatct cccggacccc cgaagtgacc     120
tgcgtggtgg tggacgtgtc ccacgaggac cctgaagtga agttcaattg gtacgtggac     180
ggcgtggaag tgcacaacgc caagaccaag cccagagagg aacagtacaa ctccacctac     240
cgggtggtgt ccgtgctgac cgtgctgcac caggactggc tgaacggcaa agagtacaag     300
tgcaaggtct ccaacaaggc cctgcccgcc tccatcgaaa agaccatctc caaggccaag     360
ggccagcccc gcgagcctca ggtgtacaca ctgccccct gcgggaaga gatgaccaag       420
aaccaggtgt ccctgtggtg tctggtgaaa ggcttctacc cctccgatat cgctgtggaa     480
tgggagtcca acggccagcc cgagaacaac tacaagacca cccccctgt gctggactcc      540
gacggctcat tcttcctgta ctccaagctg accgtggaca agtcccggtg gcagcagggc     600
aacgtgttct cctgctccgt gatgcacgag gccctgcaca accactacac ccagaaaagc     660
ttgtccctga gccccggc                                                   678
```

<210> SEQ ID NO 84
<211> LENGTH: 927
<212> TYPE: DNA

<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 84

```
gataaaaccc atacctgccc gccgtgcccg gcgccggaac tgctgggcgg cccgagcgtg      60
tttctgtttc cgccgaaacc gaaagatacc ctgatgatta gccgcacccc ggaagtgacc     120
tgcgtggtgg tggatgtgag ccatgaagat ccggaagtga aatttaactg gtatgtggat     180
ggcgtggaag tgcataacgc gaaaaccaaa ccgcgcgaag aacagtataa cagcacctat     240
cgcgtggtga gcgtgctgac cgtgctgcat caggattggc tgaacggcaa agaatataaa     300
tgcaaagtga gcaacaaagc gctgccggcg ccgattgaaa aaaccattag caaagcgaaa     360
ggccagccgc gcgaaccgca ggtgtatacc ctgccgccga gccgcgatga actgaccaaa     420
aaccaggtga gcctgacctg cctggtgaaa ggcttttatc cgagcgatat tgcggtggaa     480
tgggaaagca cggccagcc ggaaaacaac tataaaacca ccccgccggt gctggatagc     540
gatggcagct ttttctgtta tagcaaactg accgtggata aaagccgctg gcagcagggc     600
aacgtgttta gctgcagcgt gatgcatgaa gcgctgcata accattatac ccagaaaagc     660
ctgagcctga gcccgggcaa aggcggcggc ggcagcggcg gcggcggcag cggcggcggc     720
ggcagccagc tgtatagcgc gctggcgaac aaatgctgcc atgtgggctg caccaaacgc     780
agcctggcgc gcttttgcgg cggcggcggc agcggcggcg gcggcagcgg cggcggcggc     840
agcagctgga tggaagaagt gattaaactg tgtggccgcg aactggtgcg cgcgcagatt     900
gcgatttgcg gcatgagcac ctggagc                                         927
```

<210> SEQ ID NO 85
<211> LENGTH: 816
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 85

```
ggaggagcgg gtggagcttg tcctccatgc ccggcgcctg agttcgaggg cggaccctcc      60
gtgttcctgt tcccccaaa gcccaaggac accctgatga tctcccggac ccccgaagtg     120
acctgcgtgg tggtggacgt gtcccacgag gaccctgaag tgaagttcaa ttggtacgtg     180
gacggcgtgg aagtgcacaa cgccaagacc aagcccagag aggaacagta caactccacc     240
taccgggtgg tgtccgtgct gaccgtgctg caccaggact ggctgaacgg caaagagtac     300
aagtgcaagg tctccaacaa ggccctgccc gcctccatcg aaaagaccat ctccaaggcc     360
aagggccagc cccgcgagcc tcaggtgtac acactgcccc cctgccggga agatgacc      420
aagaaccagg tgtccctgtg cgtgtctgtg aaaggcttct acccctccga tatcgctgtg     480
gaatgggagt ccaacggcca gcccgagaac aactacaaga ccaccccccc tgtgctggac     540
tccgacggct cattcttcct gtactccaag ctgaccgtgg acaagtcccg gtggcagcag     600
ggcaacgtgt tctcctgctc cgtgatgcac gaggccctgc acaaccacta cacccagaag     660
tctctaagct tgagcccgg cggaggtggt ggaagcggag gaggtggctc tgagggggt       720
ggaagcggag gtgaggtgg atcccagctc tactcagcgc tcgctaataa gtgttgtcat      780
gtgggatgca caaagcggtc tctcgccaga ttctgc                                816
```

<210> SEQ ID NO 86
<211> LENGTH: 816
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 86

```
ggaggagcgg gtggagcttg tcctccatgc ccggcgcctg agttcgaggg cggaccctcc      60
gtgttcctgt tcccccaaa gcccaaggac accctgatga tctcccggac ccccgaagtg     120
acctgcgtgg tggtggacgt gtcccacgag accctgaag tgaagttcaa ttggtacgtg     180
gacggcgtgg aagtgcacaa cgccaagacc aagcccagag aggaacagta caactccacc    240
taccgggtgg tgtccgtgct gaccgtgctg caccaggact ggctgaacgg caagagtac     300 aagtgcaagg tctccaacaa ggccctgccc gcctccatcg aaaagaccat ctccaaggcc    360
aagggccagc ccgcgagcc tcaggtgtac acactgcccc ccagccggga agagatgacc     420
aagaaccagg tgtccctgtg gtgtctggtg aaaggcttct accctccga tatcgctgtg     480 gaatgggagt ccaacggcca gcccgagaac aactacaaga ccaccccccc tgtgctggac    540
tccgacggct cattcttcct gtactccaag ctgaccgtgg acaagtcccg gtggcagcag    600
ggcaacgtgt tctcctgctc cgtgatgcac gaggccctgc acaaccacta cacccagaag   660
tctctaagct tgagccccgg cggaggtggt ggaagcggag gaggtggctc tggaggggt     720 ggaagcggag gtggaggtgg atcccagctc tactcagcgc tcgctaataa gtgttgtcat    780
gtgggatgca caaagcggtc tctcgccaga ttctgc                              816
```

<210> SEQ ID NO 87
<211> LENGTH: 813
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 87

```
gacaagaccc acacctgtcc tccatgcccg gcgcctgagt tcgagggcgg accctccgtg     60
ttcctgttcc ccccaaagcc caaggacacc ctgatgatct cccggacccc cgaagtgacc    120
tgcgtggtgg tggacgtgtc ccacgaggac cctgaagtga agttcaattg gtacgtggac    180
ggcgtggaag tgcacaacgc caagaccaag cccagagagg aacagtacaa ctccacctac    240
cgggtggtgt ccgtgctgac cgtgctgcac caggactggc tgaacggcaa agagtacaag    300
tgcaaggtct ccaacaaggc cctgcccgcc tccatcgaaa agaccatctc caaggccaag    360
ggccagcccc gcgagcctca ggtgtacaca ctgcccccct gcgggaaga gatgaccaag     420 aaccaggtgt ccctgtggtg tctggtgaaa ggcttctacc cctccgatat cgctgtggaa    480
tgggagtcca acggccagcc cgagaacaac tacaagacca ccccccctgt gctggactcc    540 gacgctcat tcttcctgta ctccaagctg accgtggaca agtcccggtg gcagcagggc    600
aacgtgttct cctgctccgt gatgcacgag gccctgcaca accactacac ccagaagtct   660
ctaagcttga gccccggcgg aggtggtgga agcggaggag gtggctctgg aggggtgga     720 agcggaggtg gaggtggatc ccagctctac tcagcgctcg ctaataagtg ttgtcatgtg    780
```
ggatgcacaa agcggtctct cgccagattc tgc                            813

<210> SEQ ID NO 88
<211> LENGTH: 816
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 88
ggaggagcgg gtggagcttg tcctccatgc ccggcgcctg agttcgaggg cggaccctcc    60
gtgttcctgt tcccccaaa gcccaaggac accctgatga tctcccggac ccccgaagtg   120
acctgcgtgg tggtggacgt gtcccacgag gaccctgaag tgaagttcaa ttggtacgtg   180
gacggcgtgg aagtgcacaa cgccaagacc aagcccagag aggaacagta caactccacc   240
taccgggtgg tgtccgtgct gaccgtgctg caccaggact ggctgaacgg caaagagtac   300
aagtgcaagg tctccaacaa ggccctgccc gcctccatcg aaaagaccat ctccaaggcc   360
aagggccagc cccgcgagcc tcaggtgtgc acactgcccc ccagccggga agagatgacc   420
aagaaccagg tgtccctgtc ctgtgccgtg aaaggcttct acccctccga tatcgctgtg   480
gaatgggagt ccaacggcca gcccgagaac aactacaaga ccaccccccc tgtgctggac   540
tccgacggct cattcttcct ggtgtccaag ctgaccgtgg acaagtcccg gtggcagcag   600
ggcaacgtgt tctcctgctc cgtgatgcac gaggccctgc acaaccacta cacccagaag   660
tctctctaagct tgagccccgg cggaggtggt ggaagcggag gaggtggctc tgagggggt   720
ggaagcggag gtggaggtgg atcccagctc tactcagcgc tcgctaataa gtgttgtcat   780
gtgggatgca caaagcggtc tctcgccaga ttctgc                            816

<210> SEQ ID NO 89
<211> LENGTH: 816
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 89
ggaggagcgg gtggagcttg tcctccatgc ccggcgcctg agttcgaggg cggaccctcc    60
gtgttcctgt tcccccaaa gcccaaggac accctgatga tctcccggac ccccgaagtg   120
acctgcgtgg tggtggacgt gtcccacgag gaccctgaag tgaagttcaa ttggtacgtg   180
gacggcgtgg aagtgcacaa cgccaagacc aagcccagag aggaacagta caactccacc   240
taccgggtgg tgtccgtgct gaccgtgctg caccaggact ggctgaacgg caaagagtac   300
aagtgcaagg tctccaacaa ggccctgccc gcctccatcg aaaagaccat ctccaaggcc   360
aagggccagc cccgcgagcc tcaggtgtac acactgcccc ccagccggga agagatgacc   420
aagaaccagg tgtccctgtc ctgtgccgtg aaaggcttct acccctccga tatcgctgtg   480
gaatgggagt ccaacggcca gcccgagaac aactacaaga ccaccccccc tgtgctggac   540
tccgacggct cattcttcct ggtgtccaag ctgaccgtgg acaagtcccg gtggcagcag   600
ggcaacgtgt tctcctgctc cgtgatgcac gaggccctgc acaaccacta cacccagaag   660
tctctctaagct tgagccccgg cggaggtggt ggaagcggag gaggtggctc tgagggggt   720
ggaagcggag gtggaggtgg atcccagctc tactcagcgc tcgctaataa gtgttgtcat   780

```
gtgggatgca caaagcggtc tctcgccaga ttctgc                              816
```

<210> SEQ ID NO 90
<211> LENGTH: 825
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 90

```
gacaagaccc acacctgtcc tccatgcccg gcgcctgagt tcgagggcgg accctccgtg     60
ttcctgttcc ccccaaagcc caaggacacc ctgatgatct cccggacccc cgaagtgacc    120
tgcgtggtgg tggacgtgtc ccacgaggac cctgaagtga agttcaattg gtacgtggac    180
ggcgtggaag tgcacaacgc caagaccaag cccagagagg aacagtacaa ctccacctac    240
cgggtggtgt ccgtgctgac cgtgctgcac caggactggc tgaacggcaa agagtacaag    300
tgcaaggtct ccaacaaggc cctgcccgcc tccatcgaaa agaccatctc caaggccaag    360
ggccagcccc gcgagcctca ggtgtacaca ctgcccccct gccgggaaga gatgaccaag    420
aaccaggtgt ccctgtggtg tctggtgaaa ggcttctacc cctccgatat cgctgtggaa    480
tgggagtcca acggccagcc cgagaacaac tacaagacca ccccccctgt gctggactcc    540
gacggctcat tcttcctgta ctccaagctg accgtggaca agtcccggtg gcagcagggc    600
aacgtgttct cctgctccgt gatgcacgag gccctgcaca accactacac ccagaagtct    660
ctaagcttga gccccggcgg aggtggtgga agcggaggag gtggctctgg aggggtgga    720 agcggaggtg gaggtggatc cagctggatg gaagaagtga ttaaactgtg tggccgcgaa    780
ctggtgcgcg cgcagattgc gatttgcggc atgagcacct ggagc                   825
```

<210> SEQ ID NO 91
<211> LENGTH: 828
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 91

```
ggaggagcgg gtggagcttg tcctccatgc ccggcgcctg agttcgaggg cggaccctcc     60
gtgttcctgt tccccccaaa gcccaaggac accctgatga tctcccggac ccccgaagtg    120
acctgcgtgg tggtggacgt gtcccacgag gaccctgaag tgaagttcaa ttggtacgtg    180
gacggcgtgg aagtgcacaa cgccaagacc aagcccagag gaacagtaca actccacc    240 taccgggtgg tgtccgtgct gaccgtgctg caccaggact ggctgaacgg caaagagtac    300
aagtgcaagg tctccaacaa ggccctgccc gcctccatcg aaaagaccat ctccaaggcc    360
aagggccagc cccgcgagcc tcaggtgtac acactgcccc cctgccggga agagatgacc    420
aagaaccagg tgtccctgtg gtgtctggtg aaaggcttct acccctccga tatcgctgtg    480
gaatgggagt ccaacggcca gcccgagaac aactacaaga ccaccccccc tgtgctggac    540
tccgacggct cattcttcct gtactccaag ctgaccgtgg acaagtcccg gtggcagcag    600
ggcaacgtgt tctcctgctc cgtgatgcac gaggccctgc acaaccacta cacccagaag    660
tctctaagct tgagccccgg cggaggtggt ggaagcggag gaggtggctc tggagggggt    720
```

```
ggaagcggag gtggaggtgg atccagctgg atggaagaag tgattaaact gtgtggccgc    780
gaactggtgc gcgcgcagat tgcgatttgc ggcatgagca cctggagc                 828
```

<210> SEQ ID NO 92
<211> LENGTH: 828
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 92

```
ggaggagcgg gtggagcttg tcctccatgc ccggcgcctg agttcgaggg cggaccctcc     60
gtgttcctgt tccccccaaa gcccaaggac accctgatga tctcccggac ccccgaagtg    120
acctgcgtgg tggtggacgt gtcccacgag gaccctgaag tgaagttcaa ttggtacgtg    180
gacggcgtgg aagtgcacaa cgccaagacc aagcccagag aggaacagta caactccacc    240
taccgggtgg tgtccgtgct gaccgtgctg caccaggact ggctgaacgg caaagagtac    300
aagtgcaagg tctccaacaa ggccctgccc gcctccatcg aaaagaccat ctccaaggcc    360
aagggccagc ccgcgagcc tcaggtgtac acactgcccc cagccggga agagatgacc     420 aagaaccagg tgtccctgtg tgtctggtg aaaggcttct acccctccga tatcgctgtg    480
gaatgggagt ccaacggcca gcccgagaac aactacaaga ccaccccccc tgtgctggac    540
tccgacggct cattcttcct gtactccaag ctgaccgtgg acaagtcccg gtggcagcag    600
ggcaacgtgt tctcctgctc cgtgatgcac gaggccctgc acaaccacta cacccagaag    660
tctctaagct tgagccccgg cggaggtggt ggaagcggag gaggtggctc tgagggggt     720 ggaagcggag gtggaggtgg atccagctgg atggaagaag tgattaaact gtgtggccgc    780
gaactggtgc gcgcgcagat tgcgatttgc ggcatgagca cctggagc                 828
```

<210> SEQ ID NO 93
<211> LENGTH: 813
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 93

```
gacaagaccc ayacmtgtcc tccatgcccg gcgcctgagt tcgagggcgg accctccgtg     60
ttcctgttcc ccccaaagcc caaggacacc ctgatgatct cccggacccc cgaagtgacc    120
tgcgtggtgg tggacgtgtc ccacgaggac cctgaagtga agttcaattg gtacgtggac    180
ggcgtggaag tgcacaacgc caagaccaag cccagagagg aacagtacaa ctccacctac    240
cgggtggtgt ccgtgctgac cgtgctgcac caggactggc tgaacggcaa agagtacaag    300
tgcaaggtct ccaacaaggc cctgcccgcc tccatcgaaa agaccatctc caaggccaag    360
ggccagcccc gcgagcctca ggtgtgcaca ctgcccccca gcgggaaga gatgaccaag     420 aaccaggtgt ccctgtcctg tgccgtgaaa ggcttctacc cctccgatat cgctgtggaa    480
tgggagtcca acggccagcc cgagaacaac tacaagacca cccccctgt gctggactcc     540 gacggctcat tcttcctggt gtccaagctg accgtggaca agtcccggtg gcagcagggc    600
aacgtgttct cctgctccgt gatgcacgag gccctgcaca accactacac ccagaagtct    660
ctaagcttga gccccggcgg aggtggtgga agcggaggag gtggctctgg aggggtgga     720
```

```
agcggaggtg gaggtggatc ccagctctac tcagcgctcg ctaataagtg ttgtcatgtg    780
ggatgcacaa agcggtctct cgccagattc tgc                                 813

<210> SEQ ID NO 94
<211> LENGTH: 828
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 94
ggaggagcgg gtggagcttg tcctccatgc ccggcgcctg agttcgaggg cggaccctcc     60
gtgttcctgt tcccccaaa gcccaaggac accctgatga tctcccggac ccccgaagtg    120
acctgcgtgg tggtggacgt gtcccacgag gaccctgaag tgaagttcaa ttggtacgtg    180
gacggcgtgg aagtgcacaa cgccaagacc aagcccagag aggaacagta caactccacc    240
taccgggtgg tgtccgtgct gaccgtgctg caccaggact ggctgaacgg caaagagtac    300
aagtgcaagg tctccaacaa ggccctgccc gcctccatcg aaaagaccat ctccaaggcc    360
aagggccagc cccgcgagcc tcaggtgtgc acactgcccc ccagccggga agagatgacc    420
aagaaccagg tgtccctgtc ctgtgccgtg aaaggcttct acccctccga tatcgctgtg    480
gaatgggagt ccaacggcca gcccgagaac aactacaaga ccaccccccc tgtgctggac    540
tccgacggct cattcttcct ggtgtccaag ctgaccgtgg acaagtcccg gtggcagcag    600
ggcaacgtgt tctcctgctc cgtgatgcac gaggccctgc acaaccacta cacccagaag    660
tctctaagct tgagccccgg cggaggtggt ggaagcggag gaggtggctc tggaggggt    720 ggaagcggag gtggaggtgg atccagctgg atggaagaag tgattaaact gtgtggccgc    780
gaactggtgc gcgcgcagat tgcgatttgc ggcatgagca cctggagc                 828

<210> SEQ ID NO 95
<211> LENGTH: 828
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 95
ggaggagcgg gtggagcttg tcctccatgc ccggcgcctg agttcgaggg cggaccctcc     60
gtgttcctgt tcccccaaa gcccaaggac accctgatga tctcccggac ccccgaagtg    120
acctgcgtgg tggtggacgt gtcccacgag gaccctgaag tgaagttcaa ttggtacgtg    180
gacggcgtgg aagtgcacaa cgccaagacc aagcccagag aggaacagta caactccacc    240
taccgggtgg tgtccgtgct gaccgtgctg caccaggact ggctgaacgg caaagagtac    300
aagtgcaagg tctccaacaa ggccctgccc gcctccatcg aaaagaccat ctccaaggcc    360
aagggccagc cccgcgagcc tcaggtgtac acactgcccc ccagccggga agagatgacc    420
aagaaccagg tgtccctgtc ctgtgccgtg aaaggcttct acccctccga tatcgctgtg    480
gaatgggagt ccaacggcca gcccgagaac aactacaaga ccaccccccc tgtgctggac    540
tccgacggct cattcttcct ggtgtccaag ctgaccgtgg acaagtcccg gtggcagcag    600
ggcaacgtgt tctcctgctc cgtgatgcac gaggccctgc acaaccacta cacccagaag    660
```

```
tctctaagct tgagccccgg cggaggtggt ggaagcggag gaggtggctc tggaggggt      720 ggaagcggag gtggaggtgg atccagctgg atggaagaag tgattaaact gtgtggccgc      780
gaactggtgc gcgcgcagat tgcgatttgc ggcatgagca cctggagc                   828
```

```
<210> SEQ ID NO 96
<211> LENGTH: 825
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 96
gacaagaccc acacctgtcc tccatgcccg gcgcctgagt tcgagggcgg accctccgtg       60
ttcctgttcc ccccaaagcc caaggacacc ctgatgatct cccggacccc cgaagtgacc      120
tgcgtggtgg tggacgtgtc ccacgaggac cctgaagtga agttcaattg gtacgtggac      180
ggcgtggaag tgcacaacgc caagaccaag cccagagagg aacagtacaa ctccacctac      240
cgggtggtgt ccgtgctgac cgtgctgcac caggactggc tgaacggcaa agagtacaag      300
tgcaaggtct ccaacaaggc cctgcccgcc tccatcgaaa agaccatctc caaggccaag      360
ggccagcccc gcgagcctca ggtgtgcaca ctgcccccca gccgggaaga gatgaccaag      420
aaccaggtgt ccctgtcctg tgccgtgaaa ggcttctacc cctccgatat cgctgtggaa      480
tgggagtcca acggccagcc cgagaacaac tacaagacca ccccccctgt gctggactcc      540
gacggctcat tcttcctggt gtccaagctg accgtggaca gtcccggtg cagcagggc      600 aacgtgttct cctgctccgt gatgcacgag gccctgcaca accactacac ccagaagtct      660
ctaagcttga gccccggcgg aggtggtgga agcggaggag gtggctctgg aggggtgga      720 agcggaggtg gaggtggatc cagctggatg gaagaagtga ttaaactgtg tggccgcgaa      780
ctggtgcgcg cgcagattgc gatttgcggc atgagcacct ggagc                      825
```

```
<210> SEQ ID NO 97
<211> LENGTH: 798
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 97
gacaagaccc acacctgtcc tccatgcccg gcgcctgagt tcgagggcgg accctccgtg       60
ttcctgttcc ccccaaagcc caaggacacc ctgatgatct cccggacccc cgaagtgacc      120
tgcgtggtgg tggacgtgtc ccacgaggac cctgaagtga agttcaattg gtacgtggac      180
ggcgtggaag tgcacaacgc caagaccaag cccagagagg aacagtacaa ctccacctac      240
cgggtggtgt ccgtgctgac cgtgctgcac caggactggc tgaacggcaa agagtacaag      300
tgcaaggtct ccaacaaggc cctgcccgcc tccatcgaaa agaccatctc caaggccaag      360
ggccagcccc gcgagcctca ggtgtacaca ctgccccct gccgggaaga gatgaccaag      420
aaccaggtgt ccctgtggtg tctggtgaaa ggcttctacc cctccgatat cgctgtggaa      480
tgggagtcca acggccagcc cgagaacaac tacaagacca ccccccctgt gctggactcc      540
gacggctcat tcttcctgta ctccaagctg accgtggaca gtcccggtg cagcagggc      600 aacgtgttct cctgctccgt gatgcacgag gccctgcaca accactacac ccagaagtct      660
```

```
ctaagcttga gccccggcgg aggtggtgga agcggaggag gtggctctgg tggaggggc      720 ggatcccagc tctactcagc gctcgctaat aagtgttgtc atgtgggatg cacaaagcgg      780
tctctcgcca gattctgc                                                   798
```

<210> SEQ ID NO 98
<211> LENGTH: 810
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 98

```
gacaagaccc acacctgtcc tccatgcccg gcgcctgagt tcgagggcgg accctccgtg       60
ttcctgttcc ccccaaagcc caaggacacc ctgatgatct cccggacccc cgaagtgacc     120
tgcgtggtgg tggacgtgtc ccacgaggac cctgaagtga agttcaattg gtacgtggac     180
ggcgtggaag tgcacaacgc caagaccaag cccagagagg aacagtacaa ctccacctac     240
cgggtggtgt ccgtgctgac cgtgctgcac caggactggc tgaacggcaa agagtacaag     300
tgcaaggtct ccaacaaggc cctgcccgcc tccatcgaaa agaccatctc caaggccaag     360
ggccagcccc gcgagcctca ggtgtgcaca ctgccccca gcgggaaga gatgaccaag       420 aaccaggtgt ccctgtcctg tgccgtgaaa ggcttctacc cctccgatat cgctgtggaa     480
tgggagtcca acggccagcc cgagaacaac tacaagacca ccccccctgt gctggactcc     540
gacggctcat tcttcctggt gtccaagctg accgtggaca agtccggtg gcagcagggc      600 aacgtgttct cctgctccgt gatgcacgag gccctgcaca accactacac ccagaagtct     660
ctaagcttga gccccggcgg aggtggtgga agcggaggag gtggctctgg tggaggggc      720 ggatccagct ggatggaaga agtgattaaa ctgtgtggcc gcgaactggt gcgcgcgcag     780
attgcgattt gcggcatgag cacctggagc                                     810
```

<210> SEQ ID NO 99
<211> LENGTH: 783
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 99

```
gacaagaccc acacctgtcc tccatgcccg gcgcctgagt tcgagggcgg accctccgtg       60
ttcctgttcc ccccaaagcc caaggacacc ctgatgatct cccggacccc cgaagtgacc     120
tgcgtggtgg tggacgtgtc ccacgaggac cctgaagtga agttcaattg gtacgtggac     180
ggcgtggaag tgcacaacgc caagaccaag cccagagagg aacagtacaa ctccacctac     240
cgggtggtgt ccgtgctgac cgtgctgcac caggactggc tgaacggcaa agagtacaag     300
tgcaaggtct ccaacaaggc cctgcccgcc tccatcgaaa agaccatctc caaggccaag     360
ggccagcccc gcgagcctca ggtgtacaca ctgcccccct gcgggaaga gatgaccaag      420 aaccaggtgt ccctgtggtg tctggtgaaa ggcttctacc cctccgatat cgctgtggaa     480
tgggagtcca acggccagcc cgagaacaac tacaagacca ccccccctgt gctggactcc     540
gacggctcat tcttcctgta ctccaagctg accgtggaca agtccggtg gcagcagggc      600
```

```
aacgtgttct cctgctccgt gatgcacgag gccctgcaca accactacac ccagaagtct    660
ctaagcttga gccccggcgg aggaggtggc tctggtggag ggggcggatc ccagctctac    720
tcagcgctcg ctaataagtg ttgtcatgtg ggatgcacaa agcggtctct cgccagattc    780
tgc                                                                 783

<210> SEQ ID NO 100
<211> LENGTH: 795
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 100
gacaagaccc acacctgtcc tccatgcccg gcgcctgagt tcgagggcgg accctccgtg     60
ttcctgttcc ccccaaagcc caaggacacc ctgatgatct cccggacccc cgaagtgacc    120
tgcgtggtgg tggacgtgtc ccacgaggac cctgaagtga agttcaattg gtacgtggac    180
ggcgtggaag tgcacaacgc caagaccaag cccagagagg aacagtacaa ctccacctac    240
cgggtggtgt ccgtgctgac cgtgctgcac caggactggc tgaacggcaa agagtacaag    300
tgcaaggtct ccaacaaggc cctgcccgcc tccatcgaaa agaccatctc caaggccaag    360
ggccagcccc gcgagcctca ggtgtgcaca ctgccccca gccgggaaga gatgaccaag    420
aaccaggtgt ccctgtcctg tgccgtgaaa ggcttctacc cctccgatat cgctgtggaa    480
tgggagtcca acgccagcc cgagaacaac tacaagacca ccccccctgt gctggactcc    540
gacggctcat tcttcctggt gtccaagctg accgtggaca agtcccggtg gcagcagggc    600
aacgtgttct cctgctccgt gatgcacgag gccctgcaca accactacac ccagaagtct    660
ctaagcttga gccccggcgg aggaggtggc tctggtggag ggggcggatc cagctggatg    720
gaagaagtga ttaaactgtg tggccgcgaa ctggtgcgcg cgcagattgc gatttgcggc    780
atgagcacct ggagc                                                    795

<210> SEQ ID NO 101
<211> LENGTH: 768
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 101
gacaagaccc acacctgtcc tccatgcccg gcgcctgagt tcgagggcgg accctccgtg     60
ttcctgttcc ccccaaagcc caaggacacc ctgatgatct cccggacccc cgaagtgacc    120
tgcgtggtgg tggacgtgtc ccacgaggac cctgaagtga agttcaattg gtacgtggac    180
ggcgtggaag tgcacaacgc caagaccaag cccagagagg aacagtacaa ctccacctac    240
cgggtggtgt ccgtgctgac cgtgctgcac caggactggc tgaacggcaa agagtacaag    300
tgcaaggtct ccaacaaggc cctgcccgcc tccatcgaaa agaccatctc caaggccaag    360
ggccagcccc gcgagcctca ggtgtacaca ctgcccccct gccgggaaga gatgaccaag    420
aaccaggtgt ccctgtggtg tctggtgaaa ggcttctacc cctccgatat cgctgtggaa    480
tgggagtcca acgccagcc cgagaacaac tacaagacca ccccccctgt gctggactcc    540
gacggctcat tcttcctgta ctccaagctg accgtggaca agtcccggtg gcagcagggc    600
```

```
aacgtgttct cctgctccgt gatgcacgag gccctgcaca accactacac ccagaagtct    660
ctaagcttga gccccggcgg tggaggggc ggatcccagc tctactcagc gctcgctaat    720
aagtgttgtc atgtgggatg cacaaagcgg tctctcgcca gattctgc                768
```

<210> SEQ ID NO 102
<211> LENGTH: 780
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 102

```
gacaagaccc acacctgtcc tccatgcccg gcgcctgagt tcgagggcgg accctccgtg     60
ttcctgttcc ccccaaagcc caaggacacc ctgatgatct cccggacccc cgaagtgacc    120
tgcgtggtgg tggacgtgtc ccacgaggac cctgaagtga agttcaattg gtacgtggac    180
ggcgtggaag tgcacaacgc caagaccaag cccagagagg aacagtacaa ctccacctac    240
cgggtggtgt ccgtgctgac cgtgctgcac caggactggc tgaacggcaa agagtacaag    300
tgcaaggtct ccaacaaggc cctgcccgcc tccatcgaaa agaccatctc caaggccaag    360
ggccagcccc gcgagcctca ggtgtgcaca ctgccccca gccgggaaga gatgaccaag    420
aaccaggtgt ccctgtcctg tgccgtgaaa ggcttctacc cctccgatat cgctgtggaa    480
tgggagtcca acggccagcc cgagaacaac tacaagacca ccccccctgt gctggactcc    540
gacggctcat tcttcctggt gtccaagctg accgtggaca gtcccggtg gcagcagggc    600 aacgtgttct cctgctccgt gatgcacgag gccctgcaca accactacac ccagaagtct    660
ctaagcttga gccccggcgg tggaggggc ggatccagct ggatggaaga agtgattaaa    720
ctgtgtggcc gcgaactggt gcgcgcgcag attgcgattt gcggcatgag cacctggagc    780
```

<210> SEQ ID NO 103
<211> LENGTH: 813
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 103

```
gacaagaccc acacctgtcc tccatgcccg gcgcctgagt tcgagggcgg accctccgtg     60
ttcctgttcc ccccaaagcc caaggacacc ctgatgatct cccggacccc cgaagtgacc    120
tgcgtggtgg tggacgtgtc ccacgaggac cctgaagtga agttcaattg gtacgtggac    180
ggcgtggaag tgcacaacgc caagaccaag cccagagagg aacagtacaa ctccacctac    240
cgggtggtgt ccgtgctgac cgtgctgcac caggactggc tgaacggcaa agagtacaag    300
tgcaaggtct ccaacaaggc cctgcccgcc tccatcgaaa agaccatctc caaggccaag    360
ggccagcccc gcgagcctca ggtgtacaca ctgcccccct gccgggaaga gatgaccaag    420
aaccaggtgt ccctgtggtg tctggtgaaa ggcttctacc cctccgatat cgctgtggaa    480
tgggagtcca acggccagcc cgagaacaac tacaagacca ccccccctgt gctggactcc    540
gacggctcat tcttcctgta ctccaagctg accgtggaca gtcccggtg gcagcagggc    600 aacgtgttct cctgctccgt gatgcacgag gccctgcaca accactacac ccagaagtct    660
```

```
ctaagcttga gccccggcgc acctgctccc gcaccagccc ctgctcccgc accagcccct    720
gctcccgcac cagccggatc ccagctctac tcagcgctcg ctaataagtg ttgtcatgtg    780
ggatgcacaa agcggtctct cgccagattc tgc                                 813
```

<210> SEQ ID NO 104
<211> LENGTH: 825
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 104

```
gacaagaccc acacctgtcc tccatgcccg gcgcctgagt tcgagggcgg accctccgtg     60
ttcctgttcc ccccaaagcc caaggacacc ctgatgatct cccggacccc cgaagtgacc    120
tgcgtggtgg tggacgtgtc ccacgaggac cctgaagtga agttcaattg gtacgtggac    180
ggcgtggaag tgcacaacgc caagaccaag cccagagagg aacagtacaa ctccacctac    240
cgggtggtgt ccgtgctgac cgtgctgcac caggactggc tgaacggcaa agagtacaag    300
tgcaaggtct ccaacaaggc cctgcccgcc tccatcgaaa agaccatctc caaggccaag    360
ggccagcccc gcgagcctca ggtgtgcaca ctgccccccca gccgggaaga gatgaccaag    420
aaccaggtgt ccctgtcctg tgccgtgaaa ggcttctacc cctccgatat cgctgtggaa    480
tgggagtcca acggccagcc cgagaacaac tacaagacca ccccccctgt gctggactcc    540
gacggctcat tcttcctggt gtccaagctg accgtggaca gtcccggtg gcagcagggc    600 aacgtgttct cctgctccgt gatgcacgag gccctgcaca accactacac ccagaagtct    660
ctaagcttga gccccggcgc acctgctccc gcaccagccc ctgctcccgc accagcccct    720
gctcccgcac cagccggatc cagctggatg gaagaagtga ttaaactgtg tggccgcgaa    780
ctggtgcgcg cgcagattgc gatttgcggc atgagcacct ggagc                    825
```

<210> SEQ ID NO 105
<211> LENGTH: 798
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 105

```
gacaagaccc acacctgtcc tccatgcccg gcgcctgagt tcgagggcgg accctccgtg     60
ttcctgttcc ccccaaagcc caaggacacc ctgatgatct cccggacccc cgaagtgacc    120
tgcgtggtgg tggacgtgtc ccacgaggac cctgaagtga agttcaattg gtacgtggac    180
ggcgtggaag tgcacaacgc caagaccaag cccagagagg aacagtacaa ctccacctac    240
cgggtggtgt ccgtgctgac cgtgctgcac caggactggc tgaacggcaa agagtacaag    300
tgcaaggtct ccaacaaggc cctgcccgcc tccatcgaaa agaccatctc caaggccaag    360
ggccagcccc gcgagcctca ggtgtgcaca ctgccccccca gccgggaaga gatgaccaag    420
aaccaggtgt ccctgtcctg tgccgtgaaa ggcttctacc cctccgatat cgctgtggaa    480
tgggagtcca acggccagcc cgagaacaac tacaagacca ccccccctgt gctggactcc    540
gacggctcat tcttcctggt gtccaagctg accgtggaca gtcccggtg gcagcagggc    600 aacgtgttct cctgctccgt gatgcacgag gccctgcaca accactacac ccagaagtct    660
```

| | |
|---|---|
| ctaagcttga gccccggcgc agctcctgct cccgcaccag ccctgctcc cgcaccagcc | 720 |
| ggatcccagc tctactcagc gctcgctaat aagtgttgtc atgtgggatg cacaaagcgg | 780 |
| tctctcgcca gattctgc | 798 |

<210> SEQ ID NO 106
<211> LENGTH: 810
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 106

| | |
|---|---|
| gacaagaccc acacctgtcc tccatgcccg gcgcctgagt tcgagggcgg accctccgtg | 60 |
| ttcctgttcc ccccaaagcc caaggacacc ctgatgatct cccggacccc cgaagtgacc | 120 |
| tgcgtggtgg tggacgtgtc ccacgaggac cctgaagtga agttcaattg gtacgtggac | 180 |
| ggcgtggaag tgcacaacgc caagaccaag cccagagagg aacagtacaa ctccacctac | 240 |
| cgggtggtgt ccgtgctgac cgtgctgcac caggactggc tgaacggcaa agagtacaag | 300 |
| tgcaaggtct ccaacaaggc cctgcccgcc tccatcgaaa agaccatctc caaggccaag | 360 |
| ggccagcccc gcgagcctca ggtgtacaca ctgcccccct gccgggaaga tgaccaag | 420 |
| aaccaggtgt ccctgtggtg tctggtgaaa ggcttctacc cctccgatat cgctgtggaa | 480 |
| tgggagtcca acggccagcc cgagaacaac tacaagacca ccccccctgt gctggactcc | 540 |
| gacggctcat tcttcctgta ctccaagctg accgtggaca agtcccggtg gcagcagggc | 600 |
| aacgtgttct cctgctccgt gatgcacgag gccctgcaca accactacac ccagaagtct | 660 |
| ctaagcttga gccccggcgc agctcctgct cccgcaccag ccctgctcc cgcaccagcc | 720 |
| ggatccagct ggatggaaga agtgattaaa ctgtgtggcc gcgaactggt gcgcgcgcag | 780 |
| attgcgattt gcggcatgag cacctggagc | 810 |

<210> SEQ ID NO 107
<211> LENGTH: 783
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 107

| | |
|---|---|
| gacaagaccc acacctgtcc tccatgcccg gcgcctgagt tcgagggcgg accctccgtg | 60 |
| ttcctgttcc ccccaaagcc caaggacacc ctgatgatct cccggacccc cgaagtgacc | 120 |
| tgcgtggtgg tggacgtgtc ccacgaggac cctgaagtga agttcaattg gtacgtggac | 180 |
| ggcgtggaag tgcacaacgc caagaccaag cccagagagg aacagtacaa ctccacctac | 240 |
| cgggtggtgt ccgtgctgac cgtgctgcac caggactggc tgaacggcaa agagtacaag | 300 |
| tgcaaggtct ccaacaaggc cctgcccgcc tccatcgaaa agaccatctc caaggccaag | 360 |
| ggccagcccc gcgagcctca ggtgtacaca ctgcccccct gccgggaaga tgaccaag | 420 |
| aaccaggtgt ccctgtggtg tctggtgaaa ggcttctacc cctccgatat cgctgtggaa | 480 |
| tgggagtcca acggccagcc cgagaacaac tacaagacca ccccccctgt gctggactcc | 540 |
| gacggctcat tcttcctgta ctccaagctg accgtggaca agtcccggtg gcagcagggc | 600 |

```
aacgtgttct cctgctccgt gatgcacgag gccctgcaca accactacac ccagaagtct    660
ctaagcttga gccccggcgc accagcccct gctcccgcac cagccggatc ccagctctac    720
tcagcgctcg ctaataagtg ttgtcatgtg ggatgcacaa agcggtctct cgccagattc    780
tgc                                                                  783
```

<210> SEQ ID NO 108
<211> LENGTH: 795
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 108

```
gacaagaccc acacctgtcc tccatgcccg gcgcctgagt tcgagggcgg accctccgtg     60
ttcctgttcc ccccaaagcc caaggacacc ctgatgatct cccggacccc cgaagtgacc    120
tgcgtggtgg tggacgtgtc ccacgaggac cctgaagtga agttcaattg gtacgtggac    180
ggcgtggaag tgcacaacgc caagaccaag cccagagagg aacagtacaa ctccacctac    240
cgggtggtgt ccgtgctgac cgtgctgcac caggactggc tgaacggcaa agagtacaag    300
tgcaaggtct ccaacaaggc cctgcccgcc tccatcgaaa agaccatctc caaggccaag    360
ggccagcccc gcgagcctca ggtgtgcaca ctgccccca gcgggaaga gatgaccaag     420 aaccaggtgt ccctgtcctg tgccgtgaaa ggcttctacc cctccgatat cgctgtggaa    480
tgggagtcca acggccagcc cgagaacaac tacaagacca cccccctgt gctggactcc    540 gacggctcat tcttcctggt gtccaagctg accgtggaca agtcccggtg gcagcagggc    600
aacgtgttct cctgctccgt gatgcacgag gccctgcaca accactacac ccagaagtct    660
ctaagcttga gccccggcgc accagcccct gctcccgcac cagccggatc cagctggatg    720
gaagaagtga ttaaactgtg tggccgcgaa ctggtgcgcg cgcagattgc gatttgcggc    780
atgagcacct ggagc                                                    795
```

<210> SEQ ID NO 109
<211> LENGTH: 816
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 109

```
gacaagaccc acaccgcttg tcctccatgc ccggcgcctg agttcgaggg cggaccctcc     60
gtgttcctgt tccccccaaa gcccaaggac accctgatga tctcccggac ccccgaagtg    120
acctgcgtgg tggtggacgt gtcccacgag gaccctgaag tgaagttcaa ttggtacgtg    180
gacggcgtgg aagtgcacaa cgccaagacc aagcccagag gaacagtca acctccacc     240 taccgggtgg tgtccgtgct gaccgtgctg caccaggact ggctgaacgg caaagagtac    300
aagtgcaagg tctccaacaa ggccctgccc gcctccatcg aaaagaccat ctccaaggcc    360
aagggccagc ccgcgagcc tcaggtgtac acactgcccc cctgccggga agagatgacc    420
aagaaccagg tgtccctgtg gtgtctggtg aaaggcttct accctccga tatcgctgtg    480 gaatgggagt ccaacggcca gcccgagaac aactacaaga ccaccccccc tgtgctggac    540
tccgacggct cattcttcct gtactccaag ctgaccgtgg acaagtcccg gtggcagcag    600
```

```
ggcaacgtgt tctcctgctc cgtgatgcac gaggccctgc acaaccacta cacccagaag    660
tctctaagct tgagcccgg cggaggtggt ggaagcggag gaggtggctc tggaggggt    720 ggaagcggag gtggaggtgg atcccagctc tactcagcgc tcgctaatga gtgttgtcat    780
gtgggatgca caaagcggtc tctcgccaga ttctgc                              816
```

<210> SEQ ID NO 110
<211> LENGTH: 816
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 110

```
gacaagaccc acaccgcttg tcctccatgc ccggcgcctg agttcgaggg cggaccctcc     60
gtgttcctgt tcccccaaa gcccaaggac accctgatga tctcccggac ccccgaagtg    120
acctgcgtgg tggtggacgt gtcccacgag gaccctgaag tgaagttcaa ttggtacgtg    180
gacggcgtgg aagtgcacaa cgccaagacc aagcccagag aggaacagta caactccacc    240
taccgggtgg tgtccgtgct gaccgtgctg caccaggact ggctgaacgg caaagagtac    300
aagtgcaagg tctccaacaa ggccctgccc gcctccatcg aaaagaccat ctccaaggcc    360
aagggccagc ccgcgagcc tcaggtgtac acactgcccc cctgccggga agagatgacc    420
aagaaccagg tgtccctgtg gtgtctggtg aaaggcttct accctccga tatcgctgtg    480 gaatgggagt ccaacggcca gcccgagaac aactacaaga ccacccccccc tgtgctggac    540 tccgacggct cattcttcct gtactccaag ctgaccgtgg acaagtcccg gtggcagcag    600
ggcaacgtgt tctcctgctc cgtgatgcac gaggccctgc acaaccacta cacccagaag    660
tctctaagct tgagcccgg cggaggtggt ggaagcggag gaggtggctc tggaggggt    720 ggaagcggag gtggaggtgg atcccagctc tactcagcgc tcgctaatca ctgttgtcat    780
gtgggatgca caaagcggtc tctcgccaga ttctgc                              816
```

<210> SEQ ID NO 111
<211> LENGTH: 816
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 111

```
gacaagaccc acaccgcttg tcctccatgc ccggcgcctg agttcgaggg cggaccctcc     60
gtgttcctgt tcccccaaa gcccaaggac accctgatga tctcccggac ccccgaagtg    120
acctgcgtgg tggtggacgt gtcccacgag gaccctgaag tgaagttcaa ttggtacgtg    180
gacggcgtgg aagtgcacaa cgccaagacc aagcccagag aggaacagta caactccacc    240
taccgggtgg tgtccgtgct gaccgtgctg caccaggact ggctgaacgg caaagagtac    300
aagtgcaagg tctccaacaa ggccctgccc gcctccatcg aaaagaccat ctccaaggcc    360
aagggccagc ccgcgagcc tcaggtgtac acactgcccc cctgccggga agagatgacc    420
aagaaccagg tgtccctgtg gtgtctggtg aaaggcttct accctccga tatcgctgtg    480 gaatgggagt ccaacggcca gcccgagaac aactacaaga ccacccccccc tgtgctggac    540
```

| | |
|---|---|
| tccgacggct cattcttcct gtactccaag ctgaccgtgg acaagtcccg gtggcagcag | 600 |
| ggcaacgtgt tctcctgctc cgtgatgcac gaggccctgc acaaccacta cacccagaag | 660 |
| tctctaagct tgagccccgg cggaggtggt ggaagcggag gaggtggctc tggagggggt | 720 |
| ggaagcggag gtggaggtgg atcccagctc tactcagcgc tcgctaattt gtgttgtcat | 780 |
| gtgggatgca caaagcggtc tctcgccaga ttctgc | 816 |

<210> SEQ ID NO 112
<211> LENGTH: 816
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 112

| | |
|---|---|
| gacaagaccc acaccgcttg tcctccatgc ccggcgcctg agttcgaggg cggaccctcc | 60 |
| gtgttcctgt tccccccaaa gcccaaggac accctgatga tctcccggac ccccgaagtg | 120 |
| acctgcgtgg tggtggacgt gtcccacgag gaccctgaag tgaagttcaa ttggtacgtg | 180 |
| gacggcgtgg aagtgcacaa cgccaagacc aagcccagag aggaacagta caactccacc | 240 |
| taccgggtgg tgtccgtgct gaccgtgctg caccaggact ggctgaacgg caaagagtac | 300 |
| aagtgcaagg tctccaacaa ggccctgccc gcctccatcg aaaagaccat ctccaaggcc | 360 |
| aagggccagc cccgcgagcc tcaggtgtac acactgcccc cctgccggga agagatgacc | 420 |
| aagaaccagg tgtccctgtg cgtgtctggtg aaaggcttct accctccga tatcgctgtg | 480 |
| gaatgggagt ccaacggcca gcccgagaac aactacaaga ccacccccc tgtgctggac | 540 |
| tccgacggct cattcttcct gtactccaag ctgaccgtgg acaagtcccg gtggcagcag | 600 |
| ggcaacgtgt tctcctgctc cgtgatgcac gaggccctgc acaaccacta cacccagaag | 660 |
| tctctaagct tgagccccgg cggaggtggt ggaagcggag gaggtggctc tggagggggt | 720 |
| ggaagcggag gtggaggtgg atcccagctc tactcagcgc tcgctaatat gtgttgtcat | 780 |
| gtgggatgca caaagcggtc tctcgccaga ttctgc | 816 |

<210> SEQ ID NO 113
<211> LENGTH: 816
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 113

| | |
|---|---|
| gacaagaccc acaccgcttg tcctccatgc ccggcgcctg agttcgaggg cggaccctcc | 60 |
| gtgttcctgt tccccccaaa gcccaaggac accctgatga tctcccggac ccccgaagtg | 120 |
| acctgcgtgg tggtggacgt gtcccacgag gaccctgaag tgaagttcaa ttggtacgtg | 180 |
| gacggcgtgg aagtgcacaa cgccaagacc aagcccagag aggaacagta caactccacc | 240 |
| taccgggtgg tgtccgtgct gaccgtgctg caccaggact ggctgaacgg caaagagtac | 300 |
| aagtgcaagg tctccaacaa ggccctgccc gcctccatcg aaaagaccat ctccaaggcc | 360 |
| aagggccagc cccgcgagcc tcaggtgtac acactgcccc cctgccggga agagatgacc | 420 |
| aagaaccagg tgtccctgtg cgtgtctggtg aaaggcttct accctccga tatcgctgtg | 480 |
| gaatgggagt ccaacggcca gcccgagaac aactacaaga ccacccccc tgtgctggac | 540 |

```
tccgacggct cattcttcct gtactccaag ctgaccgtgg acaagtcccg gtggcagcag    600
ggcaacgtgt tctcctgctc cgtgatgcac gaggccctgc acaaccacta cacccagaag    660
tctctaagct tgagccccgg cggaggtggt ggaagcggag gaggtggctc tggaggggt     720 ggaagcggag gtggaggtgg atcccagctc tactcagcgc tcgctaataa gtgttgtcat    780
gtgggatgca caaaggagtc tctcgccaga ttctgc                              816
```

<210> SEQ ID NO 114
<211> LENGTH: 816
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 114

```
gacaagaccc acaccgcttg tcctccatgc ccggcgcctg agttcgaggg cggaccctcc     60
gtgttcctgt tccccccaaa gcccaaggac accctgatga tctcccggac ccccgaagtg    120
acctgcgtgg tggtggacgt gtcccacgag gaccctgaag tgaagttcaa ttggtacgtg    180
gacggcgtgg aagtgcacaa cgccaagacc aagcccagag aggaacagta caactccacc    240
taccgggtgg tgtccgtgct gaccgtgctg caccaggact ggctgaacgg caaagagtac    300
aagtgcaagg tctccaacaa ggccctgccc gcctccatcg aaaagaccat ctccaaggcc    360
aagggccagc cccgcgagcc tcaggtgtac acactgcccc cctgccggga agagatgacc    420
aagaaccagg tgtccctgtg gtgtctggtg aaaggcttct acccctccga tatcgctgtg    480
gaatgggagt ccaacggcca gcccgagaac aactacaaga ccaccccccc tgtgctggac    540
tccgacggct cattcttcct gtactccaag ctgaccgtgg acaagtcccg gtggcagcag    600
ggcaacgtgt tctcctgctc cgtgatgcac gaggccctgc acaaccacta cacccagaag    660
tctctaagct tgagccccgg cggaggtggt ggaagcggag gaggtggctc tggaggggt     720 ggaagcggag gtggaggtgg atcccagctc tactcagcgc tcgctaataa gtgttgtcat    780
gtgggatgca caaagcactc tctcgccaga ttctgc                              816
```

<210> SEQ ID NO 115
<211> LENGTH: 813
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 115

```
gacaagaccc acacctgtcc tccatgcccg gcgcctgagt tcgagggcgg accctccgtg     60
ttcctgttcc ccccaaagcc caaggacacc ctgatgatct cccggacccc cgaagtgacc    120
tgcgtggtgg tggacgtgtc ccacgaggac cctgaagtga agttcaattg gtacgtggac    180
ggcgtggaag tgcacaacgc caagaccaag cccagagagg aacagtacaa ctccacctac    240
cgggtggtgt ccgtgctgac cgtgctgcac caggactggc tgaacggcaa agagtacaag    300
tgcaaggtct ccaacaaggc cctgcccgcc tccatcgaaa agaccatctc caaggccaag    360
ggccagcccc gcgagcctca ggtgtacaca ctgccccct gccgggaaga gatgaccaag    420
aaccaggtgt ccctgtggtg tctggtgaaa ggcttctacc cctccgatat cgctgtggaa    480
```

```
tgggagtcca acggccagcc cgagaacaac tacaagacca ccccccctgt gctggactcc    540
gacggctcat tcttcctgta ctccaagctg accgtggaca agtcccggtg gcagcagggc    600
aacgtgttct cctgctccgt gatgcacgag gccctgcaca accactacac ccagaagtct    660
ctaagcttga gccccggcgg aggtggtgga agcggaggag gtggctctgg aggggggtgga    720 agcggaggtg gaggtggatc ccagctctac tcagcgctcg ctaataagtg ttgtcatgtg    780
ggatgcacaa agcggtctct cgccgccttc tgc                                 813
```

<210> SEQ ID NO 116
<211> LENGTH: 813
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 116

```
gacaagaccc acacctgtcc tccatgcccg gcgcctgagt tcgagggcgg accctccgtg     60
ttcctgttcc ccccaaagcc caaggacacc ctgatgatct cccggacccc cgaagtgacc    120
tgcgtggtgg tggacgtgtc ccacgaggac cctgaagtga agttcaattg gtacgtggac    180
ggcgtggaag tgcacaacgc caagaccaag cccagagagg aacagtacaa ctccacctac    240
cgggtggtgt ccgtgctgac cgtgctgcac caggactggc tgaacggcaa agagtacaag    300
tgcaaggtct ccaacaaggc cctgcccgcc tccatcgaaa agaccatctc caaggccaag    360
ggccagcccc gcgagcctca ggtgtacaca ctgcccccct gcgggaaga gatgaccaag    420 aaccaggtgt ccctgtggtg tctggtgaaa ggcttctacc cctccgatat cgctgtggaa    480
tgggagtcca acggccagcc cgagaacaac tacaagacca ccccccctgt gctggactcc    540
gacggctcat tcttcctgta ctccaagctg accgtggaca agtcccggtg gcagcagggc    600
aacgtgttct cctgctccgt gatgcacgag gccctgcaca accactacac ccagaagtct    660
ctaagcttga gccccggcgg aggtggtgga agcggaggag gtggctctgg aggggggtgga    720 agcggaggtg gaggtggatc ccagctctac tcagcgctcg ctaataagtg ttgtcatgtg    780
ggatgcacaa agcggtctct cgccatcttc tgc                                 813
```

<210> SEQ ID NO 117
<211> LENGTH: 813
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 117

```
gacaagaccc acacctgtcc tccatgcccg gcgcctgagt tcgagggcgg accctccgtg     60
ttcctgttcc ccccaaagcc caaggacacc ctgatgatct cccggacccc cgaagtgacc    120
tgcgtggtgg tggacgtgtc ccacgaggac cctgaagtga agttcaattg gtacgtggac    180
ggcgtggaag tgcacaacgc caagaccaag cccagagagg aacagtacaa ctccacctac    240
cgggtggtgt ccgtgctgac cgtgctgcac caggactggc tgaacggcaa agagtacaag    300
tgcaaggtct ccaacaaggc cctgcccgcc tccatcgaaa agaccatctc caaggccaag    360
ggccagcccc gcgagcctca ggtgtacaca ctgcccccct gcgggaaga gatgaccaag    420 aaccaggtgt ccctgtggtg tctggtgaaa ggcttctacc cctccgatat cgctgtggaa    480
```

```
tgggagtcca acggccagcc cgagaacaac tacaagacca ccccccctgt gctggactcc    540
gacggctcat tcttcctgta ctccaagctg accgtggaca agtcccggtg gcagcagggc    600
aacgtgttct cctgctccgt gatgcacgag gccctgcaca accactacac ccagaagtct    660
ctaagcttga gccccggcgg aggtggtgga agcggaggag gtggctctgg aggggggtgga    720 agcggaggtg gaggtggatc ccagctctac tcagcgctcg ctaataagtg ttgtcatgtg    780
ggatgcacaa agcggtctct cgccatgttc tgc                                 813
```

<210> SEQ ID NO 118
<211> LENGTH: 813
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic polynucleotide"

<400> SEQUENCE: 118

```
gacaagaccc acacctgtcc tccatgcccg gcgcctgagt tcgagggcgg accctccgtg     60
ttcctgttcc ccccaaagcc caaggacacc ctgatgatct cccggacccc cgaagtgacc    120
tgcgtggtgg tggacgtgtc ccacgaggac cctgaagtga agttcaattg gtacgtggac    180
ggcgtggaag tgcacaacgc caagaccaag cccagagagg aacagtacaa ctccacctac    240
cgggtggtgt ccgtgctgac cgtgctgcac caggactggc tgaacggcaa agagtacaag    300
tgcaaggtct ccaacaaggc cctgcccgcc tccatcgaaa agaccatctc caaggccaag    360
ggccagcccc gcgagcctca ggtgtacaca ctgcccccct gccgggaaga gatgaccaag    420
aaccaggtgt ccctgtggtg tctggtgaaa ggcttctacc cctccgatat cgctgtggaa    480
tgggagtcca acggccagcc cgagaacaac tacaagacca ccccccctgt gctggactcc    540
gacggctcat tcttcctgta ctccaagctg accgtggaca agtcccggtg gcagcagggc    600
aacgtgttct cctgctccgt gatgcacgag gccctgcaca accactacac ccagaagtct    660
ctaagcttga gccccggcgg aggtggtgga agcggaggag gtggctctgg aggggggtgga    720 agcggaggtg gaggtggatc ccagctctac tcagcgctcg ctaataagtg ttgtcatgtg    780
ggatgcacaa agcggtctct cgcccagttc tgc                                 813
```

<210> SEQ ID NO 119
<211> LENGTH: 813
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic polynucleotide"

<400> SEQUENCE: 119

```
gacaagaccc acacctgtcc tccatgcccg gcgcctgagt tcgagggcgg accctccgtg     60
ttcctgttcc ccccaaagcc caaggacacc ctgatgatct cccggacccc cgaagtgacc    120
tgcgtggtgg tggacgtgtc ccacgaggac cctgaagtga agttcaattg gtacgtggac    180
ggcgtggaag tgcacaacgc caagaccaag cccagagagg aacagtacaa ctccacctac    240
cgggtggtgt ccgtgctgac cgtgctgcac caggactggc tgaacggcaa agagtacaag    300
tgcaaggtct ccaacaaggc cctgcccgcc tccatcgaaa agaccatctc caaggccaag    360
ggccagcccc gcgagcctca ggtgtacaca ctgcccccct gccgggaaga gatgaccaag    420
```

```
aaccaggtgt ccctgtggtg tctggtgaaa ggcttctacc cctccgatat cgctgtggaa    480
tgggagtcca acggccagcc cgagaacaac tacaagacca ccccccctgt gctggactcc    540
gacggctcat tcttcctgta ctccaagctg accgtggaca agtcccggtg gcagcagggc    600
aacgtgttct cctgctccgt gatgcacgag gccctgcaca accactacac ccagaagtct    660
ctaagcttga gccccggcgg aggtggtgga agcggaggag gtggctctgg aggggggtgga    720 agcggaggtg gaggtggatc ccagctctac tcagcgctcg ctaataagtg ttgtcatgtg    780
ggatgcacaa agcggtctct cgcctccttc tgc                                 813

<210> SEQ ID NO 120
<211> LENGTH: 813
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 120
gacaagaccc acacctgtcc tccatgcccg gcgcctgagt tcgagggcgg accctccgtg     60
ttcctgttcc ccccaaagcc caaggacacc ctgatgatct cccggacccc cgaagtgacc    120
tgcgtggtgg tggacgtgtc ccacgaggac cctgaagtga agttcaattg gtacgtggac    180
ggcgtggaag tgcacaacgc caagaccaag cccagagagg aacagtacaa ctccacctac    240
cgggtggtgt ccgtgctgac cgtgctgcac caggactggc tgaacggcaa agagtacaag    300
tgcaaggtct ccaacaaggc cctgcccgcc tccatcgaaa agaccatctc caaggccaag    360
ggccagcccc gcgagcctca ggtgtacaca ctgccccct gccgggaaga gatgaccaag    420
aaccaggtgt ccctgtggtg tctggtgaaa ggcttctacc cctccgatat cgctgtggaa    480
tgggagtcca acggccagcc cgagaacaac tacaagacca ccccccctgt gctggactcc    540
gacggctcat tcttcctgta ctccaagctg accgtggaca agtcccggtg gcagcagggc    600
aacgtgttct cctgctccgt gatgcacgag gccctgcaca accactacac ccagaagtct    660
ctaagcttga gccccggcgg aggtggtgga agcggaggag gtggctctgg aggggggtgga    720 agcggaggtg gaggtggatc ccagctctac tcagcgctcg ctaataagtg ttgtcatgtg    780
ggatgcacaa agcggtctct cgcctacttc tgc                                 813

<210> SEQ ID NO 121
<211> LENGTH: 813
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 121
gacaagaccc acacctgtcc tccatgcccg gcgcctgagt tcgagggcgg accctccgtg     60
ttcctgttcc ccccaaagcc caaggacacc ctgatgatct cccggacccc cgaagtgacc    120
tgcgtggtgg tggacgtgtc ccacgaggac cctgaagtga agttcaattg gtacgtggac    180
ggcgtggaag tgcacaacgc caagaccaag cccagagagg aacagtacaa ctccacctac    240
cgggtggtgt ccgtgctgac cgtgctgcac caggactggc tgaacggcaa agagtacaag    300
tgcaaggtct ccaacaaggc cctgcccgcc tccatcgaaa agaccatctc caaggccaag    360
ggccagcccc gcgagcctca ggtgtacaca ctgccccct gccgggaaga gatgaccaag    420
```

```
aaccaggtgt ccctgtggtg tctggtgaaa ggcttctacc cctccgatat cgctgtggaa      480
tgggagtcca acggccagcc cgagaacaac tacaagacca cccccctgt gctggactcc      540 gacggctcat tcttcctgta ctccaagctg accgtggaca agtcccggtg gcagcagggc      600
aacgtgttct cctgctccgt gatgcacgag gccctgcaca accactacac ccagaagtct      660
ctaagcttga gccccggcgg aggtggtgga agcggaggag gtggctctgg aggggtgga      720 agcggaggtg gaggtggatc ccagctctac tcagcgctcg ctaataagtg ttgtcatgtg      780
ggatgcacaa agcggtctct cgccagagag tgc                                  813
```

```
<210> SEQ ID NO 122
<211> LENGTH: 813
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 122
gacaagaccc acacctgtcc tccatgcccg gcgcctgagt tcgagggcgg accctccgtg       60
ttcctgttcc ccccaaagcc caaggacacc ctgatgatct cccggacccc cgaagtgacc      120
tgcgtggtgg tggacgtgtc ccacgaggac cctgaagtga agttcaattg gtacgtggac      180
ggcgtggaag tgcacaacgc caagaccaag cccagagagg aacagtacaa ctccacctac      240
cgggtggtgt ccgtgctgac cgtgctgcac caggactggc tgaacggcaa agagtacaag      300
tgcaaggtct ccaacaaggc cctgcccgcc tccatcgaaa agaccatctc caaggccaag      360
ggccagcccc gcgagcctca ggtgtacaca ctgccccct gccgggaaga tgaccaag       420 aaccaggtgt ccctgtggtg tctggtgaaa ggcttctacc cctccgatat cgctgtggaa      480
tgggagtcca acggccagcc cgagaacaac tacaagacca cccccctgt gctggactcc      540 gacggctcat tcttcctgta ctccaagctg accgtggaca agtcccggtg gcagcagggc      600
aacgtgttct cctgctccgt gatgcacgag gccctgcaca accactacac ccagaagtct      660
ctaagcttga gccccggcgg aggtggtgga agcggaggag gtggctctgg aggggtgga      720 agcggaggtg gaggtggatc ccagctctac tcagcgctcg ctaataagtg ttgtcatgtg      780
ggatgcacaa agcggtctct cgccagaatc tgc                                  813
```

```
<210> SEQ ID NO 123
<211> LENGTH: 924
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 123
gacaagaccc acacctgtcc tccatgcccg gcgcctgagt tcgagggcgg accctccgtg       60
ttcctgttcc ccccaaagcc caaggacacc ctgatgatct cccggacccc cgaagtgacc      120
tgcgtggtgg tggacgtgtc ccacgaggac cctgaagtga agttcaattg gtacgtggac      180
ggcgtggaag tgcacaacgc caagaccaag cccagagagg aacagtacaa ctccacctac      240
cgggtggtgt ccgtgctgac cgtgctgcac caggactggc tgaacggcaa agagtacaag      300
tgcaaggtct ccaacaaggc cctgcccgcc tccatcgaaa agaccatctc caaggccaag      360
```

```
ggccagcccc gcgagcctca ggtgtacaca ctgcccccct gccgggaaga gatgaccaag    420
aaccaggtgt ccctgtggtg tctggtgaaa ggcttctacc cctccgatat cgctgtggaa    480
tgggagtcca acggccagcc cgagaacaac tacaagacca ccccccctgt gctggactcc    540
gacggctcat tcttcctgta ctccaagctg accgtggaca agtcccggtg gcagcagggc    600
aacgtgttct cctgctccgt gatgcacgag gccctgcaca accactacac ccagaagtct    660
ctaagcttga gccccggcgg aggtggtgga agcggaggag gtggctctgg aggggggtgga    720 agcggaggtg gaggtggatc ctcctggatg gaggaggtta tcaagctgtg tggacgcgaa    780
ctggtgcgcg ctcagatcgc gatatgcggg atgtccacat ggtcaggcgg cggcagcggc    840
ggcggcagcg gccagctcta ctcagcgctc gctaataagt gttgtcatgt gggatgcaca    900
aagcggtctc tcgccagatt ctgc                                           924
```

<210> SEQ ID NO 124
<211> LENGTH: 924
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 124

```
gacaagaccc acacctgtcc tccatgcccg gcgcctgagt tcgagggcgg accctccgtg    60
ttcctgttcc ccccaaagcc caaggacacc ctgatgatct cccggacccc cgaagtgacc    120
tgcgtggtgg tggacgtgtc ccacgaggac cctgaagtga agttcaattg gtacgtggac    180
ggcgtggaag tgcacaacgc caagaccaag cccagagagg aacagtacaa ctccacctac    240
cgggtggtgt ccgtgctgac cgtgctgcac caggactggc tgaacggcaa agagtacaag    300
tgcaaggtct ccaacaaggc cctgcccgcc tccatcgaaa agaccatctc caaggccaag    360
ggccagcccc gcgagcctca ggtgtgcaca ctgcccccca gccgggaaga gatgaccaag    420
aaccaggtgt ccctgtcctg tgccgtgaaa ggcttctacc cctccgatat cgctgtggaa    480
tgggagtcca acggccagcc cgagaacaac tacaagacca ccccccctgt gctggactcc    540
gacggctcat tcttcctggt gtccaagctg accgtggaca agtcccggtg gcagcagggc    600
aacgtgttct cctgctccgt gatgcacgag gccctgcaca accactacac ccagaagtct    660
ctaagcttga gccccggcgg aggtggtgga agcggaggag gtggctctgg aggggggtgga    720 agcggaggtg gaggtggatc ctcctggatg gaggaggtta tcaagctgtg tggacgcgaa    780
ctggtgcgcg ctcagatcgc gatatgcggg atgtccacat ggtcaggcgg cggcagcggc    840
ggcggcagcg gccagctcta ctcagcgctc gctaataagt gttgtcatgt gggatgcaca    900
aagcggtctc tcgccagatt ctgc                                           924
```

<210> SEQ ID NO 125
<211> LENGTH: 819
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 125

```
tcctggatgg aagaagtgat caagctctgc ggcagagaac tcgtgcgggc ccagatcgct    60
atctgcggca tgtctacttg gagcgcggcc gcgggtggag gtggatccgg aggaggtgga    120
```

```
agcggaggag gtggaagcgg aggaggtgga agcgcttgtc ctccatgccc ggcgcctgag      180
ttcgagggcg gaccctccgt gttcctgttc ccccaaagc ccaaggacac cctgatgatc      240
tcccggaccc ccgaagtgac ctgcgtggtg gtggacgtgt cccacgagga ccctgaagtg      300
aagttcaatt ggtacgtgga cggcgtggaa gtgcacaacg ccaagaccaa gcccagagag      360
gaacagtaca actccaccta ccgggtggtg tccgtgctga ccgtgctgca ccaggactgg      420
ctgaacggca aagagtacaa gtgcaaggtc tccaacaagg ccctgcccgc ctccatcgaa      480
aagaccatct ccaaggccaa gggccagccc cgcgagcctc aggtgtgcac actgccccc      540 agccgggaag atgaccaaga accaggtgt cccctgtcct gtgccgtgaa aggcttctac      600
ccctccgata tcgctgtgga atgggagtcc aacggccagc cgagaacaa ctacaagacc      660 accccccctg tgctggactc cgacggctca ttcttcctgg tgtccaagct gaccgtggac      720
aagtcccggt ggcagcaggg caacgtgttc tcctgctccg tgatgcacga ggccctgcac      780
aaccactaca cccagaagtc tctgtccctg agccccggc                             819
```

<210> SEQ ID NO 126
<211> LENGTH: 807
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 126

```
cagctgtact ctgccctggc caacaagtgt tgccacgtgg gctgcaccaa gagatccctg       60
gccagattct gtgcggccgc gggtggaggt ggatccggag gaggtggaag cggaggaggt      120
ggaagcggag gaggtggaag cgcttgtcct ccatgcccgg cgcctgagtt cgagggcgga      180
ccctccgtgt tcctgttccc cccaaagccc aaggacaccc tgatgatctc ccggaccccc      240
gaagtgacct gcgtggtggt ggacgtgtcc cacgaggacc ctgaagtgaa gttcaattgg      300
tacgtggacg gcgtggaagt gcacaacgcc aagaccaagc ccagagagga acagtacaac      360
tccacctacc gggtggtgtc cgtgctgacc gtgctgcacc aggactggct gaacggcaaa      420
gagtacaagt gcaaggtctc caacaaggcc ctgcccgcct ccatcgaaaa gaccatctcc      480
aaggccaagg ccagccccg cgagcctcag gtgtacacac tgccccctg ccgggaagag      540 atgaccaaga accaggtgtc cctgtggtgt ctggtgaaag gcttctaccc ctccgatatc      600
gctgtggaat gggagtccaa cggccagccc gagaacaact acaagaccac ccccctgtg      660 ctggactccg acggctcatt cttcctgtac tccaagctga ccgtggacaa gtcccggtgg      720
cagcagggca acgtgttctc ctgctccgtg atgcacgagg ccctgcacaa ccactacacc      780
cagaagtctc tgtccctgag ccccggc                                          807
```

<210> SEQ ID NO 127
<211> LENGTH: 942
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 127

```
cagctgtact ctgccctggc caacaagtgt tgccacgtgg gctgcaccaa gagatccctg       60
```

```
gccagattct gtgcggccgc gggtggaggt ggatccggag gaggtggaag cggaggaggt    120
ggaagcggag gaggtggaag cgcttgtcct ccatgcccgg cgcctgagtt cgagggcgga    180
ccctccgtgt tcctgttccc cccaaagccc aaggacaccc tgatgatctc ccggaccccc    240
gaagtgacct gcgtggtggt ggacgtgtcc cacgaggacc ctgaagtgaa gttcaattgg    300
tacgtggacg gcgtggaagt gcacaacgcc aagaccaagc cagagagga acagtacaac    360 tccacctacc gggtggtgtc cgtgctgacc gtgctgcacc aggactggct gaacggcaaa    420
gagtacaagt gcaaggtctc caacaaggcc ctgcccgcct ccatcgaaaa gaccatctcc    480
aaggccaagg gccagccccg cgagcctcag gtgtacacac tgcccccctg ccgggaagag    540
atgaccaaga accaggtgtc cctgtggtgt ctggtgaaag gcttctaccc ctccgatatc    600
gctgtggaat gggagtccaa cggccagccc gagaacaact acaagaccac cccccctgtg    660
ctggactccg acggctcatt cttcctgtac tccaagctga ccgtggacaa gtcccggtgg    720
cagcagggca acgtgttctc ctgctccgtg atgcacgagg ccctgcacaa ccactacacc    780
cagaagtctc taagcttgag ccccggcgga ggtggtggaa gcggaggagg tggctctgga    840 ggggggtggaa gcggaggtgg aggtggatcc cagctctact cagcgctcgc taataagtgt    900
tgtcatgtgg gatgcacaaa gcggtctctc gccagattct gc                      942

<210> SEQ ID NO 128
<211> LENGTH: 966
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 128
tcctggatgg aagaagtgat caagctctgc ggcagagaac tcgtgcgggc ccagatcgct     60
atctgcggca tgtctacttg gagcgcggcc gcgggtggag gtggatccgg aggaggtgga    120
agcggaggag gtggaagcgg aggaggtgga agcgcttgtc ctccatgccc ggcgcctgag    180
ttcgagggcg gaccctccgt gttcctgttc cccccaaagc caaggacac cctgatgatc    240 tcccggaccc ccgaagtgac ctgcgtggtg gtggacgtgt cccacgagga ccctgaagtg    300
aagttcaatt ggtacgtgga cggcgtgaa gtgcacaacg ccaagaccaa gccagagag    360 gaacagtaca actccaccta ccgggtggtg tccgtgctga ccgtgctgca ccaggactgg    420
ctgaacggca aagagtacaa gtgcaaggtc tccaacaagg ccctgcccgc ctccatcgaa    480
aagaccatct ccaaggccaa gggccagccc cgcgagcctc aggtgtgcac actgccccc    540 agccgggaag atgaccaa gaaccaggtg tccctgtcct gtgccgtgaa aggcttctac    600
ccctccgata tcgctgtgga atgggagtcc aacggccagc cgagaacaa ctacaagacc    660 accccccctg tgctggactc cgacggctca ttcttcctgg tgtccaagct gaccgtggac    720
aagtcccggt ggcagcaggg caacgtgttc tcctgctccg tgatgcacga ggccctgcac    780
aaccactaca cccagaagtc tctaagcttg agccccggcg gaggtggtgg aagcggagga    840
ggtggctctg gaggggtgg aagcggaggt ggaggtggat ccagctggat ggaagaagtg    900
attaaactgt gtggccgcga actggtgcgc gcgcagattg cgatttgcgg catgagcacc    960
tggagc                                                              966

<210> SEQ ID NO 129
<211> LENGTH: 819
```

<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 129

| | | | | | |
|---|---|---|---|---|---|
| gacaagaccc | acacctgtcc | tccatgcccg | gcgcctgagt | tcgagggcgg | accctccgtg | 60 |
| ttcctgttcc | ccccaaagcc | caaggacacc | ctgatgatct | cccggacccc | cgaagtgacc | 120 |
| tgcgtggtgg | tggacgtgtc | ccacgaggac | cctgaagtga | agttcaattg | gtacgtggac | 180 |
| ggcgtggaag | tgcacaacgc | caagaccaag | cccagagagg | aacagtacaa | ctccacctac | 240 |
| cgggtggtgt | ccgtgctgac | cgtgctgcac | caggactggc | tgaacggcaa | agagtacaag | 300 |
| tgcaaggtct | ccaacaaggc | cctgcccgcc | tccatcgaaa | agaccatctc | caaggccaag | 360 |
| ggccagcccc | gcgagcctca | ggtgtgcaca | ctgccccca | gcgggaaga | gatgaccaag | 420 |
| aaccaggtgt | ccctgtcctg | tgccgtgaaa | ggcttctacc | cctccgatat | cgctgtggaa | 480 |
| tgggagtcca | acggccagcc | cgagaacaac | tacaagacca | cccccctgt | gctggactcc | 540 |
| gacggctcat | tcttcctggt | gtccaagctg | accgtggaca | agtcccggtg | gcagcagggc | 600 |
| aacgtgttct | cctgctccgt | gatgcacgag | gccctgcaca | accactacac | ccagaagtct | 660 |
| ctaagcttga | gccccggcgg | aggtggtgga | agcggaggag | gtggctctgg | aggggtgga | 720 |
| agcggaggtg | gaggtggatc | cagctggatg | gaagaagtga | ttaaactgtg | tggccgcgaa | 780 |
| ctggtgcgcg | cgcagattgc | gatttgcggc | atgagcacc | | | 819 |

<210> SEQ ID NO 130
<211> LENGTH: 816
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 130

| | | | | | |
|---|---|---|---|---|---|
| gacaagaccc | acacctgtcc | tccatgcccg | gcgcctgagt | tcgagggcgg | accctccgtg | 60 |
| ttcctgttcc | ccccaaagcc | caaggacacc | ctgatgatct | cccggacccc | cgaagtgacc | 120 |
| tgcgtggtgg | tggacgtgtc | ccacgaggac | cctgaagtga | agttcaattg | gtacgtggac | 180 |
| ggcgtggaag | tgcacaacgc | caagaccaag | cccagagagg | aacagtacaa | ctccacctac | 240 |
| cgggtggtgt | ccgtgctgac | cgtgctgcac | caggactggc | tgaacggcaa | agagtacaag | 300 |
| tgcaaggtct | ccaacaaggc | cctgcccgcc | tccatcgaaa | agaccatctc | caaggccaag | 360 |
| ggccagcccc | gcgagcctca | ggtgtgcaca | ctgccccca | gcgggaaga | gatgaccaag | 420 |
| aaccaggtgt | ccctgtcctg | tgccgtgaaa | ggcttctacc | cctccgatat | cgctgtggaa | 480 |
| tgggagtcca | acggccagcc | cgagaacaac | tacaagacca | cccccctgt | gctggactcc | 540 |
| gacggctcat | tcttcctggt | gtccaagctg | accgtggaca | agtcccggtg | gcagcagggc | 600 |
| aacgtgttct | cctgctccgt | gatgcacgag | gccctgcaca | accactacac | ccagaagtct | 660 |
| ctaagcttga | gccccggcgg | aggtggtgga | agcggaggag | gtggctctgg | aggggtgga | 720 |
| agcggaggtg | gaggtggatc | cagctggatg | gaagaagtga | ttaaactgtg | tggccgcgaa | 780 |
| ctggtgcgcg | cgcagattgc | gatttgcggc | atgagc | | | 816 |

<210> SEQ ID NO 131

<211> LENGTH: 1482
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 131

```
gaggtgcagc tgctcgagtc aggggagggc ttggtacagc cggggggtc cctgagactc      60 tcctgtacaa cctctggatt caccttaac acgtatgcca tgagttgggt ccgccaggct     120
ccagggaagg ggctgaatg gctctcaggt attaataaca atggtcggac tgcattctac     180
gcagactccg tgaagggccg cttcaccatc tccagagaca actccaaaaa cacactttat    240
ctgcaaatta atagtctgag agcggacgac acggccgttt atttctgtgc gaaagatgtc    300
agatttatcg cagtgcctgg tgactcctgg ggccaggaa ccctggtcac cgtctcctca     360
gcctccacca agggcccatc ggtcttcccc ctggccccca gcagcaagag caccagcggc    420
ggcacagccg ccctgggctg cctggtgaag gactacttcc ccgagcccgt gaccgtgtcc    480
tggaacagcg gagccctgac ctccggcgtg cacaccttcc cggccgtgct gcagagcagc    540
ggcctgtaca gcctgagcag cgtggtgaca gtgccaagca gcagcctggg cacccagacc    600
tacatctgca acgtgaacca caagcccagc aacaccaagg tggacaagag agttgagccc    660
aaatcttgtg acaagaccca cacctgtcct ccatgcccgg cgcctgagtt cgagggcgga    720
ccctccgtgt tcctgttccc cccaaagccc aaggacaccc tgatgatctc ccggaccccc    780
gaagtgacct gcgtggtggt ggacgtgtcc cacgaggacc ctgaagtgaa gttcaattgg    840
tacgtggacg gcgtggaagt gcacaacgcc aagaccaagc ccagagagga acagtacaac    900
tccacctacc gggtggtgtc cgtgctgacc gtgctgcacc aggactggct gaacggcaaa    960
gagtacaagt gcaaggtctc caacaaggcc ctgcccgcct ccatcgaaaa gaccatctcc   1020
aaggccaagg gccagccccg cgagcctcag gtgtacacac tgccccctg ccgggaagag   1080 atgaccaaga accaggtgtc cctgtggtgt ctggtgaaag gcttctaccc ctccgatatc   1140
gctgtggaat gggagtccaa cggccagccc gagaacaact acaagaccac cccccctgtg   1200
ctggactccg acggctcatt cttcctgtac tccaagctga ccgtggacaa gtcccggtgg   1260
cagcagggca acgtgttctc ctgctccgtg atgcacgagg ccctgcacaa ccactacacc   1320
cagaagtctc taagcttgag ccccggcgga ggtggtggaa gcggaggagg tggctctgga   1380
gggggtggaa gcggaggtgg aggtggatcc cagctctact cagcgctcgc taataagtgt   1440
tgtcatgtgg gatgcacaaa gcggtctctc gccagattct gc                       1482
```

<210> SEQ ID NO 132
<211> LENGTH: 1494
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 132

```
gaggtgcagc tgctcgagtc aggggagggc ttggtacagc cggggggtc cctgagactc      60 tcctgtacaa cctctggatt caccttaac acgtatgcca tgagttgggt ccgccaggct     120
ccagggaagg ggctgaatg gctctcaggt attaataaca atggtcggac tgcattctac     180
gcagactccg tgaagggccg cttcaccatc tccagagaca actccaaaaa cacactttat    240
```

```
ctgcaaatta atagtctgag agcggacgac acggccgttt atttctgtgc gaaagatgtc      300
agatttatcg cagtgcctgg tgactcctgg ggccagggaa ccctggtcac cgtctcctca      360
gcctccacca agggcccatc ggtcttcccc ctggccccca gcagcaagag caccagcggc      420
ggcacagccg ccctgggctg cctggtgaag gactacttcc ccgagcccgt gaccgtgtcc      480
tggaacagcg gagccctgac ctccggcgtg cacaccttcc ccgccgtgct gcagagcagc      540
ggcctgtaca gcctgagcag cgtggtgaca gtgccaagca gcagcctggg cacccagacc      600
tacatctgca acgtgaacca caagcccagc aacaccaagg tggacaagag agttgagccc      660
aaatcttgtg acaagaccca cacctgtcct ccatgcccgg cgcctgagtt cgagggcgga      720
ccctccgtgt tcctgttccc cccaaagccc aaggacaccc tgatgatctc ccggaccccc      780
gaagtgacct gcgtggtggt ggacgtgtcc cacgaggacc ctgaagtgaa gttcaattgg      840
tacgtggacg gcgtggaagt gcacaacgcc aagaccaagc cagagagga acagtacaac      900 tccacctacc gggtggtgtc cgtgctgacc gtgctgcacc aggactggct gaacggcaaa      960
gagtacaagt gcaaggtctc caacaaggcc ctgcccgcct ccatcgaaaa gaccatctcc     1020
aaggccaagg gccagccccg cgagcctcag gtgtgcacac tgcccccag ccggaagag      1080 atgaccaaga accaggtgtc cctgtcctgt gccgtgaaag gcttctaccc ctccgatatc     1140
gctgtggaat gggagtccaa cggccagccc gagaacaact acaagaccac cccccctgtg     1200
ctggactccg acggctcatt cttcctggtg tccaagctga ccgtggacaa gtcccggtgg     1260
cagcagggca acgtgttctc ctgctccgtg atgcacgagg ccctgcacaa ccactacacc     1320
cagaagtctc taagcttgag ccccggcgga ggtggtggaa gcggaggagg tggctctgga     1380
gggggtggaa gcggaggtgg aggtggatcc agctggatgg aagaagtgat taaactgtgt     1440
ggccgcgaac tggtgcgcgc gcagattgcg atttgcggca tgagcacctg gagc           1494
```

<210> SEQ ID NO 133
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 133

```
gagctcgtgt tgactcagcc tgcctccgtg tctgggtctc ctggacagtc gatcaccatc       60
tcctgcactg gaaccagcag tgacgttggt ggttataact atgtctcctg gtaccaacag      120
cacccaggca agcccccaa actcatgatt tatgatgtca gtaagcggcc ctcagggtt       180 tctaatcgct tctctggctc caagtctggc aacacggcct ccctgaccat ctctgggctc      240
caggctgagg acgaggctga ttattactgc agctcatata caagcagcag cactttggta      300
ttcggcggag ggaccaagct gaccgtccta ggtcagccca aggctgcccc ctcggtcact      360
ctgttcccgc cctcctctga ggagcttcaa gccaacaagg ccacactggt gtgtctcata      420
agtgacttct acccgggagc cgtgacagtg gcctggaagg cagatagcag ccccgtcaag      480
gcgggagtgg agaccaccac accctccaaa caaagcaaca caagtacgc ggccagcagc      540 tatctgagcc tgacgcctga gcagtggaag tcccacagaa gctacagctg ccaggtcacg      600
catgaaggga gcaccgtgga aaagacagtg gcccctacag aatgttca                   648
```

<210> SEQ ID NO 134

<211> LENGTH: 876
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 134

| | | | | | |
|---|---|---|---|---|---|
| gataaaaccc | atacctgccc | gccgtgcccg | gcgccggaac | tgctgggcgg | cccgagcgtg | 60 |
| tttctgtttc | cgccgaaacc | gaaagatacc | ctgatgatta | gccgcacccc | ggaagtgacc | 120 |
| tgcgtggtgg | tggatgtgag | ccatgaagat | ccggaagtga | aatttaactg | gtatgtggat | 180 |
| ggcgtggaag | tgcataacgc | gaaaaccaaa | ccgcgcgaag | aacagtataa | cagcacctat | 240 |
| cgcgtggtga | gcgtgctgac | cgtgctgcat | caggattggc | tgaacggcaa | agaatataaa | 300 |
| tgcaaagtga | gcaacaaagc | gctgccggcg | ccgattgaaa | aaaccattag | caaagcgaaa | 360 |
| ggccagccgc | gcgaaccgca | ggtgtatacc | ctgccgccga | gccgcgatga | actgaccaaa | 420 |
| aaccaggtga | gcctgacctg | cctggtgaaa | ggctttttatc | cgagcgatat | tgcggtggaa | 480 |
| tgggaaagca | acggccagcc | ggaaaacaac | tataaaacca | ccccgccggt | gctggatagc | 540 |
| gatggcagct | tttttctgta | tagcaaactg | accgtggata | aaagccgctg | gcagcagggc | 600 |
| aacgtgttta | gctgcagcgt | gatgcatgaa | gcgctgcata | accattatac | ccagaaaagc | 660 |
| ctgagcctga | gcccgggcaa | aggcggcagc | ccgcagctgt | atagcgcgct | ggcgaacaaa | 720 |
| tgctgccatg | tgggctgcac | caaacgcagc | ctggcgcgct | tttgcggcgg | cggcagcggc | 780 |
| ggcggcagcg | gcagctggat | ggaagaagtg | attaaactgt | gtggccgcga | actggtgcgc | 840 |
| gcgcagattg | cgatttgcgg | catgagcacc | tggagc | | | 876 |

<210> SEQ ID NO 135
<211> LENGTH: 885
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 135

| | | | | | |
|---|---|---|---|---|---|
| gataagacac | acacctgtcc | tccatgtcct | gctccagaac | tgctcggcgg | accctctgtg | 60 |
| ttcctgtttc | ctccaaagcc | taaggacacc | ctgatgatct | ctcggacccc | tgaagtgacc | 120 |
| tgcgtggtgg | tggatgtgtc | tcacgaggat | cccgaagtga | agttcaattg | gtacgtggac | 180 |
| ggcgtggaag | tgcacaacgc | caagaccaag | cctagagagg | aacagtacaa | ctccacctac | 240 |
| agagtggtgt | ccgtgctgac | cgtgctgcac | caggattggc | tgaacggcaa | agagtacaag | 300 |
| tgcaaggtgt | ccaacaaggc | cctgcctgct | cctatcgaaa | agaccatctc | caaggctaag | 360 |
| ggccagcctc | gggaacctca | ggtttacaca | ctgcctccat | ctcggacga | gctgaccaag | 420 |
| aatcaggtgt | ccctgacctg | cctggtcaag | ggcttctacc | cttccgatat | cgccgtggaa | 480 |
| tgggagtcca | atggccagcc | tgagaacaac | tacaagacca | cacctcctgt | gctggactcc | 540 |
| gacggctcat | tcttcctgta | ctccaagctg | acagtggaca | agtctcggtg | gcagcagggc | 600 |
| aacgtgttct | cctgttctgt | gatgcacgag | gccctgcaca | accactacac | ccagaagtcc | 660 |
| ctgtctctgt | ccctggaaa | aggcggttcc | ggtggctctc | ctcagctgta | ctctgccctg | 720 |
| gccaacaagt | gttgtcacgt | gggctgcacc | aagcggtccc | tggctagatt | ttgtggcggt | 780 |
| ggaagtggcg | gcggatccgg | ctcttggatg | gaagaggtta | tcaagctgtg | cggcagagaa | 840 |

```
ctcgtgcggg cccagatcgc tatctgtggc atgtccacct ggtcc            885
```

<210> SEQ ID NO 136
<211> LENGTH: 894
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic polynucleotide"

<400> SEQUENCE: 136

```
gataagacac atacctgtcc tccatgtcct gctccagagc tgctcggagg cccttccgtg   60
tttctgttcc ctccaaagcc taaggacacc ctgatgatct ctcggacccc tgaagtgacc  120
tgcgtggtgg tggatgtgtc tcacgaggat cccgaagtga agttcaattg gtacgtggac  180
ggcgtggaag tgcacaacgc caagaccaag cctagagagg aacagtacaa ctccacctac  240
agagtggtgt ccgtgctgac cgtgctgcac caggattggc tgaacggcaa agagtacaag  300
tgcaaggtgt ccaacaaggc cctgcctgct cctatcgaaa agaccatctc caaggccaag  360
ggccagccta gggaacccca ggtttacacc ttgcctccat ctcgggacga gctgaccaag  420
aaccaggtgt ccctgacctg tctggtcaag ggcttctacc cctccgatat cgccgtggaa  480
tgggagtcta atggccagcc tgagaacaac tacaagacca cacctcctgt gctggactcc  540
gacggctcat tcttcctgta ctccaagctg acagtggaca agtccagatg gcagcagggc  600
aacgtgttct cctgctccgt gatgcacgag gccctgcaca atcactacac ccagaagtcc  660
ctgtctctgt cccctggcaa aggtggcagc ggaggttccg gaggatctcc tcagctgtac  720
tctgccctgg ccaacaagtg ttgccacgtg gctgcacca agatccct ggccagattt  780
tgtggcggcg gatctggcgg aggttccggc tcttggatgg aagaagtgat caagctctgc  840
ggcagagaac tcgtgcgggc ccagatcgct atctgcggca tgtctacctg gtcc        894
```

<210> SEQ ID NO 137
<211> LENGTH: 516
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic polynucleotide"

<400> SEQUENCE: 137

```
ttcaattggt acgtggacgg cgtggaagtg cacaacgcca agaccaagcc cagagaggaa   60
cagtacaact ccacctaccg ggtggtgtcc gtgctgaccg tgctgcacca ggactggctg  120
aacggcaaag agtacaagtg caaggtctcc aacaaggccc tgcccgcctc catcgaaaag  180
accatctcca aggccaaggg ccagccccgc gagcctcagg tgtacacact gccccccagc  240
cgggaagaga tgaccaagaa ccaggtgtcc ctgacctgtc tggtgaaagg cttctacccc  300
tccgatatcg ctgtggaatg ggagtccaac ggccagcccg agaacaacta caagaccacc  360
ccccctgtgc tggactccga cggctcattc ttcctgtact ccaagctgac cgtggacaag  420
tcccggtggc agcagggcaa cgtgttctcc tgctccgtga tgcacgaggc cctgcacaac  480
cactacaccc agaagtctct gtccctgagc cccggc                           516
```

<210> SEQ ID NO 138
<211> LENGTH: 828
<212> TYPE: DNA

<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 138

```
gacaagaccc acaccgcttg tcctccatgc ccggcgcctg agttcgaggg cggaccctcc      60
gtgttcctgt tcccccaaa gcccaaggac accctgatga tctcccggac ccccgaagtg     120
acctgcgtgg tggtggacgt gtcccacgag gaccctgaag tgaagttcaa ttggtacgtg     180
gacggcgtgg aagtgcacaa cgccaagacc aagcccagag aggaacagta caactccacc     240
taccgggtgg tgtccgtgct gaccgtgctg caccaggact ggctgaacgg caaagagtac     300
aagtgcaagg tctccaacaa ggccctgccc gcctccatcg aaaagaccat ctccaaggcc     360
aagggccagc ccgcgagcc tcaggtgtgc acactgcccc cagccggga agagatgacc     420
aagaaccagg tgtccctgtc ctgtgccgtg aaaggcttct acccctccga tatcgctgtg     480
gaatgggagt ccaacggcca gcccgagaac aactacaaga ccacccccccc tgtgctggac     540
tccgacggct cattcttcct ggtgtccaag ctgaccgtgg acaagtcccg gtggcagcag     600
ggcaacgtgt tctcctgctc cgtgatgcac gaggccctgc acaaccacta cacccagaag     660
tctctaagct tgagccccgg cggaggtggt ggaagcggag gaggtggctc tggagggggt     720
ggaagcggag gtggaggtgg atccagctgg atggaagaag tgattaaact gtgtggccgc     780
gaactggtgc gcgcgcagat tgcgatttgc ggcatgagca cctggagc                    828
```

<210> SEQ ID NO 139
<211> LENGTH: 816
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 139

```
gacaagaccc acaccgcttg tcctccatgc ccggcgcctg agttcgaggg cggaccctcc      60
gtgttcctgt tcccccaaa gcccaaggac accctgatga tctcccggac ccccgaagtg     120
acctgcgtgg tggtggacgt gtcccacgag gaccctgaag tgaagttcaa ttggtacgtg     180
gacggcgtgg aagtgcacaa cgccaagacc aagcccagag aggaacagta caactccacc     240
taccgggtgg tgtccgtgct gaccgtgctg caccaggact ggctgaacgg caaagagtac     300
aagtgcaagg tctccaacaa ggccctgccc gcctccatcg aaaagaccat ctccaaggcc     360
aagggccagc ccgcgagcc tcaggtgtac acactgcccc cctgccggga agagatgacc     420
aagaaccagg tgtccctgtg gtgtctggtg aaaggcttct acccctccga tatcgctgtg     480
gaatgggagt ccaacggcca gcccgagaac aactacaaga ccacccccccc tgtgctggac     540
tccgacggct cattcttcct gtactccaag ctgaccgtgg acaagtcccg gtggcagcag     600
ggcaacgtgt tctcctgctc cgtgatgcac gaggccctgc acaaccacta cacccagaag     660
tctctaagct tgagccccgg cggaggtggt ggaagcggag gaggtggctc tggagggggt     720
ggaagcggag gtggaggtgg atcccagctc tactcagcgc tcgctaataa gtgttgtcga     780
gtgggatgca caaagcggtc tctcgccaga ttctgc                                816
```

<210> SEQ ID NO 140
<211> LENGTH: 813

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 140
gacaagaccc acacctgtcc tccatgcccg gcgcctgagt tcgagggcgg accctccgtg      60
ttcctgttcc ccccaaagcc caaggacacc ctgatgatct cccggacccc cgaagtgacc     120
tgcgtggtgg tggacgtgtc ccacgaggac cctgaagtga agttcaattg gtacgtggac     180
ggcgtggaag tgcacaacgc caagaccaag cccagagagg aacagtacaa ctccacctac     240
cgggtggtgt ccgtgctgac cgtgctgcac caggactggc tgaacggcaa agagtacaag     300
tgcaaggtct ccaacaaggc cctgcccgcc tccatcgaaa agaccatctc caaggccaag     360
ggccagcccc gcgagcctca ggtgtacaca ctgccccct gccgggaaga gatgaccaag     420
aaccaggtgt ccctgtggtg tctggtgaaa ggcttctacc cctccgatat cgctgtggaa     480
tgggagtcca acggccagcc cgagaacaac tacaagacca ccccccctgt gctggactcc     540
gacggctcat tcttcctgta ctccaagctg accgtggaca gtcccggtg gcagcagggc     600
aacgtgttct cctgctccgt gatgcacgag gccctgcaca accactacac ccagaagtct     660
ctaagcttga gccccggcgg aggtggtgga agcggaggag gtggctctgg aggggtgga     720
agcggaggtg gaggtggatc ccagctctac tcagcgctcg ctaataagtg ttgtcatgtg     780
ggatgcacaa agcggtctct cgccagagcg tgc                                 813
```